US011499146B2

(12) United States Patent
Babe et al.

(10) Patent No.: US 11,499,146 B2
(45) Date of Patent: Nov. 15, 2022

(54) *BACILLUS GIBSONII*-CLADE SERINE PROTEASES

(71) Applicant: DANISCO US INC., Palo Alto, CA (US)

(72) Inventors: Lilia Maria Babe, Emerald Hills, CA (US); Richard R. Bott, Kirkland, WA (US); David A. Estell, San Mateo, CA (US); Harm Mulder, Voorhout (NL); Frits Goedegebuur, Vlaardingen (NL); Jian Yao, Sunnyvale, CA (US); Sina Pricelius, Leiden (NL); Miles Scotcher, San Ramon, CA (US)

(73) Assignee: DANISCO US INC., Palo Alto, CA (US)

( * ) Notice: Subject to any disclaimer, the term of this patent is extended or adjusted under 35 U.S.C. 154(b) by 367 days.

(21) Appl. No.: 15/736,401

(22) PCT Filed: Jun. 17, 2016

(86) PCT No.: PCT/US2016/038245
§ 371 (c)(1),
(2) Date: Dec. 14, 2017

(87) PCT Pub. No.: WO2016/205755
PCT Pub. Date: Dec. 22, 2016

(65) Prior Publication Data

US 2018/0237761 A1 Aug. 23, 2018

Related U.S. Application Data

(60) Provisional application No. 62/180,673, filed on Jun. 17, 2015.

(51) Int. Cl.
*C12N 9/54* (2006.01)
*C11D 3/386* (2006.01)

(52) U.S. Cl.
CPC ................ *C12N 9/54* (2013.01); *C11D 3/386* (2013.01); *C11D 3/38663* (2013.01); *C12Y 304/21062* (2013.01)

(58) Field of Classification Search
CPC ...... C12N 9/54; C11D 3/386; C11D 3/38663; C12Y 304/21062; A61P 43/00
See application file for complete search history.

(56) References Cited

U.S. PATENT DOCUMENTS

| | | | | |
|---|---|---|---|---|
| 7,262,042 B2 | 8/2007 | Weber et al. | | |
| 7,507,569 B2 * | 3/2009 | Minning | ............ | C11D 3/38636 435/221 |

FOREIGN PATENT DOCUMENTS

| | | |
|---|---|---|
| WO | 2009/037258 A1 | 3/2009 |
| WO | 2015/089447 A1 | 6/2015 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Goddette et al., Gen Bank accession No. P29599, Oct. 1, 1993.*
Copeland et al., Gen Bank accession No. ABR36072, Jun. 27, 2007.*
Ma et al., Gen Bank accession No. AKG74460, May 11, 2015.*
Database Accession No. ABW46664, Sequence 3 from U.S. Pat. No. 7262042, Oct. 19, 2007.
International Search Report and Written Opinion, PCT/US2016/038245, dated Sep. 16, 2016.

* cited by examiner

*Primary Examiner* — Delia M Ramirez

(57) ABSTRACT

Disclosed herein is one or more subtilisin variant, nucleic acid encoding same, and compositions and methods related to the production and use thereof, including one or more *Bacillus gibsonii*-clade subtilisin variant that has improved stability and/or soil removal compared to one or more reference subtilisin.

10 Claims, 47 Drawing Sheets

Figure 1:
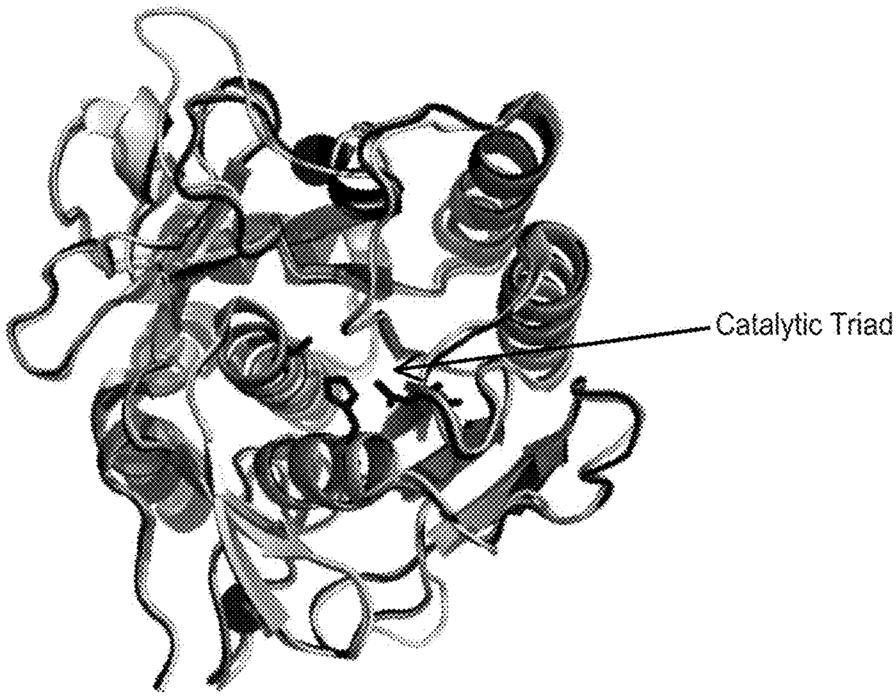

Specification includes a Sequence Listing.

| FIG. 6A-1 |
|---|
| FIG. 6A-2 |

FIG. 6A

FIG. 6A-1

```
                                       1                                                 50
        B_amyloliquefaciens_CAA24990  (1) AQSVPYGVSQIKAPALHSQGYTGSNVKVAVIDSGIDSSHPDLKVAGGASM
        G_stearothermophilus_ABY25856 (1) AQSVPYGVSQIKAPALHSQGFTGSNVKVAVIDSGIDSSHPDLKVAGGASM
                  B_subtilis_BAN09118 (1) AQSVPYGISQIKAPALHSQGYTGSNVKVAVIDSGIDSSHPDLNVRGGASF
             B_atrophaeus_YP003972439 (1) AQSVPYGISQIKAPAVHSQGYTGSNVKVAVIDSGIDSSHPDLKVSGGASF
                B_circulans_ADN04910  (1) AQTVPYGIPQIKAPAVHAQGYKGANVKVAVLDTGIHAAHPDLNVAGGASF
                   B_pumilus_ADK11996 (1) AQTVPYGIPQIKAPAVHAQGYKGANVKVAVLDTGIHAAHPDLNVAGGASF
         B_licheniformis_CAJ70731.1   (1) AQTVPYGIPLIKADKVQAQGFKGANVKVAVLDTGIQASHPDLNVVGGASF
                Bacillus_sp_BAD11988  (1) AQTTPWGVTHINAHRAHSSGVTGSGVKVAILDTGIHASHPDLNVRGGASF
                Bacillus_sp_AAC43580  (1) AQTVPWGIPHIKADKAHAAGVTGSGVKVAILDTGIDANHADLNVKGGASF
                Bacillus_sp_BAA05540  (1) SQTVPWGISFINTQQAHNRGIFGNGARVAVLDTGIA-SHPDLRIAGGASF
                    B_lentus_P29600   (1) AQSVPWGISRVQAPAAHNRGLTGSGVKVAVLDTGIS-THPDLNIRGGASF
                          Bgi02446    (1) QQTVPWGITRVQAPAVHNRGITGSGVRVAILDSGIS-AHSDLNIRGGASF
                 B_gibsonii_DSM9728   (1) QQTVPWGITRVQAPAVHNRGVTGSGVRVAILDSGIS-THSDLTIRGGASF
                 B_gibsonii_DSM9729   (1) QQTVPWGITRVQAPAVHNRGITGSGVRVAILDSGIS-AHSDLNIRGGASF
                 B_gibsonii_DSM9730   (1) QQTVPWGITRVQAPAVHNRGVTGSGVRVAILDSGIS-THSDLTIRGGASF
                 B_gibsonii_DSM9731   (1) QQTVPWGITRVQAPAVHNRGVTGSGVRVAILDSGIS-THSDLTIRGGASF
                   WO03054184-0001    (1) QQTVPWGITRVQAPAVHNRGVTGSGVRVAILDSGIS-THSDLTIRGGASF
                   WO03054185-0001    (1) QQTVPWGITRVQAPTVHNRGITGSGVKVAILDTGIA-QHSDLTIRGGASF
                 WO2007131657-0001    (1) QQTVPWGITRVQAPAVHNRGVTGSGVRVAILDSGIS-QHSDLTIRGGASF
                 WO2008086916-0001    (1) QQTVPWGITRVQAPAVHNRGVTGSGVRVAILDSGIS-QHSDLTIRGGASF
                         BSP-01537    (1) QQTVPWGITRVQAPAVHNRGVTGSGVRVAILDSGIS-AHSDLNIRGGASF
                         BSP-01757    (1) QQTVPWGITRVQAPAVHNRGITGSGVRVAILDSGIS-AHSDLTIRGGASF
                         BSP-01531    (1) AQTVPWGITRVQAPAVHNRGITGSGVRVAILDSGIS-AHSDLNIRGGASF
```

| | | |
|---|---|---|
| BSP-02320 | (1) | QQTVPWGITRVQAPAVHNRGITGSGVRVAILDSGIS-AHSDLNIRGGASF |
| BSP-02389 | (1) | QQTVPWGITRVQAPAVHNRGITGSGVRVAILDSGIS-AHSDLNIRGGASF |
| BSP-02355 | (1) | QQTVPWGITRVQAPAVHNRGITGSGVRVAILDSGIS-AHSDLNIRGGASF |
| BSP-02354 | (1) | QQTVPWGITRVQAPAVHNRGITGSGVRVAILDSGIS-AHSDLNIRGGASF |
| BSP-02380 | (1) | QQTVPWGITRVQAPAVHNRGITGSGVRVAILDSGIS-AHSDLNIRGGASF |
| BSP-03007 | (1) | QQTVPWGITRVQAPAVHNRGITGSGVRVAILDSGIS-AHSDLNIRGGASF |
| BSP-02411 | (1) | QQTVPWGITRVQAPAVHNRGITGSGVRVAILDSGIS-AHSDLNIRGGASF |
| BSP-02195 | (1) | QQTVPWGITRVQAPAVHNRGITGSGVRVAILDSGIS-AHSDLNIRGGASF |
| BSP-02400 | (1) | QQTVPWGITRVQAPAVHNRGITGSGVRVAILDSGIS-AHSDLNIRGGASF |
| BSP-02301 | (1) | QQTVPWGITRVQAPAVHNRGITGSGVKVAILDSGIS-AHSDLNIRGGASF |
| BSP-03027 | (1) | QQTVPWGITRVQAPAVHNRGITGSGVKVAILDSGIS-AHSDLNIRGGASF |
| BSP-02412 | (1) | QQTVPWGITRVQAPAVHNRGITGSGVKVAILDSGIS-AHSDLNIRGGASF |
| BSP-02391 | (1) | QQTVPWGITRVQAPAVHNRGITGSGVKVAILDSGIS-AHSDLNIRGGASF |
| BSP-02227 | (1) | QQTVPWGITRVQAPAVHNRGITGSGVRVAILDSGIS-AHSDLNIRGGASF |
| BSP-02725 | (1) | QQTVPWGITRVQAPAVHNRGITGSGVRVAILDSGIS-AHSDLNIRGGASF |
| BSP-03048 | (1) | QQTVPWGITRVQAPAVHNRGITGSGVRVAILDSGIS-AHSDLNIRGGASF |
| BSP-03024 | (1) | QQTVPWGITRVQAPAVHNRGITGSGVRVAILDSGIS-AHSDLNIRGGASF |
| BSP-03033 | (1) | QQTVPWGITRVQAPAVHNRGITGSGVRVAILDSGIS-AHSDLNIRGGASF |
| Consensus | (1) | QQTVPWGITRVQAPAVHNRGITGSGVRVAILDSGIS AHSDLNIRGGASF |

| | | 51 100 |
|---|---|---|
| B_amyloliquefaciens_CAA24990 | (51) | VPSETNPFQDNNSHGTHVAGTVAALNNSIGVLGVAPSASLYAVKVLGADG |
| G_stearothermophilus_ABY25856 | (51) | VPSETNPFQDNNSHGTHVAGTVAALNNSVGVLGVAPSASLYAVKVLGADG |
| B_subtilis_BAN09118 | (51) | VPSETNPYQDGSSHGTHVAGTVAALNNTIGVLGVAPSASLYAVKVLDSTG |
| B_atrophaeus_YP003972439 | (51) | VPSEPNPFQDGNSHGTHVAGTVAALNNSVGVLGVAPSASLYAVKVLSSSG |
| B_circulans_ADN04910 | (51) | VPSEPNATQDFQSHGTHVAGTIAALDNTIGVLGVAPSASLYAVKVLDRNG |
| B_pumilus_ADK11996 | (51) | VPSEPNATQDFQSHGTHVAGTIAALDNTIGVLGVAPSASLYAVKVLDRNG |
| B_licheniformis_CAJ70731.1 | (51) | VAGEAY-NTDGNGHGTHVAGTVAALDNTTGVLGVAPSVSLYAVKVLNSSG |
| Bacillus_sp_BAD11988 | (51) | ISGESNPYIDSNGHGTHVAGTVAALNNTVGVLGVAYNAELYAVKVLSASG |
| Bacillus_sp_AAC43580 | (51) | VSGEPNALQDGNGHGTHVAGTVAALNNTTGVLGVAYNADLYAVKVLSASG |
| Bacillus_sp_BAA05540 | (50) | ISSEPS-YHDNNGHGTHVAGTIAALNNSIGVLGVAPSADLYAVKVLDRNG |
| B_lentus_P29600 | (50) | VPGEPS-TQDGNGHGTHVAGTIAALNNSIGVLGVAPSAELYAVKVLGASG |
| Bgi02446 | (50) | VPGEPT-TADLNGHGTHVAGTVAALNNSIGVIGVAPNAELYAVKVLGANG |
| B_gibsonii_DSM9728 | (50) | VPGEPT-TADLNGHGTHVAGTVAALNNSIGVIGVAPSADLYAVKVLGANG |
| B_gibsonii_DSM9729 | (50) | VPGEPT-TADLNGHGTHVAGTVAALNNSIGVIGVAPNADLYAVKVLGANG |
| B_gibsonii_DSM9730 | (50) | VPGEPT-TADLNGHGTHVAGTVAALNNSIGVIGVAPSADLYAVKVLGANG |
| B_gibsonii_DSM9731 | (50) | VPGEPT-TADLNGHGTHVAGTVAALNNSIGVIGVAPSADLYAVKVLGANG |
| WO03054184-0001 | (50) | VPGEPT-TADLNGHGTHVAGTVAALNNSIGVIGVAPSADLYAVKVLGANG |
| WO03054185-0001 | (50) | VPGEST-TADLNGHGTHVAGTVAALNNSIGVIGVAPSADLYAVKVLGANG |
| WO2007131657-0001 | (50) | IPGEPT-TADLNGHGTHVAGTVAALNNSIGVIGVAPSADLYAVKVLGANG |
| WO2008086916-0001 | (50) | VPGEPT-TEDLNGHGTHVAGTVAALNNSFGVIGVAPSADLYAVKVLGAGG |
| BSP-01537 | (50) | VPGEPT-TADLNGHGTHVAGTVAALNNSIGVVGVAPSADLYAVKVLGANG |
| BSP-01757 | (50) | VPGEPT-TADLNGHGTHVAGTVAALNNSIGVVGVAPSADLYAVKVLGANG |
| BSP-01531 | (50) | VPGEPT-TADLNGHGTHVAGTVAALNNSIGVVGVAPNAELYAVKVLGANG |

```
BSP-02320   (50) VPGEPT-TADLNGHGTHVAGTVAALDNSIGVVGVAPSADLYAVKVLGANG
BSP-02389   (50) VPGEPT-TADLNGHGTHVAGTVAALDNSIGVVGVAPSADLYAVKVLGANG
BSP-02355   (50) VPGEPT-TADLNGHGTHVAGTVAALNNSIGVIGVAPSADLYAVKVLGANG
BSP-02354   (50) VPGEPT-TADLNGHGTHVAGTVAALDNSIGVVGVAPSADLYAVKVLGANG
BSP-02380   (50) VPGEPT-TADLNGHGTHVAGTVAALDNSIGVVGVAPSADLYAVKVLGANG
BSP-03007   (50) VPGEPT-TADLNGHGTHVAGTVAALDNSIGVVGVAPSADLYAVKVLGANG
BSP-02411   (50) VPGEPT-TADLNGHGTHVAGTVAALDNSIGVIGVAPSADLYAVKVLGANG
BSP-02195   (50) VPGEPT-TADLNGHGTHVAGTVAALDNSIGVIGVAPNAELYAVKVLGANG
BSP-02400   (50) VPGEPT-TADLNGHGTHVAGTVAALDNSIGVVGVAPNAELYAVKVLGANG
BSP-02301   (50) VPGEPT-TADLNGHGTHVAGTVAALNNSIGVIGVAPNAELYAVKVLGANG
BSP-03027   (50) VPGEPT-TADLNGHGTHVAGTVAALNNSIGVIGVAPNAELYAVKVLGANG
BSP-02412   (50) VPGEPT-TADLNGHGTHVAGTVAALDNSIGVIGVAPNAELYAVKVLGANG
BSP-02391   (50) VPGEPT-TADLNGHGTHVAGTVAALDNSIGVIGVAPNAELYAVKVLGANG
BSP-02227   (50) VPGEPT-TADLNGHGTHVAGTVAALDNSIGVVGVAPNAELYAVKVLGANG
BSP-02725   (50) VPGEPT-TADLNGHGTHVAGTVAALNNSIGVIGVAPSADLYAVKVLGANG
BSP-03048   (50) VPGEPT-TADLNGHGTHVAGTVAALNNSIGVVGVAPSADLYAVKVLGANG
BSP-03024   (50) VPGEPT-TADLNGHGTHVAGTVAALDNSIGVVGVAPSADLYAVKVLGANG
BSP-03033   (50) VPGEPT-TADLNGHGTHVAGTVAALDNSIGVVGVAPSADLYAVKVLGANG
Consensus   (51) VPGEPT TADLNGHGTHVAGTVAALNNSIGV GVAPSADLYAVKVLGANG
```

| | | 101 150 |
|---|---|---|
| B_amyloliquefaciens_CAA24990 | (101) | SGQYSWIINGIEWAIANNMDVINMSLGGPSGSAALKAAVDKAVASGVVVV |
| G_stearothermophilus_ABY25856 | (101) | SGQYSWIINGIEWAIAYNMDVINMSLGGPSGSAALKAAVDKAVASGIVVV |
| B_subtilis_BAN09118 | (101) | SGQYSWIINGIEWAISNNMDVINMSLGGPTGSTALKTVVDKAVASGIVVV |
| B_atrophaeus_YP003972439 | (101) | SGDYSWIINGIEWAISNNMDVINMSLGGPQGSTALKAVVDKAVSQGIVVV |
| B_circulans_ADN04910 | (101) | DGQYSWIISGIEWAVANNMDVINMSLGGPNGSTALKNAVDTANNRGVVVV |
| B_pumilus_ADK11996 | (101) | DGQYSWIISGIEWAVANNMDVINMSLGGASGSTALKNAVDTANNRGVVVV |
| B_licheniformis_CAJ70731.1 | (100) | SGSYSGIVSGIEWATTNGMDVINMSLGGASGSTAMKQAVDNAYARGVVVV |
| Bacillus_sp_BAD11988 | (101) | SGTLSGIAQGVEWSIANKMDVINMSLGGSSGSTALQRAVDNAYRNNIVVV |
| Bacillus_sp_AAC43580 | (101) | SGTLSGIAQGIEWSISNGMNVINMSLGGSSGSTALQQACNNAYNRGIVVI |
| Bacillus_sp_BAA05540 | (99) | SGSLASVAQGIEWAINNNMHIINMSLGSTSGSSTLELAVNRANNAGILLV |
| B_lentus_P29600 | (99) | SGSVSSIAQGLEWAGNNGMHVANLSLGSPSPSATLEQAVNSATSRGVLVV |
| Bgi02446 | (99) | SGSVSGIAQGLEWAATNNMHIANMSLGSDFPSSTLERAVNYATSRDVLVI |
| B_gibsonii_DSM9728 | (99) | RGSVSGIAQGLEWAAANNMHIANMSLGSDAPSTTLERAVNYATSQGVLVI |
| B_gibsonii_DSM9729 | (99) | SGSVSGIAQGLEWAATNNMHIANMSLGSDFPSSTLERAVNYATSRDVLVI |
| B_gibsonii_DSM9730 | (99) | RGSVSGIAQGLEWAAANNMHIANMSLGSDAPSTTLERAVNYATSQGVLVI |
| B_gibsonii_DSM9731 | (99) | RGSVSGIAQGLEWAAANNMHIANMSLGSDAPSTTLERAVNYATSQGVLVI |
| WO03054184-0001 | (99) | RGSVSGIAQGLEWAAANNMHIANMSLGSDAPSITLERAVNYATSQGVLVI |
| WO03054185-0001 | (99) | RGSVSGIAQGLEWAATNNMHIANMSLGSDAPSTTLERAVNYATSRGVLVI |
| WO2007131657-0001 | (99) | RGSVSGIAQGLEWAAANNMHIANMSLGADAPSSTLERAVNYATSQGVLVI |
| WO2008086916-0001 | (99) | RGSVSGIAQGLEWAAANNMHIANMSLGADAPSSTLERAVNYATSRGVLVI |
| BSP-01537 | (99) | SGSVSGIAQGLEWAATNNIHIANMSLGSDAPSTTLERAVNYATSQGVLVI |
| BSP-01757 | (99) | SGSVSGIAQGLEWAAANNMHIANMSLGSDAPSSTLERAVNYATSQGVLVI |
| BSP-01531 | (99) | SGSVSGIAQGLEWAATNNMHIANMSLGSDAPSTTLERAVNYATSAGVLVI |

```
BSP-02320   (99) SGSVSGIAQGLEWAATNNMHIANMSLGSDFPSSTLERAVNYATSRDVLVI
BSP-02389   (99) RGSISGIAQGLEWAATNNMHIANMSLGSDFPSSTLERAVNYATSRDVLVI
BSP-02355   (99) RGSISGIAQGLEWAAQNNMHIANMSLGSDFPSSTLERAVNYATSRDVLVI
BSP-02354   (99) RGSISGIAQGLEWAATNNMHIANMSLGTDAPSSTLERAVNYATSADVLVI
BSP-02380   (99) RGSISGIAQGLEWAAQNNMHIANMSLGSDFPSSTLERAVNYATSADVLVI
BSP-03007   (99) RGSISGIAQGLEWAATNNMHIANMSLGSDFPSSTLERAVNYATSRDVLVI
BSP-02411   (99) RGSISGIAQGLEWAATNNMHIANMSLGTDAPSSTLERAVNYATSRDVLVI
BSP-02195   (99) RGSISGIAQGLEWAATNNMHIANMSLGTDAPSSTLERAVNYATSADVLVI
BSP-02400   (99) RGSISGIAQGLEWAAQNNMHVANMSLGTDAPSSTLERAVNYATSRDVLVI
BSP-02301   (99) RGSISGIAQGLEWAAQNNMHVANMSLGTDAPSSTLERAVNYATSRDVLVI
BSP-03027   (99) RGSISGIAQGLEWAATNNMHIANMSLGTDAPSSTLERAVNYATSADVLVI
BSP-02412   (99) RGSISGIAQGLEWAATNNMHVANMSLGTDAPSSTLERAVNYATSADVLVI
BSP-02391   (99) RGSISGIAQGLEWAAQNNMHIANMSLGTDAPSSTLERAVNYATSRDVLVI
BSP-02227   (99) RGSISGIAQGLEWAAQNNMHIANMSLGTDAPSSTLERAVNYATSADVLVI
BSP-02725   (99) RGSVSGIAQGLEWAAQNNMHVANMSLGTDAPSSTLERAVNYATSADVLVI
BSP-03048   (99) RGSISGIAQGLEWAAQNNMHVANMSLGTDAPSSTLERAVNYATSADVLVI
BSP-03024   (99) RGSVSGIAQGLEWAAQNNMHIANMSLGTDAPSSTLERAVNYATSADVLVI
BSP-03033   (99) RGSISGIAQGLEWAAQNNMHIANMSLGTDAPSSTLERAVNYATSRDVLVI
Consensus  (101) RGS SGIAQGLEWAA NNMHIANMSLG DAPSSTLERAVNYATS  VLVI
```

| | | 151 200 |
|---|---|---|
| B_amyloliquefaciens_CAA24990 | (151) | AAAGNEGTSGSSSTVGYPGKYPSVIAVGAVDSSNQRASFSSVGPELDVMA |
| G_stearothermophilus_ABY25856 | (151) | AAAGNEGTSGSSSTVGYPGKYPSVIAVGAVNSSNQRASFSSVGSELDVMA |
| B_subtilis_BAN09118 | (151) | AAAGNEGSSGSTSTVGYPAKYPSTIAVGAVNSSNQRASFSSAGSELDVMA |
| B_atrophaeus_YP003972439 | (151) | AAAGNSGSSGSTSTVGYPAKYPSVIAVGAVDSNNQRASFSSAGSELDVMA |
| B_circulans_ADN04910 | (151) | AAAGNSGSTGSTSTVGYPAKYDSTIAVANVNSSNVRNSSSSAGPELDVSA |
| B_pumilus_ADK11996 | (151) | AAAGNSGSSGSRSTVGYPAKYESTIAVANVNSNNVRNSSSSAGPELDVSA |
| B_licheniformis_CAJ70731.1 | (150) | AAAGNSGSSGNTNTIGYPAKYDSVIAVGAVDSNSNRASFSSVGAELEVMA |
| Bacillus_sp_BAD11988 | (151) | AAAGNSGAQGNRNTIGYPARYSSVIAVGAVDSNNNRASFSSVGSELEVMA |
| Bacillus_sp_AAC43580 | (151) | AAAGNSGSSGNRNTMGYPARYSSVIAVGAVSSNNTRASFSSVGSELEVMA |
| Bacillus_sp_BAA05540 | (149) | GAAGNTGRQG----VNYPARYSGVMAVAAVDQNGQRASFSTYGPEIEISA |
| B_lentus_P29600 | (149) | AASGNSGAGS----ISYPARYANAMAVGATDQNNNRASFSQYGAGLDIVA |
| Bgi02446 | (149) | AATGNNGSGS----VGYPARYANAMAVGATDQNNRRANFSQYGTGIDIVA |
| B_gibsonii_DSM9728 | (149) | AATGNNGSGS----VGYPARYANAMAVGATDQNNRRANFSQYGTGIDIVA |
| B_gibsonii_DSM9729 | (149) | AATGNNGSGS----VGYPARYANAMAVGATDQNNRRANFSQYGTGIDIVA |
| B_gibsonii_DSM9730 | (149) | AATGNNGSGS----VGYPARYANAMAVGATDQNNRRANFSQYGTGIDIVA |
| B_gibsonii_DSM9731 | (149) | AATGNNGSGS----VGYPARYANAMAVGATDQNNRRANFSQYGSGIDIVA |
| WO03054184-0001 | (149) | AATGNNGSGS----VGYPARYANAMAVGATDQNNRRANFSQYGTGIDIVA |
| WO03054185-0001 | (149) | AATGNNGTGS----IGYPARYANAMAVGATDQNNRRASFSQYGTGIDIVA |
| WO2007131657-0001 | (149) | AATGNNGSGS----VGYPARYANAMAVGATDQNNRRANFSQYGTGIDIVA |
| WO2008086916-0001 | (149) | AATGNNGSGS----VGYPARYANAMAVGATDQNNRRANFSQYGTGIDIVA |
| BSP-01537 | (149) | AATGNNGSGS----VGYPARYANAMAVGATDQNNRRANFSQYGTGIDIVA |
| BSP-01757 | (149) | AATGNNGSGT----ISYPARYANAMAVGATDQNNRRANFSQYGTGIDIVA |
| BSP-01531 | (149) | AATGNNGSGS----VGYPARYANALAVGATDQNNRRANFSQYGTGLDIVA |

| | | |
|---|---|---|
| BSP-02320 | (149) | AATGNNGSGT----VGYPARYANAMAVGATDQNNRRANFSQYGTGIDIVA |
| BSP-02389 | (149) | AATGNNGSGT----IGYPARYANAMAVGATDQNNRRANFSQYGTGIDIVA |
| BSP-02355 | (149) | AATGNNGSGT----ISYPARYANAMAVGATDQNNRRANFSQYGTGIDIVA |
| BSP-02354 | (149) | AATGNNGSGS----VGYPARYANAMAVGATDQNNRRANFSQYGTGLDIVA |
| BSP-02380 | (149) | AATGNNGSGS----VGYPARYANAMAVGATDQNNRRANFSQYGTGLDIVA |
| BSP-03007 | (149) | AATGNNGSGS----VGYPARYANAMAVGATDQNNRRANFSQYGTGLDIVA |
| BSP-02411 | (149) | AATGNNGSGS----VGYPARYANAMAVGATDQNNRRANFSQYGTGLDIVA |
| BSP-02195 | (149) | AATGNNGSGT----VGYPARYANAMAVGATDQNNRRANFSQYGTGIDIVA |
| BSP-02400 | (149) | AATGNNGSGT----VSYPARYANAMAVGATDQNNRRANFSQYGTGIDIVA |
| BSP-02301 | (149) | AATGNNGSGT----ISYPARYANAMAVGATDQNNRRANFSQYGAGIDIVA |
| BSP-03027 | (149) | AATGNNGSGT----ISYPARYANAMAVGATDQNNRRANFSQYGTGIDIVA |
| BSP-02412 | (149) | AATGNNGSGS----VSYPARYANAMAVGATDQNNRRANFSQYGTGIDIVA |
| BSP-02391 | (149) | AATGNNGSGS----VGYPARYANAMAVGATDQNNRRANFSQYGAGLDIVA |
| BSP-02227 | (149) | AATGNNGSGS----VGYPARYANAMAVGATDQNNRRANFSQYGTGIDIVA |
| BSP-02725 | (149) | AATGNNGSGS----VSYPARYANAMAVGATDQNNRRANFSQYGTGIDIVA |
| BSP-03048 | (149) | AATGNNGSGS----VGYPARYANAMAVGATDQNNRRANFSQYGTGIDIVA |
| BSP-03024 | (149) | AATGNNGSGS----VGYPARYANAMAVGATDQNNRRANFSQYGTGIDIVA |
| BSP-03033 | (149) | AATGNNGSGS----VGYPARYANAMAVGATDQNNRRANFSQYGTGIDIVA |
| Consensus | (151) | AATGNNGSGS    VGYPARYANAMAVGATDQNNRRANFSQYGTGIDIVA |

| | | 201 250 |
|---|---|---|
| B_amyloliquefaciens_CAA24990 | (201) | PGVSIQSTLPGNKYGAYNGTSMASPHVAGAAALILSKHPNWTNTQVRSSL |
| G_stearothermophilus_ABY25856 | (201) | PGVSIQSTLPGNKYGAYNGTSMASPHVAGAAALILSKHPNWTNTQVRSSL |
| B_subtilis_BAN09118 | (201) | PGVSIQSTLPGGTYGSYNGTSMATPHVAGAAALILSKHPTWSNAQVRDRL |
| B_atrophaeus_YP003972439 | (201) | PGVSIQSTLPGSSYGSYNGTSMASPHVAGAAALVLSKHPNWTNSQVRNSL |
| B_circulans_ADN04910 | (201) | PGTSILSTVPSRGYTSYTGTSMASPHVAGAAALILSKNPNLSNSQVRQRL |
| B_pumilus_ADK11996 | (201) | PGTSILSTVPSSGYTSYTGTSMASPHVAGAAALILSKNPNLTNSQVRQRL |
| B_licheniformis_CAJ70731.1 | (200) | PGAGVYSTYPTNTYATLNGTSMASPHVAGAAALILSKHPNLSASQVRNRL |
| Bacillus_sp_BAD11988 | (201) | PGVSILSTVPGSSYASYNGTSMASPHVAGAAALLKAKYPNWSAAQIRNKL |
| Bacillus_sp_AAC43580 | (201) | PGVNILSTTPGNNYASFNGTSMAAPHVAGAAALIKAKYPSMTNVQIRERL |
| Bacillus_sp_BAA05540 | (195) | PGVNVNSTYTGNRYVSLSGTSMATPHVAGVAALVKSRYPSYTNNQIRQRI |
| B_lentus_P29600 | (195) | PGVNVQSTYPGSTYASLNGTSMATPHVAGAAALVKQKNPSWSNVQIRNHL |
| Bgi02446 | (195) | PGVNVQSTYPGNRYVSMNGTSMATPHVAGAAALVKQRYPSWNATQIRNHL |
| B_gibsonii_DSM9728 | (195) | PGVNVQSTYPGNRYASLNGTSMATPHVAGAAALVKQRYPSWNATQIRNHL |
| B_gibsonii_DSM9729 | (195) | PGVNVQSTYPGNRYVSMNGTSMATPHVAGAAALVKQRYPSWNATQIRNHL |
| B_gibsonii_DSM9730 | (195) | PGVNVQSTYPGNRYVSMNGTSMATPHVAGAAALVKQRYPSWNATQIRNHL |
| B_gibsonii_DSM9731 | (195) | PGVNVQSTYPGNRYVSMNGTSMATPHVAGAAALVKQRYPSWNATQIRNHL |
| WO03054184-0001 | (195) | PGVNVQSTYPGNRYASLNGTSMATPHVAGAAALVKQRYPSWNATQIRNHL |
| WO03054185-0001 | (195) | PGVGIQSTYLNNSYASMPGTSMATPHVAGVAALVKQKNPSWNATQIRNHL |
| WO2007131657-0001 | (195) | PGVNVQSTYPGNRYASLNGTSMATPHVAGAAALVKQRNPSWNATQIRNHL |
| WO2008086916-0001 | (195) | PGVNVQSTYPGNRYASLNGTSMATPHVAGVAALVKQRNPSWNATQIRNHL |
| BSP-01537 | (195) | PGVNVQSTYPGNRYVSMNGTSMATPHVAGVAALVKQRYPSWNATQIRNHL |
| BSP-01757 | (195) | PGVGVQSTYPGNRYVSMNGTSMATPHVAGAAALVKQRYPSWNATQIRNHL |
| BSP-01531 | (195) | PGVNVQSTYPGNRYVSMNGTSMATPHVAGAAALVKQRYPSWNATQIRNHL |

```
BSP-02320  (195) PGVNVQSTYPGNRYVSMNGTSMATPHVAGAAALVKQRYPSWNATQIRDHL
BSP-02389  (195) PGVNVQSTYPGNRYVSMNGTSMATPHVAGAAALVKQRYPSWNATQIRDHL
BSP-02355  (195) PGVNVQSTYPGNRYVSMSGTSMATPHVAGAAALVKQRYPSWNATQIRDHL
BSP-02354  (195) PGVNVQSTYPGNRYVSMNGTSMATPHVAGAAALVKQRYPSWNATQIRDHL
BSP-02380  (195) PGVNVQSTYPGNRYVSMNGTSMATPHVAGAAALVKQRYPSWNATQIRDHL
BSP-03007  (195) PGVNVQSTYPGNRYVSMNGTSMATPHVAGAAALVKQRYPSWNATQIRDHL
BSP-02411  (195) PGVNVQSTYPGNRYVSMNGTSMATPHVAGAAALVKQRYPSWNATQIRDHL
BSP-02195  (195) PGVNVQSTYPGNRYVSMSGTSMATPHVAGAAALVKQRYPSWNATQIRNHL
BSP-02400  (195) PGVNVQSTYPGNRYVSMSGTSMATPHVAGAAALVKQRYPSWNATQIRNHL
BSP-02301  (195) PGVNVQSTYPGNRYVSMNGTSMATPHVAGAAALVKQRYPSWNATQIRDHL
BSP-03027  (195) PGVNVQSTYPGNRYVSMNGTSMATPHVAGAAALVKQRYPSWNATQIRNHL
BSP-02412  (195) PGVNVQSTYPGNRYVSMSGTSMATPHVAGAAALVKQRYPSWNATQIRDHL
BSP-02391  (195) PGVNVQSTYPGNRYVSMSGTSMATPHVAGAAALVKQRYPSWNATQIRDHL
BSP-02227  (195) PGVNVQSTYPGNRYVSMSGTSMATPHVAGAAALVKQRYPSWNATQIRDHL
BSP-02725  (195) PGVNVQSTYPGNRYVSMNGTSMATPHVAGAAALVKQRYPSWNATQIRNHL
BSP-03048  (195) PGVNVQSTYPGNRYVSMNGTSMATPHVAGAAALVKQRYPSWNATQIRDHL
BSP-03024  (195) PGVNVQSTYPGNRYVSMNGTSMATPHVAGAAALVKQRYPSWNATQIRDHL
BSP-03033  (195) PGVNVQSTYPGNRYVSMNGTSMATPHVAGAAALVKQRYPSWNATQIRDHL
Consensus  (201) PGVNVQSTYPGNRYVSMNGTSMATPHVAGAAALVKQRYPSWNATQIR HL
```

```
                                      251                      275
B_amyloliquefaciens_CAA24990   (251) ENTTTKLGDSFYYGKGLINVQAAAQ   SEQ ID NO:74
G_stearothermophilus_ABY25856  (251) ENTTTKLGDAFYYGKGLINVQAAAQ   SEQ ID NO:75
B_subtilis_BAN09118            (251) ESTATNLGSSFYYGKGLINVQAAAQ   SEQ ID NO:76
B_atrophaeus_YP003972439       (251) ESTATNLGNSFYYGKGLINVQAAAQ   SEQ ID NO:77
B_circulans_ADN04910           (251) ENTATPLGNSFYYGKGLINVQAASN   SEQ ID NO:78
B_pumilus_ADK11996             (251) ENTATPLGDSFYYGKGLINVQAASN   SEQ ID NO:79
B_licheniformis_CAJ70731.1     (250) SSTATYLGSSFYYGKGLINVEAAAQ   SEQ ID NO:80
Bacillus_sp_BAD11988           (251) NSTTTYLGSSFYYGNGVINVERALQ   SEQ ID NO:81
Bacillus_sp_AAC43580           (251) KNTATNLGDPFFYGKGVINVESALQ   SEQ ID NO:82
Bacillus_sp_BAA05540           (245) NQTATYLGSPSLYGNGLVHAGRATQ   SEQ ID NO:83
B_lentus_P29600                (245) KNTATSLGSTNLYGSGLVNAEAATR   SEQ ID NO:84
Bgi02446                       (245) KNTATNLGNSSQFGSGLVNAEAATR   SEQ ID NO:85
B_gibsonii_DSM9728             (245) KNTATNLGNSSQFGSGLVNAEAATR   SEQ ID NO:86
B_gibsonii_DSM9729             (245) KNTATNLGNSSQFGSGLVNAEAATR   SEQ ID NO:87
B_gibsonii_DSM9730             (245) KNTATNLGNSSQFGSGLVNAEAATR   SEQ ID NO:88
B_gibsonii_DSM9731             (245) KNTATNLGNSSQFGSGLVNAEAATR   SEQ ID NO:89
WO03054184-0001                (245) KNTATNLGNSSQFGSGLVNAEAATR   SEQ ID NO:90
WO03054185-0001                (245) KNTATNLGNSSQFGSGLVNADAATR   SEQ ID NO:91
WO2007131657-0001              (245) KNTATNLGNSSQFGSGLVNAEAATR   SEQ ID NO:92
WO2008086916-0001              (245) KNTATNLGNSSQFGSGLVNAEAAIR   SEQ ID NO:93
BSP-01537                      (245) KNTATNLGNSSQFGSGLVNAEAATR   SEQ ID NO:94
BSP-01757                      (245) KNTATNLGNSSQFGSGLVNAEAATR   SEQ ID NO:95
BSP-01531                      (245) KNTATNLGNTNLYGSGLVNAEAATR   SEQ ID NO:96
```

| | | | |
|---|---|---|---|
| BSP-02320 | (245) | KNTATNLGNSSQFGSGLVNAEAATR | SEQ ID NO:97 |
| BSP-02389 | (245) | KNTATNLGNSSQYGSGLVNAEAATR | SEQ ID NO:98 |
| BSP-02355 | (245) | KNTATNLGNSSQYGSGLVNAEAATR | SEQ ID NO:99 |
| BSP-02354 | (245) | KNTATNLGNSSQYGSGLVNAEAATR | SEQ ID NO:100 |
| BSP-02380 | (245) | KNTATNLGNSSQYGSGLVNAEAATR | SEQ ID NO:101 |
| BSP-03007 | (245) | KNTATNLGNSSQYGSGLVNAEAATR | SEQ ID NO:102 |
| BSP-02411 | (245) | KNTATNLGNSSQYGSGLVNAEAATR | SEQ ID NO:103 |
| BSP-02195 | (245) | KNTATNLGNSSQFGSGLVNAEAATR | SEQ ID NO:104 |
| BSP-02400 | (245) | KNTATNLGNSSQYGSGLVNAEAATR | SEQ ID NO:105 |
| BSP-02301 | (245) | KNTATNLGNSSQFGSGLVNAEAATR | SEQ ID NO:106 |
| BSP-03027 | (245) | KNTATNLGNSSQFGSGLVNAEAATR | SEQ ID NO:107 |
| BSP-02412 | (245) | KNTATNLGNSSQFGSGLVNAEAATR | SEQ ID NO:108 |
| BSP-02391 | (245) | KNTATNLGNSSQFGSGLVNAEAATR | SEQ ID NO:109 |
| BSP-02227 | (245) | KNTATNLGNSSQFGSGLVNAEAATR | SEQ ID NO:110 |
| BSP-02725 | (245) | KNTATNLGNSSQYGSGLVNAEAATR | SEQ ID NO:111 |
| BSP-03048 | (245) | KNTATNLGNSSQFGSGLVNAEAATR | SEQ ID NO:112 |
| BSP-03024 | (245) | KNTATNLGNSSQFGSGLVNAEAATR | SEQ ID NO:113 |
| BSP-03033 | (245) | KNTATNLGNSSQFGSGLVNAEAATR | SEQ ID NO:114 |
| Consensus | (251) | KNTATNLGNSSQFGSGLVNAEAATR | SEQ ID NO:115 |

```
                                     1                                                50
B_amyloliquefaciens_CAA24990    (1) AQSVPYGVSQIKAPALHSQGYTGSNVKVAVIDSGIDSSHPDLKVAGGASM
G_stearothermophilus_ABY25856   (1) AQSVPYGVSQIKAPALHSQGFTGSNVKVAVIDSGIDSSHPDLKVAGGASM
B_subtilis_BAN09118             (1) AQSVPYGISQIKAPALHSQGYTGSNVKVAVIDSGIDSSHPDLNVRGGASF
B_atrophaeus_YP003972439        (1) AQSVPYGISQIKAPAVHSQGYTGSNVKVAVIDSGIDSSHPDLKVSGGASF
B_circulans_ADN04910            (1) AQTVPYGIPQIKAPAVHAQGYKGANVKVAVLDTGIHAAHPDLNVAGGASF
B_pumilus_ADK11996              (1) AQTVPYGIPQIKAPAVHAQGYKGANVKVAVLDTGIHAAHPDLNVAGGASF
B_licheniformis_CAJ70731.1      (1) AQTVPYGIPLIKADKVQAQGFKGANVKVAVLDTGIQASHPDLNVVGGASF
Bacillus_sp_BAD11988            (1) AQTTPWGVTHINAHRAHSSGVTGSGVKVAILDTGIHASHPDLNVRGGASF
Bacillus_sp_AAC43580            (1) AQTVPWGIPHIKADKAHAAGVTGSGVKVAILDTGIDANHADLNVKGGASF
Bacillus_sp_BAA05540            (1) SQTVPWGISFINTQQAHNRGIFGNGARVAVLDTGIA-SHPDLRIAGGASF
B_lentus_P29600                 (1) AQSVPWGISRVQAPAAHNRGLTGSGVKVAVLDTGIS-THPDLNIRGGASF
Bgi02446                        (1) QQTVPWGITRVQAPAVHNRGITGSGVRVAILDSGIS-AHSDLNIRGGASF
BSP-02107                       (1) QQTVPWGITRVQAPAVHNRGITGSGVRVAILDSGIS-THEDLNIRGGASF
BSP-02233                       (1) QQTVPWGITRVQAPAVHNRGITGSGVRVAILDSGIS-THEDLNIRGGASF
BSP-02209                       (1) QQTVPWGITRVQAPAVHNRGITGSGVRVAILDSGIS-THEDLTIRGGASF
BSP-02235                       (1) QQTVPWGITRVQAPAVHNRGITGSGVRVAILDSGIS-THEDLTIRGGASF
BSP-02310                       (1) QQTVPWGITRVQAPAVHNRGITGSGVKVAILDSGIS-THEDLNIRGGVSF
BSP-02364                       (1) QQTVPWGITRVQAPAVHNRGITGSGVRVAILDSGIS-THEDLNIRGGVSF
BSP-02112                       (1) QQTVPWGITRVQAPAVHNRGITGSGVRVAILDSGIS-THEDLNVRGGVSF
BSP-02203                       (1) QQTVPWGITRVQAPAVHNRGITGSGVRVAILDSGIS-THEDLNVRGGVSF
BSP-02249                       (1) QQTVPWGITRVQAPAVHNRGITGSGVRVAILDSGIS-THEDLNVRGGVSF
BSP-02132                       (1) QQTVPWGITRVQAPAVHNRGITGSGVRVAILDSGIS-THEDLNIRGGASF
BSP-02438                       (1) QQTVPWGITRVQAPAVHNRGITGFGVRVAILDSGIS-THEDLNIRGGVSF
BSP-02423                       (1) QQTVPWGITRVQAPAVHNRGITGSGVRVAILDSGIS-THEDLTIRGGVSF
BSP-02443                       (1) QQTVPWGITRVQAPAVHNRGITGSGVRVAILDSGIS-THEDLTIRGGVSF
BSP-02524                       (1) QQTVPWGITRVQAPAVHNRGITGSGVRVAILDSGIS-THEDLTIRGGVSF
BSP-02540                       (1) QQTVPWGITRVQAPAVHNRGITGSGVRVAILDSGIS-THEDLTIRGGVSF
BSP-02677                       (1) QQTVPWGITRVQAPAVHNRGITGSGVKVAILDSGIS-THEDLNIRGGVSF
BSP-02542                       (1) QQTVPWGITRVQAPAVHNRGITGSGVRVAILDSGIS-THEDLNIRGGVSF
```

```
BSP-02565    (1) QQTVPWGITRVQAPAVHNRGITGSGVRVAILDSGIS-THEDLNIRGGVSF
BSP-02500    (1) QQTVPWGITRVQAPAVHNRGITGSGVRVAILDSGIS-THEDLNVRGGVSF
BSP-02507    (1) QQTVPWGITRVQAPAVHNRGITGSGVRVAILDSGIS-THEDLNVRGGVSF
BSP-02569    (1) QQTVPWGITRVQAPAVHNRGITGSGVRVAILDSGIS-THEDLNVRGGVSF
BSP-02521    (1) QQTVPWGITRVQAPAVHNRGITGSGVRVAILDSGIS-THEDLNVRGGVSF
BSP-02537    (1) QQTVPWGITRVQAPAVHNRGITGSGVRVAILDSGIS-THEDLNVRGGVSF
BSP-03079    (1) QQTVPWGITRVQAPAVHNRGITGSGVRVAILDSGIS-THEDLNVRGGVSF
BSP-02508    (1) QQTVPWGITRVQAPAVHNRGITGSGVRVAILDSGIS-THEDLNVRGGVSF
BSP-02539    (1) QQTVPWGITRVQAPAVHNRGITGSGVRVAILDSGIS-THEDLNVRGGVSF
BSP-02480    (1) QQTVPWGITRVQAPAVHNRGITGSGVRVAILDSGIS-THEDLNVRGGVSF
BSP-02504    (1) QQTVPWGITRVQAPAVHNRGITGSGVRVAILDSGIS-THEDLNVRGGVSF
BSP-02513    (1) QQTVPWGITRVQAPAVHNRGITGSGVRVAILDSGIS-THEDLNVRGGVSF
BSP-02525    (1) QQTVPWGITRVQAPAVHNRGITGSGVRVAILDSGIS-THEDLNVRGGVSF
BSP-02781    (1) QQTVPWGITRVQAPAVHNRGITGSGVRVAILDSGIA-AHEDLNVRGGVSF
BSP-02814    (1) QQTVPWGITRVQAPAVHNRGITGSGVRVAILDSGIA-AHEDLNVRGGVSF
BSP-02828    (1) QQTVPWGITRVQAPAVHNRGITGSGVRVAILDSGIA-AHEDLNVRGGVSF
BSP-02791    (1) QQTVPWGITRVQAPAVHNRGITGSGVRVAILDSGIS-AHEDLNVRGGVSF
BSP-02829    (1) QQTVPWGITRVQAPAVHNRGITGSGVRVAILDSGIS-AHEDLNVRGGVSF
BSP-02035    (1) QQTVPWGITRVQAPAVHNRGITGSGVRVAILDSGIS-THEDLNVRGGVSF
BSP-02060    (1) QQTVPWGITRVQAPAVHNRGITGSGVRVAILDSGIS-THEDLNVRGGVSF
BSP-02979    (1) QQTVPWGITRVQAPAVHNRGITGSGVRVAILDSGIS-THEDLNVRGGVSF
BSP-02043    (1) QQTVPWGITRVQAPAVHNRGITGSGVRVAILDSGIS-THEDLNVRGGVSF
BSP-03009    (1) QQTVPWGITRVQAPAVHNRGITGSGVRVAILDSGIS-THEDLNVRGGVSF
BSP-02052    (1) QQTVPWGITRVQAPAVHNRGITGSGVRVAILDSGIS-THEDLNVRGGVSF
BSP-02086    (1) QQTVPWGITRVQAPAVHNRGITGSGVRVAILDSGIS-THEDLNVRGGVSF
BSP-02073    (1) QQTVPWGITRVQAPAVHNRGITGSGVRVAILDSGIS-THEDLNVRGGVSF
BSP-03070    (1) QQTVPWGITRVQAPAVHNRGITGSGVRVAILDSGIS-THEDLTIRGGVSF
BSP-02514    (1) QQTVPWGITRVQAPAVHNRGITGSGVRVAILDSGIS-THEDLNVRGGVSF
BSP-02471    (1) QQTVPWGITRVQAPAVHNRGITGSGVRVAILDSGIS-THEDLNVRGGVSF
BSP-00801    (1) QQTVPWGITRVQAPAVHNRGITGSGVRVAILDSGIS-THEDLNVRGGVSF
BSP-02768    (1) QQTVPWGISRVQAPAVHNRGITGSGVRVAILDSGIS-THEDLNVRGGVSF
BSP-02805    (1) QQTVPWGITRVQAPAVHNRGITGSGVRVAILDSGIS-THEDLNVRGGVSF
BSP-03098    (1) QQTIPWGITRVQAPAVHNRGITGSGVRVAILDSGIS-THEDLNVRGGVSF
Consensus    (1) QQTVPWGITRVQAPAVHNRGITGSGVRVAILDSGIS THEDLNVRGGVSF
```

FIG. 7A-2

FIG. 7B

| FIG. 7B-1 |
|---|
| FIG. 7B-2 |

FIG. 7B-1

```
                                         51                                               100
B_amyloliquefaciens_CAA24990   (51) VPSETNPFQDNNSHGTHVAGTVAALNNSIGVLGVAPSASLYAVKVLGADG
G_stearothermophilus_ABY25856  (51) VPSETNPFQDNNSHGTHVAGTVAALNNSVGVLGVAPSASLYAVKVLGADG
         B_subtilis_BAN09118   (51) VPSETNPYQDGSSHGTHVAGTVAALNNTIGVLGVAPSASLYAVKVLDSTG
    B_atrophaeus_YP003972439   (51) VPSEPNPFQDGNSHGTHVAGTVAALNNSVGVLGVAPSASLYAVKVLSSSG
        B_circulans_ADN04910   (51) VPSEPNATQDFQSHGTHVAGTIAALDNTIGVLGVAPSASLYAVKVLDRNG
          B_pumilus_ADK11996   (51) VPSEPNATQDFQSHGTHVAGTIAALDNTIGVLGVAPSASLYAVKVLDRNG
   B_licheniformis_CAJ70731.1  (51) VAGEAY-NTDGNGHGTHVAGTVAALDNTTGVLGVAPSVSLYAVKVLNSSG
        Bacillus_sp_BAD11988   (51) ISGESNPYIDSNGHGTHVAGTVAALNNTVGVLGVAYNAELYAVKVLSASG
        Bacillus_sp_AAC43580   (51) VSGEPNALQDGNGHGTHVAGTVAALNNTTGVLGVAYNADLYAVKVLSASG
        Bacillus_sp_BAA05540   (50) ISSEPS-YHDNNGHGTHVAGTIAALNNSIGVLGVAPSADLYAVKVLDRNG
            B_lentus_P29600    (50) VPGEPS-TQDGNGHGTHVAGTIAALNNSIGVLGVAPSAELYAVKVLGASG
                  Bgi02446     (50) VPGEPT-TADLNGHGTHVAGTVAALNNSIGVIGVAPNAELYAVKVLGANG
                 BSP-02107     (50) VPGEPT-TADLNGHGTHVAGTVAALNNSIGVIGVAPNAELYAVKVLGANG
                 BSP-02233     (50) VPGEPT-TADLNGHGTHVAGTVAALDNSIGVIGVAPNAELYAVKVLGANG
                 BSP-02209     (50) VPGEPT-TADLNGHGTHVAGTVAALNNSIGVIGVAPNAELYAVKVLGANG
                 BSP-02235     (50) VPGEPT-TADLNGHGTHVAGTVAALDNSIGVIGVAPNAELYAVKVLGANG
                 BSP-02310     (50) VPGEPG-YADLNGHGTHVAGTVAALDNSIGVIGVAPNAELYAVKVLGANG
                 BSP-02364     (50) VPGEPT-TADLNGHGTHVAGTVAALNNSIGVIGVAPNAELYAVKVLGANG
                 BSP-02112     (50) VPGEPG-TADLNGHGTHVAGTVAALNNSIGVIGVAPNAELYAVKVLGANG
                 BSP-02203     (50) VPGEPG-TADLNGHGTHVAGTVAALDNSIGVVGVAPNAELYAVKVLGANG
                 BSP-02249     (50) VPGEPT-TADLNGHGTHVAGTVAALDNSIGVVGVAPNAELYAVKVLGANG
                 BSP-02132     (50) VPGEPT-TADLNGHGTHVAGTVAALDNSIGVVGVAPSADLYAVKVLGANG
                 BSP-02438     (50) VPGEPT-TADLNGHGTHVAGTVAALDNSIGVVGVAPSADLYAVKVLGANG
                 BSP-02423     (50) VPGEPT-YADLNGHGTHVAGTVAALDNSIGVVGVAPSADLYAVKVLGANG
                 BSP-02443     (50) VPGEPT-TADLNGHGTHVAGTVAALDNSIGVVGVAPSADLYAVKVLGANG
                 BSP-02524     (50) VPGEPT-TADLNGHGTHVAGTVAALNNSIGVVGVAPSADLYAVKVLGANG
                 BSP-02540     (50) VPGEPG-TADLNGHGTHVAGTVAALNNSIGVVGVAPSADLYAVKVLGANG
                 BSP-02677     (50) VPGEPT-TADLNGHGTHVAGTVAALNNSIGVVGVAPSADLYAVKVLGANG
                 BSP-02542     (50) VPGEPT-TADLNGHGTHVAGTVAALNNSIGVVGVAPSADLYAVKVLGANG
```

| | | |
|---|---|---|
| BSP-02565 | (50) | VPGEPT-TADLNGHGTHVAGTVAALNNSIGVVGVAPSADLYAVKVLGANG |
| BSP-02500 | (50) | VPGEPT-TADLNGHGTHVAGTVAALNNSIGVVGVAPSADLYAVKVLGANG |
| BSP-02507 | (50) | VPGEPT-TADLNGHGTHVAGTVAALNNSIGVVGVAPSADLYAVKVLGANG |
| BSP-02569 | (50) | VPGEPG-TADLNGHGTHVAGTVAALNNSIGVVGVAPSADLYAVKVLGANG |
| BSP-02521 | (50) | VPGEPT-TADLNGHGTHVAGTVAALNNSIGVVGVAPSADLYAVKVLGANG |
| BSP-02537 | (50) | VPGEPG-TADLNGHGTHVAGTVAALNNSIGVVGVAPSADLYAVKVLGANG |
| BSP-03079 | (50) | VPGEPT-TADLNGHGTHVAGTVAALNNSIGVVGVAPSADLYAVKVLGANG |
| BSP-02508 | (50) | VPGEPT-TADLNGHGTHVAGTVAALNNSIGVVGVAPSADLYAVKVLGANG |
| BSP-02539 | (50) | VPGEPT-TADLNGHGTHVAGTVAALNNSIGVVGVAPSADLYAVKVLGANG |
| BSP-02480 | (50) | VPGEPT-TADLNGHGTHVAGTVAALNNSIGVVGVAPSADLYAVKVLGANG |
| BSP-02504 | (50) | VPGEPT-TADLNGHGTHVAGTVAALNNSIGVVGVAPSADLYAVKVLGANG |
| BSP-02513 | (50) | VPGEPT-TADLNGHGTHVAGTVAALNNSIGVVGVAPSADLYAVKVLGANG |
| BSP-02525 | (50) | VPGEPT-YADLNGHGTHVAGTVAALNNSIGVVGVAPSADLYAVKVLGANG |
| BSP-02781 | (50) | VPGEPM-TADLNGHGTHVAGTVAALNNSIGVVGVAPSADLYAVKVLGANG |
| BSP-02814 | (50) | VPGEPT-TADLNGHGTHVAGTVAALNNSIGVVGVAPSADLYAVKVLGANG |
| BSP-02828 | (50) | VPGEPT-TADLNGHGTHVAGTVAALNNSIGVVGVAPSADLYAVKVLGANG |
| BSP-02791 | (50) | VPGEPT-TADLNGHGTHVAGTVAALNNSIGVVGVAPSADLYAVKVLGANG |
| BSP-02829 | (50) | VPGEPT-TADLNGHGTHVAGTVAALNNSIGVVGVAPSADLYAVKVLGANG |
| BSP-02035 | (50) | VPGEPT-TADLNGHGTHVAGTVAALDNSIGVIGVAPSADLYAVKVLGANG |
| BSP-02060 | (50) | VPGEPT-TADLNGHGTHVAGTVAALDNSIGVIGVAPSADLYAVKVLGANG |
| BSP-02979 | (50) | VPGEPT-TADLNGHGTHVAGTVAALDNSIGVIGVAPSADLYAVKVLGANG |
| BSP-02043 | (50) | VPGEPT-TADLNGHGTHVAGTVAALDNSIGVVGVAPSADLYAVKVLGANG |
| BSP-03009 | (50) | VPGEPT-TADLNGHGTHVAGTVAALDNSIGVVGVAPSADLYAVKVLGANG |
| BSP-02052 | (50) | VPGEPT-TADLNGHGTHVAGTVAALDNSIGVIGVAPSADLYAVKVLGANG |
| BSP-02086 | (50) | VPGEPT-TADLNGHGTHVAGTVAALDNSIGVVGVAPSADLYAVKVLGANG |
| BSP-02073 | (50) | VPGEPT-TADLNGHGTHVAGTVAALDNSIGVVGVAPSADLYAVKVLGANG |
| BSP-03070 | (50) | VPGEPT-TADLNGHGTHVAGTVAALNNSIGVVGVAPSADLYAVKVLGANG |
| BSP-02514 | (50) | VPGEPT-TADLNGHGTHVAGTVAALNNSIGVVGVAPSADLYAVKVLGANG |
| BSP-02471 | (50) | VPGEPT-TADLNGHGTHVAGTVAALNNSIGVVGVAPSADLYAVKVLGANG |
| BSP-00801 | (50) | VPGEPT-TADLNGHGTHVAGTVAALNNSIGVVGVAPSADLYAVKVLGANG |
| BSP-02768 | (50) | VPGEPT-TADLNGHGTHVAGTVAALNNSIGVVGVAPSADLYAVKVLGANG |
| BSP-02805 | (50) | VPGEPT-TADLNGHGTHVAGTVAALNNSIGVVGVAPSADLYAVKVLGANG |
| BSP-03098 | (50) | VPGEPT-TADLNGHGTHVAGTVAALNNSIGVVGVAPSADLYAVKVLGANG |
| Consensus | (51) | VPGEPT TADLNGHGTHVAGTVAALNNSIGVVGVAPSADLYAVKVLGANG |

| | | 101 150 |
|---|---|---|
| B_amyloliquefaciens_CAA24990 | (101) | SGQYSWIINGIEWAIANNMDVINMSLGGPSGSAALKAAVDKAVASGVVVV |
| G_stearothermophilus_ABY25856 | (101) | SGQYSWIINGIEWAIAYNMDVINMSLGGPSGSAALKAAVDKAVASGIVVV |
| B_subtilis_BAN09118 | (101) | SGQYSWIINGIEWAISNNMDVINMSLGGPTGSTALKTVVDKAVASGIVVV |
| B_atrophaeus_YP003972439 | (101) | SGDYSWIINGIEWAISNNMDVINMSLGGPQGSTALKAVVDKAVSQGIVVV |
| B_circulans_ADN04910 | (101) | DGQYSWIISGIEWAVANNMDVINMSLGGPNGSTALKNAVDTANNRGVVVV |
| B_pumilus_ADK11996 | (101) | DGQYSWIISGIEWAVANNMDVINMSLGGASGSTALKNAVDTANNRGVVVV |
| B_licheniformis_CAJ70731.1 | (100) | SGSYSGIVSGIEWATTNGMDVINMSLGGASGSTAMKQAVDNAYARGVVVV |
| Bacillus_sp_BAD11988 | (101) | SGTLSGIAQGVEWSIANKMDVINMSLGGSSGSTALQRAVDNAYRNNIVVV |
| Bacillus_sp_AAC43580 | (101) | SGTLSGIAQGIEWSISNGMNVINMSLGGSSGSTALQQACNNAYNRGIVVI |
| Bacillus_sp_BAA05540 | (99) | SGSLASVAQGIEWAINNNMHIINMSLGSTSGSSTLELAVNRANNAGILLV |
| B_lentus_P29600 | (99) | SGSVSSIAQGLEWAGNNGMHVANLSLGSPSPSATLEQAVNSATSRGVLVV |
| Bgi02446 | (99) | SGSVSGIAQGLEWAATNNMHIANMSLGSDFPSSTLERAVNYATSRDVLVI |
| BSP-02107 | (99) | RGSISGIAQGLEWAAQNNMHIANMSLGTDAPSSTLERAVNYATSADVLVI |
| BSP-02233 | (99) | RGSISGIAQGLEWAATNNMHIANMSLGTDAPSSTLERAVNYATSADVLVI |
| BSP-02209 | (99) | RGSISGIAQGLEWAAQNNMHIANMSLGTDAPSSTLERAVNYATSRDVLVI |
| BSP-02235 | (99) | RGSISGIAQGLEWAATNNMHIANMSLGTDAPSSTLERAVNYATSRDVLVI |
| BSP-02310 | (99) | RGSISGIAQGLEWAATNNMHIANMSLGTDAPSSTLERAVNYATSRDVLVI |
| BSP-02364 | (99) | RGSISGIAQGLEWAAANNMHVANMSLGTDAPSSTLERAVNYATSADVLVI |
| BSP-02112 | (99) | RGSISGIAQGLEWAAQNNMHIANMSLGTDAPSSTLERAVNYATSRDVLVI |
| BSP-02203 | (99) | RGSISGIAQGLEWAAQNNMHIANMSLGTDAPSSTLERAVNYATSRDVLVI |
| BSP-02249 | (99) | RGSISGIAQGLEWAAQNNMHIANMSLGTDAPSSTLERAVNYATSRDVLVI |
| BSP-02132 | (99) | RGSISGIAQGLEWAAQNNMHIANMSLGTDAPSSTLERAVNYATSADVLVI |
| BSP-02438 | (99) | RGSVSGIAQGLEWAAQNNMHIANMSLGTDAPSSTLERAVNYATSRDVLVI |
| BSP-02423 | (99) | RGSVSGIAQGLEWAAQNNMHIANMSLGTDAPSSTLERAVNYATSRDVLVI |
| BSP-02443 | (99) | RGSVSGIAQGLEWAAQNNMHIANMSLGSDAPSSTLERAVNYATSRDVLVI |
| BSP-02524 | (99) | RGSISGIAQGLEWAAQNNMHIANMSLGSDAPSSTLERAVNYATSRDVLVI |
| BSP-02540 | (99) | RGSVSGIAQGLEWAAQNNMHIANMSLGSDAPSSTLERAVNYATSRDVLVI |
| BSP-02677 | (99) | RGSVSGIAQGLEWAAQNNMHIANMSLGSDAPSSTLERAVNYATSRDVLVI |
| BSP-02542 | (99) | RGSVSGIAQGLEWAAQNNMHIANMSLGSDAPSSTLERAVNYATSADVLVI |

```
BSP-02565   (99) RGSISGIAQGLEWAAQNNMHIANMSLGSDAPSSTLERAVNYATSADVLVI
BSP-02500   (99) RGSVSGIAQGLEWAAQNNMHIANMSLGTDAPSSTLERAVNYATSADVLVI
BSP-02507   (99) RGSVSGIAQGLEWAAQNNMHIANMSLGTDAPSSTLERAVNYATSADVLVI
BSP-02569   (99) RGSVSGIAQGLEWAAQNNMHIANMSLGTDAPSSTLERAVNYATSRDVLVI
BSP-02521   (99) RGSISGIAQGLEWAAQNNMHIANMSLGTDAPSSTLERAVNYATSRDVLVI
BSP-02537   (99) RGSISGIAQGLEWAAQNNMHIANMSLGSDAPSSTLERAVNYATSADVLVI
BSP-03079   (99) RGSISGIAQGLEWAAQNNMHIANMSLGSDAPSSTLERAVNYATSRDVLVI
BSP-02508   (99) RGSVSGIAQGLEWAAQNNMHIANMSLGSDAPSSTLERAVNYATSRDVLVI
BSP-02539   (99) RGSVSGIAQGLEWAAQNNMHIANMSLGSDAPSSTLERAVNYATSRDVLVI
BSP-02480   (99) RGSVSGIAQGLEWAAANNMHIANMSLGTDAPSSTLERAVNYATSRDVLVI
BSP-02504   (99) RGSVSGIAQGLEWAAANNMHIANMSLGTDAPSSTLERAVNYATSRDVLVI
BSP-02513   (99) RGSVSGIAQGLEWAAANNMHIANMSLGSDAPSSTLERAVNYATSRDVLVI
BSP-02525   (99) RGSVSGIAQGLEWAAANNMHIANMSLGSDAPSSTLERAVNYATSRDVLVI
BSP-02781   (99) RGSVSGIAQGLEWAAANNMHIANMSLGSDAPSSTLERAVNYATSRDVLVI
BSP-02814   (99) RGSVSGIAQGLEWAAANNMHIASMSLGSDAPSSTLERAVNYATSQDVLVI
BSP-02828   (99) RGSVSGIAQGLEWAAANNMHIANMSLGSDAPSSTLERAVNYATSRDVLVI
BSP-02791   (99) RGSVSGIAQGLEWAAANNMHIANMSLGSDAPSSTLERAVNYATSRDVLVI
BSP-02829   (99) RGSVSGIAQGLEWAAANNMHIANMSLGSDAPSSTLERAVNYATSQDVLVI
BSP-02035   (99) RGSVSGIAQGLEWAAANNMHIANMSLGTDAPSSTLERAVNYATSRDVLVI
BSP-02060   (99) RGSVSGIAQGLEWAAANNMHIANMSLGSDAPSSTLERAVNYATSRDVLVI
BSP-02979   (99) RGSVSGIAQGLEWAAANNMHIANMSLGTDAPSSTLERAVNYATSRDVLVI
BSP-02043   (99) RGSVSGIAQGLEWAAANNMHIANMSLGSDAPSSTLERAVNYATSRDVLVI
BSP-03009   (99) RGSVSGIAQGLEWAAANNMHIANMSLGSDAPSSTLERAVNYATSRDVLVI
BSP-02052   (99) RGSVSGIAQGLEWAAANNMHIANMSLGSDAPSSTLERAVNYATSRDVLVI
BSP-02086   (99) RGSVSGIAQGLEWAAANNMHIANMSLGSDAPSSTLERAVNYATSRDVLVI
BSP-02073   (99) RGSVSGIAQGLEWAAANNMHIANMSLGSDAPSSTLERAVNYATSRDVLVI
BSP-03070   (99) RGSVSGIAQGLEWAAANNMHIANMSLGSDAPSSTLERAVNYATSRDVLVI
BSP-02514   (99) RGSISGIAQGLEWAAANNMHIANMSLGSDAPSSTLERAVNYATSRDVLVI
BSP-02471   (99) RGSVSGIAQGLEWAAANNMHIANMSLGTDAPSSTLERAVNYATSRDVLVI
BSP-00801   (99) RGSVSGIAQGLEWAAANNMHIANMSLGSDAPSSTLERAVNYATSRDVLVI
BSP-02768   (99) RGSVSGIAQGLEWAAANNMHIANMSLGSDAPSSTLERAVNYATSRDVLVI
BSP-02805   (99) RGSVSGIAQGLEWAAANNMHIANMSLGSDAPSSTLERAVNYATSRDVLVI
BSP-03098   (99) RGSVSGIAQGLEWAAANNMHIANMSLGSDAPSSTLERAVNYATSRDVLVI
Consensus  (101) RGSVSGIAQGLEWAA NNMHIANMSLGSDAPSSTLERAVNYATSRDVLVI
```

| | | 151 200 |
|---|---|---|
| B_amyloliquefaciens_CAA24990 | (151) | AAAGNEGTSGSSSTVGYPGKYPSVIAVGAVDSSNQRASFSSVGPELDVMA |
| G_stearothermophilus_ABY25856 | (151) | AAAGNEGTSGSSSTVGYPGKYPSVIAVGAVNSSNQRASFSSVGSELDVMA |
| B_subtilis_BAN09118 | (151) | AAAGNEGSSGSTSTVGYPAKYPSTIAVGAVNSSNQRASFSSAGSELDVMA |
| B_atrophaeus_YP003972439 | (151) | AAAGNSGSSGSTSTVGYPAKYPSVIAVGAVDSNNQRASFSSAGSELDVMA |
| B_circulans_ADN04910 | (151) | AAAGNSGSTGSTSTVGYPAKYDSTIAVANVNSSNVRNSSSSAGPELDVSA |
| B_pumilus_ADK11996 | (151) | AAAGNSGSSGSRSTVGYPAKYESTIAVANVNSNNVRNSSSSAGPELDVSA |
| B_licheniformis_CAJ70731.1 | (150) | AAAGNSGSSGNTNTIGYPAKYDSVIAVGAVDSNSNRASFSSVGAELEVMA |
| Bacillus_sp_BAD11988 | (151) | AAAGNSGAQGNRNTIGYPARYSSVIAVGAVDSNNNRASFSSVGSELEVMA |
| Bacillus_sp_AAC43580 | (151) | AAAGNSGSSGNRNTMGYPARYSSVIAVGAVSSNNTRASFSSVGSELEVMA |
| Bacillus_sp_BAA05540 | (149) | GAAGNTGRQG----VNYPARYSGVMAVAAVDQNGQRASFSTYGPEIEISA |
| B_lentus_P29600 | (149) | AASGNSGAGS----ISYPARYANAMAVGATDQNNNRASFSQYGAGLDIVA |
| Bgi02446 | (149) | AATGNNGSGS----VGYPARYANAMAVGATDQNNRRANFSQYGTGIDIVA |
| BSP-02107 | (149) | AATGNNGSGS----VGYPARYANAMAVGATDQNNRRANFSQYGTGIDIVA |
| BSP-02233 | (149) | AATGNNGSGS----VGYPARYANAMAVGATDQNNRRANFSQYGTGIDIVA |
| BSP-02209 | (149) | AATGNNGSGS----VGYPARYANAMAVGATDQNNRRANFSQYGTGIDIVA |
| BSP-02235 | (149) | AATGNNGSGT----VGYPARYANAMAVGATDQNNRRANFSQYGTGIDIVA |
| BSP-02310 | (149) | AATGNNGSGS----VGYPARYANAMAVGATDQNNRRANFSQYGTGIDIVA |
| BSP-02364 | (149) | AATGNNGSGT----VSYPARYANAMAVGATDQNNRRANFSQYGTGIDIVA |
| BSP-02112 | (149) | AATGNNGSGS----VGYPARYANAMAVGATDQNNRRANFSQYGTGIDIVA |
| BSP-02203 | (149) | AATGNNGSGS----VGYPARYANAMAVGATDQNNRRANFSQYGTGIDIVA |
| BSP-02249 | (149) | AATGNNGSGS----VGYPARYANAMAVGATDQNNRRANFSQYGTGIDIVA |
| BSP-02132 | (149) | AATGNNGSGS----VGYPARYANAMAVGATDQNNRRANFSQYGTGIDIVA |
| BSP-02438 | (149) | AATGNNGSGS----VGYPARYANAMAVGATDQNNRRANFSQYGTGIDIVA |
| BSP-02423 | (149) | AATGNNGSGS----VGYPARYANAMAVGATDQNNRRANFSQYGTGIDIVA |
| BSP-02443 | (149) | AATGNNGSGS----VGYPARYANAMAVGATDQNNRRANFSQYGTGIDIVA |
| BSP-02524 | (149) | AATGNNGSGS----VGYPARYANAMAVGATDQNNRRANFSQYGTGIDIVA |
| BSP-02540 | (149) | AATGNNGSGS----VGYPARYANAMAVGATDQNNRRANFSQYGTGIDIVA |
| BSP-02677 | (149) | AATGNNGSGS----VGYPARYANAMAVGATDQNNRRANFSQYGTGIDIVA |
| BSP-02542 | (149) | AATGNNGSGS----VGYPARYANAMAVGATDQNNRRANFSQYGTGIDIVA |

```
BSP-02565  (149) AATGNNGSGS----VGYPARYANAMAVGATDQNNRRANFSQYGTGIDIVA
BSP-02500  (149) AATGNNGSGS----VGYPARYANAMAVGATDQNNRRANFSQYGTGIDIVA
BSP-02507  (149) AATGNNGSGS----VGYPARYANAMAVGATDQNNRRANFSQYGTGIDIVA
BSP-02569  (149) AATGNNGSGS----VGYPARYANAMAVGATDQNNRRANFSQYGTGIDIVA
BSP-02521  (149) AATGNNGSGS----VGYPARYANAMAVGATDQNNRRANFSQYGTGIDIVA
BSP-02537  (149) AATGNNGSGS----VGYPARYANAMAVGATDQNNRRANFSQYGTGIDIVA
BSP-03079  (149) AATGNNGSGS----VGYPARYANAMAVGATDQNNRRANFSQYGTGIDIVA
BSP-02508  (149) AATGNNGSGS----VGYPARYANAMAVGATDQNNRRANFSQYGTGIDIVA
BSP-02539  (149) AATGNNGSGS----VGYPARYANAMAVGATDQNNRRANFSQYGTGIDIVA
BSP-02480  (149) AATGNNGSGS----VGYPARYANAMAVGATDQNNRRANFSQYGTGIDIVA
BSP-02504  (149) AATGNNGSGS----VGYPARYANAMAVGATDQNNRRANFSQYGTGIDIVA
BSP-02513  (149) AATGNNGSGS----VGYPARYANAMAVGATDQNNRRANFSQYGTGIDIVA
BSP-02525  (149) AATGNNGSGS----VGYPARYANAMAVGATDQNNRRANFSQYGTGIDIVA
BSP-02781  (149) AATGNNGSGS----VGYPARYANAMAVGATDQNNRRANFSQYGTGIDIVA
BSP-02814  (149) AATGNNGSGS----VGYPARYANAMAVGATDQNNRRANFSQYGTGIDIVA
BSP-02828  (149) AATGNNGSGS----VGYPARYANAMAVGATDQNNRRANFSQYGTGIDIVA
BSP-02791  (149) AATGNNGSGS----VGYPARYANAMAVGATDQNNRRANFSQYGTGIDIVA
BSP-02829  (149) AATGNNGSGS----VGYPARYANAMAVGATDQNNRRANFSQYGTGIDIVA
BSP-02035  (149) AATGNNGSGT----VGYPARYANAMAVGATDQNNRRANFSQYGTGIDIVA
BSP-02060  (149) AATGNNGSGT----VGYPARYANAMAVGATDQNNRRANFSQYGTGIDIVA
BSP-02979  (149) AATGNNGSGS----VGYPARYANAMAVGATDQNNRRANFSQYGTGIDIVA
BSP-02043  (149) AATGNNGSGT----VGYPARYANAMAVGATDQNNRRANFSQYGTGIDIVA
BSP-03009  (149) AATGNNGSGS----VGYPARYANAMAVGATDQNNRRANFSQYGTGIDIVA
BSP-02052  (149) AATGNNGSGS----VGYPARYANAMAVGATDQNNRRANFSQYGTGIDIVA
BSP-02086  (149) AATGNNGSGS----VGYPARYANAMAVGATDQNNRRANFSQYGTGIDIVA
BSP-02073  (149) AATGNNGSGS----VGYPARYANAMAVGATDQNNRRANFSQYGTGIDIVA
BSP-03070  (149) AATGNNGSGT----VGYPARYANAMAVGATDQNNRRANFSQYGTGIDIVA
BSP-02514  (149) AATGNNGSGS----VGYPARYANAMAVGATDQNNRRANFSQYGTGIDIVA
BSP-02471  (149) AATGNNGSGS----VGYPARYANAMAVGATDQNNRRANFSQYGTGIDIVA
BSP-00801  (149) AATGNNGSGS----VGYPARYANAMAVGATDQNNRRANFSQYGTGIDIVA
BSP-02768  (149) AATGNNGSGS----VGYPARYANAMAVGATDQNNRRANFSQYGTGIDIVA
BSP-02805  (149) AATGNNGSGS----VGYPARYANAMAVGATDQNNRRANFSQYGTGLDIVA
BSP-03098  (149) AATGNNGSGS----VGYPARYANAMAVGATDQNNRRASFSQYGTGIDIVA
Consensus  (151) AATGNNGSGS    VGYPARYANAMAVGATDQNNRRANFSQYGTGIDIVA
```

| | | 201 250 |
|---|---|---|
| B_amyloliquefaciens_CAA24990 | (201) | PGVSIQSTLPGNKYGAYNGTSMASPHVAGAAALILSKHPNWTNTQVRSSL |
| G_stearothermophilus_ABY25856 | (201) | PGVSIQSTLPGNKYGAYNGTSMASPHVAGAAALILSKHPNWTNTQVRSSL |
| B_subtilis_BAN09118 | (201) | PGVSIQSTLPGGTYGSYNGTSMATPHVAGAAALILSKHPTWSNAQVRDRL |
| B_atrophaeus_YP003972439 | (201) | PGVSIQSTLPGSSYGSYNGTSMASPHVAGAAALVLSKHPNWTNSQVRNSL |
| B_circulans_ADN04910 | (201) | PGTSILSTVPSRGYTSYTGTSMASPHVAGAAALILSKNPNLSNSQVRQRL |
| B_pumilus_ADK11996 | (201) | PGTSILSTVPSSGYTSYTGTSMASPHVAGAAALILSKNPNLTNSQVRQRL |
| B_licheniformis_CAJ70731.1 | (200) | PGAGVYSTYPTNTYATLNGTSMASPHVAGAAALILSKHPNLSASQVRNRL |
| Bacillus_sp_BAD11988 | (201) | PGVSILSTVPGSSYASYNGTSMASPHVAGAAALLKAKYPNWSAAQIRNKL |
| Bacillus_sp_AAC43580 | (201) | PGVNILSTTPGNNYASFNGTSMAAPHVAGAAALIKAKYPSMTNVQIRERL |
| Bacillus_sp_BAA05540 | (195) | PGVNVNSTYTGNRYVSLSGTSMATPHVAGVAALVKSRYPSYTNNQIRQRI |
| B_lentus_P29600 | (195) | PGVNVQSTYPGSTYASLNGTSMATPHVAGAAALVKQKNPSWSNVQIRNHL |
| Bgi02446 | (195) | PGVNVQSTYPGNRYVSMNGTSMATPHVAGAAALVKQRYPSWNATQIRNHL |
| BSP-02107 | (195) | PGVNVQSTYPGNRYVSMSGTSMATPHVAGAAALVKQRYPSWNATQIRDHL |
| BSP-02233 | (195) | PGVNVQSTYPGNRYVSMSGTSMATPHVAGAAALVKQRYPSWNATQIRDHL |
| BSP-02209 | (195) | PGVNVQSTYPGNRYVSMNGTSMATPHVAGAAALVKQRYPSWNATQIRDHL |
| BSP-02235 | (195) | PGVNVQSTYPGNRYVSMNGTSMATPHVAGAAALVKQRYPSWNATQIRDHL |
| BSP-02310 | (195) | PGVNVQSTYPGNRYVSMNGTSMATPHVAGAAALVKQRYPSWNATQIRDHL |
| BSP-02364 | (195) | PGVNVQSTYPGNRYVSMSGTSMATPHVAGAAALVKQRYPSWNATQIRNHL |
| BSP-02112 | (195) | PGVNVQSTYPGNRYVSMSGTSMATPHVAGAAALVKQRYPSWNATQIRNHL |
| BSP-02203 | (195) | PGVNVQSTYPGNRYVSMNGTSMATPHVAGAAALVKQRYPSWNATQIRNHL |
| BSP-02249 | (195) | PGVNVQSTYPGNRYVSMNGTSMATPHVAGAAALVKQRYPSWNATQIRDHL |
| BSP-02132 | (195) | PGVNVQSTYPGNRYVSMNGTSMATPHVAGAAALVKQRYPSWNATQIRNHL |
| BSP-02438 | (195) | PGVNVQSTYPGNRYVSMSGTSMATPHVAGAAALVKQRYPSWNATQIRNHL |
| BSP-02423 | (195) | PGVNVQSTYPGNRYVSMNGTSMATPHVAGAAALVKQRYPSWNATQIRNHL |
| BSP-02443 | (195) | PGVNVQSTYPGNRYVSMNGTSMATPHVAGAAALVKQRYPSWNATQIRDHL |
| BSP-02524 | (195) | PGVNVQSTYPGNRYVSMNGTSMATPHVAGAAALVKQRYPSWNATQIRDHL |
| BSP-02540 | (195) | PGVNVQSTYPGNRYVSMSGTSMATPHVAGAAALVKQRYPSWNATQIRDHL |
| BSP-02677 | (195) | PGVNVQSTYPGNRYVSMSGTSMATPHVAGAAALVKQRYPSWNATQIRDHL |
| BSP-02542 | (195) | PGVNVQSTYPGNRYVSMNGTSMATPHVAGAAALVKQRYPSWNATQIRDHL |

| | | |
|---|---|---|
| BSP-02565 | (195) | PGVNVQSTYPGNRYVSMNGTSMATPHVAGAAALVKQRYPSWNATQIRDHL |
| BSP-02500 | (195) | PGVNVQSTYPGNRYVSMNGTSMATPHVAGAAALVKQRYPSWNATQIRDHL |
| BSP-02507 | (195) | PGVNVQSTYPGNRYVSMNGTSMATPHVAGAAALVKQRYPSWNATQIRNHL |
| BSP-02569 | (195) | PGVNVQSTYPGNRYVSMNGTSMATPHVAGAAALVKQRYPSWNATQIRNHL |
| BSP-02521 | (195) | PGVNVQSTYPGNRYVSMNGTSMATPHVAGAAALVKQRYPSWNATQIRDHL |
| BSP-02537 | (195) | PGVNVQSTYPGNRYVSMNGTSMATPHVAGAAALVKQRYPSWNATQIRNHL |
| BSP-03079 | (195) | PGVNVQSTYPGNRYVSMNGTSMATPHVAGAAALVKQRYPSWNATQIRNHL |
| BSP-02508 | (195) | PGVNVQSTYPGNRYVSMNGTSMATPHVAGAAALVKQRYPSWNATQIRDHL |
| BSP-02539 | (195) | PGVNVQSTYPGNRYVSMSGTSMATPHVAGAAALVKQRYPSWNATQIRDHL |
| BSP-02480 | (195) | PGVNVQSTYPGNRYVSMNGTSMATPHVAGAAALVKQRYPSWNATQIRDHL |
| BSP-02504 | (195) | PGVNVQSTYPGNRYVSMNGTSMATPHVAGAAALVKQRYPSWNTTQIRDHL |
| BSP-02513 | (195) | PGVNVQSTYPGNRYVSMNGTSMATPHVAGAAALVKQRYPSWNATQIRDHL |
| BSP-02525 | (195) | PGVNVQSTYPGNRYVSMNGTSMATPHVAGAAALVKQRYPSWNATQIRDHL |
| BSP-02781 | (195) | PGVNVQSTYPGNRYVSMNGTSMATPHVAGAAALVKQRYPSWNATQIRNHL |
| BSP-02814 | (195) | PGVNVQSTYPGNRYVSMNGTSMATPHVAGAAALVKQRYPSWNATQIRNHL |
| BSP-02828 | (195) | PGVNVQSTYPGNRYVSMSGTSMATPHVAGAAALVKQRYPSWNATQIRNHL |
| BSP-02791 | (195) | PGVNVQSTYPGNRYVSMSGTSMATPHVAGAAALVKQRYPSWNATQIRNHL |
| BSP-02829 | (195) | PGVNVQSTYPGNRYVSMNGTSMATPHVAGAAALVKQRYPSWNATQIRDHL |
| BSP-02035 | (195) | PGVNVQSTYPGNRYVSMSGTSMATPHVAGAAALVKQRYPSWNATQIRNHL |
| BSP-02060 | (195) | PGVNVQSTYPGNRYVSMSGTSMATPHVAGAAALVKQRYPSWNATQIRNHL |
| BSP-02979 | (195) | PGVNVQSTYPGNRYVSMSGTSMATPHVAGAAALVKQRYPSWNATQIRNHL |
| BSP-02043 | (195) | PGVNVQSTYPGNRYVSMSGTSMATPHVAGAAALVKQRYPSWNATQIRNHL |
| BSP-03009 | (195) | PGVNVQSTYPGNRYVSMSGTSMATPHVAGAAALVKQRYPSWNATQIRNHL |
| BSP-02052 | (195) | PGVNVQSTYPGNRYVSMSGTSMATPHVAGAAALVKQRYPSWNATQIRQHL |
| BSP-02086 | (195) | PGVNVQSTYPGNRYVSMSGTSMATPHVAGAAALVKQRYPSWNATQIRNHL |
| BSP-02073 | (195) | PGVNVQSTYPGNRYVSMSGTSMATPHVAGAAALVKQRYPSWNATQIRQHL |
| BSP-03070 | (195) | PGVNVQSTYPGNRYVSMSGTSMATPHVAGAAALVKQRYPSWNATQIRNHL |
| BSP-02514 | (195) | PGVNVQSTYPGNRYVSMSGTSMATPHVAGAAALVKQRYPSWNATQIRNHL |
| BSP-02471 | (195) | PGVNVQSTYPGNRYVSMSGTSMATPHVAGAAALVKQRYPSWNATQIRNHL |
| BSP-00801 | (195) | PGVNVQSTYPGNRYVSMNGTSMATPHVAGAAALVKQRYPSWNATQIRNHL |
| BSP-02768 | (195) | PGINVQSTYPGNRYVSMNGTSMATPHVAGAAALVKQRYPSWNATQIRNHL |
| BSP-02805 | (195) | PGVNVQSTYPGNRYVSMNGTSMATPHVAGVAALVKQRYPSWNATQIRNHL |
| BSP-03098 | (195) | PGVNVQSTYPGNRYVSMNGTSMATPHVAGAAALVKQRYPSWNATQIRNHL |
| Consensus | (201) | PGVNVQSTYPGNRYVSMNGTSMATPHVAGAAALVKQRYPSWNATQIRNHL |

| | | 251 275 | |
|---|---|---|---|
| B_amyloliquefaciens_CAA24990 | (251) | ENTTTKLGDSFYYGKGLINVQAAAQ | SEQ ID NO:74 |
| G_stearothermophilus_ABY25856 | (251) | ENTTTKLGDAFYYGKGLINVQAAAQ | SEQ ID NO:75 |
| B_subtilis_BAN09118 | (251) | ESTATNLGSSFYYGKGLINVQAAAQ | SEQ ID NO:76 |
| B_atrophaeus_YP003972439 | (251) | ESTATNLGNSFYYGKGLINVQAAAQ | SEQ ID NO:77 |
| B_circulans_ADN04910 | (251) | ENTATPLGNSFYYGKGLINVQAASN | SEQ ID NO:78 |
| B_pumilus_ADK11996 | (251) | ENTATPLGDSFYYGKGLINVQAASN | SEQ ID NO:79 |
| B_licheniformis_CAJ70731.1 | (250) | SSTATYLGSSFYYGKGLINVEAAAQ | SEQ ID NO:80 |
| Bacillus_sp_BAD11988 | (251) | NSTTTYLGSSFYYGNGVINVERALQ | SEQ ID NO:81 |
| Bacillus_sp_AAC43580 | (251) | KNTATNLGDPFFYGKGVINVESALQ | SEQ ID NO:82 |
| Bacillus_sp_BAA05540 | (245) | NQTATYLGSPSLYGNGLVHAGRATQ | SEQ ID NO:83 |
| B_lentus_P29600 | (245) | KNTATSLGSTNLYGSGLVNAEAATR | SEQ ID NO:84 |
| Bgi02446 | (245) | KNTATNLGNSSQFGSGLVNAEAATR | SEQ ID NO:85 |
| BSP-02107 | (245) | KNTATNLGNSSQFGSGLVNAEAATR | SEQ ID NO:116 |
| BSP-02233 | (245) | KNTATNLGNSSQFGSGLVNAEAATR | SEQ ID NO:117 |
| BSP-02209 | (245) | KNTATNLGNSSQFGSGLVNAEAATR | SEQ ID NO:118 |
| BSP-02235 | (245) | KNTATNLGNSSQFGSGLVNAEAATR | SEQ ID NO:26 |
| BSP-02310 | (245) | KNTATNLGNSSQFGSGLVNAEAATR | SEQ ID NO:30 |
| BSP-02364 | (245) | KNTATNLGNSSQFGSGLVNAEAATR | SEQ ID NO:119 |
| BSP-02112 | (245) | KNTATNLGNSSQFGSGLVNAEAATR | SEQ ID NO:120 |
| BSP-02203 | (245) | KNTATNLGNSSQFGSGLVNAEAATR | SEQ ID NO:24 |
| BSP-02249 | (245) | KNTATNLGNSSQFGSGLVNAEAATR | SEQ ID NO:28 |
| BSP-02132 | (245) | KNTATNLGNSSQFGSGLVNAEAATR | SEQ ID NO:121 |
| BSP-02438 | (245) | KNTATNLGNSSQFGSGLVNAEAATR | SEQ ID NO:122 |
| BSP-02423 | (245) | KNTATNLGNSSQFGSGLVNAEAATR | SEQ ID NO:32 |
| BSP-02443 | (245) | KNTATNLGNSSQFGSGLVNAEAATR | SEQ ID NO:124 |
| BSP-02524 | (245) | KNTATNLGNSSQFGSGLVNAEAATR | SEQ ID NO:125 |
| BSP-02540 | (245) | KNTATNLGNSSQFGSGLVNAEAATR | SEQ ID NO:126 |
| BSP-02677 | (245) | KNTATNLGNSSQFGSGLVNAEAATR | SEQ ID NO:127 |
| BSP-02542 | (245) | KNTATNLGNSSQFGSGLVNAEAATR | SEQ ID NO:128 |

| | | | |
|---|---|---|---|
| BSP-02565 | (245) | KNTATNLGNSSQFGSGLVNAEAATR | SEQ ID NO:129 |
| BSP-02500 | (245) | KNTATNLGNSSQFGSGLVNAEAATR | SEQ ID NO:130 |
| BSP-02507 | (245) | KNTATNLGNSSQFGSGLVNAEAATR | SEQ ID NO:40 |
| BSP-02569 | (245) | KNTATNLGNSSQFGSGLVNAEAATR | SEQ ID NO:52 |
| BSP-02521 | (245) | KNTATNLGNSSQFGSGLVNAEAATR | SEQ ID NO:133 |
| BSP-02537 | (245) | KNTATNLGNSSQFGSGLVNAEAATR | SEQ ID NO:134 |
| BSP-03079 | (245) | KNTATNLGNSSQFGSGLVNAEAATR | SEQ ID NO:135 |
| BSP-02508 | (245) | KNTATNLGNSSQFGSGLVNAEAATR | SEQ ID NO:42 |
| BSP-02539 | (245) | KNTATNLGNSSQFGSGLVNAEAATR | SEQ ID NO:136 |
| BSP-02480 | (245) | KNTATNLGNSSQFGSGLVNAEAATR | SEQ ID NO:38 |
| BSP-02504 | (245) | KNTATNLGNSSQFGSGLVNAEAATR | SEQ ID NO:137 |
| BSP-02513 | (245) | KNTATNLGNSSQFGSGLVNAEAATR | SEQ ID NO:138 |
| BSP-02525 | (245) | KNTATNLGNSSQFGSGLVNAEAATR | SEQ ID NO:139 |
| BSP-02781 | (245) | KNTATNLGNSSQFGSGLVNAEAATR | SEQ ID NO:140 |
| BSP-02814 | (245) | KNTATNLGNSSQFGSGLVNAEAATR | SEQ ID NO:141 |
| BSP-02828 | (245) | KNTATNLGNSNQFGSGLVNAEAATR | SEQ ID NO:142 |
| BSP-02791 | (245) | LSTATNLGNSSQFGSGLVNAEAATR | SEQ ID NO:143 |
| BSP-02829 | (245) | KKTATNLGNSSQFGSGLVNAEAATR | SEQ ID NO:144 |
| BSP-02035 | (245) | KNTATNLGNSSQFGSGLVNAEAATR | SEQ ID NO:145 |
| BSP-02060 | (245) | KNTATNLGNSSQFGSGLVNAEAATR | SEQ ID NO:146 |
| BSP-02979 | (245) | KNTATNLGNSSQFGSGLVNAEAATR | SEQ ID NO:147 |
| BSP-02043 | (245) | KNTATNLGNSSQFGSGLVNAEAATR | SEQ ID NO:148 |
| BSP-03009 | (245) | KNTATNLGNSSQFGSGLVNAEAATR | SEQ ID NO:149 |
| BSP-02052 | (245) | LNTATNLGNSSQFGSGLVNAEAATR | SEQ ID NO:150 |
| BSP-02086 | (245) | LNTATNLGNSSQFGSGLVNAEAATR | SEQ ID NO:151 |
| BSP-02073 | (245) | KNTATNLGNSSQFGSGLVNAEAATR | SEQ ID NO:152 |
| BSP-03070 | (245) | KNTATNLGNSSQFGSGLVNAEAATR | SEQ ID NO:153 |
| BSP-02514 | (245) | KNTATNLGNSSQFGSGLVNAEAATR | SEQ ID NO:154 |
| BSP-02471 | (245) | KNTATNLGNSSQFGSGLVNAEAATR | SEQ ID NO:155 |
| BSP-00801 | (245) | KNTATNLGNSSQFGSGLVNAEAATR | SEQ ID NO:18 |
| BSP-02768 | (245) | KNTATNLGNSSQFGSGLVNAEAATR | SEQ ID NO:156 |
| BSP-02805 | (245) | KNTATNLGNSSQFGSGLVNAEAATR | SEQ ID NO:157 |
| BSP-03098 | (245) | KNTATNLGNSSQFGSGLVNAEAATR | SEQ ID NO:158 |
| Consensus | (251) | KNTATNLGNSSQFGSGLVNAEAATR | SEQ ID NO:159 |

FIG. 7F-2

```
                                                 1                                                  50
  B_amyloliquefaciens_CAA24990    (1) AQSVPYGVSQIKAPALHSQGYTGSNVKVAVIDSGIDSSHPDLKVAGGASM
G_stearothermophilus_ABY25856    (1) AQSVPYGVSQIKAPALHSQGFTGSNVKVAVIDSGIDSSHPDLKVAGGASM
            B_subtilis_BAN09118    (1) AQSVPYGISQIKAPALHSQGYTGSNVKVAVIDSGIDSSHPDLNVRGGASF
      B_atrophaeus_YP003972439    (1) AQSVPYGISQIKAPAVHSQGYTGSNVKVAVIDSGIDSSHPDLKVSGGASF
           B_circulans_ADN04910    (1) AQTVPYGIPQIKAPAVHAQGYKGANVKVAVLDTGIHAAHPDLNVAGGASF
             B_pumilus_ADK11996    (1) AQTVPYGIPQIKAPAVHAQGYKGANVKVAVLDTGIHAAHPDLNVAGGASF
     B_licheniformis_CAJ70731.1    (1) AQTVPYGIPLIKADKVQAQGFKGANVKVAVLDTGIQASHPDLNVVGGASF
           Bacillus_sp_AAC43580    (1) AQTVPWGIPHIKADKAHAAGVTGSGVKVAILDTGIDANHADLNVKGGASF
           Bacillus_sp_BAD11988    (1) AQTTPWGVTHINAHRAHSSGVTGSGVKVAILDTGIHASHPDLNVRGGASF
           Bacillus_sp_BAA05540    (1) SQTVPWGISFINTQQAHNRGIFGNGARVAVLDTGIA-SHPDLRIAGGASF
                B_lentus_P29600    (1) AQSVPWGISRVQAPAAHNRGLTGSGVKVAVLDTGIS-THPDLNIRGGASF
                       Bgi02446    (1) QQTVPWGITRVQAPAVHNRGITGSGVRVAILDSGIS-AHSDLNIRGGASF
                      BSP-00801    (1) QQTVPWGITRVQAPAVHNRGITGSGVRVAILDSGIS-THEDLNVRGGVSF
                      BSP-02235    (1) QQTVPWGITRVQAPAVHNRGITGSGVRVAILDSGIS-THEDLTIRGGASF
                      BSP-02310    (1) QQTVPWGITRVQAPAVHNRGITGSGVKVAILDSGIS-THEDLNIRGGVSF
                      BSP-02203    (1) QQTVPWGITRVQAPAVHNRGITGSGVRVAILDSGIS-THEDLNVRGGVSF
                      BSP-02249    (1) QQTVPWGITRVQAPAVHNRGITGSGVRVAILDSGIS-THEDLNVRGGVSF
                      BSP-02106    (1) QQTVPWGITRVQAPAVHNRGITGSGVRVAILDSGIS-THEDLNIRGGVSF
                      BSP-02429    (1) QQTVPWGITRVQAPAVHNRGITGSGVRVAILDSGIS-THEDLNVRGGVSF
                      BSP-02423    (1) QQTVPWGITRVQAPAVHNRGITGSGVRVAILDSGIS-THEDLTIRGGVSF
                      BSP-02508    (1) QQTVPWGITRVQAPAVHNRGITGSGVRVAILDSGIS-THEDLNVRGGVSF
                      BSP-02521    (1) QQTVPWGITRVQAPAVHNRGITGSGVRVAILDSGIS-THEDLNVRGGVSF
                      BSP-02550    (1) QQTVPWGITRVQAPAVHNRGITGSGVRVAILDSGIS-THEDLNVRGGVSF
                      BSP-02611    (1) QQTVPWGITRVQAPAVHNRGITGSGVKVAILDSGIS-THEDLNVRGGVSF
                      BSP-02658    (1) QQTVPWGITRVQAPAVHNRGITGSGVKVAILDSGIS-THEDLNIRGGVSF
                      BSP-03095    (1) QQTVPWGITRVQAPAVHNRGITGSGVRVAILDSGIS-THEDLNVRGGVSF
                      BSP-02983    (1) QQTVPWGITRVQAPAVHNRGITGSGVRVAILDSGIS-THEDLNVRGGVSF
                      BSP-02795    (1) QQTIPWGISRVQAPAVHNRGITGSGVRVAILDSGIS-THEDLNVRGGVSF
                      BSP-03159    (1) QQTVPWGITRVQAPAVHNRGITGSGVRVAILDSGIS-THEDLNVRGGVSF
                      BSP-02035    (1) QQTVPWGITRVQAPAVHNRGITGSGVRVAILDSGIS-THEDLNVRGGVSF
                      BSP-02445    (1) QQTVPWGITRVQAPAVHNRGITGSGVRVAILDSGIS-THEDLNVRGGVSF
                      BSP-02480    (1) QQTVPWGITRVQAPAVHNRGITGSGVRVAILDSGIS-THEDLNVRGGVSF
                      BSP-02676    (1) QQTVPWGITRVQAPAVHNRGITGSGVKVAILDSGIS-THEDLNVRGGVSF
                      BSP-02552    (1) QQTVPWGITRVQAPAVHNRGITGSGVRVAILDSGIS-THEDLTVSGGVSF
                      BSP-02567    (1) QQTVPWGITRVQAPAVHNRGITGSGVRVAILDSGIS-THEDLTVSGGVSF
                      BSP-02635    (1) QQTVPWGITRVQAPAVHNRGITGSGVRVAILDSGIS-THEDLNVRGGVSF
                      BSP-02507    (1) QQTVPWGITRVQAPAVHNRGITGSGVRVAILDSGIS-THEDLNVRGGVSF
                      BSP-02684    (1) QQTVPWGITRVQAPAVHNRGITGSGVRVAILDSGIS-THEDLNVRGGVSF
                      BSP-02569    (1) QQTVPWGITRVQAPAVHNRGITGSGVRVAILDSGIS-THEDLNVRGGVSF
                      Consensus    (1) QQTVPWGITRVQAPAVHNRGITGSGVRVAILDSGIS THEDLNVRGGVSF
```

FIG. 8A

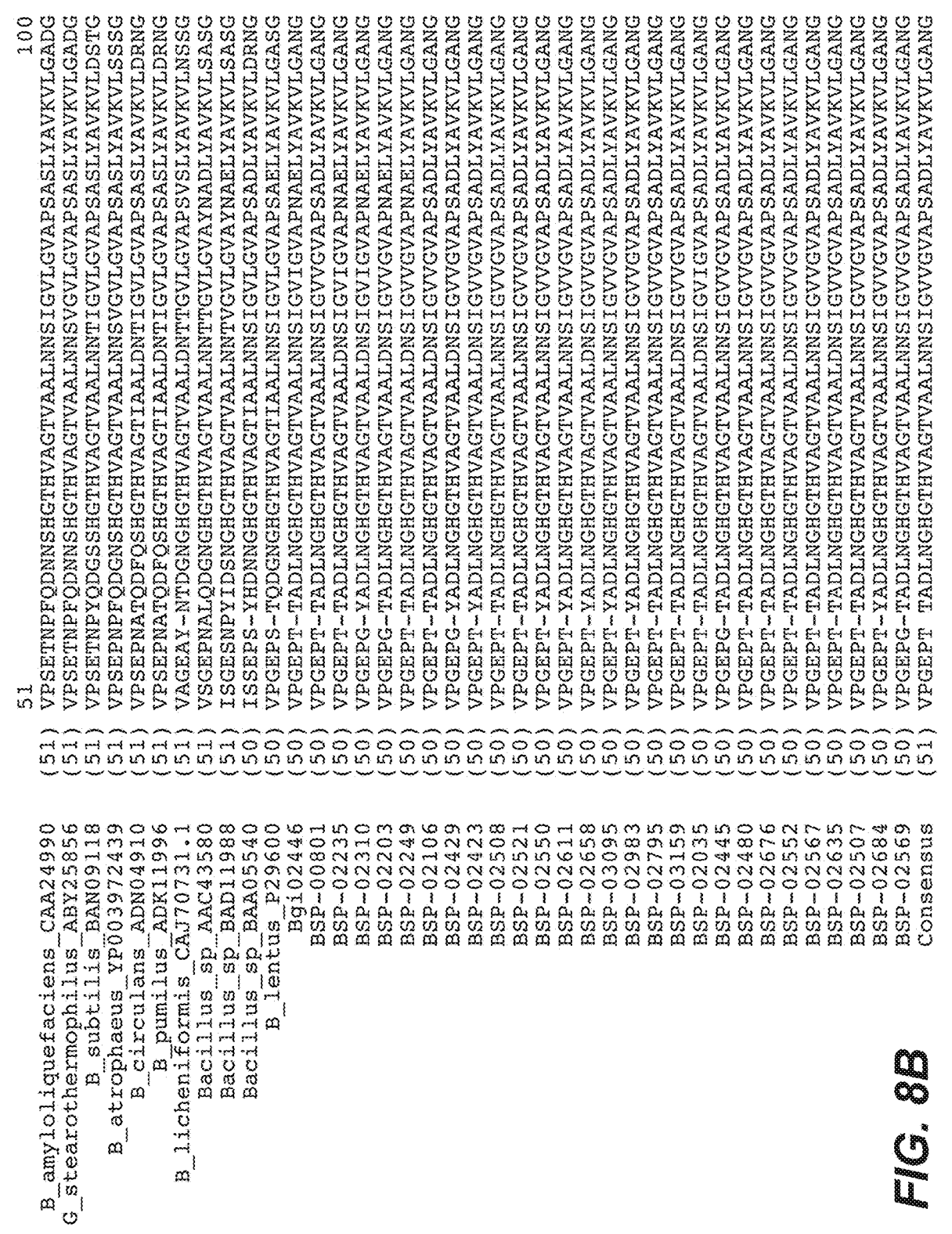

```
                                      51                                                100
B_amyloliquefaciens_CAA24990    (51) VPSETNPFQDNNSHGTHVAGTVAALNNSIGVLGVAPSASLYAVKVLGADG
G_stearothermophilus_ABY25856   (51) VPSETNPFQDNNSHGTHVAGTVAALNNSVGVLGVAPSASLYAVKVLGADG
B_subtilis_BAN09118             (51) VPSETNPYQDGSSHGTHVAGTVAALNNTIGVLGVAPSASLYAVKVLDSTG
B_atrophaeus_YP003972439        (51) VPSEPNPFQDGNSHGTHVAGTVAALNNSVGVLGVAPSASLYAVKVLSSSG
B_circulans_ADN04910            (51) VPSEPNATQDFQSHGTHVAGTIAALDNTIGVLGVAPSASLYAVKVLDRNG
B_pumilus_ADK11996              (51) VPSEPNATQDFQSHGTHVAGTIAALDNTIGVLGVAPSASLYAVKVLDRNG
B_licheniformis_CAJ70731.1      (51) VAGEAY-NTDGNGHGTHVAGTVAALDNTTGVLGVAPSVSLYAVKVLNSSG
Bacillus_sp_AAC43580            (51) VSGEPNALQDGNGHGTHVAGTVAALNNTTGVLGVAYNADLYAVKVLSASG
Bacillus_sp_BAD11988            (51) ISGESNPYIDSNGHGTHVAGTVAALNNTVGVLGVAYNAELYAVKVLSASG
Bacillus_sp_BAA05540            (50) ISSEPS-YHDNNGHGTHVAGTIAALNNSIGVLGVAPSADLYAVKVLDRNG
B_lentus_P29600                 (50) VPGEPS-TQDGNGHGTHVAGTIAALNNSIGVLGVAPSAELYAVKVLGASG
Bgi02446                        (50) VPGEPT-TADLNGHGTHVAGTVAALNNSIGVIGVAPNAELYAVKVLGANG
BSP-00801                       (50) VPGEPT-TADLNGHGTHVAGTVAALNNSIGVVGVAPSADLYAVKVLGANG
BSP-02235                       (50) VPGEPT-TADLNGHGTHVAGTVAALDNSIGVIGVAPNAELYAVKVLGANG
BSP-02310                       (50) VPGEPG-YADLNGHGTHVAGTVAALDNSIGVIGVAPNAELYAVKVLGANG
BSP-02203                       (50) VPGEPG-TADLNGHGTHVAGTVAALDNSIGVVGVAPNAELYAVKVLGANG
BSP-02249                       (50) VPGEPT-TADLNGHGTHVAGTVAALDNSIGVVGVAPNAELYAVKVLGANG
BSP-02106                       (50) VPGEPT-TADLNGHGTHVAGTVAALDNSIGVVGVAPSADLYAVKVLGANG
BSP-02429                       (50) VPGEPG-YADLNGHGTHVAGTVAALDNSIGVVGVAPSADLYAVKVLGANG
BSP-02423                       (50) VPGEPT-YADLNGHGTHVAGTVAALDNSIGVVGVAPSADLYAVKVLGANG
BSP-02508                       (50) VPGEPT-TADLNGHGTHVAGTVAALNNSIGVVGVAPSADLYAVKVLGANG
BSP-02521                       (50) VPGEPT-TADLNGHGTHVAGTVAALNNSIGVVGVAPSADLYAVKVLGANG
BSP-02550                       (50) VPGEPT-YADLNGHGTHVAGTVAALNNSIGVVGVAPSADLYAVKVLGANG
BSP-02611                       (50) VPGEPT-YADLNGHGTHVAGTVAALNNSIGVVGVAPSADLYAVKVLGANG
BSP-02658                       (50) VPGEPT-YADLNGHGTHVAGTVAALDNSIGVVGVAPSADLYAVKVLGANG
BSP-03095                       (50) VPGEPT-YADLNGHGTHVAGTVAALNNSIGVVGVAPSADLYAVKVLGANG
BSP-02983                       (50) VPGEPT-YADLNGHGTHVAGTVAALNNSIGVVGVAPSADLYAVKVLGANG
BSP-02795                       (50) VPGEPT-TADLNGHGTHVAGTVAALNNSIGVVGVAPSADLYAVKVLGANG
BSP-03159                       (50) VPGEPT-TADLNGHGTHVAGTVAALDNSIGVVGVAPSADLYAVKVLGANG
BSP-02035                       (50) VPGEPT-TADLNGHGTHVAGTVAALDNSIGVIGVAPSADLYAVKVLGANG
BSP-02445                       (50) VPGEPG-TADLNGHGTHVAGTVAALNNSIGVVGVAPSADLYAVKVLGANG
BSP-02480                       (50) VPGEPT-TADLNGHGTHVAGTVAALNNSIGVVGVAPSADLYAVKVLGANG
BSP-02676                       (50) VPGEPT-TADLNGHGTHVAGTVAALNNSIGVVGVAPSADLYAVKVLGANG
BSP-02552                       (50) VPGEPT-TADLNGHGTHVAGTVAALDNSIGVVGVAPSADLYAVKVLGANG
BSP-02567                       (50) VPGEPT-TADLNGHGTHVAGTVAALNNSIGVVGVAPSADLYAVKVLGANG
BSP-02635                       (50) VPGEPT-TADLNGHGTHVAGTVAALDNSIGVVGVAPSADLYAVKVLGANG
BSP-02507                       (50) VPGEPT-TADLNGHGTHVAGTVAALNNSIGVVGVAPSADLYAVKVLGANG
BSP-02684                       (50) VPGEPT-YADLNGHGTHVAGTVAALNNSIGVVGVAPSADLYAVKVLGANG
BSP-02569                       (50) VPGEPG-TADLNGHGTHVAGTVAALNNSIGVVGVAPSADLYAVKVLGANG
Consensus                       (51) VPGEPT TADLNGHGTHVAGTVAALNNSIGVVGVAPSADLYAVKVLGANG
```

FIG. 8B

```
                                   101                                              150
B_amyloliquefaciens_CAA24990 (101) SGQYSWIINGIEWAIANNMDVINMSLGGPSGSAALKAAVDKAVASGVVVV
G_stearothermophilus_ABY25856 (101) SGQYSWIINGIEWAIAYNMDVINMSLGGPSGSAALKAAVDKAVASGIVVV
B_subtilis_BAN09118 (101) SGQYSWIINGIEWAISNNMDVINMSLGGPTGSTALKTVVDKAVASGIVVV
B_atrophaeus_YP003972439 (101) SGDYSWIINGIEWAISNNMDVINMSLGGPQGSTALKAVVDKAVSQGIVVV
B_circulans_ADN04910 (101) DGQYSWIISGIEWAVANNMDVINMSLGGPNGSTALKNAVDTANNRGVVVV
B_pumilus_ADK11996 (101) DGQYSWIISGIEWAVANNMDVINMSLGGASGSTALKNAVDTANNRGVVVV
B_licheniformis_CAJ70731.1 (100) SGSYSGIVSGIEWATTNGMDVINMSLGGASGSTAMKQAVDNAYARGVVVV
Bacillus_sp_AAC43580 (101) SGTLSGIAQGIEWSISNGMNVINMSLGGSSGSTALQQACNNAYNRGIVVI
Bacillus_sp_BAD11988 (101) SGTLSGIAQGVEWSIANKMDVINMSLGGSSGSTALQRAVDNAYRNNIVVV
Bacillus_sp_BAA05540 (99) SGSLASVAQGIEWAINNNMHIINMSLGSTSGSSTLELAVNRANNAGILLV
B_lentus_P29600 (99) SGSVSSIAQGLEWAGNNGMHVANLSLGSPSPSATLEQAVNSATSRGVLVV
Bgi02446 (99) SGSVSGIAQGLEWAATNNMHIANMSLGSDFPSSTLERAVNYATSRDVLVI
BSP-00801 (99) RGSVSGIAQGLEWAAANNMHIANMSLGSDAPSSTLERAVNYATSRDVLVI
BSP-02235 (99) RGSISGIAQGLEWAATNNMHIANMSLGTDAPSSTLERAVNYATSRDVLVI
BSP-02310 (99) RGSISGIAQGLEWAATNNMHIANMSLGTDAPSSTLERAVNYATSRDVLVI
BSP-02203 (99) RGSISGIAQGLEWAAQNNMHIANMSLGTDAPSSTLERAVNYATSRDVLVI
BSP-02249 (99) RGSISGIAQGLEWAAQNNMHIANMSLGTDAPSSTLERAVNYATSRDVLVI
BSP-02106 (99) RGSISGIAQGLEWAAQNNMHIANMSLGTDAPSSTLERAVNYATSRDVLVI
BSP-02429 (99) RGSISGIAQGLEWAAQNNMHIANMSLGTDAPSSTLERAVNYATSRDVLVI
BSP-02423 (99) RGSVSGIAQGLEWAAQNNMHIANMSLGTDAPSSTLERAVNYATSRDVLVI
BSP-02508 (99) RGSVSGIAQGLEWAAQNNMHIANMSLGSDAPSSTLERAVNYATSRDVLVI
BSP-02521 (99) RGSISGIAQGLEWAAQNNMHIANMSLGTDAPSSTLERAVNYATSRDVLVI
BSP-02550 (99) RGSVSGIAQGLEWAAQNNMHIANMSLGTDAPSSTLERAVNYATSRDVLVI
BSP-02611 (99) RGSVSGIAQGLEWAAQNNMHIANMSLGTDAPSSTLERAVNYATSRDVLVI
BSP-02658 (99) RGSVSGIAQGLEWAAQNNMHVANMSLGTDAPSSTLERAVNYATSRDVLVI
BSP-03095 (99) RGSVSGIAQGLEWAAQNNMHVANMSLGTDAPSSTLERAVNYATSRDVLVI
BSP-02983 (99) RGSVSGIAQGLEWAAQNNMHIANMSLGTDAPSSTLERAVNYATSRDVLVI
BSP-02795 (99) RGSVSGIAQGLEWAAANNMHIANMSLGSDAPSSTLERAVNYATSRDVLVI
BSP-03159 (99) RGSISGIAQGLEWAAANNMHIANMSLGSDAPSSTLERAVNYATSQDVLVI
BSP-02035 (99) RGSVSGIAQGLEWAAANNMHIANMSLGTDAPSSTLERAVNYATSRDVLVI
BSP-02445 (99) RGSISGIAQGLEWAAANNMHIANMSLGTDAPSSTLERAVNYATSRDVLVI
BSP-02480 (99) RGSVSGIAQGLEWAAANNMHIANMSLGTDAPSSTLERAVNYATSRDVLVI
BSP-02676 (99) RGSVSGIAQGLEWAAANNMHIANMSLGTDAPSSTLERAVNYATSRDVLVI
BSP-02552 (99) RGSVSGIAQGLEWAAANNMHIANMSLGTDAPSSTLERAVNYATSRDVLVI
BSP-02567 (99) RGSVSGIAQGLEWAAANNMHIANMSLGTDAPSSTLERAVNYATSRDVLVI
BSP-02635 (99) RGSVSGIAQGLEWAAANNMHIANMSLGTDAPSSTLERAVNYATSRDVLVI
BSP-02507 (99) RGSVSGIAQGLEWAAQNNMHIANMSLGTDAPSSTLERAVNYATSADVLVI
BSP-02684 (99) RGSVSGIAQGLEWAAANNMHIANMSLGTDAPSSTLERAVNYATSADVLVI
BSP-02569 (99) RGSVSGIAQGLEWAAQNNMHIANMSLGTDAPSSTLERAVNYATSRDVLVI
Consensus (101) RGSVSGIAQGLEWAA NNMHIANMSLGTDAPSSTLERAVNYATSRDVLVI
```

FIG. 8C

| | | 151 200 |
|---|---|---|
| B_amyloliquefaciens_CAA24990 | (151) | AAAGNEGTSGSSSTVGYPGKYPSVIAVGAVDSSNQRASFSSVGPELDVMA |
| G_stearothermophilus_ABY25856 | (151) | AAAGNEGTSGSSSTVGYPGKYPSVIAVGAVNSSNQRASFSSVGSELDVMA |
| B_subtilis_BAN09118 | (151) | AAAGNEGSSGSTSTVGYPAKYPSTIAVGAVNSSNQRASFSSAGSELDVMA |
| B_atrophaeus_YP003972439 | (151) | AAAGNSGSSGSTSTVGYPAKYPSVIAVGAVDSNNQRASFSSAGSELDVMA |
| B_circulans_ADN04910 | (151) | AAAGNSGSTGSTSTVGYPAKYDSTIAVANVNSSNVRNSSSSAGPELDVSA |
| B_pumilus_ADK11996 | (151) | AAAGNSGSSGSRSTVGYPAKYESTIAVANVNSNNVRNSSSSAGPELDVSA |
| B_licheniformis_CAJ70731.1 | (150) | AAAGNSGSSGNTNTIGYPAKYDSVIAVGAVDSNSNRASFSSVGAELEVMA |
| Bacillus_sp_AAC43580 | (151) | AAAGNSGSSGNRNTMGYPARYSSVIAVGAVSSNNTRASFSSVGSELEVMA |
| Bacillus_sp_BAD11988 | (151) | AAAGNSGAQGNRNTIGYPARYSSVIAVGAVDSNNNRASFSSVGSELEVMA |
| Bacillus_sp_BAA05540 | (149) | GAAGNTGRQG----VNYPARYSGVMAVAAVDQNGQRASFSTYGPEIEISA |
| B_lentus_P29600 | (149) | AASGNSGAGS----ISYPARYANAMAVGATDQNNNRASFSQYGAGLDIVA |
| Bgi02446 | (149) | AATGNNGSGS----VGYPARYANAMAVGATDQNNRRANFSQYGTGIDIVA |
| BSP-00801 | (149) | AATGNNGSGS----VGYPARYANAMAVGATDQNNRRANFSQYGTGIDIVA |
| BSP-02235 | (149) | AATGNNGSGT----VGYPARYANAMAVGATDQNNRRANFSQYGTGIDIVA |
| BSP-02310 | (149) | AATGNNGSGS----VGYPARYANAMAVGATDQNNRRANFSQYGTGIDIVA |
| BSP-02203 | (149) | AATGNNGSGS----VGYPARYANAMAVGATDQNNRRANFSQYGTGIDIVA |
| BSP-02249 | (149) | AATGNNGSGS----VGYPARYANAMAVGATDQNNRRANFSQYGTGIDIVA |
| BSP-02106 | (149) | AATGNNGSGT----VGYPARYANAMAVGATDQNNRRANFSQYGTGIDIVA |
| BSP-02429 | (149) | AATGNNGSGS----VGYPARYANAMAVGATDQNNRRANFSQYGTGIDIVA |
| BSP-02423 | (149) | AATGNNGSGS----VGYPARYANAMAVGATDQNNRRANFSQYGTGIDIVA |
| BSP-02508 | (149) | AATGNNGSGS----VGYPARYANAMAVGATDQNNRRANFSQYGTGIDIVA |
| BSP-02521 | (149) | AATGNNGSGS----VGYPARYANAMAVGATDQNNRRANFSQYGTGIDIVA |
| BSP-02550 | (149) | AATGNNGSGT----VGYPARYANAMAVGATDQNNRRANFSQYGTGIDIVA |
| BSP-02611 | (149) | AATGNNGSGT----VSYPARYANAMAVGATDQNNRRANFSQYGTGIDIVA |
| BSP-02658 | (149) | AATGNNGSGS----VGYPARYANAMAVGATDQNNRRANFSQYGTGIDIVA |
| BSP-03095 | (149) | AATGNNGSGS----VGYPARYANAMAVGATDQNNRRANFSQYGTGIDIVA |
| BSP-02983 | (149) | AATGNNGSGS----VGYPARYANAMAVGATDQNNRRANFSQYGTGIDIVA |
| BSP-02795 | (149) | AATGNNGSGS----VGYPARYANAMAVGATDQNNRRANFSQYGTGIDIVA |
| BSP-03159 | (149) | AATGNNGSGT----VGYPARYANAMAVGATDQNNRRANFSQYGTGIDIVA |
| BSP-02035 | (149) | AATGNNGSGT----VGYPARYANAMAVGATDQNNRRANFSQYGTGIDIVA |
| BSP-02445 | (149) | AATGNNGSGT----VGYPARYANAMAVGATDQNNRRANFSQYGTGIDIVA |
| BSP-02480 | (149) | AATGNNGSGS----VGYPARYANAMAVGATDQNNRRANFSQYGTGIDIVA |
| BSP-02676 | (149) | AATGNNGSGS----VGYPARYANAMAVGATDQNNRRANFSQYGTGIDIVA |
| BSP-02552 | (149) | AATGNNGSGS----VGYPARYANAMAVGATDQNNRRANFSQYGTGIDIVA |
| BSP-02567 | (149) | AATGNNGSGS----VGYPARYANAMAVGATDQNNRRANFSQYGTGIDIVA |
| BSP-02635 | (149) | AATGNNGSGS----VGYPARYANAMAVGATDQNNRRANFSQYGTGIDIVA |
| BSP-02507 | (149) | AATGNNGSGS----VGYPARYANAMAVGATDQNNRRANFSQYGTGIDIVA |
| BSP-02684 | (149) | AATGNNGSGS----VGYPARYANAMAVGATDQNNRRANFSQYGTGIDIVA |
| BSP-02569 | (149) | AATGNNGSGS----VGYPARYANAMAVGATDQNNRRANFSQYGTGIDIVA |
| Consensus | (151) | AATGNNGSGS VGYPARYANAMAVGATDQNNRRANFSQYGTGIDIVA |

FIG. 8D

```
                                         201                                              250
     B_amyloliquefaciens_CAA24990  (201) PGVSIQSTLPGNKYGAYNGTSMASPHVAGAAALILSKHPNWTNTQVRSSL
   G_stearothermophilus_ABY25856  (201) PGVSIQSTLPGNKYGAYNGTSMASPHVAGAAALILSKHPNWTNTQVRSSL
              B_subtilis_BAN09118  (201) PGVSIQSTLPGGTYGSYNGTSMATPHVAGAAALILSKHPTWSNAQVRDRL
         B_atrophaeus_YP003972439  (201) PGVSIQSTLPGSSYGSYNGTSMASPHVAGAAALVLSKHPNWTNSQVRNSL
             B_circulans_ADN04910  (201) PGTSILSTVPSRGYTSYTGTSMASPHVAGAAALILSKNPNLSNSQVRQRL
               B_pumilus_ADK11996  (201) PGTSILSTVPSSGYTSYTGTSMASPHVAGAAALILSKNPNLTNSQVRQRL
       B_licheniformis_CAJ70731.1  (200) PGAGVYSTYPTNTYATLNGTSMASPHVAGAAALILSKHPNLSASQVRNRL
             Bacillus_sp_AAC43580  (201) PGVNILSTTPGNNYASFNGTSMAAPHVAGAAALIKAKYPSMTNVQIRERL
             Bacillus_sp_BAD11988  (201) PGVSILSTVPGSSYASYNGTSMASPHVAGAAALLKAKYPNWSAAQIRNKL
             Bacillus_sp_BAA05540  (195) PGVNVNSTYTGNRYVSLSGTSMATPHVAGVAALVKSRYPSYTNNQIRQRI
                 B_lentus_P29600  (195) PGVNVQSTYPGSTYASLNGTSMATPHVAGAAALVKQKNPSWSNVQIRNHL
                        Bgi02446  (195) PGVNVQSTYPGNRYVSMNGTSMATPHVAGAAALVKQRYPSWNATQIRNHL
                       BSP-00801  (195) PGVNVQSTYPGNRYVSMNGTSMATPHVAGAAALVKQRYPSWNATQIRNHL
                       BSP-02235  (195) PGVNVQSTYPGNRYVSMNGTSMATPHVAGAAALVKQRYPSWNATQIRDHL
                       BSP-02310  (195) PGVNVQSTYPGNRYVSMNGTSMATPHVAGAAALVKQRYPSWNATQIRDHL
                       BSP-02203  (195) PGVNVQSTYPGNRYVSMNGTSMATPHVAGAAALVKQRYPSWNATQIRNHL
                       BSP-02249  (195) PGVNVQSTYPGNRYVSMNGTSMATPHVAGAAALVKQRYPSWNATQIRDHL
                       BSP-02106  (195) PGVNVQSTYPGNRYVSMNGTSMATPHVAGAAALVKQRYPSWNATQIRDHL
                       BSP-02429  (195) PGVNVQSTYPGNRYVSMNGTSMATPHVAGAAALVKQRYPSWNATQIRDHL
                       BSP-02423  (195) PGVNVQSTYPGNRYVSMNGTSMATPHVAGAAALVKQRYPSWNATQIRNHL
                       BSP-02508  (195) PGVNVQSTYPGNRYVSMNGTSMATPHVAGAAALVKQRYPSWNATQIRDHL
                       BSP-02521  (195) PGVNVQSTYPGNRYVSMNGTSMATPHVAGAAALVKQRYPSWNATQIRDHL
                       BSP-02550  (195) PGVNVQSTYPGNRYVSMNGTSMATPHVAGAAALVKQRYPSWNATQIRDHL
                       BSP-02611  (195) PGVNVQSTYPGNRYVSMNGTSMATPHVAGAAALVKQRYPSWNATQIRDHL
                       BSP-02658  (195) PGVNVQSTYPGNRYVSMNGTSMATPHVAGAAALVKQRYPSWNATQIRDHL
                       BSP-03095  (195) PGVNVQSTYPGNRYVSMNGTSMATPHVAGAAALVKQRYPSWNATQIRDHL
                       BSP-02983  (195) PGVNVQSTYPGNRYVSMNGTSMATPHVAGAAALVKQRYPSWNATQIRDHL
                       BSP-02795  (195) PGVNVQSTYPGNRYVSMNGTSMATPHVAGVAALVKQRYPSWNATQIRNHL
                       BSP-03159  (195) PGVNVQSTYPGNRYVSMNGTSMATPHVAGVAALVKQRYPSWNATQIRNHL
                       BSP-02035  (195) PGVNVQSTYPGNRYVSMSGTSMATPHVAGAAALVKQRYPSWNATQIRNHL
                       BSP-02445  (195) PGVNVQSTYPGNRYVSMNGTSMATPHVAGAAALVKQRYPSWNATQIRNHL
                       BSP-02480  (195) PGVNVQSTYPGNRYVSMNGTSMATPHVAGAAALVKQRYPSWNATQIRDHL
                       BSP-02676  (195) PGVNVQSTYPGNRYVSMNGTSMATPHVAGAAALVKQRYPSWNATQIRDHL
                       BSP-02552  (195) PGVNVQSTYPGNRYVSMNGTSMATPHVAGAAALVKQRYPSWNATQIRNHL
                       BSP-02567  (195) PGVNVQSTYPGNRYVSMNGTSMATPHVAGAAALVKQRYPSWNATQIRDHL
                       BSP-02635  (195) PGVNVQSTYPGNRYVSMNGTSMATPHVAGAAALVKQRYPSWNATQIRDHL
                       BSP-02507  (195) PGVNVQSTYPGNRYVSMNGTSMATPHVAGAAALVKQRYPSWNATQIRNHL
                       BSP-02684  (195) PGVNVQSTYPGNRYVSMNGTSMATPHVAGAAALVKQRYPSWNATQIRNHL
                       BSP-02569  (195) PGVNVQSTYPGNRYVSMNGTSMATPHVAGAAALVKQRYPSWNATQIRNHL
                       Consensus  (201) PGVNVQSTYPGNRYVSMNGTSMATPHVAGAAALVKQRYPSWNATQIR HL
```

FIG. 8E

| | | 251 275 | |
|---|---|---|---|
| B_amyloliquefaciens_CAA24990 | (251) | ENTTTKLGDSFYYGKGLINVQAAAQ | SEQ ID NO:74 |
| G_stearothermophilus_ABY25856 | (251) | ENTTTKLGDAFYYGKGLINVQAAAQ | SEQ ID NO:75 |
| B_subtilis_BAN09118 | (251) | ESTATNLGSSFYYGKGLINVQAAAQ | SEQ ID NO:76 |
| B_atrophaeus_YP003972439 | (251) | ESTATNLGNSFYYGKGLINVQAAAQ | SEQ ID NO:77 |
| B_circulans_ADN04910 | (251) | ENTATPLGNSFYYGKGLINVQAASN | SEQ ID NO:78 |
| B_pumilus_ADK11996 | (251) | ENTATPLGDSFYYGKGLINVQAASN | SEQ ID NO:79 |
| B_licheniformis_CAJ70731.1 | (250) | SSTATYLGSSFYYGKGLINVEAAAQ | SEQ ID NO:80 |
| Bacillus_sp_AAC43580 | (251) | KNTATNLGDPFFYGKGVINVESALQ | SEQ ID NO:81 |
| Bacillus_sp_BAD11988 | (251) | NSTTTYLGSSFYYGNGVINVERALQ | SEQ ID NO:82 |
| Bacillus_sp_BAA05540 | (245) | NQTATYLGSPSLYGNGLVHAGRATQ | SEQ ID NO:83 |
| B_lentus_P29600 | (245) | KNTATSLGSTNLYGSGLVNAEAATR | SEQ ID NO:84 |
| Bgi02446 | (245) | KNTATNLGNSSQFGSGLVNAEAATR | SEQ ID NO:85 |
| BSP-00801 | (245) | KNTATNLGNSSQFGSGLVNAEAATR | SEQ ID NO:18 |
| BSP-02235 | (245) | KNTATNLGNSSQFGSGLVNAEAATR | SEQ ID NO:119 |
| BSP-02310 | (245) | KNTATNLGNSSQFGSGLVNAEAATR | SEQ ID NO:120 |
| BSP-02203 | (245) | KNTATNLGNSSQFGSGLVNAEAATR | SEQ ID NO:123 |
| BSP-02249 | (245) | KNTATNLGNSSQFGSGLVNAEAATR | SEQ ID NO:124 |
| BSP-02106 | (245) | KNTATNLGNSSQFGSGLVNAEAATR | SEQ ID NO:22 |
| BSP-02429 | (245) | KNTATNLGNSSQFGSGLVNAEAATR | SEQ ID NO:34 |
| BSP-02423 | (245) | KNTATNLGNSSQFGSGLVNAEAATR | SEQ ID NO127 |
| BSP-02508 | (245) | KNTATNLGNSSQFGSGLVNAEAATR | SEQ ID NO:140 |
| BSP-02521 | (245) | KNTATNLGNSSQFGSGLVNAEAATR | SEQ ID NO:137 |
| BSP-02550 | (245) | KNTATNLGNSSQFGSGLVNAEAATR | SEQ ID NO:44 |
| BSP-02611 | (245) | KNTATNLGNSSQYGSGLVNAEAATR | SEQ ID NO:54 |
| BSP-02658 | (245) | KNTATNLGNSSQYGSGLVNAEAATR | SEQ ID NO:58 |
| BSP-03095 | (245) | KNTATNLGNSSQFGSGLVNAEAATR | SEQ ID NO:68 |
| BSP-02983 | (245) | KNTATNLGNSSQFGSGLVNAEAATR | SEQ ID NO:66 |
| BSP-02795 | (245) | LNTATNLGNSNQFGSGLVNAEAATR | SEQ ID NO:64 |
| BSP-03159 | (245) | KNTATNLGNSNQFGSGLVNAEAATR | SEQ ID NO:70 |
| BSP-02035 | (245) | KNTATNLGNSSQFGSGLVNAEAATR | SEQ ID NO:151 |
| BSP-02445 | (245) | KNTATNLGNSSQFGSGLVNAEAATR | SEQ ID NO:36 |
| BSP-02480 | (245) | KNTATNLGNSSQFGSGLVNAEAATR | SEQ ID NO:38 |
| BSP-02676 | (245) | KNTATNLGNSSQFGSGLVNAEAATR | SEQ ID NO:60 |
| BSP-02552 | (245) | KNTATNLGNSSQFGSGLVNAEAATR | SEQ ID NO:46 |
| BSP-02567 | (245) | KNTATNLGNSSQFGSGLVNAEAATR | SEQ ID NO:50 |
| BSP-02635 | (245) | KNTATNLGNSSQFGSGLVNAEAATR | SEQ ID NO:56 |
| BSP-02507 | (245) | KNTATNLGNSSQFGSGLVNAEAATR | SEQ ID NO:135 |
| BSP-02684 | (245) | KNTATNLGNSSQFGSGLVNAEAATR | SEQ ID NO:62 |
| BSP-02569 | (245) | KNTATNLGNSSQFGSGLVNAEAATR | SEQ ID NO:136 |
| Consensus | (251) | KNTATNLGNSSQFGSGLVNAEAATR | SEQ ID NO:198 |

FIG. 8F

```
                      1                                                50
 Bgi02446        (1)  QQTVPWGITRVQAPAVHNRGITGSGVRVAILDSGISAHSDLNIRGGASFV
BSP-01531        (1)  AQTVPWGITRVQAPAVHNRGITGSGVRVAILDSGISAHSDLNIRGGASFV
BSP-01757        (1)  QQTVPWGITRVQAPAVHNRGITGSGVRVAILDSGISAHSDLTIRGGASFV
BSP-01537        (1)  QQTVPWGITRVQAPAVHNRGVTGSGVRVAILDSGISAHSDLNIRGGASFV
BSP-02320        (1)  QQTVPWGITRVQAPAVHNRGITGSGVRVAILDSGISAHSDLNIRGGASFV
BSP-02389        (1)  QQTVPWGITRVQAPAVHNRGITGSGVRVAILDSGISAHSDLNIRGGASFV
BSP-02355        (1)  QQTVPWGITRVQAPAVHNRGITGSGVRVAILDSGISAHSDLNIRGGASFV
BSP-02354        (1)  QQTVPWGITRVQAPAVHNRGITGSGVRVAILDSGISAHSDLNIRGGASFV
BSP-02380        (1)  QQTVPWGITRVQAPAVHNRGITGSGVRVAILDSGISAHSDLNIRGGASFV
BSP-03007        (1)  QQTVPWGITRVQAPAVHNRGITGSGVRVAILDSGISAHSDLNIRGGASFV
BSP-02411        (1)  QQTVPWGITRVQAPAVHNRGITGSGVRVAILDSGISAHSDLNIRGGASFV
BSP-02725        (1)  QQTVPWGITRVQAPAVHNRGITGSGVRVAILDSGISAHSDLNIRGGASFV
BSP-03024        (1)  QQTVPWGITRVQAPAVHNRGITGSGVRVAILDSGISAHSDLNIRGGASFV
BSP-03033        (1)  QQTVPWGITRVQAPAVHNRGITGSGVRVAILDSGISAHSDLNIRGGASFV
BSP-03048        (1)  QQTVPWGITRVQAPAVHNRGITGSGVRVAILDSGISAHSDLNIRGGASFV
BSP-02301        (1)  QQTVPWGITRVQAPAVHNRGITGSGVKVAILDSGISAHSDLNIRGGASFV
BSP-03027        (1)  QQTVPWGITRVQAPAVHNRGITGSGVKVAILDSGISAHSDLNIRGGASFV
BSP-02195        (1)  QQTVPWGITRVQAPAVHNRGITGSGVRVAILDSGISAHSDLNIRGGASFV
BSP-02227        (1)  QQTVPWGITRVQAPAVHNRGITGSGVRVAILDSGISAHSDLNIRGGASFV
BSP-02391        (1)  QQTVPWGITRVQAPAVHNRGITGSGVKVAILDSGISAHSDLNIRGGASFV
BSP-02412        (1)  QQTVPWGITRVQAPAVHNRGITGSGVKVAILDSGISAHSDLNIRGGASFV
BSP-02400        (1)  QQTVPWGITRVQAPAVHNRGITGSGVRVAILDSGISAHSDLNIRGGASFV
Consensus        (1)  QQTVPWGITRVQAPAVHNRGITGSGVRVAILDSGISAHSDLNIRGGASFV
                      51                                              100
 Bgi02446       (51)  PGEPTTADLNGHGTHVAGTVAALNNSIGVIGVAPNAELYAVKVLGANGSG
BSP-01531       (51)  PGEPTTADLNGHGTHVAGTVAALNNSIGVVGVAPNAELYAVKVLGANGSG
BSP-01757       (51)  PGEPTTADLNGHGTHVAGTVAALNNSIGVVGVAPSADLYAVKVLGANGSG
BSP-01537       (51)  PGEPTTADLNGHGTHVAGTVAALNNSIGVVGVAPSADLYAVKVLGANGSG
BSP-02320       (51)  PGEPTTADLNGHGTHVAGTVAALDNSIGVVGVAPSADLYAVKVLGANGSG
BSP-02389       (51)  PGEPTTADLNGHGTHVAGTVAALDNSIGVVGVAPSADLYAVKVLGANGRG
BSP-02355       (51)  PGEPTTADLNGHGTHVAGTVAALNNSIGVIGVAPSADLYAVKVLGANGRG
BSP-02354       (51)  PGEPTTADLNGHGTHVAGTVAALDNSIGVVGVAPSADLYAVKVLGANGRG
BSP-02380       (51)  PGEPTTADLNGHGTHVAGTVAALDNSIGVVGVAPSADLYAVKVLGANGRG
BSP-03007       (51)  PGEPTTADLNGHGTHVAGTVAALDNSIGVVGVAPSADLYAVKVLGANGRG
BSP-02411       (51)  PGEPTTADLNGHGTHVAGTVAALDNSIGVIGVAPSADLYAVKVLGANGRG
BSP-02725       (51)  PGEPTTADLNGHGTHVAGTVAALNNSIGVIGVAPSADLYAVKVLGANGRG
BSP-03024       (51)  PGEPTTADLNGHGTHVAGTVAALDNSIGVVGVAPSADLYAVKVLGANGRG
BSP-03033       (51)  PGEPTTADLNGHGTHVAGTVAALDNSIGVVGVAPSADLYAVKVLGANGRG
BSP-03048       (51)  PGEPTTADLNGHGTHVAGTVAALNNSIGVVGVAPSADLYAVKVLGANGRG
BSP-02301       (51)  PGEPTTADLNGHGTHVAGTVAALNNSIGVIGVAPNAELYAVKVLGANGRG
BSP-03027       (51)  PGEPTTADLNGHGTHVAGTVAALNNSIGVIGVAPNAELYAVKVLGANGRG
BSP-02195       (51)  PGEPTTADLNGHGTHVAGTVAALDNSIGVIGVAPNAELYAVKVLGANGRG
BSP-02227       (51)  PGEPTTADLNGHGTHVAGTVAALDNSIGVVGVAPNAELYAVKVLGANGRG
BSP-02391       (51)  PGEPTTADLNGHGTHVAGTVAALDNSIGVIGVAPNAELYAVKVLGANGRG
BSP-02412       (51)  PGEPTTADLNGHGTHVAGTVAALDNSIGVIGVAPNAELYAVKVLGANGRG
BSP-02400       (51)  PGEPTTADLNGHGTHVAGTVAALDNSIGVVGVAPNAELYAVKVLGANGRG
Consensus       (51)  PGEPTTADLNGHGTHVAGTVAALDNSIGVVGVAPSADLYAVKVLGANGRG
```

FIG. 12A

```
                   101                                               150
 Bgi02446  (101) SVSGIAQGLEWAATNNMHIANMSLGSDFPSSTLERAVNYATSRDVLVIAA
BSP-01531  (101) SVSGIAQGLEWAATNNMHIANMSLGSDAPSTTLERAVNYATSAGVLVIAA
BSP-01757  (101) SVSGIAQGLEWAAANNMHIANMSLGSDAPSSTLERAVNYATSQGVLVIAA
BSP-01537  (101) SVSGIAQGLEWAATNNIHIANMSLGSDAPSTTLERAVNYATSQGVLVIAA
BSP-02320  (101) SVSGIAQGLEWAATNNMHIANMSLGSDFPSSTLERAVNYATSRDVLVIAA
BSP-02389  (101) SISGIAQGLEWAATNNMHIANMSLGSDFPSSTLERAVNYATSRDVLVIAA
BSP-02355  (101) SISGIAQGLEWAAQNNMHIANMSLGSDFPSSTLERAVNYATSRDVLVIAA
BSP-02354  (101) SISGIAQGLEWAATNNMHIANMSLGTDAPSSTLERAVNYATSADVLVIAA
BSP-02380  (101) SISGIAQGLEWAAQNNMHIANMSLGSDFPSSTLERAVNYATSADVLVIAA
BSP-03007  (101) SISGIAQGLEWAATNNMHIANMSLGSDFPSSTLERAVNYATSRDVLVIAA
BSP-02411  (101) SISGIAQGLEWAATNNMHIANMSLGTDAPSSTLERAVNYATSRDVLVIAA
BSP-02725  (101) SVSGIAQGLEWAAQNNMHVANMSLGTDAPSSTLERAVNYATSADVLVIAA
BSP-03024  (101) SVSGIAQGLEWAAQNNMHIANMSLGTDAPSSTLERAVNYATSADVLVIAA
BSP-03033  (101) SISGIAQGLEWAAQNNMHIANMSLGTDAPSSTLERAVNYATSRDVLVIAA
BSP-03048  (101) SISGIAQGLEWAAQNNMHVANMSLGTDAPSSTLERAVNYATSADVLVIAA
BSP-02301  (101) SISGIAQGLEWAAQNNMHVANMSLGTDAPSSTLERAVNYATSRDVLVIAA
BSP-03027  (101) SISGIAQGLEWAATNNMHIANMSLGTDAPSSTLERAVNYATSADVLVIAA
BSP-02195  (101) SISGIAQGLEWAATNNMHIANMSLGTDAPSSTLERAVNYATSADVLVIAA
BSP-02227  (101) SISGIAQGLEWAAQNNMHIANMSLGTDAPSSTLERAVNYATSADVLVIAA
BSP-02391  (101) SISGIAQGLEWAAQNNMHIANMSLGTDAPSSTLERAVNYATSRDVLVIAA
BSP-02412  (101) SISGIAQGLEWAATNNMHVANMSLGTDAPSSTLERAVNYATSADVLVIAA
BSP-02400  (101) SISGIAQGLEWAAQNNMHVANMSLGTDAPSSTLERAVNYATSRDVLVIAA
Consensus  (101) SISGIAQGLEWAATNNMHIANMSLGTDAPSSTLERAVNYATS DVLVIAA
                   151                                               200
 Bgi02446  (151) TGNNGSGSVGYPARYANAMAVGATDQNNRRANFSQYGTGIDIVAPGVNVQ
BSP-01531  (151) TGNNGSGSVGYPARYANALAVGATDQNNRRANFSQYGTGLDIVAPGVNVQ
BSP-01757  (151) TGNNGSGTISYPARYANAMAVGATDQNNRRANFSQYGTGIDIVAPGVGVQ
BSP-01537  (151) TGNNGSGSVGYPARYANAMAVGATDQNNRRANFSQYGTGIDIVAPGVNVQ
BSP-02320  (151) TGNNGSGTVGYPARYANAMAVGATDQNNRRANFSQYGTGIDIVAPGVNVQ
BSP-02389  (151) TGNNGSGTIGYPARYANAMAVGATDQNNRRANFSQYGTGIDIVAPGVNVQ
BSP-02355  (151) TGNNGSGTISYPARYANAMAVGATDQNNRRANFSQYGTGIDIVAPGVNVQ
BSP-02354  (151) TGNNGSGSVGYPARYANAMAVGATDQNNRRANFSQYGTGLDIVAPGVNVQ
BSP-02380  (151) TGNNGSGSVGYPARYANAMAVGATDQNNRRANFSQYGTGLDIVAPGVNVQ
BSP-03007  (151) TGNNGSGSVGYPARYANAMAVGATDQNNRRANFSQYGTGLDIVAPGVNVQ
BSP-02411  (151) TGNNGSGSVGYPARYANAMAVGATDQNNRRANFSQYGTGLDIVAPGVNVQ
BSP-02725  (151) TGNNGSGSVSYPARYANAMAVGATDQNNRRANFSQYGTGIDIVAPGVNVQ
BSP-03024  (151) TGNNGSGSVGYPARYANAMAVGATDQNNRRANFSQYGTGIDIVAPGVNVQ
BSP-03033  (151) TGNNGSGSVGYPARYANAMAVGATDQNNRRANFSQYGTGIDIVAPGVNVQ
BSP-03048  (151) TGNNGSGSVGYPARYANAMAVGATDQNNRRANFSQYGTGIDIVAPGVNVQ
BSP-02301  (151) TGNNGSGTISYPARYANAMAVGATDQNNRRANFSQYGAGIDIVAPGVNVQ
BSP-03027  (151) TGNNGSGTISYPARYANAMAVGATDQNNRRANFSQYGTGIDIVAPGVNVQ
BSP-02195  (151) TGNNGSGTVGYPARYANAMAVGATDQNNRRANFSQYGTGIDIVAPGVNVQ
BSP-02227  (151) TGNNGSGSVGYPARYANAMAVGATDQNNRRANFSQYGTGIDIVAPGVNVQ
BSP-02391  (151) TGNNGSGSVGYPARYANAMAVGATDQNNRRANFSQYGAGLDIVAPGVNVQ
BSP-02412  (151) TGNNGSGSVSYPARYANAMAVGATDQNNRRANFSQYGTGIDIVAPGVNVQ
BSP-02400  (151) TGNNGSGTVSYPARYANAMAVGATDQNNRRANFSQYGTGIDIVAPGVNVQ
Consensus  (151) TGNNGSGSVGYPARYANAMAVGATDQNNRRANFSQYGTGIDIVAPGVNVQ
```

FIG. 12B

```
                   201                                               250
 Bgi02446   (201) STYPGNRYVSMNGTSMATPHVAGAAALVKQRYPSWNATQIRNHLKNTATN
BSP-01531   (201) STYPGNRYVSMNGTSMATPHVAGAAALVKQRYPSWNATQIRNHLKNTATN
BSP-01757   (201) STYPGNRYVSMNGTSMATPHVAGAAALVKQRYPSWNATQIRNHLKNTATN
BSP-01537   (201) STYPGNRYVSMNGTSMATPHVAGVAALVKQRYPSWNATQIRNHLKNTATN
BSP-02320   (201) STYPGNRYVSMNGTSMATPHVAGAAALVKQRYPSWNATQIRDHLKNTATN
BSP-02389   (201) STYPGNRYVSMNGTSMATPHVAGAAALVKQRYPSWNATQIRDHLKNTATN
BSP-02355   (201) STYPGNRYVSMSGTSMATPHVAGAAALVKQRYPSWNATQIRDHLKNTATN
BSP-02354   (201) STYPGNRYVSMNGTSMATPHVAGAAALVKQRYPSWNATQIRDHLKNTATN
BSP-02380   (201) STYPGNRYVSMNGTSMATPHVAGAAALVKQRYPSWNATQIRDHLKNTATN
BSP-03007   (201) STYPGNRYVSMNGTSMATPHVAGAAALVKQRYPSWNATQIRDHLKNTATN
BSP-02411   (201) STYPGNRYVSMNGTSMATPHVAGAAALVKQRYPSWNATQIRDHLKNTATN
BSP-02725   (201) STYPGNRYVSMNGTSMATPHVAGAAALVKQRYPSWNATQIRNHLKNTATN
BSP-03024   (201) STYPGNRYVSMNGTSMATPHVAGAAALVKQRYPSWNATQIRDHLKNTATN
BSP-03033   (201) STYPGNRYVSMNGTSMATPHVAGAAALVKQRYPSWNATQIRDHLKNTATN
BSP-03048   (201) STYPGNRYVSMNGTSMATPHVAGAAALVKQRYPSWNATQIRDHLKNTATN
BSP-02301   (201) STYPGNRYVSMNGTSMATPHVAGAAALVKQRYPSWNATQIRDHLKNTATN
BSP-03027   (201) STYPGNRYVSMNGTSMATPHVAGAAALVKQRYPSWNATQIRNHLKNTATN
BSP-02195   (201) STYPGNRYVSMSGTSMATPHVAGAAALVKQRYPSWNATQIRNHLKNTATN
BSP-02227   (201) STYPGNRYVSMSGTSMATPHVAGAAALVKQRYPSWNATQIRDHLKNTATN
BSP-02391   (201) STYPGNRYVSMSGTSMATPHVAGAAALVKQRYPSWNATQIRDHLKNTATN
BSP-02412   (201) STYPGNRYVSMSGTSMATPHVAGAAALVKQRYPSWNATQIRDHLKNTATN
BSP-02400   (201) STYPGNRYVSMSGTSMATPHVAGAAALVKQRYPSWNATQIRNHLKNTATN
Consensus   (201) STYPGNRYVSMNGTSMATPHVAGAAALVKQRYPSWNATQIRDHLKNTATN
                  251                269
 Bgi02446   (251) LGNSSQFGSGLVNAEAATR   SEQ ID NO:85
BSP-01531   (251) LGNTNLYGSGLVNAEAATR   SEQ ID NO:96
BSP-01757   (251) LGNSSQFGSGLVNAEAATR   SEQ ID NO:95
BSP-01537   (251) LGNSSQFGSGLVNAEAATR   SEQ ID NO:94
BSP-02320   (251) LGNSSQFGSGLVNAEAATR   SEQ ID NO:97
BSP-02389   (251) LGNSSQYGSGLVNAEAATR   SEQ ID NO:98
BSP-02355   (251) LGNSSQYGSGLVNAEAATR   SEQ ID NO:99
BSP-02354   (251) LGNSSQYGSGLVNAEAATR   SEQ ID NO:100
BSP-02380   (251) LGNSSQYGSGLVNAEAATR   SEQ ID NO:101
BSP-03007   (251) LGNSSQYGSGLVNAEAATR   SEQ ID NO:102
BSP-02411   (251) LGNSSQYGSGLVNAEAATR   SEQ ID NO:103
BSP-02725   (251) LGNSSQYGSGLVNAEAATR   SEQ ID NO:111
BSP-03024   (251) LGNSSQFGSGLVNAEAATR   SEQ ID NO:113
BSP-03033   (251) LGNSSQFGSGLVNAEAATR   SEQ ID NO:114
BSP-03048   (251) LGNSSQFGSGLVNAEAATR   SEQ ID NO:112
BSP-02301   (251) LGNSSQFGSGLVNAEAATR   SEQ ID NO:106
BSP-03027   (251) LGNSSQFGSGLVNAEAATR   SEQ ID NO:107
BSP-02195   (251) LGNSSQFGSGLVNAEAATR   SEQ ID NO:104
BSP-02227   (251) LGNSSQFGSGLVNAEAATR   SEQ ID NO:110
BSP-02391   (251) LGNSSQFGSGLVNAEAATR   SEQ ID NO:109
BSP-02412   (251) LGNSSQFGSGLVNAEAATR   SEQ ID NO:108
BSP-02400   (251) LGNSSQYGSGLVNAEAATR   SEQ ID NO:105
Consensus   (251) LGNSSQFGSGLVNAEAATR   SEQ ID NO:199
```

FIG. 12C

```
                      1                                                50
  Bgi02446      (1)   QQTVPWGITRVQAPAVHNRGITGSGVRVAILDSGISAHSDLNIRGGASFV
Bgi02446-Q      (1)   -QTVPWGITRVQAPAVHNRGITGSGVRVAILDSGISAHSDLNIRGGASFV
 BSP-00801      (1)   QQTVPWGITRVQAPAVHNRGITGSGVRVAILDSGISTHEDLNVRGGVSFV
 BSP-03304      (1)   QQTVPWGITRVQAPAVHNRGITGSGVRVAILDSGISAHEDLNIRGGASFV
 BSP-03309      (1)   QQTVPWGITRVQAPAVHNRGITGSGVRVAILDSGISAHEDLNIRGGASFV
 BSP-03311      (1)   QQTVPWGITRVQAPAVHNRGITGSGVRVAILDSGISAHEDLNIRGGASFV
 BSP-03318      (1)   QQTVPWGITRVQAPAVHNRGITGSGVRVAILDSGISAHEDLNIRGGASFV
 BSP-03321      (1)   QQTVPWGITRVQAPAVHNRGITGSGVRVAILDSGISAHSDLNIRGGASFV
 BSP-03324      (1)   QQTVPWGITRVQAPAVHNRGITGSGVRVAILDSGISAHEDLNIRGGASFV
 BSP-03331      (1)   QQTVPWGITRVQAPAVHNRGITGSGVRVAILDSGISAHSDLNIRGGASFV
 BSP-03333      (1)   QQTVPWGITRVQAPAVHNRGITGSGVRVAILDSGISAHSDLNIRGGASFV
 BSP-03334      (1)   QQTVPWGITRVQAPAVHNRGITGSGVRVAILDSGISAHEDLNIRGGASFV
 BSP-03343      (1)   QQTVPWGITRVQAPAVHNRGITGSGVRVAILDSGISAHSDLNIRGGASFV
 BSP-03344      (1)   QQTVPWGITRVQAPAVHNRGITGSGVRVAILDSGISAHSDLNIRGGASFV
 BSP-03346      (1)   QQTVPWGITRVQAPAVHNRGITGSGVRVAILDSGISAHSDLNIRGGASFV
 BSP-03351      (1)   QQTVPWGITRVQAPAVHNRGITGSGVRVAILDSGISAHSDLNIRGGASFV
 BSP-03372      (1)   QQTVPWGITRVQAPAVHNRGITGSGVRVAILDSGISAHSDLNIRGGASFV
 BSP-03393      (1)   QQTVPWGITRVQAPAVHNRGITGSGVRVAILDSGISAHEDLNIRGGASFV
 BSP-03394      (1)   QQTVPWGITRVQAPAVHNRGITGSGVRVAILDSGISAHEDLNIRGGASFV
 BSP-03396      (1)   QQTVPWGITRVQAPAVHNRGITGSGVRVAILDSGISAHSDLNIRGGASFV
 BSP-03397      (1)   QQTVPWGITRVQAPAVHNRGITGSGVRVAILDSGISAHEDLNIRGGASFV
 BSP-03398      (1)   QQTVPWGITRVQAPAVHNRGITGSGVRVAILDSGISAHEDLNIRGGASFV
 BSP-03435      (1)   QQTVPWGITRVQAPAVHNRGITGSGVRVAILDSGISAHSDLNIRGGASFV
 BSP-03463      (1)   QQTVPWGITRVQAPAVHNRGITGSGVRVAILDSGISAHEDLNIRGGVSFV
 BSP-03473      (1)   QQTVPWGITRVQAPAVHNRGITGSGVRVAILDSGISTHEDLNIRGGASFV
 BSP-03476      (1)   QQTVPWGITRVQAPAVHNRGITGSGVRVAILDSGISAHEDLNIRGGASFV
 BSP-03477      (1)   QQTVPWGITRVQAPAVHNRGITGSGVRVAILDSGISAHEDLNIRGGASFV
 BSP-03482      (1)   QQTVPWGITRVQAPAVHNRGITGSGVRVAILDSGISTHEDLNIRGGASFV
 BSP-03493      (1)   QQTVPWGITRVQAPAVHNRGITGSGVRVAILDSGISTHEDLNIRGGASFV
 BSP-03503      (1)   QQTVPWGITRVQAPAVHNRGITGSGVRVAILDSGISTHEDLNIRGGVSFV
 BSP-03512      (1)   QQTVPWGITRVQAPAVHNRGITGSGVRVAILDSGISTHEDLNIRGGASFV
 BSP-03559      (1)   QQTVPWGITRVQAPAVHNRGITGSGVRVAILDSGISTHEDLNIRGGVSFV
 BSP-03562      (1)   QQTVPWGITRVQAPAVHNRGITGSGVRVAILDSGISAHEDLNIRGGVSFV
 BSP-03563      (1)   QQTVPWGITRVQAPAVHNRGITGSGVRVAILDSGISAHEDLNIRGGASFV
 BSP-03575      (1)   QQTVPWGITRVQAPAVHNRGITGSGVRVAILDSGISAHEDLNIRGGASFV
 BSP-03604      (1)   QQTVPWGITRVQAPAVHNRGITGSGVRVAILDSGISTHEDLNIRGGASFV
 BSP-03623      (1)   QQTVPWGITRVQAPAVHNRGITGSGVRVAILDSGISTHEDLNIRGGVSFV
 BSP-03631      (1)   QQTVPWGITRVQAPAVHNRGITGSGVRVAILDSGISAHEDLNIRGGVSFV
 BSP-03639      (1)   QQTVPWGITRVQAPAVHNRGITGSGVRVAILDSGISTHEDLNIRGGASFV
 BSP-03647      (1)   QQTVPWGITRVQAPAVHNRGITGSGVRVAILDSGISTHEDLNIRGGVSFV
 BSP-03652      (1)   QQTVPWGITRVQAPAVHNRGITGSGVRVAILDSGISAHEDLNIRGGVSFV
 BSP-03653      (1)   QQTVPWGITRVQAPAVHNRGITGSGVRVAILDSGISTHEDLNIRGGASFV
 BSP-03662      (1)   QQTVPWGITRVQAPAVHNRGITGSGVRVAILDSGISAHEDLNIRGGASFV
 BSP-03663      (1)   QQTVPWGITRVQAPAVHNRGITGSGVRVAILDSGISAHEDLNIRGGVSFV
 BSP-03675      (1)   QQTVPWGITRVQAPAVHNRGITGSGVRVAILDSGISTHEDLNIRGGASFV
 BSP-03678      (1)   QQTVPWGITRVQAPAVHNRGITGSGVRVAILDSGISAHEDLNIRGGASFV
 BSP-03688      (1)   QQTVPWGITRVQAPAVHNRGITGSGVRVAILDSGISAHEDLNIRGGASFV
 Consensus      (1)   QQTVPWGITRVQAPAVHNRGITGSGVRVAILDSGISAHEDLNIRGGASFV
```

FIG. 14A

| | | 51 100 |
|---|---|---|
| Bgi02446 | (51) | PGEPTTADLNGHGTHVAGTVAALNNSIGVIGVAPNAELYAVKVLGANGSG |
| Bgi02446-Q | (50) | PGEPTTADLNGHGTHVAGTVAALNNSIGVIGVAPNAELYAVKVLGANGSG |
| BSP-00801 | (51) | PGEPTTADLNGHGTHVAGTVAALNNSIGVVGVAPSADLYAVKVLGANGRG |
| BSP-03304 | (51) | PGEPTTADLNGHGTHVAGTVAALNNSIGVIGVAPNADLYAVKVLGANGSG |
| BSP-03309 | (51) | PGEPTTADLNGHGTHVAGTVAALNNSIGVIGVAPNADLYAVKVLGANGSG |
| BSP-03311 | (51) | PGEPTTADLNGHGTHVAGTVAALNNSIGVIGVAPNADLYAVKVLGANGRG |
| BSP-03318 | (51) | PGEPTTADLNGHGTHVAGTVAALNNSIGVIGVAPNADLYAVKVLGANGRG |
| BSP-03321 | (51) | PGEPTYADLNGHGTHVAGTVAALNNSIGVIGVAPNAELYAVKVLGANGRG |
| BSP-03324 | (51) | PGEPTTADLNGHGTHVAGTVAALNNSIGVIGVAPNADLYAVKVLGANGRG |
| BSP-03331 | (51) | PGEPTTADLNGHGTHVAGTVAALNNSIGVIGVAPNAELYAVKVLGANGRG |
| BSP-03333 | (51) | PGEPTTADLNGHGTHVAGTVAALNNSIGVIGVAPNAELYAVKVLGANGRG |
| BSP-03334 | (51) | PGEPTYADLNGHGTHVAGTVAALNNSIGVIGVAPNADLYAVKVLGANGSG |
| BSP-03343 | (51) | PGEPTYADLNGHGTHVAGTVAALNNSIGVIGVAPNAELYAVKVLGANGSG |
| BSP-03344 | (51) | PGEPTTADLNGHGTHVAGTVAALNNSIGVIGVAPNAELYAVKVLGANGRG |
| BSP-03346 | (51) | PGEPTYADLNGHGTHVAGTVAALNNSIGVIGVAPNAELYAVKVLGANGSG |
| BSP-03351 | (51) | PGEPTYADLNGHGTHVAGTVAALNNSIGVIGVAPNAELYAVKVLGANGRG |
| BSP-03372 | (51) | PGEPTTADLNGHGTHVAGTVAALNNSIGVIGVAPNAELYAVKVLGANGRG |
| BSP-03393 | (51) | PGEPTTADLNGHGTHVAGTVAALNNSIGVIGVAPNAELYAVKVLGANGRG |
| BSP-03394 | (51) | PGEPTYADLNGHGTHVAGTVAALNNSIGVIGVAPNAELYAVKVLGANGRG |
| BSP-03396 | (51) | PGEPTTADLNGHGTHVAGTVAALNNSIGVIGVAPNAELYAVKVLGANGSG |
| BSP-03397 | (51) | PGEPTTADLNGHGTHVAGTVAALNNSIGVIGVAPNAELYAVKVLGANGRG |
| BSP-03398 | (51) | PGEPTTADLNGHGTHVAGTVAALNNSIGVIGVAPNAELYAVKVLGANGRG |
| BSP-03435 | (51) | PGEPTTADLNGHGTHVAGTVAALNNSIGVIGVAPNAELYAVKVLGANGRG |
| BSP-03463 | (51) | PGEPTYADLNGHGTHVAGTVAALNNSIGVIGVAPNADLYAVKVLGANGRG |
| BSP-03473 | (51) | PGEPTTADLNGHGTHVAGTVAALNNSIGVIGVAPNAELYAVKVLGANGRG |
| BSP-03476 | (51) | PGEPTTADLNGHGTHVAGTVAALNNSIGVIGVAPNADLYAVKVLGANGRG |
| BSP-03477 | (51) | PGEPTYADLNGHGTHVAGTVAALNNSIGVIGVAPNADLYAVKVLGANGRG |
| BSP-03482 | (51) | PGEPTTADLNGHGTHVAGTVAALNNSIGVVGVAPSADLYAVKVLGANGRG |
| BSP-03493 | (51) | PGEPTYADLNGHGTHVAGTVAALNNSIGVIGVAPNAELYAVKVLGANGRG |
| BSP-03503 | (51) | PGEPTTADLNGHGTHVAGTVAALNNSIGVVGVAPSADLYAVKVLGANGRG |
| BSP-03512 | (51) | PGEPTTADLNGHGTHVAGTVAALNNSIGVIGVAPNADLYAVKVLGANGRG |
| BSP-03559 | (51) | PGEPTYADLNGHGTHVAGTVAALNNSIGVIGVAPNAELYAVKVLGANGRG |
| BSP-03562 | (51) | PGEPTTADLNGHGTHVAGTVAALNNSIGVIGVAPNADLYAVKVLGANGRG |
| BSP-03563 | (51) | PGEPTTADLNGHGTHVAGTVAALNNSIGVIGVAPSAELYAVKVLGANGRG |
| BSP-03575 | (51) | PGEPTTADLNGHGTHVAGTVAALNNSIGVIGVAPNAELYAVKVLGANGRG |
| BSP-03604 | (51) | PGEPTYADLNGHGTHVAGTVAALNNSIGVIGVAPNAELYAVKVLGANGRG |
| BSP-03623 | (51) | PGEPTYADLNGHGTHVAGTVAALNNSIGVIGVAPNAELYAVKVLGANGRG |
| BSP-03631 | (51) | PGEPTYADLNGHGTHVAGTVAALNNSIGVIGVAPNADLYAVKVLGANGRG |
| BSP-03639 | (51) | PGEPTYADLNGHGTHVAGTVAALNNSIGVIGVAPSAELYAVKVLGANGRG |
| BSP-03647 | (51) | PGEPTYADLNGHGTHVAGTVAALNNSIGVIGVAPNADLYAVKVLGANGRG |
| BSP-03652 | (51) | PGEPTYADLNGHGTHVAGTVAALNNSIGVIGVAPSADLYAVKVLGANGRG |
| BSP-03653 | (51) | PGEPTYADLNGHGTHVAGTVAALNNSIGVIGVAPSADLYAVKVLGANGRG |
| BSP-03662 | (51) | PGEPTYADLNGHGTHVAGTVAALNNSIGVIGVAPNAELYAVKVLGANGRG |
| BSP-03663 | (51) | PGEPTTADLNGHGTHVAGTVAALNNSIGVVGVAPNADLYAVKVLGANGRG |
| BSP-03675 | (51) | PGEPTYADLNGHGTHVAGTVAALNNSIGVIGVAPSADLYAVKVLGANGRG |
| BSP-03678 | (51) | PGEPTTADLNGHGTHVAGTVAALNNSIGVIGVAPNAELYAVKVLGANGRG |
| BSP-03688 | (51) | PGEPTTADLNGHGTHVAGTVAALNNSIGVIGVAPNAELYAVKVLGANGRG |
| Consensus | (51) | PGEPTTADLNGHGTHVAGTVAALNNSIGVIGVAPNAELYAVKVLGANGRG |

FIG. 14B

```
                   101                                                150
  Bgi02446  (101) SVSGIAQGLEWAATNNMHIANMSLGSDFPSSTLERAVNYATSRDVLVIAA
Bgi02446-Q  (100) SVSGIAQGLEWAATNNMHIANMSLGSDFPSSTLERAVNYATSRDVLVIAA
 BSP-00801  (101) SVSGIAQGLEWAAANNMHIANMSLGSDAPSSTLERAVNYATSRDVLVIAA
 BSP-03304  (101) SVSGIAQGLEWAATNNMHIANMSLGSDFPSSTLERAVNYATSRDVLVIAA
 BSP-03309  (101) SVSGIAQGLEWAATNNMHIANMSLGSDFPSSTLERAVNYATSRDVLVIAA
 BSP-03311  (101) SVSGIAQGLEWAATNNMHIANMSLGSDAPSSTLERAVNYATSRDVLVIAA
 BSP-03318  (101) SVSGIAQGLEWAATNNMHIANMSLGSDAPSSTLERAVNYATSRDVLVIAA
 BSP-03321  (101) SVSGIAQGLEWAAQNNMHIANMSLGSDAPSSTLERAVNYATSRDVLVIAA
 BSP-03324  (101) SVSGIAQGLEWAATNNMHIANMSLGTDFPSSTLERAVNYATSRDVLVIAA
 BSP-03331  (101) SVSGIAQGLEWAATNNMHIANMSLGTDFPSSTLERAVNYATSRDVLVIAA
 BSP-03333  (101) SVSGIAQGLEWAATNNMHIANMSLGTDFPSSTLERAVNYATSRDVLVIAA
 BSP-03334  (101) SVSGIAQGLEWAAQNNMHIANMSLGSDFPSSTLERAVNYATSRDVLVIAA
 BSP-03343  (101) SVSGIAQGLEWAAQNNMHIANMSLGSDFPSSTLERAVNYATSRDVLVIAA
 BSP-03344  (101) SVSGIAQGLEWAATNNMHIANMSLGSDAPSSTLERAVNYATSRDVLVIAA
 BSP-03346  (101) SVSGIAQGLEWAAQNNMHIANMSLGSDFPSSTLERAVNYATSRDVLVIAA
 BSP-03351  (101) SVSGIAQGLEWAAQNNMHIANMSLGTDFPSSTLERAVNYATSRDVLVIAA
 BSP-03372  (101) SVSGIAQGLEWAATNNMHIANMSLGSDAPSSTLERAVNYATSRDVLVIAA
 BSP-03393  (101) SVSGIAQGLEWAATNNMHIANMSLGTDAPSSTLERAVNYATSRDVLVIAA
 BSP-03394  (101) SVSGIAQGLEWAATNNMHIANMSLGTDAPSSTLERAVNYATSRDVLVIAA
 BSP-03396  (101) SVSGIAQGLEWAATNNMHIANMSLGTDAPSSTLERAVNYATSRDVLVIAA
 BSP-03397  (101) SVSGIAQGLEWAATNNMHIANMSLGTDFPSSTLERAVNYATSRDVLVIAA
 BSP-03398  (101) SVSGIAQGLEWAATNNMHIANMSLGSDAPSSTLERAVNYATSRDVLVIAA
 BSP-03435  (101) SVSGIAQGLEWAATNNMHIANMSLGTDAPSSTLERAVNYATSRDVLVIAA
 BSP-03463  (101) SVSGIAQGLEWAAQNNMHIANMSLGTDAPSSTLERAVNYATSRDVLVIAA
 BSP-03473  (101) SVSGIAQGLEWAAQNNMHIANMSLGTDAPSSTLERAVNYATSRDVLVIAA
 BSP-03476  (101) SVSGIAQGLEWAATNNMHIANMSLGTDAPSSTLERAVNYATSRDVLVIAA
 BSP-03477  (101) SVSGIAQGLEWAATNNMHIANMSLGTDAPSSTLERAVNYATSRDVLVIAA
 BSP-03482  (101) SVSGIAQGLEWAAQNNMHIANMSLGTDAPSSTLERAVNYATSRDVLVIAA
 BSP-03493  (101) SVSGIAQGLEWAATNNMHIANMSLGTDAPSSTLERAVNYATSRDVLVIAA
 BSP-03503  (101) SVSGIAQGLEWAAANNMHIANMSLGTDAPSSTLERAVNYATSRDVLVIAA
 BSP-03512  (101) SVSGIAQGLEWAAANNMHIANMSLGSDAPSSTLERAVNYATSRDVLVIAA
 BSP-03559  (101) SVSGIAQGLEWAAQNNMHIANMSLGTDAPSSTLERAVNYATSRDVLVIAA
 BSP-03562  (101) SVSGIAQGLEWAAQNNMHIANMSLGTDAPSSTLERAVNYATSRDVLVIAA
 BSP-03563  (101) SVSGIAQGLEWAATNNMHIANMSLGSDAPSSTLERAVNYATSRDVLVIAA
 BSP-03575  (101) SVSGIAQGLEWAAQNNMHIANMSLGSDAPSSTLERAVNYATSRDVLVIAA
 BSP-03604  (101) SVSGIAQGLEWAAQNNMHIANMSLGTDAPSSTLERAVNYATSRDVLVIAA
 BSP-03623  (101) SVSGIAQGLEWAAANNMHIANMSLGTDAPSSTLERAVNYATSRDVLVIAA
 BSP-03631  (101) SVSGIAQGLEWAAANNMHIANMSLGTDAPSSTLERAVNYATSRDVLVIAA
 BSP-03639  (101) SVSGIAQGLEWAAQNNMHIANMSLGTDAPSSTLERAVNYATSRDVLVIAA
 BSP-03647  (101) SVSGIAQGLEWAAANNMHIANMSLGTDAPSSTLERAVNYATSRDVLVIAA
 BSP-03652  (101) SVSGIAQGLEWAAQNNMHIANMSLGTDAPSSTLERAVNYATSRDVLVIAA
 BSP-03653  (101) SVSGIAQGLEWAAQNNMHIANMSLGSDAPSSTLERAVNYATSRDVLVIAA
 BSP-03662  (101) SVSGIAQGLEWAATNNMHIANMSLGSDAPSSTLERAVNYATSRDVLVIAA
 BSP-03663  (101) SVSGIAQGLEWAAANNMHIANMSLGTDAPSSTLERAVNYATSRDVLVIAA
 BSP-03675  (101) SVSGIAQGLEWAAANNMHIANMSLGTDAPSSTLERAVNYATSRDVLVIAA
 BSP-03678  (101) SVSGIAQGLEWAAANNMHIANMSLGTDFPSSTLERAVNYATSRDVLVIAA
 BSP-03688  (101) SVSGIAQGLEWAAQNNMHIANMSLGTDAPSSTLERAVNYATSRDVLVIAA
 Consensus  (101) SVSGIAQGLEWAA NNMHIANMSLGTDAPSSTLERAVNYATSRDVLVIAA
```

FIG. 14C

| | | |
|---|---|---|
| | | 151 200 |
| Bgi02446 | (151) | TGNNGSGSVGYPARYANAMAVGATDQNNRRANFSQYGTGIDIVAPGVNVQ |
| Bgi02446-Q | (150) | TGNNGSGSVGYPARYANAMAVGATDQNNRRANFSQYGTGIDIVAPGVNVQ |
| BSP-00801 | (151) | TGNNGSGSVGYPARYANAMAVGATDQNNRRANFSQYGTGIDIVAPGVNVQ |
| BSP-03304 | (151) | TGNNGSGSVGYPARYANAMAVGATDQNNRRANFSQYGTGIDIVAPGVNVQ |
| BSP-03309 | (151) | TGNNGSGSVGYPARYANAMAVGATDQNNRRANFSQYGTGIDIVAPGVNVQ |
| BSP-03311 | (151) | TGNNGSGSVGYPARYANAMAVGATDQNNRRANFSQYGTGIDIVAPGVNVQ |
| BSP-03318 | (151) | TGNNGSGSVGYPARYANAMAVGATDQNNRRANFSQYGTGIDIVAPGVNVQ |
| BSP-03321 | (151) | TGNNGSGSVGYPARYANAMAVGATDQNNRRANFSQYGTGIDIVAPGVNVQ |
| BSP-03324 | (151) | TGNNGSGSVGYPARYANAMAVGATDQNNRRANFSQYGTGIDIVAPGVNVQ |
| BSP-03331 | (151) | TGNNGSGSVGYPARYANAMAVGATDQNNRRANFSQYGTGIDIVAPGVNVQ |
| BSP-03333 | (151) | TGNNGSGSVGYPARYANAMAVGATDQNNRRANFSQYGTGIDIVAPGVNVQ |
| BSP-03334 | (151) | TGNNGSGSVGYPARYANAMAVGATDQNNRRANFSQYGTGIDIVAPGVNVQ |
| BSP-03343 | (151) | TGNNGSGSVGYPARYANAMAVGATDQNNRRANFSQYGTGIDIVAPGVNVQ |
| BSP-03344 | (151) | TGNNGSGSVGYPARYANAMAVGATDQNNRRANFSQYGTGIDIVAPGVNVQ |
| BSP-03346 | (151) | TGNNGSGSVGYPARYANAMAVGATDQNNRRANFSQYGTGIDIVAPGVNVQ |
| BSP-03351 | (151) | TGNNGSGSVGYPARYANAMAVGATDQNNRRANFSQYGTGIDIVAPGVNVQ |
| BSP-03372 | (151) | TGNNGSGSVGYPARYANAMAVGATDQNNRRANFSQYGTGIDIVAPGVNVQ |
| BSP-03393 | (151) | TGNNGSGSVGYPARYANAMAVGATDQNNRRANFSQYGTGIDIVAPGVNVQ |
| BSP-03394 | (151) | TGNNGSGSVGYPARYANAMAVGATDQNNRRANFSQYGTGIDIVAPGVNVQ |
| BSP-03396 | (151) | TGNNGSGSVGYPARYANAMAVGATDQNNRRANFSQYGTGIDIVAPGVNVQ |
| BSP-03397 | (151) | TGNNGSGSVGYPARYANAMAVGATDQNNRRANFSQYGTGIDIVAPGVNVQ |
| BSP-03398 | (151) | TGNNGSGSVGYPARYANAMAVGATDQNNRRANFSQYGTGIDIVAPGVNVQ |
| BSP-03435 | (151) | TGNNGSGSVGYPARYANAMAVGATDQNNRRANFSQYGTGIDIVAPGVNVQ |
| BSP-03463 | (151) | TGNNGSGSVGYPARYANAMAVGATDQNNRRANFSQYGTGIDIVAPGVNVQ |
| BSP-03473 | (151) | TGNNGSGSVGYPARYANAMAVGATDQNNRRANFSQYGTGIDIVAPGVNVQ |
| BSP-03476 | (151) | TGNNGSGSVGYPARYANAMAVGATDQNNRRANFSQYGTGIDIVAPGVNVQ |
| BSP-03477 | (151) | TGNNGSGSVGYPARYANAMAVGATDQNNRRANFSQYGTGIDIVAPGVNVQ |
| BSP-03482 | (151) | TGNNGSGSVGYPARYANAMAVGATDQNNRRANFSQYGTGIDIVAPGVNVQ |
| BSP-03493 | (151) | TGNNGSGSVGYPARYANAMAVGATDQNNRRANFSQYGTGIDIVAPGVNVQ |
| BSP-03503 | (151) | TGNNGSGSVGYPARYANAMAVGATDQNNRRANFSQYGTGIDIVAPGVNVQ |
| BSP-03512 | (151) | TGNNGSGSVGYPARYANAMAVGATDQNNRRANFSQYGTGIDIVAPGVNVQ |
| BSP-03559 | (151) | TGNNGSGSVGYPARYANAMAVGATDQNNRRANFSQYGTGIDIVAPGVNVQ |
| BSP-03562 | (151) | TGNNGSGSVGYPARYANAMAVGATDQNNRRANFSQYGTGIDIVAPGVNVQ |
| BSP-03563 | (151) | TGNNGSGSVGYPARYANAMAVGATDQNNRRANFSQYGTGIDIVAPGVNVQ |
| BSP-03575 | (151) | TGNNGSGSVGYPARYANAMAVGATDQNNRRANFSQYGTGIDIVAPGVNVQ |
| BSP-03604 | (151) | TGNNGSGSVGYPARYANAMAVGATDQNNRRANFSQYGTGIDIVAPGVNVQ |
| BSP-03623 | (151) | TGNNGSGSVGYPARYANAMAVGATDQNNRRANFSQYGTGIDIVAPGVNVQ |
| BSP-03631 | (151) | TGNNGSGSVGYPARYANAMAVGATDQNNRRANFSQYGTGIDIVAPGVNVQ |
| BSP-03639 | (151) | TGNNGSGSVGYPARYANAMAVGATDQNNRRANFSQYGTGIDIVAPGVNVQ |
| BSP-03647 | (151) | TGNNGSGSVGYPARYANAMAVGATDQNNRRANFSQYGTGIDIVAPGVNVQ |
| BSP-03652 | (151) | TGNNGSGSVGYPARYANAMAVGATDQNNRRANFSQYGTGIDIVAPGVNVQ |
| BSP-03653 | (151) | TGNNGSGSVGYPARYANAMAVGATDQNNRRANFSQYGTGIDIVAPGVNVQ |
| BSP-03662 | (151) | TGNNGSGSVGYPARYANAMAVGATDQNNRRANFSQYGTGIDIVAPGVNVQ |
| BSP-03663 | (151) | TGNNGSGSVGYPARYANAMAVGATDQNNRRANFSQYGTGIDIVAPGVNVQ |
| BSP-03675 | (151) | TGNNGSGSVGYPARYANAMAVGATDQNNRRANFSQYGTGIDIVAPGVNVQ |
| BSP-03678 | (151) | TGNNGSGSVGYPARYANAMAVGATDQNNRRANFSQYGTGIDIVAPGVNVQ |
| BSP-03688 | (151) | TGNNGSGSVGYPARYANAMAVGATDQNNRRANFSQYGTGIDIVAPGVNVQ |
| Consensus | (151) | TGNNGSGSVGYPARYANAMAVGATDQNNRRANFSQYGTGIDIVAPGVNVQ |

FIG. 14D

| | | 201 250 |
|---|---|---|
| Bgi02446 | (201) | STYPGNRYVSMNGTSMATPHVAGAAALVKQRYPSWNATQIRNHLKNTATN |
| Bgi02446-Q | (200) | STYPGNRYVSMNGTSMATPHVAGAAALVKQRYPSWNATQIRNHLKNTATN |
| BSP-00801 | (201) | STYPGNRYVSMNGTSMATPHVAGAAALVKQRYPSWNATQIRNHLKNTATN |
| BSP-03304 | (201) | STYPGNRYVSMNGTSMATPHVAGAAALVKQRYPSWNATQIRNHLKNTATN |
| BSP-03309 | (201) | STYPGNRYVSMNGTSMATPHVAGAAALVKQRYPSWNATQIRDHLKNTATN |
| BSP-03311 | (201) | STYPGNRYVSMNGTSMATPHVAGAAALVKQRYPSWNATQIRNHLKNTATN |
| BSP-03318 | (201) | STYPGNRYVSMNGTSMATPHVAGAAALVKQRYPSWNATQIRDHLKNTATN |
| BSP-03321 | (201) | STYPGNRYVSMNGTSMATPHVAGAAALVKQRYPSWNATQIRNHLKNTATN |
| BSP-03324 | (201) | STYPGNRYVSMNGTSMATPHVAGAAALVKQRYPSWNATQIRNHLKNTATN |
| BSP-03331 | (201) | STYPGNRYVSMNGTSMATPHVAGAAALVKQRYPSWNATQIRNHLKNTATN |
| BSP-03333 | (201) | STYPGNRYVSMNGTSMATPHVAGAAALVKQRYPSWNATQIRDHLKNTATN |
| BSP-03334 | (201) | STYPGNRYVSMNGTSMATPHVAGAAALVKQRYPSWNATQIRNHLKNTATN |
| BSP-03343 | (201) | STYPGNRYVSMNGTSMATPHVAGAAALVKQRYPSWNATQIRDHLKNTATN |
| BSP-03344 | (201) | STYPGNRYVSMNGTSMATPHVAGAAALVKQRYPSWNATQIRNHLKNTATN |
| BSP-03346 | (201) | STYPGNRYVSMNGTSMATPHVAGAAALVKQRYPSWNATQIRNHLKNTATN |
| BSP-03351 | (201) | STYPGNRYVSMNGTSMATPHVAGAAALVKQRYPSWNATQIRNHLKNTATN |
| BSP-03372 | (201) | STYPGNRYVSMNGTSMATPHVAGAAALVKQRYPSWNATQIRDHLKNTATN |
| BSP-03393 | (201) | STYPGNRYVSMNGTSMATPHVAGAAALVKQRYPSWNATQIRNHLKNTATN |
| BSP-03394 | (201) | STYPGNRYVSMNGTSMATPHVAGAAALVKQRYPSWNATQIRNHLKNTATN |
| BSP-03396 | (201) | STYPGNRYVSMNGTSMATPHVAGAAALVKQRYPSWNATQIRNHLKNTATN |
| BSP-03397 | (201) | STYPGNRYVSMNGTSMATPHVAGAAALVKQRYPSWNATQIRNHLKNTATN |
| BSP-03398 | (201) | STYPGNRYVSMNGTSMATPHVAGAAALVKQRYPSWNATQIRNHLKNTATN |
| BSP-03435 | (201) | STYPGNRYVSMNGTSMATPHVAGAAALVKQRYPSWNATQIRNHLKNTATN |
| BSP-03463 | (201) | STYPGNRYVSMNGTSMATPHVAGAAALVKQRYPSWNATQIRDHLKNTATN |
| BSP-03473 | (201) | STYPGNRYVSMNGTSMATPHVAGAAALVKQRYPSWNATQIRDHLKNTATN |
| BSP-03476 | (201) | STYPGNRYVSMNGTSMATPHVAGAAALVKQRYPSWNATQIRNHLKNTATN |
| BSP-03477 | (201) | STYPGNRYVSMNGTSMATPHVAGAAALVKQRYPSWNATQIRNHLKNTATN |
| BSP-03482 | (201) | STYPGNRYVSMNGTSMATPHVAGAAALVKQRYPSWNATQIRDHLKNTATN |
| BSP-03493 | (201) | STYPGNRYVSMNGTSMATPHVAGAAALVKQRYPSWNATQIRDHLKNTATN |
| BSP-03503 | (201) | STYPGNRYVSMNGTSMATPHVAGAAALVKQRYPSWNATQIRNHLKNTATN |
| BSP-03512 | (201) | STYPGNRYVSMNGTSMATPHVAGAAALVKQRYPSWNATQIRNHLKNTATN |
| BSP-03559 | (201) | STYPGNRYVSMNGTSMATPHVAGAAALVKQRYPSWNATQIRNHLKNTATN |
| BSP-03562 | (201) | STYPGNRYVSMNGTSMATPHVAGAAALVKQRYPSWNATQIRDHLKNTATN |
| BSP-03563 | (201) | STYPGNRYVSMNGTSMATPHVAGAAALVKQRYPSWNATQIRNHLKNTATN |
| BSP-03575 | (201) | STYPGNRYVSMNGTSMATPHVAGAAALVKQRYPSWNATQIRNHLKNTATN |
| BSP-03604 | (201) | STYPGNRYVSMNGTSMATPHVAGAAALVKQRYPSWNATQIRDHLKNTATN |
| BSP-03623 | (201) | STYPGNRYVSMNGTSMATPHVAGAAALVKQRYPSWNATQIRNHLKNTATN |
| BSP-03631 | (201) | STYPGNRYVSMNGTSMATPHVAGAAALVKQRYPSWNATQIRDHLKNTATN |
| BSP-03639 | (201) | STYPGNRYVSMNGTSMATPHVAGAAALVKQRYPSWNATQIRDHLKNTATN |
| BSP-03647 | (201) | STYPGNRYVSMNGTSMATPHVAGAAALVKQRYPSWNATQIRDHLKNTATN |
| BSP-03652 | (201) | STYPGNRYVSMNGTSMATPHVAGAAALVKQRYPSWNATQIRNHLKNTATN |
| BSP-03653 | (201) | STYPGNRYVSMNGTSMATPHVAGAAALVKQRYPSWNATQIRNHLKNTATN |
| BSP-03662 | (201) | STYPGNRYVSMNGTSMATPHVAGAAALVKQRYPSWNATQIRNHLKNTATN |
| BSP-03663 | (201) | STYPGNRYVSMNGTSMATPHVAGAAALVKQRYPSWNATQIRDHLKNTATN |
| BSP-03675 | (201) | STYPGNRYVSMNGTSMATPHVAGAAALVKQRYPSWNATQIRDHLKNTATN |
| BSP-03678 | (201) | STYPGNRYVSMNGTSMATPHVAGAAALVKQRYPSWNATQIRNHLKNTATN |
| BSP-03688 | (201) | STYPGNRYVSMNGTSMATPHVAGAAALVKQRYPSWNATQIRDHLKNTATN |
| Consensus | (201) | STYPGNRYVSMNGTSMATPHVAGAAALVKQRYPSWNATQIRNHLKNTATN |

FIG. 14E

| | | | |
|---|---|---|---|
| | | 251 269 | |
| Bgi02446 | (251) | LGNSSQFGSGLVNAEAATR | SEQ ID NO:85 |
| Bgi02446-Q | (250) | LGNSSQFGSGLVNAEAATR | SEQ ID NO:19 |
| BSP-00801 | (251) | LGNSSQFGSGLVNAEAATR | SEQ ID NO:18 |
| BSP-03304 | (251) | LGNSSQFGSGLVNAEAATR | SEQ ID NO:213 |
| BSP-03309 | (251) | LGNSSQFGSGLVNAEAATR | SEQ ID NO:214 |
| BSP-03311 | (251) | LGNSSQFGSGLVNAEAATR | SEQ ID NO:215 |
| BSP-03318 | (251) | LGNSSQFGSGLVNAEAATR | SEQ ID NO:216 |
| BSP-03321 | (251) | LGNSSQFGSGLVNAEAATR | SEQ ID NO:217 |
| BSP-03324 | (251) | LGNSSQFGSGLVNAEAATR | SEQ ID NO:218 |
| BSP-03331 | (251) | LGNSSQFGSGLVNAEAATR | SEQ ID NO:219 |
| BSP-03333 | (251) | LGNSSQFGSGLVNAEAATR | SEQ ID NO:220 |
| BSP-03334 | (251) | LGNSSQFGSGLVNAEAATR | SEQ ID NO:221 |
| BSP-03343 | (251) | LGNSSQFGSGLVNAEAATR | SEQ ID NO:222 |
| BSP-03344 | (251) | LGNSSQFGSGLVNAEAATR | SEQ ID NO:223 |
| BSP-03346 | (251) | LGNSSQFGSGLVNAEAATR | SEQ ID NO:224 |
| BSP-03351 | (251) | LGNSSQFGSGLVNAEAATR | SEQ ID NO:225 |
| BSP-03372 | (251) | LGNSSQFGSGLVNAEAATR | SEQ ID NO:226 |
| BSP-03393 | (251) | LGNSSQFGSGLVNAEAATR | SEQ ID NO:227 |
| BSP-03394 | (251) | LGNSSQFGSGLVNAEAATR | SEQ ID NO:228 |
| BSP-03396 | (251) | LGNSSQFGSGLVNAEAATR | SEQ ID NO:229 |
| BSP-03397 | (251) | LGNSSQFGSGLVNAEAATR | SEQ ID NO:230 |
| BSP-03398 | (251) | LGNSSQFGSGLVNAEAATR | SEQ ID NO:231 |
| BSP-03435 | (251) | LGNSSQFGSGLVNAEAATR | SEQ ID NO:232 |
| BSP-03463 | (251) | LGNSSQFGSGLVNAEAATR | SEQ ID NO:233 |
| BSP-03473 | (251) | LGNSSQFGSGLVNAEAATR | SEQ ID NO:234 |
| BSP-03476 | (251) | LGNSSQFGSGLVNAEAATR | SEQ ID NO:235 |
| BSP-03477 | (251) | LGNSSQFGSGLVNAEAATR | SEQ ID NO:236 |
| BSP-03482 | (251) | LGNSSQFGSGLVNAEAATR | SEQ ID NO:237 |
| BSP-03493 | (251) | LGNSSQFGSGLVNAEAATR | SEQ ID NO:238 |
| BSP-03503 | (251) | LGNSSQFGSGLVNAEAATR | SEQ ID NO:239 |
| BSP-03512 | (251) | LGNSSQFGSGLVNAEAATR | SEQ ID NO:240 |
| BSP-03559 | (251) | LGNSSQFGSGLVNAEAATR | SEQ ID NO:241 |
| BSP-03562 | (251) | LGNSSQFGSGLVNAEAATR | SEQ ID NO:242 |
| BSP-03563 | (251) | LGNSSQFGSGLVNAEAATR | SEQ ID NO:243 |
| BSP-03575 | (251) | LGNSSQFGSGLVNAEAATR | SEQ ID NO:244 |
| BSP-03604 | (251) | LGNSSQFGSGLVNAEAATR | SEQ ID NO:245 |
| BSP-03623 | (251) | LGNSSQFGSGLVNAEAATR | SEQ ID NO:246 |
| BSP-03631 | (251) | LGNSSQFGSGLVNAEAATR | SEQ ID NO:247 |
| BSP-03639 | (251) | LGNSSQFGSGLVNAEAATR | SEQ ID NO:248 |
| BSP-03647 | (251) | LGNSSQFGSGLVNAEAATR | SEQ ID NO:249 |
| BSP-03652 | (251) | LGNSSQFGSGLVNAEAATR | SEQ ID NO:250 |
| BSP-03653 | (251) | LGNSSQFGSGLVNAEAATR | SEQ ID NO:251 |
| BSP-03662 | (251) | LGNSSQFGSGLVNAEAATR | SEQ ID NO:252 |
| BSP-03663 | (251) | LGNSSQFGSGLVNAEAATR | SEQ ID NO:253 |
| BSP-03675 | (251) | LGNSSQFGSGLVNAEAATR | SEQ ID NO:254 |
| BSP-03678 | (251) | LGNSSQFGSGLVNAEAATR | SEQ ID NO:255 |
| BSP-03688 | (251) | LGNSSQFGSGLVNAEAATR | SEQ ID NO:256 |
| Consensus | (251) | LGNSSQFGSGLVNAEAATR | SEQ ID NO:257 |

FIG. 14F

*BACILLUS GIBSONII*-CLADE SERINE PROTEASES

Disclosed herein is one or more subtilisin variant, nucleic acid encoding same, and compositions and methods related to the production and use thereof, including one or more *Bacillus gibsonii*-clade subtilisin variant that has improved stability and/or soil removal compared to one or more reference subtilisin. Compositions containing the serine proteases are suitable for use in cleaning fabrics and hard surfaces, as well as in a variety of industrial applications.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *B. subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

The present variants, compositions and methods relate to recombinant serine proteases generated through conventional molecular biology techniques (see, e.g., Sambrook et al, Molecular Cloning: Cold Spring Harbor Laboratory Press). Compositions containing the *B. gibsonii*-clade serine proteases disclosed herein are suitable for use in cleaning fabrics and hard surfaces, as well as in a variety of industrial applications.

Some embodiments are directed to a subtilisin variant comprising an amino acid sequence comprising two, three, or four or more variations versus SEQ ID NO:85 at positions selected from: (i) 1, 4, 9, 21, 24, 27, 36, 37, 39, 42, 43, 44, 47, 54, 55, 56, 74, 80, 85, 87, 99, 102, 114, 117, 119, 121, 126, 128, 131, 143, 144, 158, 159, 160, 169, 182, 188, 190, 197, 198, 212, 224, 231, 232, 237, 242, 245, 246, 254, 255, 256, and 257; (ii) 37, 39, 47, 56, 80, 85, 87, 99, 114, 126, 128, and 242; (iii) 39, 99, 126, and 128; (iv) 39 in combination with one or more variation at a position selected from 37, 47, 56, 80, 85, 87, 99, 114, 126, 128, and 242; (v) 56 in combination with one or more variation at a position selected from 37, 39, 47, 80, 85, 87, 99, 114, 126, 128, and 242; (vi) 114 in combination with one or more variation at a position selected from 37, 39, 47, 56, 80, 85, 87, 99, 126, 128, and 242; (vii) 126 in combination with one or more variation at a position selected from 37, 39, 47, 56, 80, 85, 87, 99, 114, 128, and 242; (viii) 242 in combination with one or more variation at a position selected from 37, 39, 47, 56, 80, 85, 87, 99, 114, 126, and 128; (ix) 99+128 in combination with one or more variation at a position selected from 39, 56, 114, 126 and 242; (x) 39+242 in combination with one or more variation at a position selected from 37, 47, 56, 80, 85, 87, 99, 114, 126, and 128; or (xi) 39+99+128 in combination with one or more variation at a position selected from 37, 47, 56, 80, 85, 87, 114, 126, and 242; with the proviso that one or more of said two, three, or four or more variations is non-naturally occurring; and wherein the amino acid positions of the variant are numbered by correspondence with the amino acid sequence of SEQ ID NO:85.

Other embodiments are directed to a subtilisin variant comprising an amino acid sequence comprising two, three, or four or more amino acid substitutions at positions selected from: (i) 1, 4, 9, 21, 24, 27, 36, 37, 39, 42, 43, 44, 47, 54, 55, 56, 74, 80, 85, 87, 99, 102, 114, 117, 119, 121, 126, 128, 131, 143, 144, 158, 159, 160, 169, 182, 188, 190, 197, 198, 212, 224, 231, 232, 237, 242, 245, 246, 254, 255, 256, and 257; (ii) 37, 39, 47, 56, 80, 85, 87, 99, 114, 126, 128, and 242; (iii) 39, 99, 126, and 128; (iv) 39 in combination with one or more amino acid substitution at a position selected from 37, 47, 56, 80, 85, 87, 99, 114, 126, 128, and 242; (v) 56 in combination with one or more amino acid substitution at a position selected from 37, 39, 47, 80, 85, 87, 99, 114, 126, 128, and 242; (vi) 114 in combination with one or more amino acid substitution at a position selected from 37, 39, 47, 56, 80, 85, 87, 99, 126, 128, and 242; (vii) A/S126 in combination with one or more amino acid substitution at a position selected from 37, 39, 47, 56, 80, 85, 87, 99, 114, 128, and 242; (viii) N242 in combination with one or more amino acid substitution at a position selected from 37, 39, 47, 56, 80, 85, 87, 99, 114, 126, and 128; (ix) 99+128 in combination with one or more amino acid substitution at a position selected from 39, 56, 114, 126 and 242; (x) 39+242 in combination with one or more amino acid substitution at a position selected from 37, 47, 56, 80, 85, 87, 99, 114, 126, and 128; or (xi) 39+99+128 in combination with one or more amino acid substitution at a position selected from 37, 47, 56, 80, 85, 87, 114, 126, and 242; with the proviso that one or more of said two, three, or four or more substitutions is non-naturally occurring; and wherein the amino acid positions of the variant are numbered by correspondence with the amino acid sequence of SEQ ID NO:85.

A further embodiment is directed to a subtilisin variant comprising an amino acid sequence comprising: (i) one or more variation versus SEQ ID NO:85 at positions selected from 56, 114, and 126; (ii) one or more variation versus SEQ ID NO:85 at positions selected from 56N/Y, 114A/P/Q, and 126T; (iii) one or more amino acid substitution at positions selected from 56, 114, and 126; (iv) one or more amino acid substitution at positions selected from T56, A/T114, and A/S126; (v) one or more amino acids substitutions selected from: 56N/Y, 114A/P/Q, and 126T; or (vi) one or more amino acids substitutions selected from: T56N/Y, A/T114A/P/Q, and A/S126T; with the proviso that one or more of said two, three, or four or more substitutions or variations is non-naturally occurring; and wherein the amino acid positions of the variant are numbered by correspondence with the amino acid sequence of SEQ ID NO:85.

In another embodiment, one or more subtilisin variant described herein is a member of the *B. gibsonii*-clade. In a still further embodiment, one or more subtilisin variant described herein has 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:18 or 85. In yet a still further embodiment, at least one variant described herein has proteolytic activity or an increase in proteolytic or cleaning activity compared to the proteolytic or cleaning activity of the protease having the sequence of SEQ ID NO:18 or 85. In another embodiment, the proteolytic activity is casein hydrolysis.

Another embodiment is directed to a composition comprising a surfactant and at least one variant described herein. In some embodiments, the composition further comprises at least one calcium ion and/or zinc ion, at least one stabilizer, at least one bleaching agent, phosphate, or boron. In some embodiments, the composition is phosphate-free and/or boron-free. In some embodiments, the composition is a granular, powder, solid, bar, liquid, tablet, gel, paste or unit dose composition. In some embodiments, the composition further comprises one or more additional enzymes or enzyme derivatives.

Some embodiments are directed to a method of cleaning, comprising contacting a surface or an item with at least one composition described herein. Other embodiments are directed to a method for producing a variant described herein, comprising stably transforming a host cell with an expression vector comprising a polynucleotide encoding at least one of the variants described herein. Still further embodiments are directed to a polynucleotide comprising a nucleic acid sequence encoding at least one variant described herein.

FIG. 1 provides a comparison of the main chain folding of BSP-00801 (black lines) with *B. lentus* subtilisin (medium gray lines) and subtilisin BPN' (light gray lines). The side chains of the catalytic triad in BSP-00801 are shown for reference. Apart from a few external loops, the folding pattern in all three subtilisins is conserved.

Figure 2:
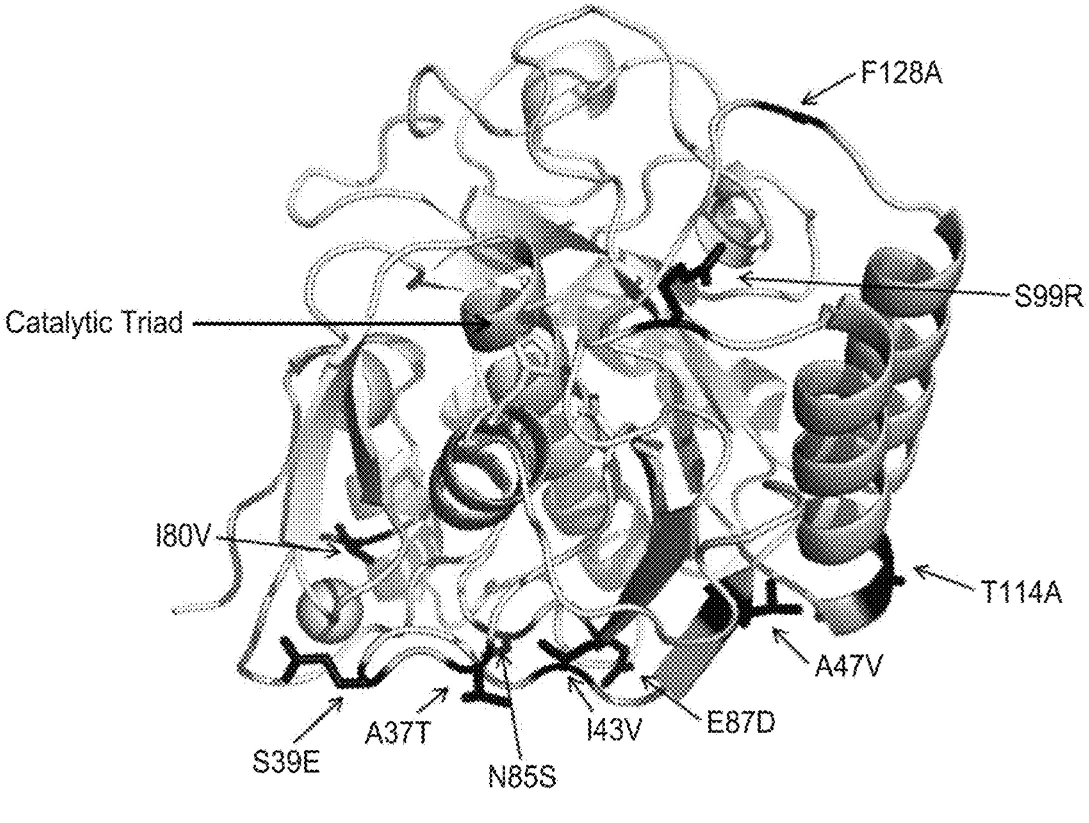

FIG. 2 provides the structural location of substitutions in *B. gibsonii*-clade subtilisin BSP-00801. Eight of the ten substitutions (A37T/N, S39E, I43V, A47V, I80V, N85S, E87D, and T114A) in BSP-00801 relative to the parent protease are found along one surface of the molecule near the first calcium binding site.

Figure 3:
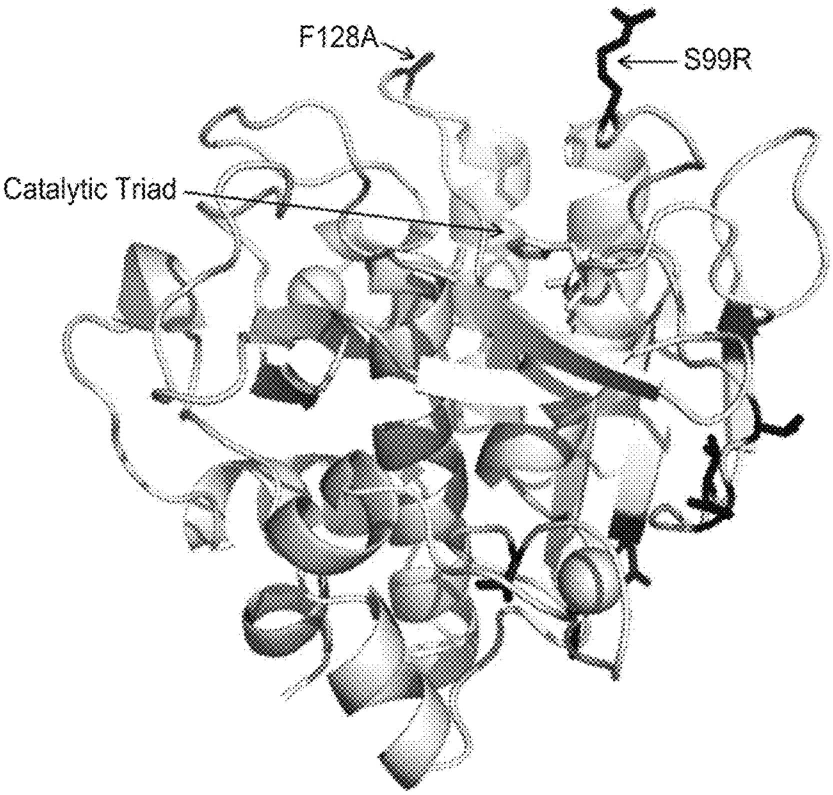

FIG. 3 provides a second view of the BSP-00801 structure with the catalytic triad shown as light sticks and the side chains of the ten substitutions shown as black sticks. This view looks down on the substrate binding surface and it is possible to see that S99R and F128A are located on two of the three loops that form the substrate binding surface corresponding to sub-sites S4-S1.

Figure 4:
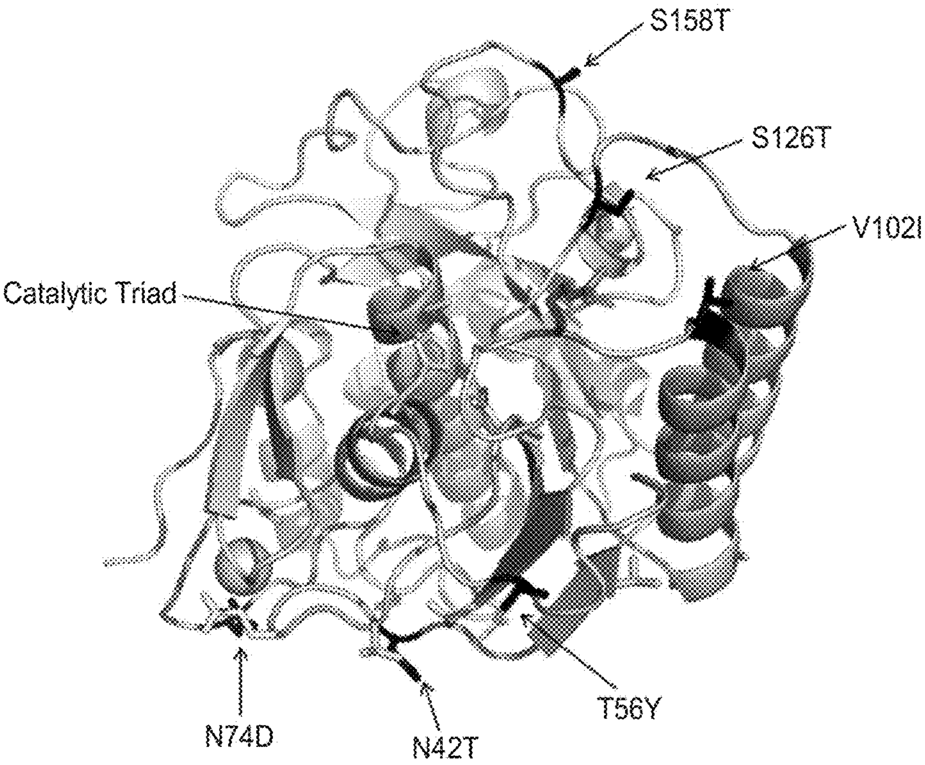

FIG. 4 provides the location of additional substitutions on BSP-00801. Six additional substitutions are found to enhance the performance of this variant. Three of these (N42T, S56Y and N74D) are found along one surface of the molecule and the other three (V102I, S126T and S158T) are found on loops that form the substrate binding region.

Figure 5:
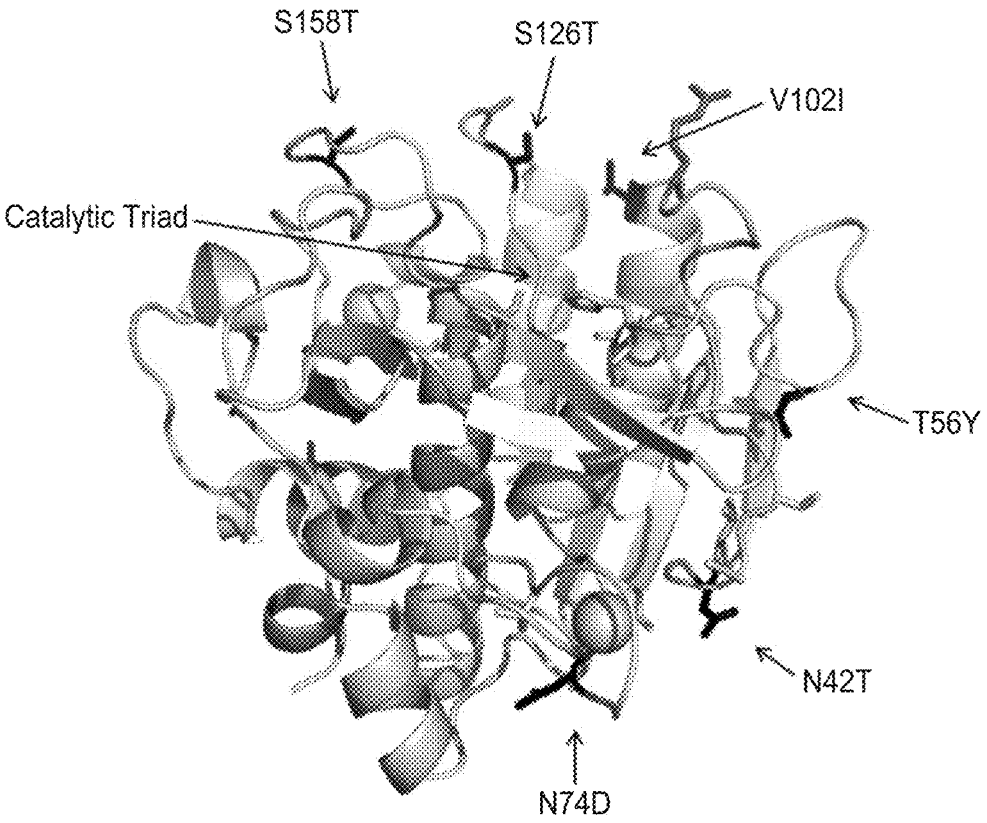

FIG. 5 provides a second view of the BSP-00801 structure with the catalytic triad, and the side chains of the 10 substitutions shown as light gray sticks. The additional sites that further enhance the performance are shown as black sticks. This view looks down the substrate binding surface and it is possible to see the location of three of the additional sites (V102I, S126T and S158T) one on each of the three loops that form the sub-sites S4-S1.

FIG. 6A-F provides an alignment of the amino acid sequences of the predicted mature forms of the *B. gibsonii*-clade subtilisins of Table 3*; B. gibsonii*-clade subtilisins DSM 9728, DSM 9729, DSM 9730, DSM 9731 and Bgi02446; and the amino acid sequences of multiple proteases listed in Tables 6-1 and 6-2. A consensus sequence is shown below the alignment.

FIG. 7A-F provides an alignment of the amino acid sequences of the predicted mature forms of the *B. gibsonii*-clade subtilisins of Table 4*; B. gibsonii*-clade subtilisin Bgi02446; and the amino acid sequences of multiple proteases listed in Table 6-1. A consensus sequence is shown below the alignment.

FIG. 8A-F provides an alignment of the amino acid sequences of the predicted mature forms of multiple *B. gibsonii*-clade BSP-00801 variant subtilisins of Table 5*; B. gibsonii*-clade subtilisin Bgi02446; and the amino acid sequences of multiple proteases listed in Table 6-1. A consensus sequence is shown below the alignment.

Figure 9:
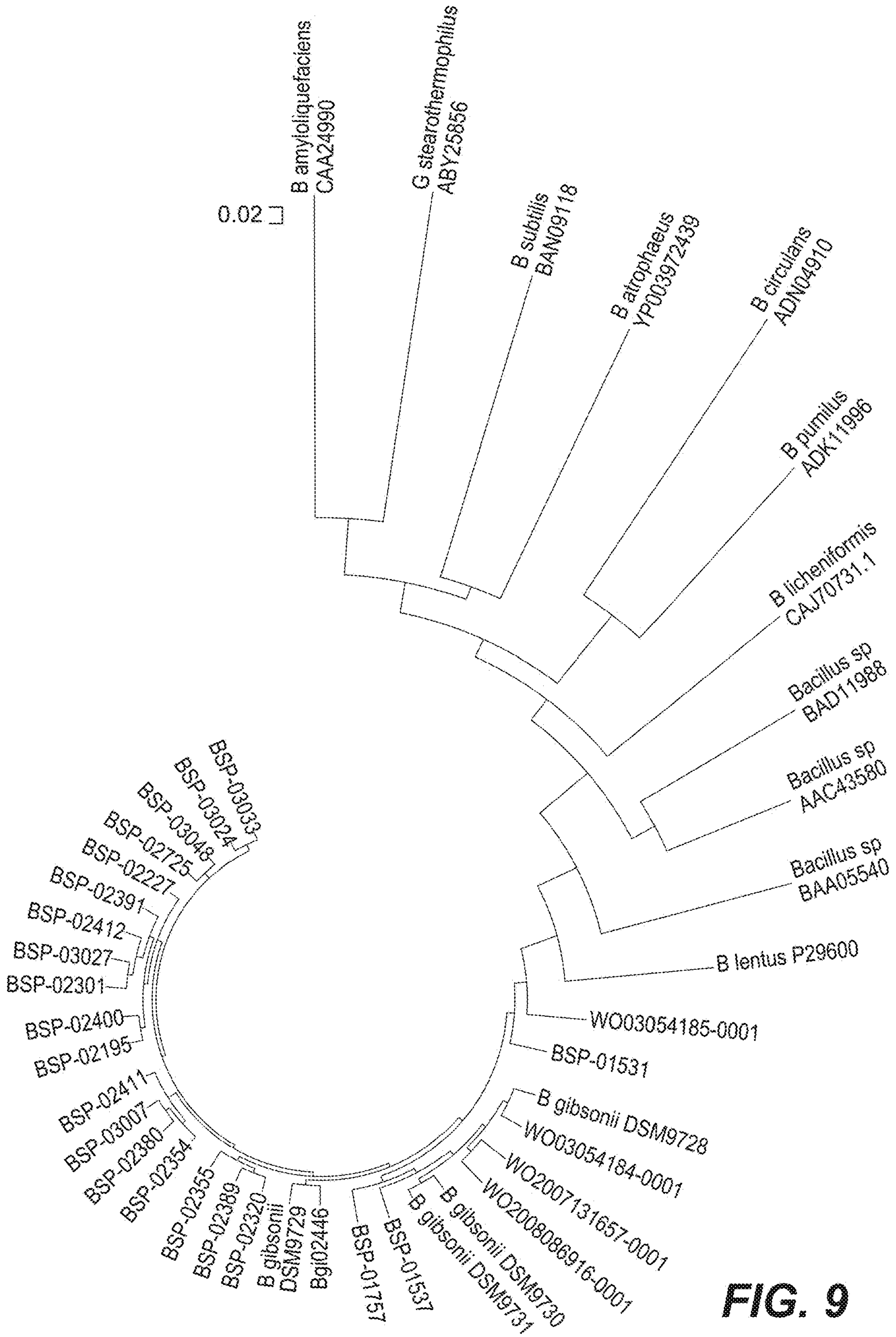

FIG. 9 provides a phylogenetic tree of the *B. gibsonii*-clade subtilisins of Table 3, the *B. gibsonii*-clade subtilisins DSM 9728, DSM 9729, DSM 9730, DSM 9731 and Bgi02446, and various other bacterial serine proteases.

Figure 10:
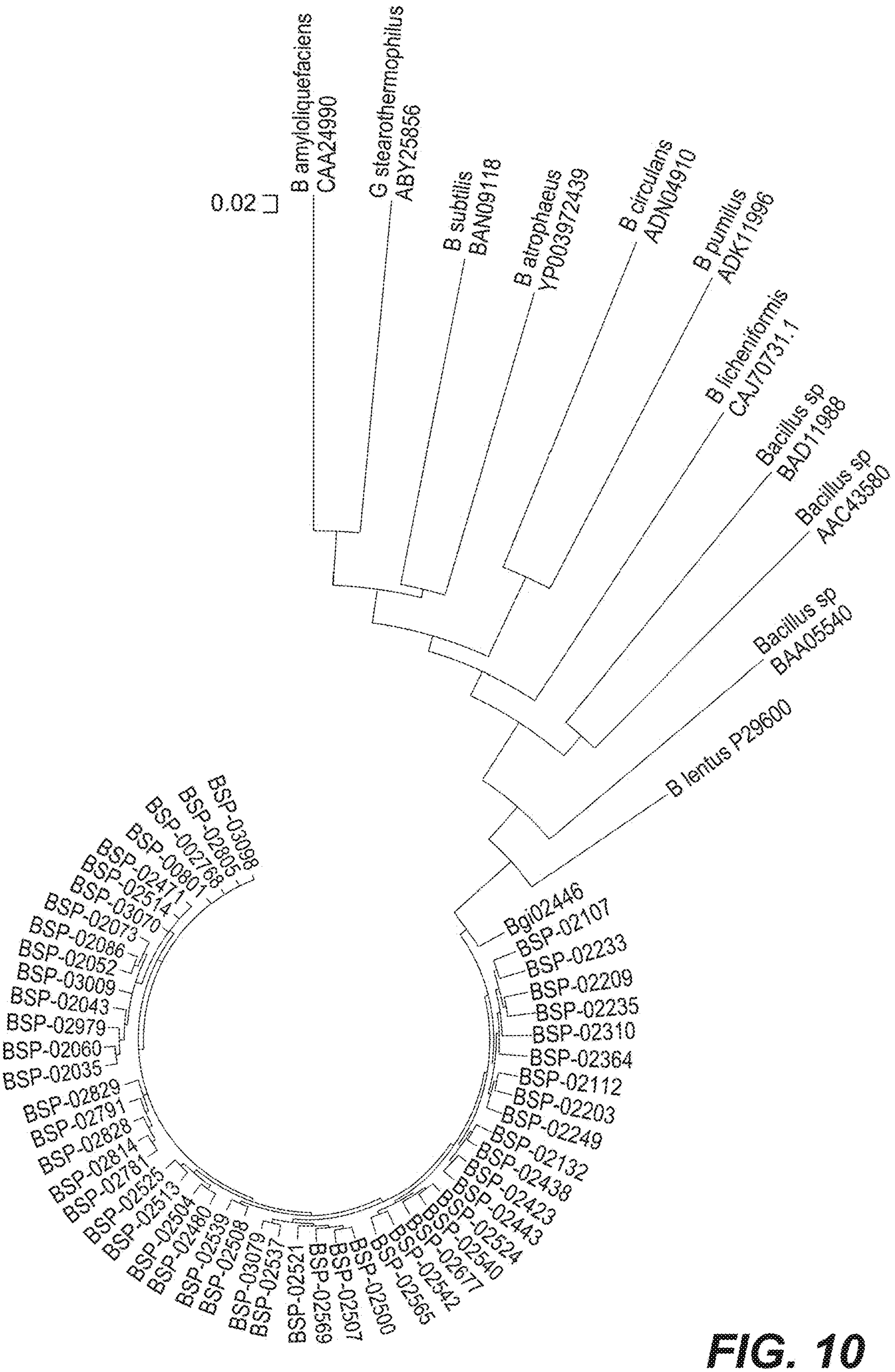

FIG. 10 provides a phylogenetic tree of the *B. gibsonii*-clade subtilisins of Table 4, *B. gibsonii*-clade subtilisin Bgi02446; and various other bacterial serine proteases.

Figure 11:
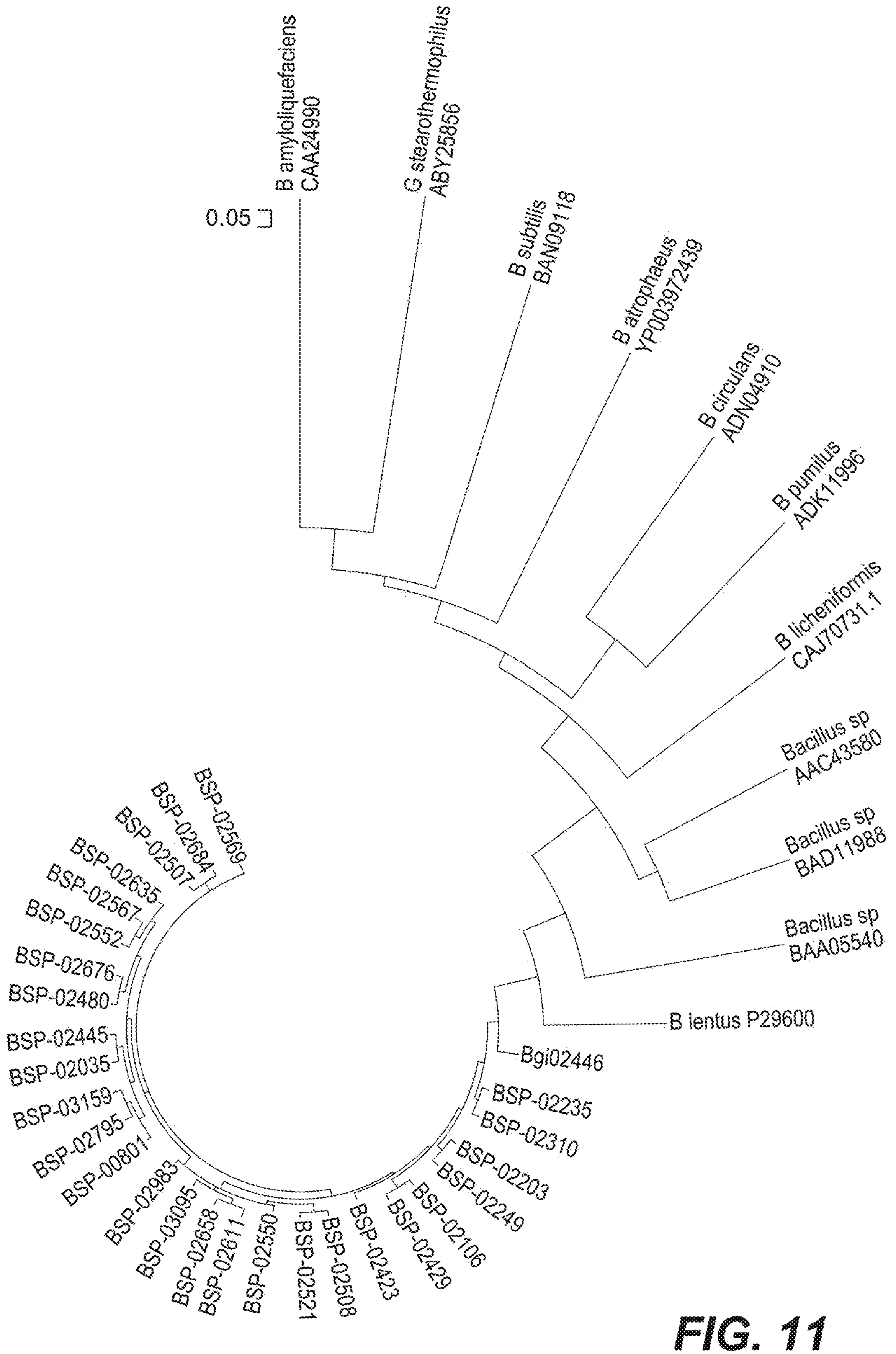

FIG. 11 provides a phylogenetic tree of multiple *B. gibsonii*-clade subtilisins of Table 5, *B. gibsonii*-clade subtilisin Bgi02446; and various other bacterial serine proteases.

FIG. 12A-C provides the structural alignment of the amino acid sequences of the predicted mature forms of the *B. gibsonii*-clade subtilisins of Table 3 and Bgi02446, wherein these sequences are shown to share a common motif extending between Asp (D)32 and His (H)65.

Figure 13:
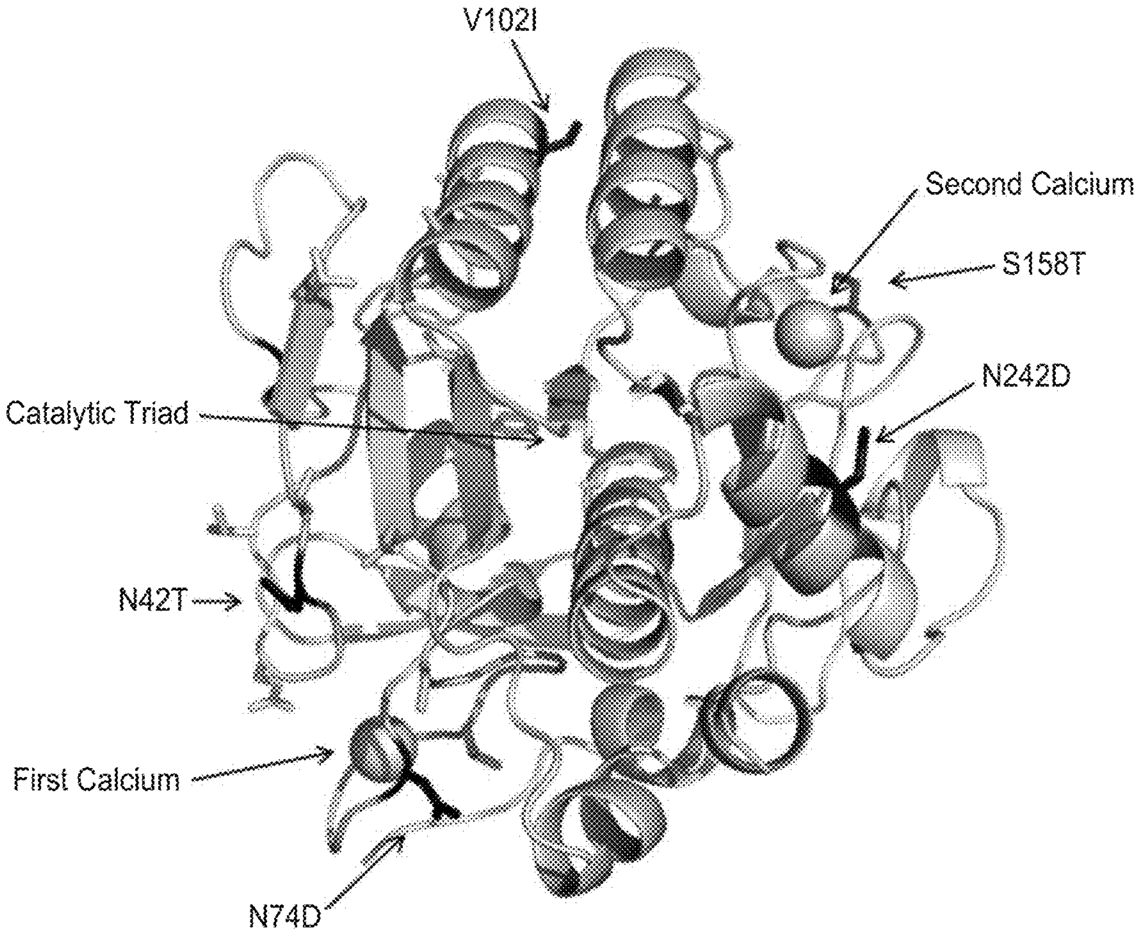

FIG. 13 provides the location of the N242D substitution relative to some of the other sites in BSP-00801 which are visible in this orientation. N242D is situated far removed from the substrate binding surface and the surface near the first calcium binding site. It is found closer to the second calcium binding site.

FIG. 14A-F provides an alignment of the amino acid sequences of Bgi02446*, B. gibsonii*-clade BSP-00801 variant subtilisin and mature forms of multiple *B. gibsonii*-clade variant subtilisins of Table 7.

Figure 15:
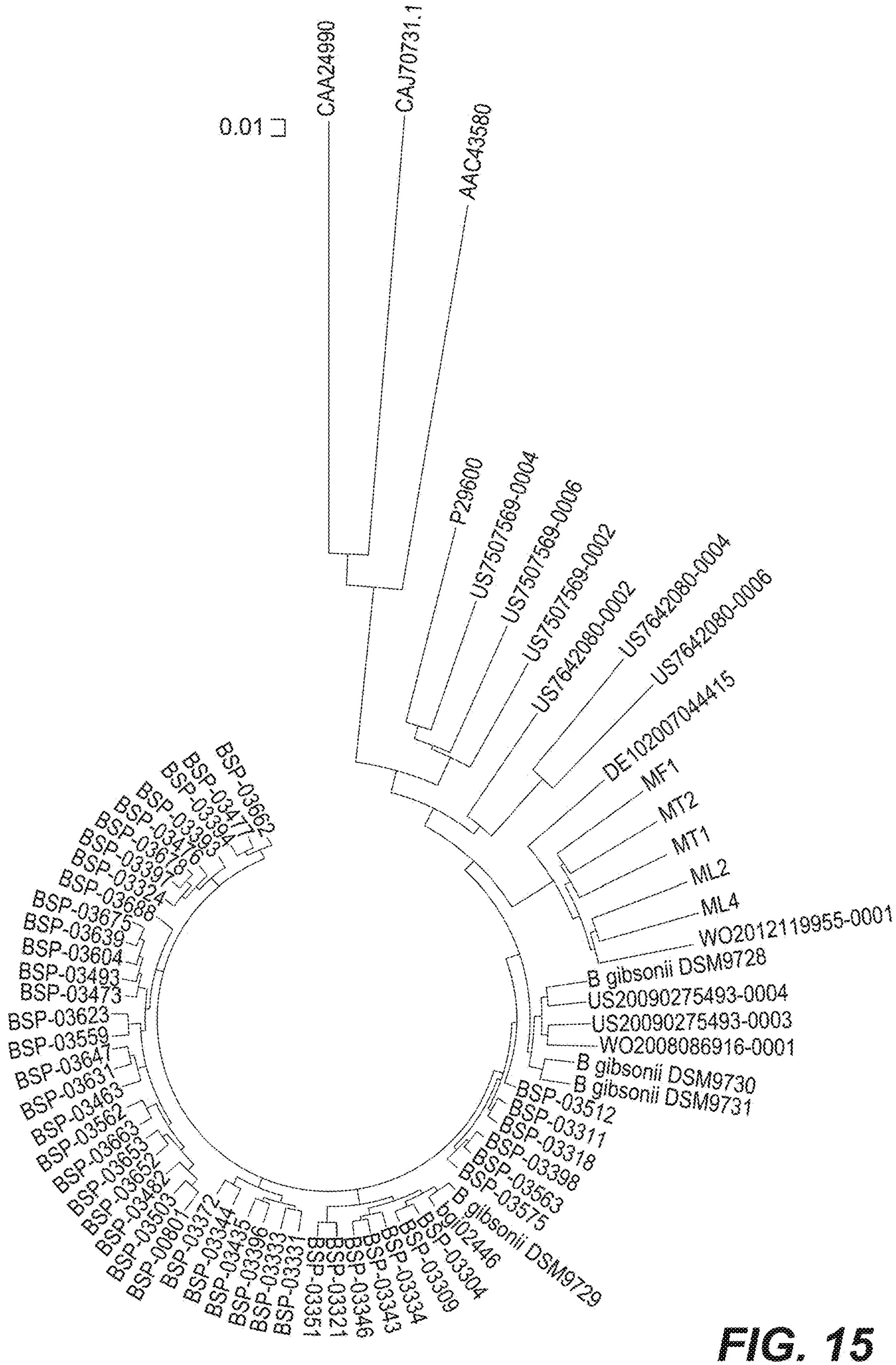

FIG. 15 provides a phylogenetic tree of the *B. gibsonii*-clade subtilisins of Table 7, the *B. gibsonii*-clade subtilisins DSM 9728, DSM 9729, DSM 9730, DSM 9731 and Bgi02446; the amino acid sequences of multiple proteases listed in Tables 6-1 and 6-2, and the amino acid sequences of BgAP variants ML2, ML4, MT1, MT2, MF1.

Described herein are variants, compositions and methods relating to recombinant serine proteases generated through conventional molecular biology techniques (see, e.g., Sambrook et al, Molecular Cloning: Cold Spring Harbor Laboratory Press). Compositions containing the serine proteases disclosed herein are suitable for use in cleaning fabrics and hard surfaces, as well as in a variety of industrial applications, such as, for example, textile, leather and feather processing. At least one *B. gibsonii*-clade serine proteases disclosed herein is also well suited for inclusion in compositions for protein degradation, including but not limited to laundry and dishwashing detergents; personal care compositions; and human food and animal feed.

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The nomenclature of the amino acid substitution(s) or variation(s) of one or more subtilisin variant described herein uses one or more of the following: position; position: amino acid substitution(s) or variation(s); or starting amino acid(s):position:amino acid substitution(s). Reference to a "position" (i.e. 5, 8, 17, 22, etc) encompasses any starting amino acid that may be present at such position, and any variation from the starting amino acid or any substitution that may be present at such position. Reference to a "position: amino acid substitution(s) and/or variation(s)" (i.e. 1S/T/G, 3G, 17T, etc) encompasses any starting amino acid that may be present at such position and the one or more amino acid(s) that may vary from the starting amino acid and/or with which such starting amino acid may be substituted. An amino acid substitution will exclude the starting amino acid, where the substituted amino acid and starting amino acid are the same. Reference to a starting amino acid or an amino acid substitution or an amino acid variation may be further expressed as several starting, substituted, or varied amino acids separated by a foreslash ("/"). For example, D275S/K indicates position 275 is substituted with serine (S) or lysine (K) and P/S197K indicates that starting amino acid proline (P) or serine (S) at position 197 is substituted with lysine (K).

The position of an amino acid residue in a given amino acid sequence is numbered by correspondence with the amino acid sequence of SEQ ID NO:85. That is, the amino acid sequence of SEQ ID NO:85 serves as a reference sequence. For example, the amino acid sequence of a BG46-clade subtilisin or one or more subtilisin variant described herein is aligned with the amino acid sequence of SEQ ID NO:85 using an alignment algorithm as described herein, and each amino acid residue in the given amino acid sequence that aligns (preferably optimally aligns) with an amino acid residue in SEQ ID NO:85 is conveniently numbered by reference to the numerical position of that corresponding amino acid residue. Sequence alignment algorithms, such as, for example, described herein will identify the location where insertions or deletions occur in a subject sequence when compared to a query sequence. Additionally, members of the *B. gibsonii*-clade with a QTVP at the N-terminus, such as, for example, SEQ ID NO:19, are for numbering purposes to be aligned with SEQ ID NO:85 as set forth in FIG. 14.

The term "variation(s)" when used in the phrase "two, three, or four or more amino acid variations versus SEQ ID NO:85" encompasses each amino acid that is different from the amino acid present at the corresponding position in SEQ ID NO:85. For example, the sequence of the variant of interest is aligned with SEQ ID NO:85 and each position in the variant compared to SEQ ID NO:85 to identify the amino acids at each position that are different from the amino acid present at the corresponding positions in SEQ ID NO:85 and each amino acid that is different from the corresponding amino acid in SEQ ID NO:85 is a variation.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. gibsonii, B. pabuli, B. cereus, B. agaradhaerens, B. akibai, B. clarkii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

As used herein, the term “mutation” refers to changes made to a reference amino acid or nucleic acid sequence. It is intended that the term encompass substitutions, insertions and deletions.

As used herein, the term “vector” refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multi-cloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein, the term “expression cassette,” “expression plasmid” or “expression vector” refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

As used herein, a “plasmid” refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term “introduced” refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is “operably linked” with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, “operably linked” DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term “gene” refers to a polynucleotide (e.g., a DNA segment), that encodes a polypeptide and includes regions preceding and following the coding regions. In some instances a gene includes intervening sequences (introns) between individual coding segments (exons).

As used herein, “recombinant” when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. “Recombination” and “recombining” of polynucleotides or nucleic acids refer generally to the assembly or combining of two or more nucleic acid or polynucleotide strands or fragments to generate a new polynucleotide or nucleic acid.

A nucleic acid or polynucleotide is said to “encode” a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms “host strain” and “host cell” refer to a suitable host for an expression vector comprising a DNA sequence of interest.

A “protein” or “polypeptide” comprises a polymeric sequence of amino acid residues. The terms “protein” and “polypeptide” are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as “G087S” or “G87S.

A “prosequence” or “propeptide sequence” refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms “signal sequence” and “signal peptide” refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide)

of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

The phrase "composition(s) substantially-free of boron" or "detergent(s) substantially-free of boron" refers to composition(s) or detergent(s), respectively, that contain trace amounts of boron, for example, less than about 1000 ppm (1 mg/kg or liter equals 1 ppm), less than about 100 ppm, less than about 50 ppm, less than about 10 ppm, or less than about 5 ppm, or less than about 1 ppm, perhaps from other compositions or detergent constituents.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

Disclosed herein is one or more subtilisin variant useful for cleaning applications and in methods of cleaning, as well as in a variety of industrial applications. In one embodiment, one or more serine protease or subtilisin variant described herein is a member of the *B. gibsonii*-clade. In another embodiment, one or more subtilisin variant described herein is an isolated, recombinant, substantially pure, and/or non-naturally occurring polypeptide. In some embodiments, one or more subtilisin variant described herein can be incorporated into one or more cleaning composition useful in one or more method of cleaning an item or a surface in need thereof.

Some embodiments are directed to a subtilisin variant comprising an amino acid sequence comprising two, three, or four or more variations versus SEQ ID NO:85 at positions selected from: (i) 1, 4, 9, 21, 24, 27, 36, 37, 39, 42, 43, 44, 47, 54, 55, 56, 74, 80, 85, 87, 99, 102, 114, 117, 119, 121, 126, 128, 131, 143, 144, 158, 159, 160, 169, 182, 188, 190, 197, 198, 212, 224, 231, 232, 237, 242, 245, 246, 254, 255, 256, and 257; (ii) 37, 39, 47, 56, 80, 85, 87, 99, 114, 126, 128, and 242; (iii) 39, 99, 126, and 128; (iv) 39 in combination with one or more variation at a position selected from 37, 47, 56, 80, 85, 87, 99, 114, 126, 128, and 242; (v) 56 in combination with one or more variation at a position selected from 37, 39, 47, 80, 85, 87, 99, 114, 126, 128, and 242; (vi) 114 in combination with one or more variation at a position selected from 37, 39, 47, 56, 80, 85, 87, 99, 126, 128, and 242; (vii) 126 in combination with one or more variation at a position selected from 37, 39, 47, 56, 80, 85, 87, 99, 114, 128, and 242; (viii) 242 in combination with one or more variation at a position selected from 37, 39, 47, 56, 80, 85, 87, 99, 114, 126, and 128; (ix) 99+128 in combination with one or more variation at a position selected from 39, 56, 114, 126 and 242; (x) 39+242 in combination with one or more variation at a position selected from 37, 47, 56, 80, 85, 87, 99, 114, 126, and 128; or (xi) 39+99+128 in combination with one or more variation at a position selected from 37, 47, 56, 80, 85, 87, 114, 126, and 242; with the proviso that one or more of said two, three, or four or more variations is non-naturally occurring; and wherein the amino acid positions of the variant are numbered by correspondence with the amino acid sequence of SEQ ID NO:85. Yet other embodiments are directed to a subtilisin variant comprising an amino acid sequence comprising two, three, or four or more variations versus SEQ ID NO:85 at positions selected from: (i) 1A, 4I, 9S, 21V, 24F, 27K, 36A, 37T/N, 39E, 42T, 43V, 44S, 47V, 54S, 55M/G, 56N/Y, 74D, 80V, 85S, 87D, 99R, 102I, 114A/P/Q, 117I, I119V, 121S, 126T, 128A, 131T, 143A/T/Q, 144G, 158T, 159I, 160S, 169L, 182S, 188A, 190L, 197I, 198G, 212S/T/K, 224I/V, 231K, 232N, 237T, 242D/Q, 245L, 246S/K, 254T, 255N, 256L, and 257Y; (ii) 37T/N, 39E, 47V, 56N/Y, 80V, 85S, 87D, 99R, 114A/P/Q, 126T, 128A, and 242D/Q; or (iii) 39E, 99R, 126T, and 128A; (iv) 39E in combination with one or more variation at a position selected from 37T/N, 47V, 56N/Y, 80V, 85S, 87D, 99R, 114A/P/Q, 126T, 128A, and 242D/Q; (v) 56N/Y in combination with one or more variation at a position selected from 37T/N, 39E, 47V, 80V, 85S, 87D, 99R, 114A/P/Q, 126T, 128A, and 242D/Q; (vi) 114A/P/Q in combination with one or more variation at a position selected from 37T/N, 39E, 47V, 56N/Y, 80V, 85S, 87D, 99R, 126T, 128A, and 242D/Q; (vii) 126T in combination with one or more variation at a position selected from 37T/N, 39E, 47V, 56N/Y, 80V, 85S, 87D, 99R, 114A/P/Q, 128A, and 242D/Q; (viii) 242D/Q in combination with one or more variation at a position selected from 37T/N, 39E, 47V, 56N/Y, 80V, 85S, 87D, 99R, 114A/P/Q, 126T, and 128A; (ix) 99R+128A in combination with one or more variation at a position selected from 39E, 56N/Y, 114A/P/Q, 126T, and 242D/Q; (x) 39E+242D/Q in combination with one or more variation at a position selected from 37T/N, 47V, 56N/Y, 80V, 85S, 87D, 99R, 114A/P/Q, 126T, and 128A; or (xi) 39E+99R+128A in combination with one or more variation at a position selected from 37T/N, 47V, 56N/Y, 80V, 85S, 87D, 114A/P/Q, 126T, and 242D/Q; with the proviso that one or more of said two, three, or four or more variations is non-naturally occurring; and wherein the amino acid positions of the variant are numbered by correspondence with the amino acid sequence of SEQ ID NO:85.

Other embodiments are directed to a subtilisin variant comprising an amino acid sequence comprising two, three, or four or more amino acid substitutions at positions selected from: (i) 1, 4, 9, 21, 24, 27, 36, 37, 39, 42, 43, 44, 47, 54, 55, 56, 74, 80, 85, 87, 99, 102, 114, 117, 119, 121, 126, 128, 131, 143, 144, 158, 159, 160, 169, 182, 188, 190, 197, 198, 212, 224, 231, 232, 237, 242, 245, 246, 254, 255, 256, and 257; (ii) 37, 39, 47, 56, 80, 85, 87, 99, 114, 126, 128, and 242; (iii) 39, 99, 126, and 128; (iv) 39 in combination with one or more amino acid substitution at a position selected from 37, 47, 56, 80, 85, 87, 99, 114, 126, 128, and 242; (v) 56 in combination with one or more amino acid substitution at a position selected from 37, 39, 47, 80, 85, 87, 99, 114, 126, 128, and 242; (vi) 114 in combination with one or more amino acid substitution at a position selected from 37, 39, 47, 56, 80, 85, 87, 99, 126, 128, and 242; (vii) A/S126 in combination with one or more amino acid substitution at a position selected from 37, 39, 47, 56, 80, 85, 87, 99, 114, 128, and 242; (viii) N242 in combination with one or more amino acid substitution at a position selected from 37, 39, 47, 56, 80, 85, 87, 99, 114, 126, and 128; (ix) 99+128 in combination with one or more amino acid substitution at a position selected from 39, 56, 114, 126 and 242; (x) 39+242 in combination with one or more amino acid substitution at a position selected from 37, 47, 56, 80, 85, 87, 99, 114, 126, and 128; or (xi) 39+99+128 in combination with one or more amino acid substitution at a position selected from 37, 47, 56, 80, 85, 87, 114, 126, and 242; with the proviso that one or more of said two, three, or four or more substitutions is non-naturally occurring; and wherein the amino acid positions of the variant are numbered by correspondence with the amino acid sequence of SEQ ID NO:85.

Still other embodiments are directed to a subtilisin variant comprising an amino acid sequence comprising two, three, or four or more amino acid substitutions at positions selected from: (i) Q1, V4, S/T9, I/V21, S24, K/R27, S36, Q/T/S/A37, S/P/T39, N/T42, I43, R/S44, A/V47, P/S54, S/T55, T56, N74, I/V80, N/585, D/E/Q87, S/R99, I/V102, A/T114, M117, I119, N121, A/S126, A/F128, I/S/T131, Q/R143, D/G144, N/S158, I/V159, G160, M169, N/S182, S/T188, 1190, V197, G/N198, N/P212, A/V224, K/R231, N/Y232, A/N237, N242, K245, N246, S254, S255, Q256, and F257; (ii) Q/T/S/A37, S/P/T39, A/V47, T56, I/V80, N/585, D/E/Q87, S/R99, A/T114, A/S126, A/F128, and N242; (iii) S/P/T39, S/R99, A/S126, and A/F128; (iv) S/P/T39 in combination with one or more amino acid substitution at a position selected from Q/T/S/A37, A/V47, T56, I/V80, N/585, D/E/Q87, S/R99, A/T114, A/S126, A/F128, and N242; (v) T56 in combination with one or more amino acid substitution at a position selected from Q/T/S/A37, S/P/T39, A/V47, I/V80, N/585, D/E/Q87, S/R99, A/T114, A/S126, A/F128, and N242; (vi) A/T114 in combination with one or more amino acid substitution at a position selected from Q/T/S/A37, S/P/T39, A/V47, T56, I/V80, N/585, D/E/Q87, S/R99, A/S126, A/F128, and N242; (vii) A/S126 in combination with one or more amino acid substitution at a position selected from Q/T/S/A37, S/P/T39, A/V47, T56, I/V80, N/S85, D/E/Q87, S/R99, A/T114, A/F128, and N242; (viii) N242 in combination with one or more amino acid substitution at a position selected from Q/T/S/A37, S/P/T39, A/V47, T56, I/V80, N/585, D/E/Q87, S/R99, A/T114, A/S126, and A/F128; (ix) S/R99+A/F128 in combination with one or more amino acid substitution at a position selected from S/P/T39, T56, A/T114, A/S126 and N242; (x) S/P/T39+N242 in combination with one or more amino acid substitution at a position selected from Q/T/S/A37, A/V47, T56, I/V80, N/585, D/E/Q87, S/R99, A/T114, A/S126, and A/F128; or (xi) S/P/T39+S/R99+A/F128 in combination with one or more amino acid substitution at a position selected from Q/T/S/A37, A/V47, T56, I/V80, N/585, D/E/Q87, A/T114, A/S126, and N242; with the proviso that one or more of said two, three, or four or more substitutions is non-naturally occurring; and wherein the amino acid positions of the variant are numbered by correspondence with the amino acid sequence of SEQ ID NO:85. Yet another embodiment is directed to a subtilisin variant comprising an amino acid sequence comprising two, three, or four or more amino acid substitutions selected from: (i) 1A, 4I, 9S, 21V, 24F, 27K, 36A, 37T/N, 39E, 42T, 43V, 44S, 47V, 54S, 55M/G, 56N/Y, 74D, 80V, 85S, 87D, 99R, 102I, 114A/P/Q, 117I, I119V, 121S, 126T, 128A, 131T, 143A/T/Q, 144G, 158T, 159I, 160S, 169L, 182S, 188A, 190L, 197I, 198G, 212S/T/K, 224I/V, 231K, 232N, 237T, 242D/Q, 245L, 246S/K, 254T, 255N, 256L, and 257Y; (ii) 37T/N, 39E, 47V, 56N/Y, 80V, 85S, 87D, 99R, 114A/P/Q, 126T, 128A, and 242D/Q; (iii) 39E, 99R, 126T, and 128A; (iv) 39E in combination with one or more substitution at a position selected from 37T/N, 47V, 56N/Y, 80V, 85S, 87D, 99R, 114A/P/Q, 126T, 128A, and 242D/Q; (v) 56N/Y in combination with one or more substitution at a position selected from 37T/N, 39E, 47V, 80V, 85S, 87D, 99R, 114A/P/Q, 126T, 128A, and 242D/Q; (vi) 114A/P/Q in combination with one or more substitution at a position selected from 37T/N, 39E, 47V, 56N/Y, 80V, 85S, 87D, 99R, 126T, 128A, and 242D/Q; (vii) 126T in combination with one or more substitution at a position selected from 37T/N, 39E, 47V, 56N/Y, 80V, 85S, 87D, 99R, 114A/P/Q, 128A, and 242D/Q; (viii) 242D/Q in combination with one or more substitution at a position selected from 37T/N, 39E, 47V, 56N/Y, 80V, 85S, 87D, 99R, 114A/P/Q, 126T, and 128A; (ix) 99R+128A in combination with one or more substitution at a position selected from 39E, 56N/Y, 114A/P/Q, 126T, and 242D/Q; (x) 39E+242D/Q in combination with one or more substitution at a position selected from 37T/N, 47V, 56N/Y, 80V, 85S, 87D, 99R, 114A/P/Q, 126T, and 128A; or (xi) 39E+99R+128A in combination with one or more substitution at a position selected from 37T/N, 47V, 56N/Y, 80V, 85S, 87D, 114A/P/Q, 126T, and 242D/Q; with the proviso that one or more of said two, three, or four or more substitutions is non-naturally occurring; and wherein the amino acid positions of the variant are numbered by correspondence with the amino acid sequence of SEQ ID NO:85. Yet still another embodiment is directed to a subtilisin variant comprising an amino acid sequence comprising two, three, or four or more amino acid substitutions selected from: Q1A, V4I, T9S, I21V, S24F, R27K, S36A, Q/T/S/A37N/T, S/P/T39E, N42T, I43V, R44S, A47V, P54S, S/T55G/M, T56N/Y, N74D, I80V, N85S, E/Q87D, S99R, V102I, A/T114A/P/Q, M117I, I119V, N121S, A/S126T, F128A, I/S131T, Q/R143A/Q/T, D144G, N/S158T, V159I, G160S, M169L, N182S, S/T188A, I190L, V197I, N198G, N/P212K/S/T, A/V224I/V, R231K, Y232N, A/N237T, N242D/Q, K245L, N246K/S, S254T, S255N, Q256L, and F257Y; (ii) Q/T/S/A37N/T, S/P/T39E, A47V, T56N/Y, I80V, N85S, E/Q87D, S99R, A/T114A/P/Q, A/S126T, F128A, and N242D/Q; (iii) S/P/T39E, S99R, A/S126T, and F128A; (iv) S/P/T39E in combination with one or more substitution at a position selected from Q/T/S/A37N/T, A47V, T56N/Y, I80V, N85S, E/Q87D, S99R, A/T114A/P/Q, A/S126T, F128A, and N242D/Q; (v) T56N/Y in combination with one or more substitution at a position selected from Q/T/S/A37N/T, S/P/T39E, A47V, I80V, N85S, E/Q87D, S99R, A/T114A/P/Q, A/S126T, F128A, and N242D/Q; (vi) A/T114A/P/Q in combination with one or more substitution at a position selected from Q/T/S/A37N/T, S/P/T39E, A47V, T56N/Y, I80V, N85S, E/Q87D, S99R, A/S126T, F128A, and N242D/Q; (vii) A/S126T in combination with one or more substitution at a position selected from Q/T/S/A37N/T, S/P/T39E, A47V, T56N/Y, I80V, N85S, E/Q87D, S99R, A/T114A/P/Q, F128A, and N242D/Q; (viii) N242D/Q in combination with one or more substitution at a position selected from Q/T/S/A37N/T, S/P/T39E, A47V, T56N/Y, I80V, N85S, E/Q87D, S99R, A/T114A/P/Q, A/S126T, and F128A; (ix) S99R+F128A in combination with one or more substitution at a position selected from S/P/T39E, T56N/Y, A/T114A/P/Q, A/S126T and N242D/Q; (x) S/P/T39E+N242D/Q in combination with one or more substitution at a position selected from Q/T/S/A37T/N, A47V, T56N/Y, I80V, N85S, E/Q87D, S99R, A/T114A/P/Q, A/S126T, and F128A; or (xi) S/P/T39E+S99R+F128A in combination with one or more substitution at a position selected from Q/T/S/A37N/T, A47V, T56N/Y, I80V, N85S, E/Q87D, A/T114A/P/Q, A/S126T, and N242D/Q; with the proviso that one or more of said two, three, or four or more substitutions is non-naturally occurring; and wherein the amino acid positions of the variant are numbered by correspondence with the amino acid sequence of SEQ ID NO:85.

Another embodiment is directed to one or more subtilisin variant described herein, with the proviso: (i) that said two, three, or four or more variations versus SEQ ID NO:85 is not S39T+I21V+M122L+N177E; (ii) that said two, three, or four or more variations versus SEQ ID NO:85 is not S39E+N74D+D87E; (iii) that said two, three, or four or more variations versus SEQ ID NO:85 is not S39E+N74D+D87E+N253D; (iv) that said two, three, or four or more variations versus SEQ ID NO:85 is not I21V+S39E+N74D+D87E+M122L+N253D; (v) that said two, three, or four or more variations versus SEQ ID NO:85 is not Q37E+Q256E; and/or (vi) that said variation versus SEQ ID NO:85 at position 21 is not a valine when said variant comprises a variation versus SEQ ID NO:85 at one or more positions selected from: 4, 36, 42, 47, 56, 87, 99, 102, 114, 188, 224, 237, 242, and 255. An even further embodiment is directed to one or more subtilisin variant described herein, with the proviso: (i) that said two, three, or four or more substitutions is not S39T+I21V+M122L+N177E; (ii) that said two, three, or four or more substitutions is not S39E+N74D+D87E; (iii) that said two, three, or four or more substitutions is not S39E+N74D+D87E+N253D; (iv) that said two, three, or four or more substitutions is not I21V+S39E+N74D+D87E+M122L+N253D; (v) that said two, three, or four or more substitutions is not Q37E+Q256E; and/or (vi) that the substitution at position 21 is not a valine when said variant comprises a substitution at one or more positions selected from: 4, 36, 42, 47, 56, 87, 99, 102, 114, 188, 224, 237, 242, and 255.

A further embodiment is directed to a subtilisin variant comprising an amino acid sequence comprising: (i) one or more variation versus SEQ ID NO:85 at positions selected from 56, 114, and 126; (ii) one or more variation versus SEQ ID NO:85 at positions selected from 56N/Y, 114A/P/Q, and 126T; (iii) one or more amino acid substitution at positions selected from 56, 114, and 126; (iv) one or more amino acid substitution at positions selected from T56, A/T114, and A/S126; (v) one or more amino acids substitutions selected from: 56N/Y, 114A/P/Q, and 126T; or (vi) one or more amino acids substitutions selected from: T56N/Y, A/T114A/P/Q, and A/S126T; with the proviso that one or more of said two, three, or four or more variations or substitutions is non-naturally occurring; and wherein the amino acid positions of the variant are numbered by correspondence with the amino acid sequence of SEQ ID NO:85.

A still even further embodiment is directed to a subtilisin variant comprising an amino acid sequence comprising one or more amino acid substitutions selected from: N074D-I080V-N085S-E087D-S099R-V102I-S158T-V159I-N242D-F257Y; N074D-N085S-E087D-S099R-V102I-S126T-F128A-I190L-N242D-F257Y; R027K-S099R-V102I-T114Q-I119V-S126T-F128A-S158T-V159I-G160S-T188A-N242D; N074D-I080V-N085S-E087D-S099R-V102I-T114Q-S126T-F128A-N242D; R027K-S099R-V102I-S126T-F128A-R143A-S158T-V159I-G160S; N074D-I080V-N085S-E087D-S099R-V102I-I190L-N242D-F257Y; N074D-I080V-N085S-E087D-S099R-V102I-T114Q-R143A-I190L-N242D-F257Y; N074D-S099R-V102I-S126T-F128A-R143A-S158T-N212S; N074D-I080V-N085S-E087D-S099R-T114Q-S126T-F128A-R143A-N242D; N085S-E087D-S099R-T114Q-I119V-S126T-F128A-R143A-G160S-F257Y; N074D-I080V-S099R-V102I-T114Q-S126T-F128A-R143A-N212S-N242D; N074D-I080V-N085S-E087D-S099R-V102I-S126T-F128A-R143A-I190L-N242D-F257Y; N074D-I080V-S099R-V102I-T114Q-I119V-S126T-F128A-S158T-G160S-N212S-F257Y; I080V-N085S-E087D-

S099R-V102I-T114Q-I119V-S126T-F128A-R143A-N242D; N085S-E087D-S099R-V102I-T114Q-S158T-V159I-G160S-N212S-N242D-F257Y; R027K-N074D-S099R-V102I-T114Q-S126T-F128A-T188A-I190L-N212S-N242D; R027K-N074D-S099R-V102I-I119V-S126T-F128A-R143A-G160S-N212S-N242D; N042T-I080V-N085S-E087D-T114A-F128A-R143Q-D144G-S158T-V159I-G160S-N198G; I021V-I080V-N085S-E087D-M117I-F128A-S131T-R143Q-D144G-A224V; N074D-I080V-N085S-E087D-S158T-N242D; Q001A-I080V-F128A-S131T-R143A-D144G-M169L-I190L-S254T-S255N-Q256L-F257Y; A037T-S039E-N042T-S099R-V102I-T114Q-S126T-F128A-N242D; A037T-S039E-S099R-V102I-T114Q-S126T-F128A-R143A-N212S-N242D; A037T-S039E-N074D-S099R-V102I-S126T-F128A-R143A-N212S-N242D; A037T-S039E-N042T-N074D-S099R-V102I-S126T-F128A-S158T-N242D; A037T-S039E-I043V-A047V-I080V-N085S-E087D-S099R-T114A-F128A; A037T-S039E-I043V-A047V-T055G-S099R-V102I-T114Q-S126T-F128A-N212S; A037T-S039E-I043V-A047V-I080V-N085S-E087D-S099R-T114Q-F128A-N242D; A037T-S039E-I043V-A047V-I080V-N085S-E087D-S099R-T114A-F128A-N242D; A037T-S039E-A047V-I080V-N085S-E087D-S099R-T114Q-F128A-R143A-N242D; S036A-S039E-I043V-A047V-T055M-I080V-N085S-E087D-S099R-T114A-F128A; A037T-S039E-I043V-A047V-I080V-N085S-E087D-S099R-V102-T114Q-F128A; A037T-S039E-I043V-A047V-N074D-N085S-E087D-S099R-T114A-F128A-S158T-N212S; A037T-S039E-N074D-I080V-N085S-E087D-S099R-V102I-T114Q-S126T-F128A-R143A; A037T-S039E-I043V-A047V-T055G-N074D-I080V-S099R-V102-T114Q-S126T-F128A; A037T-S039E-I043V-A047V-N074D-I080V-S099R-V102I-T114Q-S126T-F128A-N242D; R027K-A037T-S039E-A047V-T055G-T056Y-N074D-S099R-V102I-S126T-F128A-N242D; A037T-S039E-N042T-A047V-N074D-I080V-N085S-E087D-S099R-T114Q-F128A-N242D; A037T-S039E-I043V-A047V-I080V-N085S-E087D-S099R-T114A-S126T-F128A-N212S; A037T-S039E-I043V-A047V-I080V-N085S-E087D-S099R-T114A-S126T-F128A-N242D; A037T-S039E-I043V-A047V-I080V-N085S-E087D-S099R-T114Q-S126T-F128A-R143A; A037T-S039E-I043V-A047V-I080V-N085S-E087D-S099R-V102I-T114A-F128A-N212S; A037T-S039E-N042T-A047V-I080V-N085S-E087D-S099R-V102-T114Q-F128A-N242D; A037T-S039E-I043V-A047V-T056Y-I080V-N085S-E087D-S099R-T114A-F128A-N242D; A037T-S039E-I043V-A047V-I080V-N085S-E087D-S099R-T114Q-F128A-N212S-N242D; A037T-S039E-A047V-I080V-N085S-E087D-S099R-V102I-T114Q-F128A-R143A-N242D; A037T-S039E-I043V-A047V-T055G-I080V-N085S-E087D-S099R-T114Q-S126T-F128A; R027K-A037T-S039E-A047V-I080V-N085S-E087D-S099R-T114Q-F128A-N212S-N242D; T009S-A037T-S039E-I043V-A047V-I080V-N085S-E087D-S099R-T114A-F128A-V197I; S039E-I043V-A047V-I080V-N085S-E087D-S099R-T114A-F128A-N212S-K245L-N246S; A037T-S039E-I043V-A047V-I080V-N085S-E087D-S099R-T114A-F128A-I190L-A224V; S036A-S039E-I043V-A047V-I080V-N085S-E087D-S099R-T114A-N121S-F128A-R143Q; S036A-S039E-I043V-A047V-I080V-N085S-E087D-S099R-T114A-F128A-N212S-S255N; S039E-I043V-A047V-I080V-N085S-E087D-S099R-T114A-F128A-R143Q-N242D-N246K; A037T-S039E-I043V-A047V-N074D-N085S-E087D-S099R-T114A-S126T-F128A-N212S; A037T-S039E-I043V-A047V-N074D-I080V-N085S-E087D-S099R-T114A-F128A-N212S; A037T-S039E-N042T-A047V-I080V-N085S-E087D-S099R-T114A-F128A-S158T-N212S; V004I-A037T-S039E-I043V-A047V-I080V-N085S-E087D-S099R-T114A-F128A-N182S; A037T-S039E-I043V-A047V-N074D-N085S-E087D-S099R-T114A-S126T-F128A-S158T-N212S; A037T-S039E-I043V-A047V-N074D-I080V-N085S-E087D-S099R-T114A-F128A-S158T-N212S; A037T-S039E-I043V-A047V-N074D-N085S-E087D-S099R-T114A-F128A-N212S-N242Q-K245L; A037T-S039E-I043V-A047V-N074D-I080V-N085S-E087D-S099R-T114A-F128A-N212S-N242Q; A037T-S039E-I043V-A047V-N074D-I080V-N085S-E087D-S099R-T114A-F128A-N212S-K245L; A037T-S039E-A047V-S099R-V102I-T114A-I119V-S126T-F128A-R143A-S158T-G160S-N212S; A037T-S039E-N042T-A047V-T056Y-N074D-I080V-N085S-E087D-S099R-T114Q-S126T-F128A; S024F-A037T-S039E-A047V-N074D-I080V-N085S-E087D-S099R-T114Q-S126T-F128A-N212S; A037T-S039E-I043V-A047V-I080V-N085S-E087D-S099R-T114Q-S126T-F128A-R143A-N242D; A037T-S039E-I043V-A047V-I080V-N085S-E087D-S099R-T114A-S126T-F128A-A237T-N242D; A037T-S039E-I043V-A047V-I080V-N085S-E087D-S099R-V102I-T114Q-S126T-F128A-N242D; A037T-S039E-I043V-A047V-T055G-I080V-N085S-E087D-S099R-V102I-T114Q-F128A-R143A; A037T-S039E-N042T-A047V-T055G-I080V-N085S-E087D-S099R-T114Q-F128A-N212S-N242D; A037T-S039E-I043V-A047V-I080V-N085S-E087D-S099R-T114A-F128A; A037T-S039E-I043V-A047V-I080V-N085S-E087D-S099R-T114A-F128A-N242D; A037T-S039E-I043V-A047V-I080V-N085S-E087D-S099R-T114Q-F128A-N242D; A037T-S039E-I043V-A047V-I080V-N085S-E087D-S099R-T114A-S126T-F128A-N242D; A037T-S039E-I043V-A047V-T056Y-I080V-N085S-E087D-S099R-T114A-F128A-N242D; A037T-S039E-I043V-A047V-I080V-N085S-E087D-S099R-T114Q-S126T-F128A-R143A; A037T-S039E-I043V-A047V-T055G-I080V-N085S-E087D-S099R-T114Q-S126T-F128A; A037T-S039E-I043V-A047V-N074D-I080V-N085S-E087D-S099R-T114A-F128A-S158T-N212S; A037T-S039E-I043V-A047V-I080V-N085S-E087D-S099R-T114A-S126T-F128A-A237T-N242D; A037T-S039E-I043V-A047V-N074D-I080V-N085S-E087D-S099R-T114A-S126T-F128A-N242D; R027K-A037T-S039E-I043V-A047V-I080V-N085S-E087D-S099R-T114A-S126T-F128A-N242D; A037T-S039E-I043V-A047V-T056Y-I080V-N085S-E087D-S099R-T114A-S126T-F128A-R143A; A037T-S039E-I043V-A047V-I080V-N085S-E087D-S099R-T114A-N121S-F128A-N246S-S255N; A037T-S039E-A047V-I080V-N085S-E087D-S099R-T114Q-F128A-R143A-N242D; A037T-S039E-I043V-A047V-N074D-N085S-E087D-S099R-T114A-F128A-S158T-N212S; A037T-S039E-I043V-A047V-I080V-N085S-E087D-S099R-V102I-T114Q-S126T-F128A-N242D; A037T-S039E-I043V-A047V-T056Y-I080V-N085S-E087D-S099R-T114Q-S126T-F128A-N242D; A037T-S039E-I043V-A047V-N074D-I080V-N085S-E087D-S099R-T114Q-I119V-S126T-F128A; A037T-S039E-I043V-A047V-T055G-I080V-N085S-E087D-S099R-V102I-T114A-S126T-F128A-S158T; A037T-S039E-I043V-A047V-I080V-N085S-E087D-S099R-T114A-S126T-F128A-R143A-S158T-N242D; A037T-S039E-N042T-I043V-R044S-A047V-N074D-I080V-N085S-E087D-S099R-T114A-S126T-F128A;

A037T-S039E-N042T-I043V-R044S-A047V-I080V-N085S-E087D-S099R-T114A-S126T-F128A-N242D; A037T-S039E-I043V-A047V-I080V-N085S-E087D-S099R-V102I-T114A-I119V-S126T-F128A-F257Y; A037T-S039E-I043V-A047V-N074D-I080V-N085S-E087D-S099R-V102I-T114A-N121 S-F128A-R143Q; A037T-S039E-I043V-A047V-N074-N085S-E087D-S099R-T114A-S126T-F128A-S158T-N212S; S036A-S039E-I043V-A047V-N074D-I080V-N085S-E087D-S099R-T114A-F128A-A224V-S255N; A037T-S039E-I043V-A047V-T055G-N074D-I080V-N085S-E087D-S099R-T114Q-S126T-F128A-N242D; A037T-S039E-I043V-A047V-T055G-I080V-N085S-E087D-S099R-V102I-T114Q-S126T-F128A-R143A; A037T-S039E-I043V-A047V-I080V-N085S-E087D-S099R-V102I-T114Q-S126T-F128A-R143A-N242D; A037T-S039E-I043V-A047V-T056Y-I080V-N085S-E087D-S099R-T114Q-S126T-F128A-S158T-N242D; A037T-S039E-I043V-A047V-T056Y-I080V-N085S-E087D-S099R-T114Q-I119V-S126T-F128A-F257Y; A037T-S039E-I043V-A047V-T056Y-I080V-N085S-E087D-S099R-T114Q-I119V-S126T-F128A-N242D; A037T-S039E-I043V-A047V-N074D-I080V-N085S-E087D-S099R-T114A-S126T-F128A-S158T-N212S-N242Q; A037T-S039E-I043V-A047V-N074D-I080V-N085S-E087D-S099R-T114A-S126T-F128A-T188A-I190L-F257Y; V004I-T009S-A037T-S039E-I043V-A047V-I080V-N085S-E087D-S099R-T114A-F128A-A224V-K245L-S255N; A037T-S039E-A047V-T056Y-I080V-N085S-E087D-S099R-T114Q-R143A-N242D; A037T-S039E-N042T-A047V-T056Y-N074D-I080V-N085S-E087D-S099R-T114Q-S126T-F128A; A037T-S039E-I043V-A047V-N074D-N085S-E087D-S099R-T114A-S126T-F128A-S158T-N212S-N242Q; A037T-S039E-I043V-A047V-N074D-N085S-E087D-S099R-T114A-S126T-F128A-S158T-N212S-K245L; A037T-S039E-I043V-A047V-I080V-N085S-E087D-S099R-T114P-S126T-F128A-R143T-S158T-N212K-N242D; A037T-S039E-I043V-A047V-T056Y-N074D-I080V-N085S-E087D-S099R-T114Q-S126T-F128A-R143A-N242D; A037T-S039E-I043V-A047V-T055G-T056Y-N074D-I080V-N085S-E087D-S099R-V102I-T114Q-S126T-F128A; S036A-A037N-S039E-I043V-A047V-I080V-N085S-E087D-S099R-T114A-F128A-N242D-K245L-N246S-S255N; A037T-S039E-I043V-A047V-N074D-I080V-N085S-E087D-S099R-T114A-S126T-F128A-S158T-N212S-N242Q-K245L; A037T-S039E-I043V-A047V-I080V-N085S-E087D-S099R-T114A-I119V-S126T-F128A-S158T-G160S-N242D-F257Y; A037T-S039E-I043V-A047V-I080V-N085S-E087D-S099R-T114A-N121S-F128A-N182S-I190L-K245L-N246S-S255N; A037T-S039E-N074D-I080V-N085S-E087D-S099R-V102I-T114Q-S126T-F128A-R143A; A037T-S039E-I043V-A047V-T055G-N074D-I080V-S099R-V102I-T114Q-S126T-F128A; A037T-S039E-I043V-A047V-N074D-I080V-S099R-V102I-T114Q-S126T-F128A-N242D; A037T-S039E-A047V-N074D-I080V-N085S-E087D-S099R-V102I-T114Q-S126T-F128A-S158T-N242D; A037T-S039E-N042T-A047V-N074D-I080V-N085S-E087D-S099R-V102I-T114Q-S126T-F128A-N242D; A037T-S039E-I043V-A047V-N074D-N085S-E087D-S099R-T114A-S126T-F128A-S158T-N212S-N242Q-K245L; T009S-S036A-S039E-I043V-A047V-I080V-N085S-E087D-S099R-T114A-F128A-R143Q-N182S-T188A-I190L; A037T-S039E-I043V-A047V-T055G-N074D-I080V-N085S-E087D-S099R-V102I-T114Q-S126T-F128A-S158T-N242D; A037T-S039E-I043V-A047V-T055G-N074D-I080V-N085S-E087D-S099R-T114Q-S126T-F128A-R143A-S158T-N212S; A037T-S039E-I043V-A047V-I080V-N085S-E087D-S099R-T114A-F128A-R143Q-N212S-A224V-Y232N-K245L-N246S-S255N; V004I-T009S-A037T-S039E-I043V-A047V-I080V-N085S-E087D-S099R-T114A-N121S-F128A-R143Q-A224I-R231K-K245L; R027K-A037T-S039E-A047V-I080V-N085S-E087D-S099R-T114Q-I119V-S126T-F128A-G160S-N242D-F257Y; R027K-A037T-S039E-I043V-A047V-T056Y-I080V-N085S-E087D-S099R-T114Q-S126T-F128A-S158T-G160S-N242D-F257Y; R027K-A037T-S039E-I043V-A047V-T056Y-I080V-N085S-E087D-S099R-V102I-T114Q-S126T-F128A-T188A-I190L-F257Y; R027K-A037T-S039E-I043V-A047V-47V-T056N-I080V-N085S-E087D-S099R-T114P-S126T-F128A-R143T-V159I-N212T-F257Y; A037T-S039E-I043V-A047V-T056Y-I080V-N085S-E087D-S099R-T114Q-I119V-S126T-F128A-S158T-V159I-G160S-F257Y; A037T-S039E-I043V-A047V-T055G-T056Y-N074D-I080V-N085S-E087D-S099R-V102I-T114Q-S126T-F128A-N242D; R027K-A037T-S039E-A047V-T056Y-N074D-I080V-N085S-E087D-S099R-T114Q-I119V-S126T-F128A-N242D-F257Y; A037T-S039E-N042T-N074D-S099R-V102I-S126T-F8A-S158T-N242D; R027K-A037T-S039E-A047V-T055G-T056Y-N074D-S099R-V102I-S126T-F128A-N242D; S039E-I043V-A047V-I080V-N085S-E087D-S099R-T114A-F128A-A224V-N242D-N246S-S255N; A037T-S039E-I043V-A047V-N074D-I080V-N085S-E087D-S099R-V102I-T114A-F128A-R143Q-S158T-A224V-S255N; A037T-S039E-I043V-A047V-P054S-T056Y-A057Q-N074D-I080V-N085S-E087D-S099R-T114A-N121S-F128A-S158T-A224V-S255N; A037T-S039E-N042T-I043V-R044S-A047V-N074D-I080V-N085 S-E087D-S099R-V102I-S126T-F128A-S158T-G160S-N242D; S126T; T114Q; T056Y; S099R-F128A; S099R-S126T; S126T-F128A; T056Y-T114Q; S039E-E087D; S099R-F128A-N242D; S099R-S126T-N242D; S099R-S126T-F128A; T056Y-T114Q-N242D; S039E-S099R-S126T; S039E-S099R-F128A; S039E-E087D-N242D; T056Y-S099R-T114Q-F128A; T056Y-S099R-T114Q-S126T; S039E-T056Y-S099R-F128A; S039E-S099R-T114Q-F128A; S039E-E087D-S099R-S126T; S039E-N085S-S099R-F128A; S039E-S099R-T114A-S126T; S039E-E087D-S099R-F128A; S039E-S099R-S126T-F128A; S039E-T056Y-E087D-T114Q; S039E-E087D-S099R-S126T-F128A; S039E-T056Y-S099R-S126T-F128A; S039E-E087D-S099R-F128A-N242D; A037T-S039E-E087D-S099R-T114A-F128A; S039E-T056Y-E087D-S099R-S126T-F128A; S039E-S099R-T114Q-S126T-F128A-N242D; A037T-S039E-S099R-T114Q-S126T-F128A-N242D; A037T-S039E-T056Y-S099R-S126T-F128A-N242D; A037T-S039E-T056Y-N085S-E087D-S099R-T114Q-F128A; A037T-S039E-A047V-T056Y-S099R-T114Q-S126T-F128A; A037T-S039E-A047V-T056Y-S099R-T114A-S126T-F128A; A037T-S039E-T056Y-S099R-T114Q-S126T-F128A-N242D; S039E-A047V-E087D-S099R-T114Q-S126T-F128A-N242D; S039E-A047V-T056Y-N085S-E087D-S099R-T114Q-S126T-F128A; S039E-A047V-I080V-E087D-S099R-T114A-S126T-F128A-N242D; A037T-S039E-T056Y-N085S-S099R-T114Q-S126T-F128A-N242D; S039E-A047V-T056Y-E087D-S099R-T114A-S126T-F128A-N242D; S039E-A047V-T056Y-E087D-S099R-T114Q-S126T-F128A-N242D; A037T-S039E-A047V-I080V-N085S-E087D-S099R-T114A-S126T-F128A; A037T-S039E-I080V-N085S-E087D-S099R-T114Q-S126T-F128A-N242D;

A037T-S039E-T056Y-N085S-E087D-S099R-T114A-S126T-F128A-N242D; A037T-S039E-A047V-T056Y-E087D-S099R-T114A-S126T-F128A-N242D; and combinations thereof, wherein the amino acid positions of the variant are numbered by correspondence with the amino acid sequence of SEQ ID NO:85.

One embodiment provides one or more subtilisin variant comprising an amino acid sequence comprising amino acid substitutions S39E+S99R+F128A, where the amino acid positions of the variant are numbered by correspondence with the amino acid sequence of SEQ ID NO:85. A still further embodiment provides one or more subtilisin variant comprising an amino acid sequence comprising amino acid substitutions S39E+S99R+F128A+N242D, where the amino acid positions of the variant are numbered by correspondence with the amino acid sequence of SEQ ID NO:85. Yet a further embodiment provides one or more subtilisin variant comprising an amino acid sequence comprising amino acid substitutions S39E+S99R+F128A+I43V, where the amino acid positions of the variant are numbered by correspondence with the amino acid sequence of SEQ ID NO:85. A still further embodiment provides one or more subtilisin variant comprising an amino acid sequence comprising amino acid substitutions S39E+S99R+F128A+A47V, where the amino acid positions of the variant are numbered by correspondence with the amino acid sequence of SEQ ID NO:85. Some embodiments provide one or more subtilisin variant comprising an amino acid sequence comprising amino acid substitutions S39E+S99R+F128A+I80V, where the amino acid positions of the variant are numbered by correspondence with the amino acid sequence of SEQ ID NO:85. A still further embodiment provides one or more subtilisin variant comprising an amino acid sequence comprising amino acid substitutions S39E+S99R+F128A and one or more amino acid substitution selected from: (i) Q1A, V4I, T9S, I21V, S24F, R27K, S36A, A37T/N, N42T, I43V, R44S, A47V, P54S, T55M/G, T56N/Y, N74D, I80V, N85S, E87D, V102I, T114A/P/Q, M117I, I119V, N121S, S126T, S131T, R143A/T/Q, D144G, S158T, V159I, G160S, M169L, N182S, T188A, I190L, V197I, N198G, N212S/T/K, A224I/V, R231K, Y232N, A237T, N242D/Q, K245L, N246S/K, A254T, S255N, Q256L, and F257Y; (ii) Q1A, I21V, R27K, N42T, N74D, I80V, N85S, E87D, V102I, T114A/Q, M117I, I119V, S126T, S131T, R143A/Q, D144G, S158T, V159I, G160S, M169L, T188A, I190L, N198G, N212S, A224V, N242D, S254T, S255N, Q256L, and F257Y; (iii) V4I, T9S, S24F, R27K, S36A, A37T/N, N42T, I43V, R44S, A47V, P54S, T55M/G, T56N/Y, A57Q, N74D, I80V, N85S, E87D, V102I, T114A/P/Q, I119V, N121S, S126T, R143A/T/Q, S158T, V159I, G160S, N182S, T188A, I190L, V197I, N212S/T/K, A224I/V, R231K, Y232N, A237T, N242D/Q, K245L, N246S/K, S255N, and F257Y; (iv) T9S, R27K, A37T/N, N42T, I43V, A47V, T55G, T56Y, N74D, I80V, N85S, E87D, V102I, T114A/Q, I119V, S126T, R143A/Q, S158T, G160S, N212S, N242D, K245L, N246S, S255N, and F257Y; (v) T9S, R27K, N42T, T55G, I119V, G160S, K245L, N246S, S255N, and F257Y; (vi) N74D, V102I, R143A/Q, S158T, and N212S; (vii) A37T/N, I43V, A47V, I80V, N85S, E87D, and T114A; (viii) N42T, T56Y, N74D, V102I, S126T, S158T, and N242D; (ix) T56Y, T114Q, S126T, and N242D; (x) I43V, A47V, I80V and N242D; (xi) I43V; (xii) A47V; (xiii) I80V; (xiv) N242D; or (xv) a combination of one or more of groups (i) to (xiv); where the amino acid positions of the variant are numbered by correspondence with the amino acid sequence of SEQ ID NO:85.

A further embodiment provides one or more subtilisin variant comprising an amino acid sequence comprising amino acid substitution N242D, where the amino acid positions of the variant are numbered by correspondence with the amino acid sequence of SEQ ID NO:85. A still further embodiment provides one or more subtilisin variant comprising an amino acid sequence comprising amino acid substitution N242D and one or more amino acid substitutions selected from: (i) Q1A, V4I, T9S, I21V, S24F, R27K, S36A, A37T/N, S39E, N42T, I43V, R44S, A47V, P54S, T55M/G, T56N/Y, N74D, I80V, N85S, E87D, S99R, V102I, T114A/P/Q, M117I, I119V, N121S, S126T, F128A, S131T, R143A/T/Q, D144G, S158T, V159I, G160S, M169L, N182S, T188A, I190L, V197I, N198G, N212S/T/K, A224I/V, R231K, Y232N, A237T, K245L, N246S/K, A254T, S255N, Q256L, and F257Y; (ii) Q1A, I21V, R27K, S39E, N42T, N74D, I80V, N85S, E87D, S99R, V102I, T114A/Q, M117I, I119V, S126T, F128A, S131T, R143A/Q, D144G, S158T, V159I, G160S, M169L, T188A, I190L, N198G, N212S, A224V, S254T, S255N, Q256L, and F257Y; (iii) V4I, T9S, S24F, R27K, S36A, A37T/N, S39E, N42T, I43V, R44S, A47V, P54S, T55M/G, T56N/Y, A57Q, N74D, I80V, N85S, E87D, S99R, V102I, T114A/P/Q, I119V, N121S, S126T, F128A, R143A/T/Q, S158T, V159I, G160S, N182S, T188A, I190L, V197I, N212S/T/K, A224I/V, R231K, Y232N, A237T, K245L, N246S/K, S255N, and F257Y; (iv) T9S, R27K, A37T/N, S39E, N42T, I43V, A47V, T55G, T56Y, N74D, I80V, N85S, E87D, S99R, V102I, T114A/Q, I119V, S126T, F128A, R143A/Q, S158T, G160S, N212S, K245L, N246S, S255N, and F257Y; (v) S39E, S99R, F128A, T56Y, T114Q, and S126T; (vi) S39E, N42T, T56Y, N74D, S99R, V102I, S126T, F128A, and S158T; (vii) I43V, A47V, and I80V; (viii) I43V; (ix) A47V; (x) I80V; and/or (xi) a combination of one or more of groups (i) to (x); where the amino acid positions of the variant are numbered by correspondence with the amino acid sequence of SEQ ID NO:85.

A further embodiment provides one or more subtilisin variant comprising an amino acid sequence comprising amino acid substitution I80V, where the amino acid positions of the variant are numbered by correspondence with the amino acid sequence of SEQ ID NO:85. A still further embodiment provides one or more subtilisin variant comprising an amino acid sequence comprising amino acid substitution I80V and one or more amino acid substitution selected from: (i) Q1A, V4I, T9S, I21V, S24F, R27K, S36A, A37T/N, S39E, N42T, I43V, R44S, A47V, P54S, T55M/G, T56N/Y, N74D, N85S, E87D, S99R, V102I, T114A/P/Q, M117I, I119V, N121S, S126T, F128A, S131T, R143A/T/Q, D144G, S158T, V159I, G160S, M169L, N182S, T188A, I190L, V197I, N198G, N212S/T/K, A224I/V, R231K, Y232N, A237T, N242D, K245L, N246S/K, A254T, S255N, Q256L, and F257Y; (ii) Q1A, I21V, R27K, S39E, N42T, N74D, N85S, E87D, S99R, V102I, T114A/Q, M117I, I119V, S126T, F128A, S131T, R143A/Q, D144G, S158T, V159I, G160S, M169L, T188A, I190L, N198G, N212S, A224V, N242D, S254T, S255N, Q256L, and F257Y; (iii) V4I, T9S, S24F, R27K, S36A, A37T/N, S39E, N42T, I43V, R44S, A47V, P54S, T55M/G, T56N/Y, A57Q, N74D, N85S, E87D, S99R, V102I, T114A/P/Q, I119V, N121S, S126T, F128A, R143A/T/Q, S158T, V159I, G160S, N182S, T188A, I190L, V197I, N212S/T/K, A224I/V, R231K, Y232N, A237T, N242D, K245L, N246S/K, S255N, and F257Y; (iv) T9S, R27K, A37T/N, S39E, N42T, I43V, A47V, T55G, T56Y, N74D, N85S, E87D, S99R, V102I, T114A/Q, I119V, S126T, F128A, R143A/Q, S158T, G160S, N212S, N242D, K245L, N246S, S255N, and F257Y; (v) S39E, S99R, F128A, T56Y, T114Q, S126T, and N242D; (vi) S39E, N42T, T56Y, N74D, S99R, V102I, S126T, F128A, S158T, and N242D; (vii) I43V, A47V, and N242D; (viii) I43V; (ix) A47V; (x) N242D; and/or (xi) a combination of one or more of groups (i) to (x); where the amino acid positions of the variant are numbered by correspondence with the amino acid sequence of SEQ ID NO:85.

A still further embodiment is directed to one or more subtilisin variant described herein, wherein said variant is a member of the *Bacillus Gibsonii*-clade. Another embodiment is directed to one or more subtilisin variant described herein, wherein said variant further comprises a DXGIXXHSDLXXXGGASXXXXXPTTADLNXH GTH (SEQ ID NO:71) or DXGIXXHSDLXXXG-GASXXXXXXTTADLXXHGTH (SEQ ID NO:72) motif, wherein the initial D is the active site Aspartic acid residue, the penultimate H is the active site Histidine, and X is any amino acid.

In another embodiment, one or more variant described herein is from a parent amino acid sequence, wherein said parent is a member of the *Bacillus Gibsonii*-clade. In yet still another embodiment, one or more variant described herein is from a parent amino acid sequence comprising a DXGIXXHSDLXXXGGASXXXXXPTTADLNXHGTH (SEQ ID NO:71) or DXGIXXHSDLXXXG-GASXXXXXXTTADLXXHGTH (SEQ ID NO:72) motif, wherein the initial D is the active site Aspartic acid residue, the penultimate H is the active site Histidine, and X is any amino acid. Yet in an even still further embodiment, one or more variant described herein is from a parent amino acid sequence, wherein said parent amino acid sequence has 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO:18 or 85.

An even still further embodiment provides one or more subtilisin variant comprising an amino acid sequence comprising one or more amino acid substitutions selected from N74D, I80V, V102I, T114Q, I119V, S126T, R143A, S158T, G160S, N212S, N242D, S255N, and F257Y and a DXGIXXHSDLXXXGGASXXXXXPTTADLNXHGTH (SEQ ID NO:71) or DXGIXXHSDLXXXG-GASXXXXXXTTADLXXHGTH (SEQ ID NO:72) motif, where the initial D is the active site Aspartic acid residue, the penultimate H is the active site Histidine, and X is any amino acid, and where the amino acid positions of the variant are numbered by correspondence with the amino acid sequence of SEQ ID NO:85. Yet an even still further embodiment provides one or more subtilisin variant comprising an amino acid sequence comprising (i) one or more amino acid substitutions selected from N74D, I80V, V102I, T114Q, I119V, S126T, R143A, S158T, G160S, N212S, N242D, S255N, and F257Y; (ii) one or more amino acid substitutions selected from N42T, N85S, E87D, S99R, and F128A; and (iii) a DXGIXXHSDLXXXGGASXXXXXPT-TADLNXHGTH (SEQ ID NO:71) or DXGIXXHSDLXXXGGASXXXXXXTTADLXXHGTH (SEQ ID NO:72) motif, where the initial D is the active site Aspartic acid residue, the penultimate H is the active site Histidine, and X is any amino acid, and where the amino acid positions of the variant are numbered by correspondence with the amino acid sequence of SEQ ID NO:85. Yet another embodiment, provides one or more subtilisin variant comprising an amino acid sequence comprising one or more amino acid substitutions selected from N74D, I80V, V102I, T114Q, I119V, S126T, R143A, S158T, G160S, N212S, N242D, S255N, and F257Y and a DXGIXXHSDLXXXG-GAS XXXXXPTTADLNXHGTH (SEQ ID NO:71) motif, where the initial D is the active site Aspartic acid residue, the penultimate H is the active site Histidine, and X is any amino acid, and where the amino acid positions of the variant are numbered by correspondence with the amino acid sequence of SEQ ID NO:85. A still yet further embodiment is directed to one or more subtilisin variant comprising an amino acid sequence comprising one or more amino acid substitutions selected from N74D, I80V, V102I, T114Q, I119V, S126T, R143A, S158T, G160S, N212S, N242D, S255N, and F257Y and a DXGIXXHSDLXXXGGASXXXXXXTTADLXXH GTH (SEQ ID NO:72) motif, where the initial D is the active site Aspartic acid residue, the penultimate H is the active site Histidine, and X is any amino acid, and where the amino acid positions of the variant are numbered by correspondence with the amino acid sequence of SEQ ID NO:85. A still further embodiment provides one or more subtilisin variant comprising an amino acid sequence comprising one or more amino acid substitutions selected from N74D, I80V, V102I, T114Q, I119V, S126T, R143A, S158T, G160S, N212S, N242D, S255N, and F257Y; one or more amino acid substitutions selected from N42T, N85S, E87D, S99R, and F128A; and a DXGIXXHSDLXXXGGASXXXXXPT-TADLNXHGTH (SEQ ID NO:71) or DXGIXXHSDLXXXGGASXXXXXXTTADLXXHGTH (SEQ ID NO:72) motif, where the initial D is the active site Aspartic acid residue, the penultimate H is the active site Histidine, and X is any amino acid, and where the amino acid positions of the variant are numbered by correspondence with the amino acid sequence of SEQ ID NO:85.

In a further embodiment, one or more subtilisin variant described herein further comprises an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid identity to the amino acid sequence of SEQ ID NO:18 or 85. In other embodiments, one or more subtilisin variant described herein further comprises an amino acid sequence with 70%, 75%, 80%, 85%, 90%, 95%, 96%, 97%, 98%, or 99% amino acid sequence identity to the amino acid sequence of SEQ ID NO:18 or 85. In some embodiments, one or more subtilisin variant described herein further comprises an amino acid sequence with 70%, 75%, 80%, 85%, 90%, 95%, 96%, 97%, 98%, or 99% amino acid sequence identity to the amino acid sequence of SEQ ID NO:85. In other embodiments, one or more subtilisin variant described herein further comprises an amino acid sequence with 80%, 85%, 90%, 95%, 96%, 97%, 98%, or 99% amino acid sequence identity to the amino acid sequence of SEQ ID NO:18 or 85. In still other embodiments, one or more subtilisin variant described herein further comprises an amino acid sequence with 80%, 85%, 90%, 95%, 96%, 97%, 98%, or 99% amino acid sequence identity to the amino acid sequence of SEQ ID NO:85. In further embodiments, one or more subtilisin variant described herein further comprises an amino acid sequence with 90%, 95%, 96%, 97%, 98%, or 99% amino acid sequence identity to the amino acid sequence of SEQ ID NO:18 or 85. In yet even still other embodiments, one or more subtilisin variant described herein further comprises an amino acid sequence with 90%, 95%, 96%, 97%, 98%, or 99% amino acid sequence identity to the amino acid sequence of SEQ ID NO:85.

As noted above, one or more subtilisin variant described herein has enzymatic activity (e.g., protease activity) and thus is useful in cleaning applications, including but not limited to, methods for cleaning dishware items, tableware items, fabrics, and items having hard surfaces (e.g., the hard surface of a table, table top, wall, furniture item, floor, ceiling, etc.). Some embodiments are directed to one or more cleaning composition comprising one or more subtilisin variant described herein. The enzymatic activity (e.g., protease enzyme activity) of one or more subtilisin variant described herein can be readily determined through procedures well known to those of ordinary skill in the art. The Examples presented infra describe methods for evaluating the enzymatic activity and cleaning performance. The performance of one or more subtilisin variant described herein in removing stains (e.g., a protein stain such as blood/milk/ink or egg yolk), cleaning hard surfaces, or cleaning laundry, dishware or tableware item(s) can be readily determined using procedures well known in the art and/or by using procedures, such as, for example, those set forth in the Examples. In some embodiments, one or more subtilisin variant described herein has protease activity in the presence of a surfactant. In other embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the protease activity comprises casein hydrolysis activity. In some embodiments, the protease activity comprises dimethylcasein hydrolysis activity.

In other embodiments, one or more subtilisin variant described herein has an increase in proteolytic activity compared to the proteolytic activity of the protease having the sequence of SEQ ID NO:85 and/or an increase in cleaning activity compared to the cleaning activity of the protease having the sequence of SEQ ID NO:85. In still other embodiments, one or more subtilisin variant described herein has an increase in proteolytic activity compared to the proteolytic activity of the protease having the sequence of SEQ ID NO:18 and/or an increase in cleaning activity compared to the cleaning activity of the protease having the sequence of SEQ ID NO:18. In even further embodiments, one or more subtilisin variant described herein has one or more improved property when compared to a reference subtilisin; wherein the improved property is selected from improved protease activity, improved cleaning performance in detergent, and improved thermostability in detergent; and wherein said detergent is optionally a boron-free detergent. In yet an even further embodiment, one or more subtilisin variant described herein has one or more improved property when compared to a reference subtilisin; wherein the improved property is selected from improved protease activity, improved cleaning performance in detergent, and improved thermostability in detergent; and wherein said detergent is a boron-free detergent. In still other embodiments, one or more subtilisin variant described herein has one or more improved property when compared to a reference subtilisin; wherein the improved property is (i) improved protease activity, wherein said variant has a PI>1 on N-suc-AAPF-pNA or dimethyl casein substrate; (ii) improved cleaning performance in detergent, wherein said variant has a BMI and/or egg stain cleaning PI>1; and/or (iii) improved thermostability in detergent, wherein said variant has a stability PI>1; and wherein said detergent is optionally a boron-free detergent. In yet still an even further embodiment, one or more subtilisin variant described herein has one or more improved property when compared to a reference subtilisin; wherein the improved property is (i) improved protease activity, wherein said variant has a PI>1 on N-suc-AAPF-pNA or dimethyl casein substrate; (ii) improved cleaning performance in detergent, wherein said variant has a BMI and/or egg stain cleaning PI>1; and/or (iii) improved thermostability in detergent, wherein said variant has a stability PI>1; and wherein said detergent is a boron-free detergent. Another embodiment is directed to one or more subtilisin variant described herein, where protease activity is measured in accordance with the protease activity assay of Example 3; cleaning performance in detergent is measured in accordance with the cleaning performance in laundry and ADW detergents assay of Example 4; and/or thermostability in detergent is measured in accordance with the stability assay of Example 4. One or more subtilisin variant described herein can have protease activity over a broad range of pH conditions. In some embodiments, one or more subtilisin variant described herein has protease activity on azo-casein as a substrate. In some embodiments, one or more subtilisin variant described herein has protease activity at a pH of from about 4.0 to about 12.0. In some embodiments, one or more subtilisin variant described herein has protease activity at a pH of from about 8.0 to about 12.0. In some embodiments, one or more subtilisin variant described herein has at least 50%, 60%, 70%, 80% or 90% of maximal protease activity at a pH of from about 8.0 to about 12.0. In some embodiments, one or more subtilisin variant has protease activity at a pH above 8.0, 8.5, 9.0, 9.5, 10.0, 10.5, 11.0 or 11.5. In some embodiments, one or more subtilisin variant has protease activity at a pH below 12.0, 11.5, 11.0, 10.5, 10.0, 9.5, 9.0 or 8.5.

In some embodiments, one or more subtilisin variant described herein has protease activity at a temperature range from about 10° C. to about 90° C. In some embodiments, one or more subtilisin variant described herein has protease activity at a temperature range of from about 50° C. to about 75° C. In some embodiments, one or more subtilisin variant described herein has at least 50%, 60%, 70%, 80% or 90% of maximal protease activity at a temperature of from about 50° C. to about 75° C. In some embodiments, one or more subtilisin variant described herein has activity at a temperature above 50° C., 55° C., 60° C., 65° C., or 70° C. In some embodiments, one or more subtilisin variant described herein has activity at a temperature below 75° C., 70° C., 65° C., 60° C., or 55° C.

In some embodiments, one or more subtilisin variant described herein demonstrates cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, one or more subtilisin variant described herein demonstrates cleaning performance in automatic dishwashing (ADW) detergent compositions. In some embodiments, the cleaning performance in automatic dishwashing (ADW) detergent compositions includes cleaning of egg yolk stains. In some embodiments, one or more subtilisin variant described herein demonstrates cleaning performance in laundry detergent compositions. In some embodiments, the cleaning performance in laundry detergent compositions includes cleaning of blood/milk/ink stains. In one or more cleaning composition described herein, one or more subtilisin variant described herein demonstrates cleaning performance with or without a bleach component.

One or more subtilisin variant described herein can be subject to various changes, such as one or more amino acid insertion, deletion, and/or substitution, either conservative or non-conservative, including where such changes do not substantially alter the enzymatic activity of the polypeptide. Similarly, one or more nucleic acid described herein can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. One or more nucleic acid sequence described herein can also be modified to include one or more codons that provide for optimum expression in an expression system (e.g., bacterial expression system), while, if desired, said one or more codons still encode the same amino acid(s).

Some embodiments are directed to one or more polypeptide having the desired enzymatic activity (e.g., protease enzyme activity or cleaning performance activity) which comprise sequences having the amino acid substitutions and/or variations described herein and also which comprise one or more additional amino acid substitution or variation, such as conservative and non-conservative substitutions or variations, wherein the polypeptide exhibits, maintains, or approximately maintains the desired enzymatic activity (e.g., proteolytic activity). In some embodiments, the proteolytic activity is reflected in the cleaning activity or performance of one or more subtilisin variant described herein. For example, an amino acid substitution may include, but is not limited to, one or more non-conservative substitution, and/or one or more conservative amino acid substitution. A conservative amino acid residue substitution typically involves exchanging a member within one functional class of amino acid residues for a residue that belongs to the same functional class (conservative amino acid residues are considered functionally homologous or conserved in calculating percent functional homology). For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservative substitutions or variations of one or more subtilisin variant described herein includes substitutions or variations of a small percentage, sometimes less than 5%, 4%, 3%, 2%, or 1%, or less than 10, 9, 8, 7, 6, 5, 4, 3, 2, or 1 amino acid with a conservatively selected amino acid of the same conservative substitution group.

One or more nucleic acid described herein is useful in recombinant production (e.g., expression) of one or more subtilisin variant described herein, typically through expression of a plasmid expression vector comprising a sequence encoding one or more subtilisin variant described herein.

Some embodiments are directed to one or more nucleic acid sequence having at least 50, 60, 65, 70, 75, 80, 85, 90, 91, 92, 93, 94, 95, 96, 97, 98, 99 or 100% nucleic acid sequence identity to the nucleic acid sequence of SEQ ID NO: 15, 21, 23, 25, 27, 29, 31, 33, 35, 37, 39, 41, 43, 45, 49, 51, 53, 55, 57, 59, 61, 63, 65, 67, or 69. Other embodiments are directed to one or more polynucleotide comprising a complementary nucleic acid sequence to the nucleic acid sequence of SEQ ID NO: 15, 21, 23, 25, 27, 29, 31, 33, 35, 37, 39, 41, 43, 45, 49, 51, 53, 55, 57, 59, 61, 63, 65, 67, or 69. Still other embodiments are directed to one or more polynucleotide comprising a nucleic acid sequence that encodes one or more subtilisin variant described herein. In even further embodiments, one or more polynucleotide or nucleic acid described herein is an isolated, recombinant, substantially pure, and/or non-naturally occurring polynucleotide or nucleic acid.

Some embodiments are directed to a synthetically derived nucleic acid comprising a nucleotide sequence encoding one or more subtilisin variant described herein. In some embodiments, one or more subtilisin variant described herein is expressed recombinantly with a homologous pro-peptide sequence (e.g., Bgi02446 pro-peptide).

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984]), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. One or more nucleotide described herein may also be obtained by screening cDNA libraries using one or more oligonucleotide probes that can hybridize to or PCR-amplify polynucleotides which encode one or more subtilisin variant described herein. Procedures for screening and isolating cDNA clones and PCR amplification procedures are well known to those of skill in the art and described in standard references known to those skilled in the art. Some nucleic acids described herein can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides that can encode one or more subtilisin variant described herein, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

Some embodiments provide one or more vector comprising one or more polynucleotide described herein; one or more expression vector or expression cassette comprising one or more nucleic acid or polynucleotide described herein; one or more isolated, substantially pure, or recombinant DNA construct comprising one or more nucleic acid or polynucleotide described herein; one or more isolated or recombinant cell comprising one or more polynucleotide described herein; and one or more composition comprising one or more such vector, nucleic acid, expression vector, expression cassette, DNA construct, cell, cell culture, or any combination or mixture thereof.

Some embodiments provide one or more recombinant cell comprising one or more vector (e.g., expression vector or DNA construct) described herein which comprise one or more nucleic acid or polynucleotide described herein. Some such recombinant cells are transformed or transfected with such one or more vector, although other methods are available and known in the art. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising one or more subtilisin variant described herein.

Other embodiments provide one or more vector comprising one or more nucleic acid or polynucleotide described herein. In some embodiments, the vector is an expression vector or expression cassette in which one or more polynucleotide sequence described herein is operably linked to one or more additional nucleic acid segment required for efficient gene expression (e.g., a promoter operably linked to a polynucleotide described herein). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *B. subtilis*, in Sonenshein et al., [eds.] *B. subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments, one or more polynucleotide sequence described herein (as well as other sequences included in the vector) is integrated into the genome of the host cell; while in other embodiments, a plasmid vector comprising one or more polynucleotide sequence described herein remains as autonomous extra-chromosomal element within the cell. The invention provides both extrachromosomal nucleic acid elements as well as incoming nucleotide sequences that are integrated into the host cell genome. One or more vector described herein is useful for producing one or more subtilisin variant described herein. In some embodiments, a polynucleotide construct encoding one or more subtilisin variant described herein is present on an integrating vector that enables the integration and optionally the amplification of the polynucleotide into the host chromosome. Examples of sites for integration are well known to those skilled in the art. In some embodiments, transcription of one or more polynucleotide described herein is effectuated by a promoter that is the wild-type promoter for the selected precursor protease. In other embodiments, the promoter is heterologous to the precursor protease, but is functional in the host cell. Examples of suitable promoters for use in bacterial host cells include, but are not limited to the amyE, amyQ, amyL, pstS, sacB, pSPAC, pAprE, pVeg, pHpaII promoters; the promoter of the *B. stearothermophilus* maltogenic amylase gene; the *B. amyloliquefaciens* (BAN) amylase gene; the *B. subtilis* alkaline protease gene; the *B. clausii* alkaline protease gene the *B. pumilis* xylosidase gene; the *B. thuringiensis* cryIIIA; and the *B. licheniformis* alpha-amylase gene. Additional promoters include, but are not limited to, the A4 promoter, as well as phage Lambda PR or PL promoters, and the *E. coli* lac, trp or tac promoters.

One or more subtilisin variant described herein can be produced in host cells of any suitable microorganism, including bacteria and fungi. In some embodiments, one or more subtilisin variant described herein can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, one or more subtilisin variant described herein is produced by *Bacillus* sp. host cells. Examples of *Bacillus* sp. host cells include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii, B. megaterium, Myceliopthera* spp, and *Yarrowia* spp, as well as other organisms within the genus *Bacillus*. In some embodiments, *B. subtilis* host cells are used for production of serine protease polypeptides. U.S. Pat. Nos. 5,264,366 and 4,760,025 (U.S. Pat. No. RE 34,606) describe various *Bacillus* host strains that can be used for producing one or more subtilisin variant described herein, although other suitable strains can be used.

Several bacterial strains that can be used to produce one or more subtilisin variant described herein include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP 0134048). The use of *B. subtilis* as an expression host cell is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce one or more subtilisin variant described herein is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., US 2005/0202535).

Host cells are transformed with one or more nucleic acid described herein using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing one or more nucleic acid sequence described herein into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use herein. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising one or more nucleic acid described herein (i.e., an intermediate cell is not used to amplify, or otherwise process, the DNA construct or vector prior to introduction into the host cell). Introduction of one or more DNA construct or vector described herein into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells described herein are cultured in conventional nutrient media. The suitable specific culture conditions, such as temperature, pH and the like are known to those skilled in the art and are well described in the scientific literature. In some embodiments, the invention provides a culture (e.g., cell culture) comprising one or more subtilisin variant described herein or one or more nucleic acid described herein.

In some embodiments, host cells transformed with one or more polynucleotide sequence described herein are cultured in a suitable nutrient medium under conditions permitting the expression of one or more subtilisin variant described herein, after which the resulting variant is recovered from the culture. In some embodiments, the variant produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as one or more subtilisin variant described herein, are well known. Various assays for detecting and measuring activity of proteases (e.g., one or more subtilisin variant described herein), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., one or more mature subtilisin variant described herein) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

Some other embodiments provide methods for making or producing one or more mature subtilisin variant described herein. A mature serine protease polypeptide does not include a signal peptide or a propeptide sequence. Some methods comprise making or producing one or more subtilisin variant described herein in a recombinant bacterial host cell, such as for example, a *Bacillus* sp. cell (e.g., a *B. subtilis* cell). Some embodiments provide a method of producing one or more subtilisin variant described herein comprising cultivating a recombinant host cell comprising a recombinant expression vector comprising a nucleic acid encoding one or more subtilisin variant described herein under conditions conducive to the production of the variant. Some such methods further comprise recovering the variant from the culture.

Some embodiments provide one or more method of producing one or more subtilisin variant described herein, comprising: (a) introducing a recombinant expression vector comprising a nucleic acid encoding one or more subtilisin variant described herein into a population of cells (e.g., bacterial cells, such as *B. subtilis* cells); and (b) culturing the cells in a culture medium under conditions conducive to produce the variant encoded by the expression vector. Some such methods further comprise: (c) isolating variant from the cells or the culture medium.

Unless otherwise noted, all component or composition levels provided herein are made in reference to the active level of that component or composition, and are exclusive of impurities, for example, residual solvents or by-products, which may be present in commercially available sources. Enzyme component weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. One embodiment is directed to a composition comprising one or more adjunct material and one or more subtilisin variant described herein. The precise nature of the adjunct materials that re employed in any particular composition, and levels of incorporation thereof, will depend on the physical form of the composition and the nature of the cleaning operation for which it is to be used.

Suitable adjunct materials include, but are not limited to, bleach catalysts, an additional enzyme, enzyme stabilizers (including, for example, an enzyme stabilizing system), chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. Suitable examples of other adjunct materials and levels of use can be found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101. In embodiments in which one or more adjunct material is not compatible with one or more subtilisin variant described herein suitable methods of keeping the adjunct material(s) and variant(s) separated (i.e., not in contact with each other) can be employed until combination of the two components is appropriate. Such separation methods include any suitable method known in the art (e.g., gelcaps, encapsulation, tablets, physical separation, etc.). The aforementioned adjunct materials may constitute the balance of the cleaning compositions described herein.

One or more cleaning composition described herein is advantageously employed for example, in laundry applications, hard surface cleaning applications, dishwashing applications, including automatic dishwashing and hand dishwashing, as well as cosmetic applications such as dentures, teeth, hair and skin cleaning and disinfecting applications, such as, for example, but not limited to, disinfecting an automatic dishwashing or laundry machine. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

Another embodiment is directed to a composition comprising one or more subtilisin variant described herein. In some embodiments, the composition is a cleaning composition. In other embodiments, the composition is a detergent composition. In yet other embodiments, the composition is selected from a laundry detergent composition, an automatic dishwashing (ADW) composition, a hand (manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW composition, or a hand (manual) dishwashing detergent composition. Even still further embodiments are directed to fabric cleaning compositions, while other embodiments are directed to non-fabric cleaning compositions. In some embodiments, the cleaning composition is boron-free. In other embodiments, the cleaning composition is phosphate-free. In still other embodiments, the composition comprises one or more subtilisin variant described herein and one or more of an excipient, adjunct material, and/or additional enzyme.

In yet still a further embodiment, the composition described herein contains phosphate, is phosphate-free, contains boron, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, a boron-free composition is a composition substantially-free of boron.

One or more subtilisin variant described herein also finds use in cleaning additive products. In some embodiments, low temperature solution cleaning applications find use. Some embodiments provide cleaning additive products comprising one or more subtilisin variant described herein, which additive is ideally suited for inclusion in a wash process when additional bleaching effectiveness is desired. Such instances include, but are not limited to low temperature solution cleaning applications. In some embodiments, the additive product is in its simplest form, one or more subtilisin variant described herein. In some embodiments, the additive is packaged in dosage form for addition to a cleaning process. In some embodiments, the additive is packaged in dosage form for addition to a cleaning process where a source of peroxygen is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In another embodiment, one or more composition described herein is in a form selected from gel, tablet, powder, granular, solid, liquid, unit dose, and combinations thereof. In yet another embodiment, one or more composition described herein is in a form selected from a low water compact formula, low water HDL or UD, or high water formula or HDL. In some embodiments, the cleaning composition describe herein is in a unit dose form. In other embodiments, the unit does form is selected from pills, tablets, capsules, gelcaps, sachets, pouches, multi-compartment pouches, and pre-measured powders or liquids. In some embodiments, the unit dose format is designed to provide controlled release of the ingredients within a multi-compartment pouch (or other unit dose format). Suitable unit dose and controlled release formats are described, for example, in EP2100949; WO 02/102955; U.S. Pat. Nos. 4,765,916; 4,972,017; and WO 04/111178. In some embodiments, the unit dose form is a tablet or powder contained in a water-soluble film or pouch.

The present cleaning compositions or cleaning additives comprise an effective amount of one or more subtilisin variant described herein, alone or in combination with one or more additional enzyme. Typically the present cleaning compositions comprise at least about 0.0001 weight percent, from about 0.0001 to about 10, from about 0.001 to about 1, or from about 0.01 to about 0.1 weight percent of one or more subtilisin variant described herein. In another embodiment, one or more cleaning composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 2 mg, about 0.1 to about 1 mg, or about 0.1 to about 0.5 mg of one or more subtilisin variant described herein per gram of composition.

In some embodiments, one or more subtilisin variant described herein cleans at low temperatures. In other embodiments, one or more composition described herein cleans at low temperatures. In other embodiments, one or more composition described herein comprises an effective amount of one or more subtilisin variant described herein as useful or effective for cleaning a surface in need of proteinaceous stain removal.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. Some embodiments provide one or more cleaning composition formulated to have an alkaline pH under wash conditions, such as a pH of from about 8.0 to about 12.0, or from about 8.5 to about 11.0, or from about 9.0 to about 11.0. In some embodiments, one or more cleaning composition described herein is formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when one or more subtilisin variant described herein is employed in a granular composition or liquid, it is desirable for the variant to be in the form of an encapsulated particle to protect the variant from other components of the granular composition during storage. In addition, encapsulation is also a means of controlling the availability of the variant during the cleaning process. In some embodiments, encapsulation enhances the performance of variant and/or additional enzymes. In this regard, one or more subtilisin variant described herein is encapsulated with any suitable encapsulating material known in the art. In some embodiments, the encapsulating material typically encapsulates at least part of the variant. Typically, the encapsulating material is water-soluble and/or water-dispersible. In some embodiments, the encapsulating material has a glass transition temperature (Tg) of 0° C. or higher. Tg is described in more detail in WO97/11151. The encapsulating material is typically selected from carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM6545, PM6550, PM7220, PM7228, EXTENDOSPHERES®, LUXSIL®, Q-CEL®, and SPHERICEL® (PQ Corp., Valley Forge, Pa.).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

In some embodiments, one or more subtilisin variant described herein shows surprising wash performance in at least one set of wash conditions (e.g., water temperature, water hardness, and/or detergent concentration). In some embodiments, one or more subtilisin variant described herein is comparable in wash performance to other serine protease polypeptide proteases. In some embodiments, one or more subtilisin variant described herein exhibits enhanced oxidative stability, enhanced thermal stability, enhanced cleaning capabilities under various conditions, and/or enhanced chelator stability.

Other embodiments are directed to one or more cleaning composition comprising from about 0.00001% to about 10% by weight composition of one or more subtilisin variant described herein and from about 99.999% to about 90.0% by weight composition of one or more adjunct material. Other embodiments provide one or more cleaning composition comprises from about 0.0001% to about 10%, about 0.001% to about 5%, about 0.001% to about 2%, about 0.005% to about 0.5% by weight composition of one or more subtilisin variant described herein and from about 99.9999% to about 90.0%, about 99.999% to about 98%, about 99.995% to about 99.5% by weight composition of one or more adjunct material.

In other embodiments, the composition described herein comprises one or more subtilisin variant described herein and one or more additional enzyme. The one or more additional enzyme is selected from additional serine proteases, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, non-serine proteases, oxidases, pectate lyases, pectin acetyl esterases, pectinases, pentosanases, perhydrolase, peroxidases, phenoloxidases, phosphatases, phospholipases, phytases, polygalacturonases, pullulanases, reductases, rhamnogalacturonases, beta-glucanases, tannases, transglutaminases, xylan acetyl-esterases, xylanases, xyloglucanases, and xylosidases, or any combinations or mixtures thereof. Some embodiments are directed to a combination of enzymes (i.e., a "cocktail") comprising conventional enzymes like amylase, lipase, cutinase and/or cellulase in conjunction with one or more subtilisin variant described herein and/or one or more additional serine protease.

In another embodiment, one or more composition described herein comprises one or more subtilisin variant described herein and one or more additional protease. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Exemplary additional proteases include but are not limited to those described in WO92/21760, WO95/23221, WO2008/010925, WO09/149200, WO09/149144, WO09/149145, WO 10/056640, WO10/056653, WO2010/0566356, WO11/072099, WO2011/13022, WO11/140364, WO 12/151534, WO2015/038792, WO2015/089447, WO2015/089441, US Publ. No. 2008/0090747, U.S. Pat. Nos. 5,801,039, 5,340,735, 5,500,364, 5,855,625, RE 34,606, 5,955,340, 5,700,676 6,312,936, 6,482,628, 8,530, 219, U.S. Provisional Appl Nos. 62/180,673 and 62/161, 077, and PCT Appl Nos. PCT/US2015/021813, PCT/US2015/055900, PCT/US2015/057497, PCT/US2015/057492, PCT/US2015/057512, PCT/US2015/057526, PCT/US2015/057520, PCT/US2015/057502, PCT/US2016/022282, and PCT/US16/32514, as well as metalloproteases described in WO1999014341, WO1999033960, WO1999014342, WO1999034003, WO2007044993, WO2009058303, WO 2009058661, WO2014071410, WO2014194032, WO2014194034, WO 2014194054, and WO 2014/194117. Additional protease examples include, but are not limited to trypsin (e.g., of porcine or bovine origin), and the *Fusarium* protease described in WO89/06270. Exemplary commercial proteases include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, BLAZE®, BLAZE® EVITY®, BLAZE® EVITY® 16L, CORONASE®, SAVINASE®, SAVINASE® ULTRA, SAVINASE® EVITY®, SAVINASE® EVERIS®, PRIMASE®, DURAZYM™, POLARZYME®, OVOZYME®, KANNASE®, LIQUANASE®, LIQUANASE EVERIS®, NEUTRASE®, RELASE® and ESPERASE® (Novozymes); BLAP™ and BLAP™ variants (Henkel); and KAP (*B. alkalophilus* subtilisin (Kao). Exemplary metalloproteases include nprE, the recombinant form of neutral metalloprotease expressed in *B. subtilis* (See e.g., WO07/044993), and PMN, the purified neutral metalloprotease from *B. amyloliquefaciens.*

Another embodiment is directed to a composition comprising one or more subtilisin variant described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. Exemplary lipases include, but are not limited to those of bacterial or fungal origin. An exemplary lipase can be a chemically or genetically modified mutant. Exemplary lipases include, but are not limited to *H. lanuginosa* lipase (See e.g., EP258068 and EP305216), *Rhizomucor miehei* lipase (See e.g., EP 238 023), *Candida* lipase, such as *C. antarctica* lipase (e.g., the *C. antarctica* lipase A or B; See e.g., EP214761), *Pseudomonas* lipases such as *P. alcaligenes* and *P. pseudoalcaligenes* lipase (See e.g., EP218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase (See e.g., WO91/16422). Exemplary cloned lipases include, but not limited to *Penicillium camembertii* lipase (See, Yamaguchi et al., Gene 103:61-67 [1991]), *Geotricum candidum* lipase (See, Schimada et al., J. Biochem., 106: 383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]), and *R. oryzae* lipase. Other types of lipase polypeptide enzymes such as cutinases may also find use in some embodiments, including but not limited to the cutinase derived from *Pseudomonas mendocina* (See, WO88/09367), and the cutinase derived from *Fusarium solani pisi* (See, WO90/09446). Exemplary commercial lipases include, but are not limited to M1 LIPASE™, LUMA FAST™, and LIPOMAX™ (DuPont); LIPEX®, LIPOCLEAN®, LIPOLASE® and LIPOLASE® ULTRA (Novozymes); and LIPASE PM (Amano Pharmaceutical Co. Ltd).

A still further embodiment is directed to a composition comprising one or more subtilisin variant described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, DURAMYL®, TERMAMYL®, FUNGAMYL®, STAINZYME®, STAINZYME PLUS®, STAINZYME PLUS®, STAINZYME ULTRA® EVITY®, and BAN™ (Novozymes); EFFECTENZ™ S 1000, POWERASE™, PREFERENZ™ S 100, PREFERENZ™ S 110, EXCELLENZ™ S 2000, RAPIDASE® and MAXAMYL® P (DuPont).

Yet a still further embodiment is directed to a composition comprising one or more subtilisin variant described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find used in a composition described herein. An exemplary cellulase can be a chemically or genetically modified mutant. Exemplary cellulases include but are not limited, to those of bacterial or fungal origin, such as, for example, is described in WO2005054475, WO2005056787, U.S. Pat. Nos. 7,449,318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ™ 100, REVITALENZ™ 200/220, and REVITALENZ® 2000 (DuPont); and KAC-500(B)™ (Kao Corporation). In some embodiments, cellulases are incorporated as portions or fragments of mature wild-type or variant cellulases, wherein a portion of the N-terminus is deleted (see, e.g., U.S. Pat. No. 5,874,276).

An even still further embodiment is directed to a composition comprising one or more subtilisin variant described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO 2016/007929; U.S. Pat. Nos. 6,566,114; 6,602,842; and 6,440,991: and U.S. Provisional Appl. Nos. 62/251,516, 62/278,383, and 62/278,387. Exemplary commercial mannanases include, but are not limited to MANNAWAY® (Novozymes) and EFFECTENZ™ M 1000, PREFERENZ® M 100, MANNASTAR®, and PURABRITE™ (DuPont).

A yet even still further embodiment is directed to a composition comprising one or more subtilisin variant described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO94/12621 and WO95/01426). An exemplary peroxidase and/or oxidase can be a chemically or genetically modified mutant. Exemplary peroxidases/oxidases include, but are not limited to those of plant, bacterial, or fungal origin.

In some embodiments, additional enzymes find use, including but not limited to perhydrolases (See e.g., WO2005/056782, WO2007106293, WO2008063400, WO 2008106214, and WO2008106215).

In yet another embodiment, the one or more subtilisin variant described herein and one or more additional enzyme contained in one or more composition described herein may each independently range to about 10%, wherein the balance of the cleaning composition is one or more adjunct material.

In some embodiments, an effective amount of one or more subtilisin variant provided herein is included in compositions useful for cleaning a variety of surfaces in need of proteinaceous stain removal. Such cleaning compositions include cleaning compositions for such applications as cleaning hard surfaces, fabrics, and dishes. Indeed, some embodiments provide fabric cleaning compositions; while other embodiments provide non-fabric cleaning compositions. Some embodiment also provide cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein one or more subtilisin variant described herein finds use are described in greater detail below. In some embodiments, the cleaning composition is formulated for use in laundry machine washing method(s), wherein the composition contains at least one surfactant and at least one builder compound, as well as one or more adjunct material selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as an additional adjunct material).

The compositions described herein also find use in detergent additive products in solid or liquid form. Such additive products are intended to supplement and/or boost the performance of a conventional detergent composition and can be added at any stage of the cleaning process. In some embodiments, the density of the laundry detergent compositions herein ranges from about 400 to about 1200 g/liter, while in other embodiments it ranges from about 500 to about 950 g/liter of composition measured at 20° C.

In embodiments formulated as compositions for use in manual dishwashing methods, the compositions contain at least one surfactant and at least one additional adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with one or more subtilisin variant described herein. Thus, in some embodiments, the compositions comprising one or more subtilisin variant described herein is a compact granular fabric cleaning composition. In other embodiments, the composition is a granular fabric cleaning composition useful in the laundering of colored fabrics. In further embodiments, the composition is a granular fabric cleaning composition which provides softening through the wash capacity. In additional embodiments, the composition is a heavy duty liquid fabric cleaning composition. In some embodiments, the compositions comprising one or more subtilisin variant described herein are fabric cleaning compositions such as those described in U.S. Pat. Nos. 6,610,642 and 6,376,450. In addition, one or more subtilisin variant described herein finds use in granular laundry detergent compositions of particular utility under European or Japanese washing conditions (See e.g., U.S. Pat. No. 6,610,642).

Yet further embodiments provide a dishwashing composition comprising one or more subtilisin variant described herein. Thus, in some embodiments, a composition comprising one or more subtilisin variant described herein is a hard surface cleaning composition such as those in U.S. Pat. Nos. 6,610,642 and 6,376,450. Some further embodiments provide an oral care composition comprising one or more subtilisin variant described herein such as those in U.S. Pat. Nos. 6,376,450, and 6,376,450.

One or more cleaning composition described herein can be formulated into any suitable form and prepared by any process chosen by the formulator (See e.g., U.S. Pat. Nos. 5,879,584; 5,691,297; 5,574,005; 5,569,645; 5,565,422; 5,516,448; 5,489,392; and 5,486,303. When a low pH cleaning composition is desired, the pH of such composition is adjusted via the addition of a material such as monoethanolamine or an acidic material such as HCl.

In some embodiments, one or more cleaning composition described herein comprises an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N($CH_2COOM$)$_2$ where R is $C_{112}$ alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400 to about 1200 and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle is a highly active particle comprising a high level of amino carboxylic builder. Sulphuric acid has been found to further contribute to the stability of the final particle.

In some embodiments, one or more cleaning composition described herein comprises at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, one or more cleaning composition described herein comprises one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in one or more embodiment described herein.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in one or more composition described herein, including those known in the art (See e.g., EP 2 100 949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, one or more composition described herein contains at least one chelating agent. Suitable chelating agents include, but are not limited to copper, iron and/or manganese chelating agents and mixtures thereof. In embodiments in which at least one chelating agent is used, the cleaning compositions comprise from about 0.1% to about 15% or even from about 3.0% to about 10% chelating agent by weight composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

In some embodiments, anti-redeposition agents find use in some embodiments described herein. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949). In some embodiments, the non-ionic surfactant can be ethoxylated nonionic surfactants, epoxy-capped poly(oxyalkylated) alcohols and amine oxides surfactants.

In some embodiments, one or more cleaning composition described herein includes one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning composition comprises from about 0.0001% to about 10%, from about 0.01% to about 5%, or even from about 0.1% to about 3% by weight composition.

In some embodiments, silicates are included in one or more composition described herein. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, one or more cleaning composition described herein contains a dispersant. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in one or more composition described herein are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO07/145964). In some embodiments, reversible protease inhibitors also find use, such as boron-containing compounds (e.g., borate, 4-formyl phenyl boronic acid, and phenyl-boronic acid derivatives (such for example, those described in WO96/41859) and/or a peptide aldehyde, such as, for example, is further described in WO2009/118375 and WO2013004636.

In some embodiments, bleaches, bleach activators and/or bleach catalysts are present in one or more composition described herein. In some embodiments, one or more composition described herein comprises inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use herein (See e.g., EP 2 100 949).

In some embodiments, bleach activators are used in one or more composition described herein. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use herein (See e.g., EP2100 949).

In addition, in some embodiments and as further described herein, one or more composition described herein further comprises at least one bleach catalyst. In some embodiments, the manganese triazacyclononane and related complexes find use, as well as cobalt, copper, manganese, and iron complexes. Additional bleach catalysts find use herein (See e.g., U.S. Pat. Nos. 4,246,612; 5,227,084; 4,810,410, WO 99/06521, and EP2100949).

In some embodiments, one or more composition described herein contains one or more catalytic metal complexes. In some embodiments, a metal-containing bleach catalyst finds use herein. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, one or more composition described herein is catalyzed by means of a manganese compound. Such compounds and levels of use are well known in the art (See e.g., U.S. Pat. No. 5,576,282). In additional embodiments, cobalt bleach catalysts find use in one or more composition described herein. Various cobalt bleach catalysts are known in the art (See e.g., U.S. Pat. Nos. 5,597,936 and 5,595,967) and are readily prepared by known procedures.

In some additional embodiments, one or more composition described herein includes a transition metal complex of a macropolycyclic rigid ligand (MRL). As a practical matter, and not by way of limitation, in some embodiments, one or more composition and cleaning processes described herein are adjusted to provide on the order of at least one part per hundred million of the active MRL species in the aqueous washing medium, and in some embodiments, provides from about 0.005 ppm to about 25 ppm, from about 0.05 ppm to about 10 ppm, or from about 0.1 ppm to about 5 ppm of the MRL in the wash liquor. In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO2000/32601, and U.S. Pat. No. 6,225,464).

In some embodiments, one or more composition described herein comprises metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2100949, WO 9426860 and WO94/26859). In some embodiments, the metal care agent is a zinc salt. In some further embodiments, one or more composition described herein comprises from about 0.1% to about 5% by weight of one or more metal care agent.

In some embodiments, the cleaning composition is a high density liquid (HDL) composition comprising one or more subtilisin variant described herein. The HDL liquid laundry detergent can comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may optionally include enzymes (generally about 0.01 wt % active enzyme to 0.5 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof.

In some embodiments, one or more composition described herein is provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2100949, WO 02/102955, U.S. Pat. Nos. 4,765,916, 4,972,017, and WO 04/111178 for materials suitable for use in unit dose and controlled release formats). In some embodiments, the unit dose form is provided by tablets wrapped with a water-soluble film or water-soluble pouches. Various unit dose formats are provided in EP2100947 and WO2013/165725 and are known in the art.

In some embodiments, the cleaning composition is a high density powder (HDD) composition having a variant serine protease polypeptide protease. The HDD powder laundry detergent can comprise a detersive surfactant including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines); ampholytic surfactants; semi-polar non-ionic surfactants and mixtures thereof; builders (phosphate free builders (e.g., zeolite builders examples of which include zeolite A, zeolite X, zeolite P and zeolite MAP in the range of 0 wt % to less than 10 wt %]; phosphate builders [examples of which include sodium tri-polyphosphate in the range of 0 wt % to less than 10 wt %]; citric acid, citrate salts and nitrilotriacetic acid or salt thereof in the range of less than 15 wt %); silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 10 wt %); and bleaching agents (including photobleaches, (e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); sources of hydrogen peroxide (e.g., inorganic perhydrate salts examples of which include mono or tetra hydrate sodium salt of perborate, percarbonate, persulfate, perphosphate, or persilicate); preformed hydrophilic and/or hydrophobic peracids (e.g., percarboxylic acids and salts, percarbonic acids and salts, perimidic acids and salts, peroxymonosulfuric acids and salts), and mixtures thereof and/or bleach catalysts (e.g., imine bleach boosters (e.g., iminium cations and polyions); iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; and metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further include enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators-organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

Representative detergent formulations that can include one or more subtilisin variant described herein can be found in WO2013063460, pages 78-152, and in particular the tables of pages 94 to 152. Serine proteases are typically incorporated into a detergent composition at a level of from 0.00001% to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

Also provided are compositions and methods of treating fabrics (e.g., to desize a textile) using one or more subtilisin variant described herein. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

One or more subtilisin variant described herein can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. One or more subtilisin variant described herein can be applied during or after the weaving to remove these sizing starch or starch derivatives. After weaving, one or more subtilisin variant described herein can be used to remove the size coating before further processing the fabric to ensure a homogeneous and wash-proof result.

One or more subtilisin variant described herein can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

One or more subtilisin variant described herein finds further use in the enzyme aided removal of proteins from animals and their subsequent degradation or disposal, such as feathers, skin, hair, hide, and the like. In some instances, immersion of the animal carcass in a solution comprising one or more subtilisin variant described herein can act to protect the skin from damage in comparison to the traditional immersion in scalding water or the defeathering process. In one embodiment, feathers can be sprayed with one or more subtilisin variant described herein under conditions suitable for digesting or initiating degradation of the plumage. In some embodiments, one or more subtilisin variant described herein can be used, as above, in combination with an oxidizing agent.

In some embodiments, removal of the oil or fat associated with raw feathers is assisted by using one or more subtilisin variant described herein. In some embodiments, the serine protease polypeptides are used in compositions for cleaning the feathers as well as to sanitize and partially dehydrate the fibers. In yet other embodiments, one or more subtilisin variant described herein find use in recovering protein from plumage. In some other embodiments, the serine protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

In a further aspect of the invention, one or more subtilisin variant described herein can be used as a component of an animal feed composition, animal feed additive and/or pet food. Another embodiment relates to a method for preparing such an animal feed, animal feed additive and/or pet food composition comprising mixing one or more subtilisin variant described herein with one or more animal feed ingredient and/or animal feed additive ingredient and/or pet food ingredient. Furthermore, one or more subtilisin variant described herein may be used in the preparation of an animal feed and/or animal feed additive and/or pet food composition.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

One or more subtilisin variant described herein finds further use in the enzyme aided bleaching of paper pulps such as chemical pulps, semi-chemical pulps, kraft pulps, mechanical pulps or pulps prepared by the sulfite method. In general terms, paper pulps are incubated with one or more subtilisin variant described herein under conditions suitable for bleaching the paper pulp. In some embodiments, the pulps are chlorine free pulps bleached with oxygen, ozone, peroxide or peroxyacids. In some embodiments, the subtilisin variants are used in enzyme aided bleaching of pulps produced by modified or continuous pulping methods that exhibit low lignin contents. In some other embodiments, the subtilisin variants are applied alone or preferably in combination with xylanase and/or endoglucanase and/or alpha-galactosidase and/or cellobiohydrolase enzymes.

One or more subtilisin variant described herein finds further use in the enzyme aided debridement of tissue. This involves the removal of dead or damaged tissue, for example, removal from wounds to aid in healing.

One or more subtilisin variant described herein finds further use in tissue culture. In particular, one or more subtilisin variant described herein can be used to suspend or resuspend cells adherent to a cell culture wall, such as during the process of harvesting cells. One or more subtilisin variant described herein can be used to cleave protein bonds between cultured cells and the dish, allowing cells to become suspended in solution.

One or more subtilisin variant described herein find further use as a food additive, a digestive aide, or a food processing aid.

EXAMPLES

The following examples are provided to demonstrate and illustrate certain preferred embodiments and aspects of the present disclosure and should not be construed as limiting.

In the experimental disclosure which follows, the following abbreviations apply: ADW (automatic dish washing); BMI (blood, milk and ink), BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PAS (polyacryl swatches); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); w/v (weight to volume).

Example 1

Heterologous Expression of *B. gibsonii*-Clade Subtilisins

DNA manipulations to generate *B. gibsonii*-clade subtilisins were carried out using conventional molecular biology techniques (see, e.g., Sambrook et al, Molecular Cloning: Cold Spring Harbor Laboratory Press). All subtilisins were expressed and recovered as described in the subsequent examples. A series of artificial DNA sequences were generated, coding for mature *B. gibsonii*-clade subtilisin sequences that introduce multiple amino acid modifications into the sequence of the wildtype *B. gibsonii*-clade Bgi02446 protease, which wildtype protease is more fully described in International Patent Application No. PCT/US2014/070107, and as AprBG in Deng et al. *J. Microbiol. Biotechnol.* (2014), 24(2), 197-198 (accession number AGS78407.1).

Example 2

Expression of *B. gibsonii*-Clade BSP-00801 of Mature Subtilisin Using Either the Native Bgi02446 Propeptide Sequence, or the Propeptide Sequence from *B. lentus* Subtilisin The processed mature enzyme BSP-00801, expressed under the control of *B. lentus* pro-sequence (SEQ ID NO:5), was characterized and showed the amino acid sequence to be 269 amino acids with QQ at the N-terminus (SEQ ID NO:18 for the amino acid sequence and SEQ ID NO: 15 for the nucleotide sequence). The processed mature enzyme of BSP-00801, expressed under the control of the Bgi02446 pro-sequence (SEQ ID NO:4), was characterized and showed the amino acid sequence to be 268 amino acids with a single Q at the N-terminus (SEQ ID NO:20). The amino acid sequence of the preproenzyme of BSP-00801 is SEQ ID NO:16. The amino acid sequence of the proenzyme is SEQ ID NO:17.

The processed mature enzyme Bgi02446, expressed under the control of *B. lentus* pro-sequence (SEQ ID NO:5), was characterized and showed the amino acid sequence to be 269 amino acids with QQ at the N-terminus (SEQ ID NO:85). The processed mature enzyme of Bgi02446, expressed under the control of the Bgi02446 pro-sequence (SEQ ID NO:4), was characterized and showed the amino acid sequence to be 268 amino acids with a single Q at the N-terminus (SEQ ID NO:19).

The amino acid sequences of the processed mature enzymes identified in Tables 3, 4, and 5 were expressed under the control of the Bgi02446 pro-sequence and, based on the knowledge of the pro-mature junction in homologous serine proteases such as BPN' (Wells et al., 1983. Nucleic Acids Res, 11: 7911-25), and PB92 protease (van der Laan et al. 1991. Appl Environ Microbiol, 57:901-909), were predicted to be 269 amino acid with a QQTVP at the N-terminus, but instead QTVP was observed.

The processed mature enzyme BSP-00801 (SEQ ID NO: 18) used in Example 5 was expressed under the control of *B. lentus* pro-sequence (SEQ ID NO:5) in accordance with the process that follows. A more detailed description of the process for expressing BSP-00801 mature enzyme via the Bgi02446 pro-sequence and the *B. lentus* pro-sequence is set forth in U.S. Provisional Patent Application No. 62/181,192, filed Jun. 17, 2015.

DNA cassettes comprising *B. subtilis* aprE promoter (SEQ ID NO: 1), the *B. subtilis* aprE signal peptide sequence (SEQ ID NO:2 for nucleotide sequence and SEQ ID NO:3 for the amino acid sequence), the pro sequence from either *B. gibsonii* Bgi02446 (SEQ ID NO:4) or from *B. lentus* (SEQ ID NO:5), and the sequence corresponding to the gene for *B. gibsoni*-clade subtilisin BSP-00801 (SEQ ID NO:6) were synthesized by amplification using primers listed on Table 1. Using techniques known in the art, PCR fragments were assembled using Gibson Assembly (SGI DNA Cat #GA1100-10) to make the final expression cassettes. The cells were transformed and grown on skim milk plates under chloramphenicol selection.

TABLE 1

Primers used to construct expression cassettes encoding Bgi02446 pro-peptide or *B. lentas* pro-peptide fusions to *B. gibsoni*-clade subtilisin BSP-00801 mature gene.

| Primer | Sequence | SEQ ID NO: |
|---|---|---|
| EL1664 | GAGGATGCAGAAGTAACGACAATGCAACAAACAGTGCCATGG | 7 |
| EL1665 | CCAAGGCCGGTTTTTTATGTATCTAGATTAGCGTGTTGCCGCTTCTG CATTG | 8 |
| EL1666 | GAAGAAGACATTGAACTGTCTATTCAACAAACAGTGCCATGG | 9 |
| EL1667 | CAATGCAGAAGCGGCAACACGCTAATCTAGATACATAAAAAACCG GCCTTGG | 10 |
| EL1668 | CCATGGCACTGTTTGTTGCATTGTCGTTACTTCTGCATCCTC | 11 |
| EL1669 | CCATGGCACTGTTTGTTGAATAGACAGTTCAATGTCTTCTTC | 12 |

The *B. gibsonii*-clade subtilisins set forth in Tables 3, 4, and 5 were produced in *B. subtilis* using an expression cassette consisting of the *B. subtilis* aprE promoter, the *B. subtilis* aprE signal peptide sequence (SEQ ID NO:3), the Bgi02446 pro-sequence, the mature protease sequences for each of the artificial sequences, and a BPN' terminator. Each expression cassette was cloned into the pHYT replicating shuttle vector and transformed into a suitable *B. subtilis* strain. The pHYT vector was derived from pHY300PLK (Takara) by adding a terminator (SEQ ID NO:13) after the tetracycline resistance gene using the BstEII and EcoRI sites. The HindIII site in pHY300PLK was also removed using a linker (SEQ ID NO: 14) cloned into the BamHI and HindIII sites.

To produce the *B. gibsonii*-clade subtilisins set forth in Tables 3, 4, and 5, the *B. subtilis* host strains transformed with the various pHYT plasmids were cultivated in an enriched semi-defined media based on MOPs buffer, with urea as major nitrogen source, glucose as the main carbon source, and supplemented with 1% soytone for robust cell growth. After incubation, the secreted proteases were isolated from the growth medium by centrifugation and filtration. Clarified culture supernatants were used for assays and purification as described below.

Example 3

Protease Activity of *B. gibsonii*-Clade Subtilisins

The protease activity of Bgi02446 and *B. gibsonii*-clade subtilisins set forth in Tables 3, 4, and 5 were tested by measuring the hydrolysis of dimethyl casein (DMC) substrate. The reagent solutions used for the DMC assay were: 2.5% w/v DMC (Sigma C-9801) in 100 mM sodium carbonate buffer pH 9.5, 0.075% TNBSA (Thermo Scientific) in Reagent A. Reagent A: 45.4 g $Na_2B_4O_7.10H_2O$ (Merck) in 15 mL 4 N NaOH to reach a final volume of 1000 mL in deionised water. Protease supernatants were diluted in dilution solution: 10 mM NaCl, 0.1 mM $CaCl_2$, 0.005% Tween-80 to the desired concentration to achieve a linear response during hydrolysis over 5 min. A 96-well microtiter plate (MTP) was filled with 95 μl DMC substrate followed by the addition of 5i1 diluted protease supernatant. 100 μL of TNBSA in Reagent A was then added with slow mixing. Activity was measured at 405 nm over 5 min using a SpectraMax plate reader in kinetic mode at RT. The absorbance of a blank containing no protease was subtracted from each sample reading. The protease activity was expressed as mOD/min.

The protease activity of Bgi02446 and *B. gibsonii*-clade subtilisins set forth in Table 7 was tested by measuring hydrolysis of N-suc-AAPF-pNA or dimethyl casein (DMC). The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a substrate working solution, 1 ml suc-AAPF-pNA stock solution was added to 100 ml Tris/Ca buffer and mixed well. An enzyme sample was added to a MTP plate (Greiner 781101) containing 1 mg/suc-AAPF-pNA working solution and assayed for activity at 405 nm over 3 minutes using a SpectraMax plate reader in kinetic mode at RT. The absorbance of a blank containing no protease was subtracted from each sample reading. The protease activity was expressed as mOD $min^{-1}$.

Example 4

Measurement of Cleaning Performance and Stability of *B. gibsonii*-Clade Subtilisins The concentration of the proteases in culture supernatant was determined by UHPLC using a Zorbax 300 SB-C3 column. Culture supernatant was diluted appropriately in dilution buffer (Tris 25 mM, pH 7.4, 5 mM $CaCl_2$). The samples were eluted from the column with a gradient of Buffer A (0.1% Trifluoroacetic acid) and Buffer B (0.07% Acetonitrile). The protein concentration of the samples was calculated based on a standard curve of the purified parent enzyme.

The cleaning performance of each *B. gibsonii*-clade protease was measured in dish based applications (ADW) using GSM-B formula (see Table 2), pH 10.5 and egg yolk microswatches (PAS-38, Center for Testmaterials BV, Vlaardingen, Netherlands). The pre-punched PAS-38 swatches that were used in the ADW performance assays were either rinsed or unrinsed. To prepare rinsed PAS38 swatches, 180 μl 10 mM CAPS buffer of pH 11 was added to MTPs containing PAS38 microswatches. The plates were sealed and incubated in an iEMS incubator for 30 min at 60° C. and 1100 rpm shaking. After incubation the buffer was removed, and the swatches were rinsed with deionized water to remove any residual buffer. The plates were air dried prior to use in the performance assay. The microswatch plates were filled prior to enzyme addition with 3 g/l GSM-B solution in 374 ppm water hardness.

Laundry (HDL) cleaning performance of each *B. gibsonii*-clade protease was tested using BMI microswatches (blood/milk/ink on cotton) (EMPA-116, Center for Testmaterials BV, Vlaardingen, Netherlands). Pre-punched (to fit on MTP) and filled microswatch-containing plates were used. The microswatch plates were filled prior to enzyme addition with 2.7 g/l Persil Non-Bio (Unilever) liquid detergent in 250 ppm water hardness, which is a commercial liquid detergent that does not contain boron or enzymes and which was purchased for use in this test.

Following incubation (PAS-38 swatches incubated for 30 minutes at 40° C. and EMPA116 swatches incubated for 15 minutes at 25° C.), absorbance was read at 405 nm for EMPA-116 and PAS-38 swatches, using the SpectraMax plate reader. Absorbance results were obtained by subtracting the value for a blank control (no enzyme) from each sample value (hereinafter "blank subtracted absorbance"). For each condition and *B. gibsonii*-clade protease, a performance index (PI) was calculated by dividing the blank subtracted absorbance by that of the parent protease at the same concentration. The value for the parent protease was determined from a standard curve of the parent protease which was included in the test and which was fitted to a Langmuir fit or Hill Sigmoidal fit.

TABLE 2

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

To measure the stability, appropriate dilutions of *B. gibsonii*-clade proteases were made in stress buffer. The proteolytic activity of the proteases was subsequently measured before and after a heat incubation step using the DMC assay described in Example 3. The temperature and duration of the heat incubation step were chosen such that the reference protease showed ~30% residual activity. Stability was measured in Tris-EDTA (50 mM Tris pH9; 1 mM EDTA; 0.005% Tween) buffered condition. % Residual activities were calculated by taking a ratio of the stressed to unstressed activity and multiplying by 100. Stability PIs were obtained by dividing the residual activity of the *B. gibsonii*-clade protease by that of the parent protease.

*B. gibsoni*-clade subtilisin BSP-00801, shown on Table 4, was utilized as a parent protease and subjected to further mutagenesis to provide the BSP-00801 variants set forth in Table 5. ND as utilized in the Tables set forth hereinbelow means not determined.

TABLE 3

Cleaning Performance And Stability of *B. gibsonii*-clade Subtilisins

| | | PI versus Bgi02446 | | | | |
|---|---|---|---|---|---|---|
| *B. gibsonii*-clade Subtilisin | Mutations With Respect To Bgi02446 | ADW pH 10.5 Rinsed Egg stain | ADW pH 10.5 Unrinsed Egg Stain | Stability in EDTA | Boron-free HDL pH 8.2, BMI Stain | Amino Acid SEQ ID NO: |
| BSP-02389 | N074D-I080V-N085S-E087D-S099R-V102I-S158T-V159I-N242D-F257Y | 1.3 | 5.3 | 1.5 | 0.9 | 98 |
| BSP-02411 | N074D-N085S-E087D-S099R-V102I-S126T-F128A-I190L-N242D-F257Y | 1.5 | 5.0 | 1.4 | 1.2 | 103 |
| BSP-02301 | R027K-S099R-V102I-T114Q-I119V-S126T-F128A-S158T-V159I-G160S-T188A-N242D | 1.4 | 4.9 | 2.7 | 1.0 | 106 |

TABLE 3-continued

Cleaning Performance And Stability of *B. gibsonii*-clade Subtilisins

| *B. gibsonii*-clade Subtilisin | Mutations With Respect To Bgi02446 | PI versus Bgi02446 ADW pH 10.5 Rinsed Egg stain | ADW pH 10.5 Unrinsed Egg Stain | Stability in EDTA | Boron-free HDL pH 8.2, BMI Stain | Amino Acid SEQ ID NO: |
|---|---|---|---|---|---|---|
| BSP-03033 | N074D-I080V-N085S-E087D-S099R-V102I-T114Q-S126T-F128A-N242D | 1.4 | 4.7 | 1.1 | 1.0 | 114 |
| BSP-03027 | R027K-S099R-V102I-S126T-F128A-R143A-S158T-V159I-G160S | 1.2 | 4.6 | 2.2 | 0.7 | 107 |
| BSP-03007 | N074D-I080V-N085S-E087D-S099R-V102I-I190L-N242D-F257Y | 1.2 | 4.5 | 1.4 | 0.6 | 102 |
| BSP-02380 | N074D-I080V-N085S-E087D-S099R-V102I-T114Q-R143A-I190L-N242D-F257Y | 1.3 | 4.2 | 1.0 | 0.9 | 101 |
| BSP-02195 | N074D-S099R-V102I-S126T-F128A-R143A-S158T-N212S | 1.3 | 4.2 | 7.5 | 0.8 | 104 |
| BSP-03024 | N074D-I080V-N085S-E087D-S099R-T114Q-S126T-F128A-R143A-N242D | 1.3 | 4.1 | 1.4 | 1.2 | 113 |
| BSP-02725 | N085S-E087D-S099R-T114Q-I119V-S126T-F128A-R143A-G160S-F257Y | 1.3 | 4.1 | 1.7 | 0.8 | 111 |
| BSP-02227 | N074D-I080V-S099R-V102I-T114Q-S126T-F128A-R143A-N212S-N242D | 1.4 | 4.0 | 2.4 | 1.1 | 110 |
| BSP-02354 | N074D-I080V-N085S-E087D-S099R-V102I-S126T-F128A-R143A-I190L-N242D-F257Y | 1.4 | 4.0 | 1.5 | 1.1 | 100 |
| BSP-02400 | N074D-I080V-S099R-V102I-T114Q-I119V-S126T-F128A-S158T-G160S-N212S-F257Y | 1.3 | 3.8 | 3.0 | 0.9 | 105 |
| BSP-03048 | I080V-N085S-E087D-S099R-V102I-T114Q-I119V-S126T-F128A-R143A-N242D | 1.3 | 3.7 | 1.6 | 0.8 | 117 |
| BSP-02355 | N085S-E087D-S099R-V102I-T114Q-S158T-V159I-G160S-N212S-N242D-F257Y | 1.0 | 3.6 | 3.9 | 0.6 | 99 |
| BSP-02391 | R027K-N074D-S099R-V102I-T114Q-S126T-F128A-T188A-I190L-N212S-N242D | 1.1 | 3.5 | 3.2 | 0.9 | 109 |
| BSP-02412 | R027K-N074D-S099R-V102I-I119V-S126T-F128A-R143A-G160S-N212S-N242D | 1.3 | 2.9 | 3.1 | 1.1 | 108 |
| BSP-01757 | N042T-I080V-N085S-E087D-T114A-F128A-R143Q-D144G-S158T-V159I-G160S-N198G | 1.2 | 1.6 | 1.6 | ND | 95 |
| BSP-01537 | I021V-I080V-N085S-E087D-M117I-F128A-S131T-R143Q-D144G-A224V | 1.3 | 1.4 | 1.3 | ND | 94 |
| BSP-02320 | N074D-I080V-N085S-E087D-S158T-N242D | 1.2 | 1.2 | 1.1 | 1.4 | 97 |
| BSP-01531 | Q001A-I080V-F128A-S131T-R143A-D144G-M169L-I190L-S254T-S255N-Q256L-F257Y | 1 3 | 1.2 | 2.0 | ND | 96 |

TABLE 4

Cleaning Performance And Stability of *B. gibsonii*-clade Subtilisins

| *B. gibsonii*-clade Subtilisin | Mutations With Respect to Bgi02446 | PI versus Bgi02446 ADW pH 10.5 Rinsed Egg stain | ADW pH 10.5 Unrinsed Egg stain | Stability in EDTA | Boron-free HDL pH 8.2, BMI Stain | Amino acid SEQ ID NO: | Nucleotide SEQ ID NO: |
|---|---|---|---|---|---|---|---|
| BSP-02209 | A037T-S039E-N042T-S099R-V102I-T114Q-S126T-F128A-N242D | 1.7 | 7.2 | 7.9 | 1.0 | 118 | — |
| BSP-02107 | A037T-S039E-S099R-V102I-T114Q-S126T-F128A-R143A-N212S-N242D | 1.5 | 4.7 | 3.9 | 1.1 | 116 | — |
| BSP-02233 | A037T-S039E-N074D-S099R-V102I-S126T-F128A-R143A-N212S-N242D | 1.2 | 2.8 | 3.8 | 1.2 | 117 | — |
| BSP-02235 | A037T-S039E-N042T-N074D-S099R-V102I-S126T-F128A-S158T-N242D | 1.6 | 5.8 | 3.6 | 1.1 | 26 | 25 |
| BSP-00801 | A037T-S039E-I043V-A047V-I080V-N085S-E087D-S099R-T114A-F128A | 1.3 | 4.5 | 2.4 | 0.9 | 18 | 15 |
| BSP-02112 | A037T-S039E-I043V-A047V-T055G-S099R-V102I-T114Q-S126T-F128A-N212S | 1.3 | 4.1 | 3.5 | 0.8 | 120 | — |
| BSP-02508 | A037T-S039E-I043V-A047V-I080V-N085S-E087D-S099R-T114Q-F128A-N242D | 1.6 | 5.4 | 2.3 | 1.1 | 42 | 41 |
| BSP-02513 | A037T-S039E-I043V-A047V-I080V-N085S-E087D-S099R-T114A-F128A-N242D | 1.4 | 4.7 | 1.7 | 1.2 | 138 | — |
| BSP-02542 | A037T-S039E-A047V-I080V-N085S-E087D-S099R-T114Q-F128A-R143A-N242D | 1.4 | 4.8 | 2.6 | 1.5 | 128 | — |
| BSP-02781 | S036A-S039E-I043V-A047V-T055M-I080V-N085S-E087D-S099R-T114A-F128A | 1.3 | 4.4 | 1.8 | 1.1 | 140 | — |
| BSP-03079 | A037T-S039E-I043V-A047V-I080V-N085S-E087D-S099R-V102I-T114Q-F128A | 1.3 | 4.4 | 2.5 | 0.9 | 135 | — |

TABLE 4-continued

Cleaning Performance And Stability of *B. gibsonii*-clade Subtilisins

| | | PI versus Bgi02446 | | | | | |
|---|---|---|---|---|---|---|---|
| *B. gibsonii*-clade Subtilisin | Mutations With Respect to Bgi02446 | ADW pH 10.5 Rinsed Egg stain | ADW pH 10.5 Unrinsed Egg stain | Stability in EDTA | Boron-free HDL pH 8.2, BMI Stain | Amino acid SEQ ID NO: | Nucleotide SEQ ID NO: |
| BSP-02060 | A037T-S039E-I043V-A047V-N074D-N085S-E087D-S099R-T114A-F128A-S158T-N212S | 1.4 | 4.6 | 3.8 | 1.3 | 146 | — |
| BSP-02132 | A037T-S039E-N074D-I080V-N085S-E087D-S099R-V102I-T114Q-S126T-F128A-R143A | 1.7 | 5.6 | 4.1 | 1.6 | 121 | — |
| BSP-02203 | A037T-S039E-I043V-A047V-T055G-N074D-I080V-S099R-V102I-T114Q-S126T-F128A | 1.5 | 5.1 | 3.6 | 1.0 | 24 | 23 |
| BSP-02249 | A037T-S039E-I043V-A047V-N074D-I080V-S099R-V102I-T114Q-S126T-F128A-N242D | 1.6 | 5.8 | 3.8 | 1.0 | 28 | 27 |
| BSP-02310 | R027K-A037T-S039E-A047V-T055G-T056Y-N074D-S099R-V102I-S126T-F128A-N242D | 1.6 | 5.8 | 3.5 | 1.2 | 30 | 29 |
| BSP-02443 | A037T-S039E-N042T-A047V-N074D-I080V-N085S-E087D-S099R-T114Q-F128A-N242D | 1.4 | 4.2 | 4.0 | 1.2 | 124 | — |
| BSP-02471 | A037T-S039E-I043V-A047V-I080V-N085S-E087D-S099R-T114A-S126T-F128A-N212S | 1.2 | 4.3 | 2.8 | 1.1 | 155 | — |
| BSP-02480 | A037T-S039E-I043V-A047V-I080V-N085S-E087D-S099R-T114A-S126T-F128A-N242D | 1.5 | 5.6 | 2.1 | 1.1 | 38 | 37 |
| BSP-02507 | A037T-S039E-I043V-A047V-I080V-N085S-E087D-S099R-T114Q-S126T-F128A-R143A | 1.8 | 6.2 | 2.7 | 1.3 | 40 | 39 |
| BSP-02514 | A037T-S039E-I043V-A047V-I080V-N085S-E087D-S099R-V102I-T114A-F128A-N212S | 1.2 | 3.3 | 2.3 | 1.0 | 154 | — |
| BSP-02524 | A037T-S039E-N042T-A047V-I080V-N085S-E087D-S099R-V102I-T114Q-F128A-N242D | 1.5 | 4.3 | 2.3 | 1.2 | 125 | — |
| BSP-02525 | A037T-S039E-I043V-A047V-T056Y-I080V-N085S-E087D-S099R-T114A-F128A-N242D | 1.5 | 4.9 | 2.3 | 1.1 | 139 | — |
| BSP-02539 | A037T-S039E-I043V-A047V-I080V-N085S-E087D-S099R-T114Q-F128A-N212S-N242D | 1.3 | 3.8 | 3.1 | 1.2 | 136 | — |
| BSP-02565 | A037T-S039E-A047V-I080V-N085S-E087D-S099R-V102I-T114Q-F128A-R143A-N242D | 1.5 | 3.5 | 2.4 | 1.4 | 129 | — |
| BSP-02569 | A037T-S039E-I043V-A047V-T055G-I080V-N085S-E087D-S099R-T114Q-S126T-F128A | 1.4 | 5.6 | 2.5 | 0.9 | 52 | 51 |
| BSP-02677 | R027K-A037T-S039E-A047V-I080V-N085S-E087D-S099R-T114Q-F128A-N212S-N242D | 1.3 | 3.9 | 3.5 | 0.9 | 127 | — |
| BSP-02768 | T009S-A037T-S039E-I043V-A047V-I080V-N085S-E087D-S099R-T114A-F128A-V197I | 1.3 | 3.6 | 2.9 | 0.8 | 156 | — |
| BSP-02791 | S039E-I043V-A047V-I080V-N085S-E087D-S099R-T114A-F128A-N212S-K245L-N246S | 1.1 | 2.9 | 2.0 | 0.8 | 143 | — |
| BSP-02805 | A037T-S039E-I043V-A047V-I080V-N085S-E087D-S099R-T114A-F128A-I190L-A224V | 1.4 | 4.3 | 2.3 | 1.0 | 157 | — |
| BSP-02814 | S036A-S039E-I043V-A047V-I080V-N085S-E087D-S099R-T114A-N121S-F128A-R143Q | 1.5 | 4.3 | 1.8 | 1.0 | 141 | — |
| BSP-02828 | S036A-S039E-I043V-A047V-I080V-N085S-E087D-S099R-T114A-F128A-N212S-S255N | 1.3 | 4.2 | 4.6 | 0.9 | 142 | — |
| BSP-02829 | S039E-I043V-A047V-I080V-N085S-E087D-S099R-T114A-F128A-R143Q-N242D-N246K | 1.3 | 4.3 | 2.9 | 1.0 | 144 | — |
| BSP-02979 | A037T-S039E-I043V-A047V-N074D-N085S-E087D-S099R-T114A-S126T-F128A-N212S | 1.3 | 4.3 | 4.7 | 0.8 | 147 | — |
| BSP-03009 | A037T-S039E-I043V-A047V-N074D-I080V-N085S-E087D-S099R-T114A-F128A-N212S | 1.2 | 3.5 | 4.3 | 0.9 | 149 | — |
| BSP-03070 | A037T-S039E-N042T-A047V-I080V-N085S-E087D-S099R-T114A-F128A-S158T-N212S | 1.1 | 3.2 | 2.7 | 0.8 | 153 | — |
| BSP-03098 | V004I-A037T-S039E-I043V-A047V-I080V-N085S-E087D-S099R-T114A-F128A-N182S | 1.4 | 4.5 | 2.2 | 1.1 | 158 | — |
| BSP-02035 | A037T-S039E-I043V-A047V-N074D-N085S-E087D-S099R-T114A-S126T-F128A-S158T-N212S | 1.4 | 4.8 | 3.6 | 1.1 | 145 | — |
| BSP-02043 | A037T-S039E-I043V-A047V-N074D-I080V-N085S-E087D-S099R-T114A-F128A-S158T-N212S | 1.2 | 3.9 | 4.0 | 1.2 | 148 | — |
| BSP-02052 | A037T-S039E-I043V-A047V-N074D-N085S-E087D-S099R-T114A-F128A-N212S-N242Q-K245L | 1.2 | 3.0 | 4.2 | 1.5 | 150 | — |
| BSP-02073 | A037T-S039E-I043V-A047V-N074D-I080V-N085S-E087D-S099R-T114A-F128A-N212S-N242Q | 1.3 | 3.6 | 3.7 | 1.3 | 152 | — |
| BSP-02086 | A037T-S039E-I043V-A047V-N074D-I080V-N085S-E087D-S099R-T114A-F128A-N212S-K245L | 1.4 | 3.8 | 2.9 | 1.3 | 151 | — |
| BSP-02364 | A037T-S039E-A047V-S099R-V102I-T114A-I119V-S126T-F128A-R143A-S158T-G160S-N212S | 1.3 | 2.7 | 4.0 | 1.1 | 119 | — |
| BSP-02423 | A037T-S039E-N042T-A047V-T056Y-N074D-I080V-N085S-E087D-S099R-T114Q-S126T-F128A | 1.5 | 6.5 | 4.0 | 1.3 | 32 | 31 |
| BSP-02438 | S024F-A037T-S039E-A047V-N074D-I080V-N085S-E087D-S099R-T114Q-S126T-F128A-N212S | 1.3 | 4.8 | 5.0 | 1.0 | 122 | — |
| BSP-02500 | A037T-S039E-I043V-A047V-I080V-N085S-E087D-S099R-T114Q-S126T-F128A-R143A-N242D | 1.7 | 5.9 | 2.0 | 1.2 | 130 | — |

TABLE 4-continued

| Cleaning Performance And Stability of *B. gibsonii*-clade Subtilisins | | | | | | | |
|---|---|---|---|---|---|---|---|
| | | PI versus Bgi02446 | | | | | |
| *B. gibsonii*-clade Subtilisin | Mutations With Respect to Bgi02446 | ADW pH 10.5 Rinsed Egg stain | ADW pH 10.5 Unrinsed Egg stain | Stabil-ity in EDTA | Boron-free HDL pH 8.2, BMI Stain | Amino acid SEQ ID NO: | Nucleotide SEQ ID NO: |
| BSP-02504 | A037T-S039E-I043V-A047V-I080V-N085S-E087D-S099R-T114A-S126T-F128A-A237T-N242D | 1.7 | 5.7 | 2.9 | 1.1 | 137 | — |
| BSP-02521 | A037T-S039E-I043V-A047V-I080V-N085S-E087D-S099R-V102I-T114Q-S126T-F128A-N242D | 1.5 | 4.8 | 2.1 | 1.2 | 133 | — |
| BSP-02537 | A037T-S039E-I043V-A047V-T055G-I080V-N085S-E087D-S099R-V102I-T114Q-F128A-R143A | 1.4 | 4.6 | 2.1 | 1.2 | 134 | — |
| BSP-02540 | A037T-S039E-N042T-A047V-T055G-I080V-N085S-E087D-S099R-T114Q-F128A-N212S-N242D | 1.2 | 3.0 | 3.2 | 1.1 | 126 | — |

TABLE 5

| Cleaning Performance And Stability of *B. gibsonii*-clade Subtilisins | | | | | | | | |
|---|---|---|---|---|---|---|---|---|
| | | | PI versus BSP-00801 | | | | | |
| *B.gibsonii*-clade Subtilisin | Mutations With Respect to BSP-00801 | Mutations With Respect to Bgi02446 | ADW pH 10.5-Rinsed Egg Stain | ADW pH 10.5-Unrinsed Egg stain | Stabil-ity in EDTA | Boron-free HDL pH 8.2, BMI stain | Amino acid SEQ ID NO: | Nucleotide SEQ ID NO: |
| BSP-00801 | Parent | A037T-S039E-I043V-A047V-I080V-N085S-E087D-S099R-T114A-F128A | 1.0 | 1.0 | 1.0 | 1.0 | 18 | 15 |
| BSP-02470 | N242D | A037T-S039E-I043V-A047V-I080V-N085S-E087D-S099R-T114A-F128A-N242D | 1.1 | 1.1 | 1.1 | 1.1 | 173 | — |
| BSP-02508 | A114Q-N242D | A037T-S039E-I043V-A047V-I080V-N085S-E087D-S099R-T114Q-F128A-N242D | 1.2 | 1.2 | 1.1 | 1.1 | 42 | 41 |
| BSP-02480 | S126T-N242D | A037T-S039E-I043V-A047V-I080V-N085S-E087D-S099R-T114A-S126T-F128A-N242D | 1.1 | 1.2 | 1.1 | 1.1 | 38 | 37 |
| BSP-02525 | T056Y-N242D | A037T-S039E-I043V-A047V-T056Y-I080V-N085S-E087D-S099R-T114A-F128A-N242D | 1.1 | 1.1 | 1.1 | 1.1 | 139 | — |
| BSP-02507 | A114Q-S126T-R143A | A037T-S039E-I043V-A047V-I080V-N085S-E087D-S099R-T114Q-S126T-F128A-R143A | 1.3 | 1.3 | 1.3 | 1.3 | 40 | 39 |
| BSP-02569 | T055G-A114Q-S126T | A037T-S039E-I043V-A047V-T055G-I080V-N085S-E087D-S099R-T114Q-S126T-F128A | 1.1 | 1.2 | 1.2 | 0.9 | 52 | 51 |
| BSP-02096 | N074D-S158T-N212S | A037T-S039E-I043V-A047V-N074D-I080V-N085S-E087D-S099R-T114A-F128A-S158T-N212S | 1.1 | 1.1 | 1.6 | 1.1 | 163 | — |
| BSP-02504 | S126T-A237T-N242D | A037T-S039E-I043V-A047V-I080V-N085S-E087D-S099R-T114A-S126T-F128A-A237T-N242D | 1.3 | 1.2 | 1.4 | 1.1 | 137 | — |
| BSP-02635 | N074D-S126T-N242D | A037T-S039E-I043V-A047V-N074D-I080V-N085S-E087D-S099R-T114A-S126T-F128A-N242D | 1.1 | 1.2 | 1.6 | 1.1 | 56 | 55 |
| BSP-02676 | R027K-S126T-N242D | R027K-A037T-S039E-I043V-A047V-I080V-N085S-E087D-S099R-T114A-S126T-F128A-N242D | 1.2 | 1.1 | 1.2 | 1.1 | 60 | 59 |
| BSP-02684 | T056Y-S126T-R143A | A037T-S039E-I043V-A047V-T056Y-I080V-N085S-E087D-S099R-T114A-S126T-F128A-R143A | 1.1 | 1.1 | 1.2 | 1.2 | 62 | 61 |
| BSP-02903 | N121S-N246S-S255N | A037T-S039E-I043V-A047V-I080V-N085S-E087D-S099R-T114A-N121S-F128A-N246S-S255N | 1.1 | 1.1 | 1.2 | 1.0 | 196 | — |
| BSP-02542 | V043I-A114Q-R143A-N242D | A037T-S039E-A047V-I080V-N085S-E087D-S099R-T114Q-F128A-R143A-N242D | 1.1 | 1.0 | 1.2 | 1.4 | 128 | — |

TABLE 5-continued

| Cleaning Performance And Stability of *B. gibsonii*-clade Subtilisins | | | | | | | | |
|---|---|---|---|---|---|---|---|---|
| | | | PI versus BSP-00801 | | | | | |
| *B.gibsonii*-clade Subtilisin | Mutations With Respect to BSP-00801 | Mutations With Respect to Bgi02446 | ADW pH 10.5-Rinsed Egg Stain | ADW pH 10.5-Unrinsed Egg stain | Stability in EDTA | Boron-free HDL pH 8.2, BMI stain | Amino acid SEQ ID NO: | Nucleotide SEQ ID NO: |
| BSP-02060 | N074D-V080I-S158T-N212S | A037T-S039E-I043V-A047V-N074D-N085S-E087D-S099R-T114A-F128A-S158T-N212S | 1.0 | 1.0 | 1.8 | 1.2 | 146 | — |
| BSP-02521 | V102I-A114Q-S126T-N242D | A037T-S039E-I043V-A047V-I080V-N085S-E087D-S099R-V102I-T114Q-S126T-F128A-N242D | 1.1 | 1.0 | 1.1 | 1.2 | 133 | — |
| BSP-02983 | T056Y-A114Q-S126T-N242D | A037T-S039E-I043V-A047V-T056Y-I080V-N085S-E087D-S099R-T114Q-S126T-F128A-N242D | 1.1 | 1.3 | 1.2 | 1.0 | 66 | 65 |
| BSP-03096 | N074D-A114Q-I119V-S126T | A037T-S039E-I043V-A047V-N074D-I080V-N085S-E087D-S099R-T114Q-I119V-S126T-F128A | 1.1 | 1.0 | 1.6 | 1.1 | 197 | — |
| BSP-02445 | T055G-V102I-S126T-S158T | A037T-S039E-I043V-A047V-T055G-I080V-N085S-E087D-S099R-V102I-T114A-S126T-F128A-S158T | 1.0 | 1.0 | 1.2 | 0.8 | 36 | 35 |
| BSP-02472 | S126T-R143A-S158T-N242D | A037T-S039E-I043V-A047V-I080V-N085S-E087D-S099R-T114A-S126T-F128A-R143A-S158T-N242D | 1.1 | 1.1 | 1.3 | 1.4 | 174 | — |
| BSP-02552 | N042T-R044S-N074D-S126T | A037T-S039E-N042T-I043V-R044S-A047V-N074D-I080V-N085S-E087D-S099R-T114A-S126T-F128A | 1.2 | 1.2 | 1.8 | 1.2 | 46 | 45 |
| BSP-02567 | N042T-R044S-S126T-N242D | A037T-S039E-N042T-I043V-R044S-A047V-I080V-N085S-E087D-S099R-T114A-S126T-F128A-N242D | 1.2 | 1.2 | 1.3 | 1.1 | 50 | 49 |
| BSP-02660 | V102I-I119V-S126T-F257Y | A037T-S039E-I043V-A047V-I080V-N085S-E087D-S099R-V102I-T114A-I119V-S126T-F128A-F257Y | 1.1 | 1.0 | 1.3 | 0.9 | 183 | — |
| BSP-02890 | N074D-V102I-N121S-R143Q | A037T-S039E-I043V-A047V-N074D-I080V-N085S-E087D-S099R-V102I-T114A-N121S-F128A-R143Q | 1.1 | 1.1 | 1.3 | 1.0 | 195 | — |
| BSP-02035 | N074D-V080I-S126T-S158T-N212S | A037T-S039E-I043V-A047V-N074D-N085S-E087D-S099R-T114A-S126T-F128A-S158T-N212S | 1.1 | 1.0 | 1.8 | 1.1 | | |
| BSP-02802 | S036A-T037A-N074D-A224V-S255N | S036A-S039E-I043V-A047V-N074D-I080V-N085S-E087D-S099R-T114A-F128A-A224V-S255N | 1.0 | 1.0 | 2.6 | 1.3 | 188 | — |
| BSP-02446 | T055G-N074D-A114Q-S126T-N242D | A037T-S039E-I043V-A047V-T055G-N074D-I080V-N085S-E087D-S099R-T114Q-S126T-F128A-N242D | 1.0 | 1.2 | 1.6 | 1.1 | 170 | — |
| BSP-02456 | T055G-V102I-A114Q-S126T-R143A | A037T-S039E-I043V-A047V-T055G-I080V-N085S-E087D-S099R-V102I-T114Q-S126T-F128A-R143A | 1.1 | 1.0 | 1.0 | 1.2 | 171 | — |
| BSP-02467 | V102I-A114Q-S126T-R143A-N242D | A037T-S039E-I043V-A047V-I080V-N085S-E087D-S099R-V102I-T114Q-S126T-F128A-R143A-N242D | 1.1 | 1.1 | 1.4 | 1.1 | 172 | — |
| BSP-02550 | T056Y-A114Q-S126T-S158T-N242D | A037T-S039E-I043V-A047V-T056Y-I080V-N085S-E087D-S099R-T114Q-S126T-F128A-S158T-N242D | 1.2 | 1.2 | 1.1 | 1.1 | 44 | 43 |
| BSP-02579 | T056Y-A114Q-I119V-S126T-F257Y | A037T-S039E-I043V-A047V-T056Y-I080V-N085S-E087D-S099R-T114Q-I119V-S126T-F128A-F257Y | 1.1 | 1.2 | 1.4 | 0.7 | 178 | — |
| BSP-03095 | T056Y-A114Q-I119V-S126T-N242D | A037T-S039E-I043V-A047V-T056Y-I080V-N085S-E087D-S099R-T114Q-I119V-S126T-F128A-N242D | 1.2 | 1.1 | 1.1 | 1.1 | 68 | 67 |

TABLE 5-continued

| Cleaning Performance And Stability of *B. gibsonii*-clade Subtilisins | | | | | | | | |
|---|---|---|---|---|---|---|---|---|
| | | | PI versus BSP-00801 | | | | | |
| *B.gibsonii*-clade Subtilisin | Mutations With Respect to BSP-00801 | Mutations With Respect to Bgi02446 | ADW pH 10.5-Rinsed Egg Stain | ADW pH 10.5-Unrinsed Egg stain | Stability in EDTA | Boron-free HDL pH 8.2, BMI stain | Amino acid SEQ ID NO: | Nucleotide SEQ ID NO: |
| BSP-02023 | N074D-S126T-S158T-N212S-N242Q | A037T-S039E-I043V-A047V-N074D-I080V-N085S-E087D-S099R-T114A-S126T-F128A-S158T-N212S-N242Q | 1.1 | 1.1 | 1.7 | 1.1 | 160 | — |
| BSP-02733 | N074D-S126T-T188A-I190L-F257Y | A037T-S039E-I043V-A047V-N074D-I080V-N085S-E087D-S099R-T114A-S126T-F128A-T188A-I190L-F257Y | 1.1 | 1.1 | 2.3 | 1.1 | 186 | — |
| BSP-02795 | V004I-T009S-A224V-K245L-S255N | V004I-T009S-A037T-S039E-I043V-A047V-I080V-N085S-E087D-S099R-T114A-F128A-A224V-K245L-S255N | 1.1 | 1.0 | 1.3 | 0.8 | 64 | 63 |
| BSP-02138 | V043I-T056Y-A114Q-A128F-R143A-N242D | A037T-S039E-A047V-T056Y-I080V-N085S-E087D-S099R-T114Q-R143A-N242D | 1.1 | 1.4 | 1.3 | 1.1 | 166 | — |
| BSP-02423 | N042T-V043I-T056Y-N074D-A114Q-S126T | A037T-S039E-N042T-A047V-T056Y -N074D-I080V-N085S-E087D-S099R -T114Q-S126T-F128A | 1.1 | 1.4 | 1.9 | 1.2 | 32 | 31 |
| BSP-02058 | N074D-V080I-S126T-S158T-N212S-N242Q | A037T-S039E-I043V-A047V-N074D -N085S-E087D-S099R-T114A-S126T -F128A-S158T-N212S-N242Q | 1.1 | 1.1 | 1.9 | 1.0 | 161 | — |
| BSP-02098 | N074D-V080I-S126T-S158T-N212S-K245L | A037T-S039E-I043V-A047V-N074D -N085S-E087D-S099R-T114A-S126T-F128A-S158T-N212S-K245L | 1.1 | 1.2 | 1.7 | 1.0 | 165 | — |
| BSP-02557 | A114P-S126T-R143T-S158T-N212K-N242D | A037T-S039E-I043V-A047V-I080V-N085S-E087D-S099R-T114P-S126T-F128A-R143T-S158T-N212K-N242D | 1.2 | 1.3 | 1.4 | 1.3 | 175 | — |
| BSP-02563 | T056Y-N074D-A114Q-S126T-R143A-N242D | A037T-S039E-I043V-A047V-T056Y-N074D-I080V-N085S-E087D-S099R-T114Q-S126T-F128A-R143A-N242D | 1.0 | 1.1 | 1.8 | 1.4 | 177 | — |
| BSP-02593 | T055G-T056Y-N074D-V102I-A114Q-S126T | A037T-S039E-I043V-A047V-T055G-T056Y-N074D-I080V-N085S-E087D-S099R-V102I-T114Q-S126T-F128A | 1.0 | 1.1 | 1.5 | 1.1 | 179 | — |
| BSP-02748 | S036A-T037N-N242D-K245L-N246S-S255N | S036A-A037N-S039E-I043V-A047V-I080V-N085S-E087D-S099R-T114A-F128A-N242D-K245L-N246S-S255N | 1.2 | 1.0 | 1.2 | 0.9 | 187 | — |
| BSP-02094 | N074D-S126T-S158T-N212S-N242Q-K245L | A037T-S039E-I043V-A047V-N074D-I080V-N085S-E087D-S099R-T114A-S126T-F128A-S158T-N212S-N242Q-K245L | 1.0 | 1.0 | 1.6 | 1.0 | 162 | — |
| BSP-02605 | I119V-S126T-S158T-G160S-N242D-F257Y | A037T-S039E-I043V-A047V-I080V-N085S-E087D-S099R-T114A-I119V-S126T-F128A-S158T-G160S-N242D-F257Y | 1.1 | 1.1 | 1.2 | 1.1 | 180 | — |
| BSP-02885 | N121S-N182S-I190L-K245L-N246S-S255N | A037T-S039E-I043V-A047V-I080V-N085S-E087D-S099R-T114A-N121S-F128A-N182S-I190L-K245L-N246S-S255N | 1.1 | 1.0 | 1.2 | 1.0 | 193 | — |
| BSP-02132 | V043I-V047A-N074D-V102I-A114Q-S126T-R143A | A037T-S039E-N074D-I080V-N085S-E087D-S099R-V102I-T114Q-S126T-F128A-R143A | 1.3 | 1.2 | 2.0 | 1.6 | 121 | — |
| BSP-02203 | T055G-N074D-S085N-D087E-V102I-A114Q-S126T | A037T-S039E-I043V-A047V-T055G-N074D-I080V-S099R-V102I-T114Q-S126T-F128A | 1.1 | 1.1 | 1.7 | 0.9 | 24 | 23 |
| BSP-02249 | N074D-S085N-D087E-V102I-A114Q-S126T-N242D | A037T-S039E-I043V-A047V-N074D-I080V-S099R-V102I-T114Q-S126T-F128A-N242D | 1.2 | 1.3 | 1.9 | 1.0 | 28 | 27 |
| BSP-02106 | V043I-N074D-V102I-A114Q-S126T-S158T-N242D | A037T-S039E-A047V-N074D-I080V-N085S-E087D-S099R-V102I-T114Q-S126T-F128A-S158T-N242D | 1.2 | 1.2 | 1.8 | 1.0 | 22 | 21 |

TABLE 5-continued

Cleaning Performance And Stability of *B. gibsonii*-clade Subtilisins

| *B.gibsonii*-clade Subtilisin | Mutations With Respect to BSP-00801 | Mutations With Respect to Bgi02446 | PI versus BSP-00801 ADW pH 10.5-Rinsed Egg Stain | ADW pH 10.5-Unrinsed Egg stain | Stability in EDTA | Boron-free HDL pH 8.2, BMI stain | Amino acid SEQ ID NO: | Nucleotide SEQ ID NO: |
|---|---|---|---|---|---|---|---|---|
| BSP-02559 | N042T-V043I-N074D-V102I-A114Q-S126T-N242D | A037T-S039E-N042T-A047V-N074D-I080V-N085S-E087D-S099R-V102I-T114Q-S126T-F128A-N242D | 1.1 | 1.1 | 1.8 | 1.1 | 176 | — |
| BSP-02097 | N074D-V080I-S126T-S158T-N212S-N242Q-K245L | A037T-S039E-I043V-A047V-N074D-N085S-E087D-S099R-T114A-S126T-F128A-S158T-N212S-N242Q-K245L | 1.0 | 1.1 | 1.7 | 1.1 | 1.6 | — |
| BSP-02848 | T009S-S036A-T037A-R143Q-N182S-T188A-I190L | T009S-S036A-S039E-I043V-A047V-I080V-N085S-E087D-S099R-T114A-F128A-R143Q-N182S-T188A-I190L | 1.1 | 1.1 | 1.5 | 1.1 | 189 | — |
| BSP-02422 | T055G-N074D-V102I-A114Q-S126T-S158T-N242D | A037T-S039E-I043V-A047V-T055G-N074D-I080V-N085S-E087D-S099R-V102I-T114Q-S126T-F128A-S158T-N242D | 1.1 | 1.1 | 1.6 | 1.1 | 168 | — |
| BSP-02427 | T055G-N074D-A114Q-S126T-R143A-S158T-N212S | A037T-S039E-I043V-A047V-T055G-N074D-I080V-N085S-E087D-S099R-T114Q-S126T-F128A-R143A-S158T-N212S | 1.1 | 1.1 | 2.1 | 1.0 | 169 | — |
| BSP-02862 | R143Q-N212S-A224V-Y232N-K245L-N246S-S255N | A037T-S039E-I043V-A047V-I080V-N085S-E087D-S099R-T114A-F128A-R143Q-N212S-A224V-Y232N-K245L-N246S-S255N | 1.1 | 1.0 | 1.0 | 1.2 | 191 | — |
| BSP-02887 | V004I-T009S-N121S-R143Q-A224I-R231K-K245L | V004I-T009S-A037T-S039E-I043V-A047V-I080V-N085S-E087D-S099R-T114A-N121S-F128A-R143Q-A224I-R231K-K245L | 1.2 | 1.1 | 1.3 | 1.0 | 194 | — |
| BSP-02689 | R027K-V043I-A114Q-I119V-S126T-G160S-N242D-F257Y | R027K-A037T-S039E-A047V-I080V-N085S-E087D-S099R-T114Q-I119V-S126T-F128A-G160S-N242D-F257Y | 1.2 | 1.0 | 1.4 | 0.9 | 185 | — |
| BSP-02611 | R027K-T056Y-A114Q-S126T-S158T-G160S-N242D-F257Y | R027K-A037T-S039E-I043V-A047V-T056Y-I080V-N085S-E087D-S099R-T114Q-S126T-F128A-S158T-G160S-N242D-F257Y | 1.1 | 1.1 | 1.3 | 1.2 | 54 | 53 |
| BSP-02620 | R027K-T056Y-V102I-A114Q-S126T-T188A-I190L-F257Y | R027K-A037T-S039E-I043V-A047V-T056Y-I080V-N085S-E087D-S099R-V102I-T114Q-S126T-F128A-T188A-I190L-F257Y | 1.1 | 1.0 | 1.4 | 0.8 | 181 | — |
| BSP-02622 | R027K-T056N-A114P-S126T-R143T-V159I-N212T-F257Y | R027K-A037T-S039E-I043V-A047V-T056N-I080V-N085S-E087D-S099R-T114P-S126T-F128A-R143T-V159I-N212T-F257Y | 1.1 | 1.2 | 1.7 | 1.2 | 182 | — |
| BSP-02681 | T056Y-A114Q-I119V-S126T-S158T-V159I-G160S-F257Y | A037T-S039E-I043V-A047V-T056Y-I080V-N085S-E087D-S099R-T114Q-I119V-S126T-F128A-S158T-V159I-G160S-F257Y | 1.2 | 1.0 | 1.5 | 1.0 | 184 | — |
| BSP-02429 | T055G-T056Y-N074D-V102I-A114Q-S126T-N242D | A037T-S039E-I043V-A047V-T055G-T056Y-N074D-I080V-N085S-E087D-S099R-V102I-T114Q-S126T-F128A-N242D | 1.0 | 1.1 | 2.0 | 1.0 | 34 | 33 |
| BSP-02658 | R027K-V043I-T056Y-N074D-A114Q-I119V-S126T-N242D-F257Y | R027K-A037T-S039E-A047V-T056Y-N074D-I080V-N085S-E087D-S099R-T114Q-I119V-S126T-F128A-N242D-F257Y | 1.1 | 1.3 | 1.8 | 1.0 | 58 | 57 |
| BSP-02235 | N042T-V043I-V047A-N074D-V080I-S085N-D087E-V102I-A114T-S126T-S158T-N242D | A037T-S039E-N042T-N074D-S099R-V102I-S126T-F128A-S158T-N242D | 1.2 | 1.3 | 1.8 | 1.1 | 26 | 25 |
| BSP-02310 | R027K-V043I-V047A-T055G-T056Y-N074D-V080I-S085N-D087E-V102I-A114T-S126T-N242D | R027K-A037T-S039E-A047V-T055G-T056Y-N074D-S099R-V102I-S126T-F128A-N242D | 1.2 | 1.3 | 1.7 | 1.1 | 30 | 29 |

TABLE 5-continued

Cleaning Performance And Stability of *B. gibsonii*-clade Subtilisins

| *B.gibsonii*-clade Subtilisin | Mutations With Respect to BSP-00801 | Mutations With Respect to Bgi02446 | PI versus BSP-00801: ADW pH 10.5-Rinsed Egg Stain | PI versus BSP-00801: ADW pH 10.5-Unrinsed Egg stain | PI versus BSP-00801: Stability in EDTA | PI versus BSP-00801: Boron-free HDL pH 8.2, BMI stain | Amino acid SEQ ID NO: | Nucleotide SEQ ID NO: |
|---|---|---|---|---|---|---|---|---|
| BSP-02872 | T037A-A224V-N242D-N246S-S255N | S039E-I043V-A047V-I080V-N085S-E087D-S099R-T114A-F128A-A224V-N242D-N246S-S255N | 0.7 | 0.7 | 1.2 | 0.9 | 192 | — |
| BSP-03159 | N074D-V102I-R143Q-S158T-A224V-S255N | A037T-S039E-I043V-A047V-N074D-I080V-N085S-E087D-S099R-V102I-T114A-F128A-R143Q-S158T-A224V-S255N | 1.1 | 1.0 | 1.9 | 1.1 | 70 | 69 |
| BSP-02861 | P054S-T056Y-A057Q-N074D-N121S-S158T-A224V-S255N | A037T-S039E-I043V-A047V-P054S-T056Y-A057Q-N074D-I080V-N085S-E087D-S099R-T114A-N121S-F128A-S158T-A224V-S255N | 1.1 | 1.0 | 1.6 | 1.2 | 190 | — |
| BSP-02345 | N042T-R044S-N074D-V102I-A114T-S126T-S158T-G160S-N242D | A037T-S039E-N042T-I043V-R044S-A047V-N074D-I080V-N085S-E087D-S099R-V102I-S126T-F128A-S158T-G160S-N242D | 1.1 | 1.2 | 2.2 | 1.1 | 167 | — |

Example 5

Crystallographic Structure of *B. gibsoni*-Clade Subtilisin BSP-00801

*B. gibsoni*-clade subtilisin BSP-00801 was produced in accordance with the process set forth in Examples 1 and 2, under the control of *B. lentus* pro-sequence.

For the purification of *B. gibsoni*-clade subtilisin BSP-00801, culture supernatant was dialyzed against 25 mM MES, pH 5.4 with 1 mM calcium chloride. The sample was then filtered and applied to an anion exchange chromatography column (Source 15S, GE Healthcare, US) equilibrated with 25 mM MES pH 5.4 and 1 mM calcium chloride. Protein was eluted with a linear sodium chloride gradient. Protein of interest was isolated and propylene glycol was added to 40% final concentration.

The three-dimensional structure of *B. gibsoni*-clade subtilisin BSP-00801 (SEQ ID NO:18) was determined using X-ray crystallography. The structure of BSP-00801 subtilisin was determined in the space group $P6_122$ having 1 molecule in the asymmetric unit with unit cell dimension a=75.19, b=75.19, c=202.3 Å and $\gamma$=120° to a resolution of 2.5 Å. The crystals were obtained by the hanging drop method starting with a 22.2 mg/mL protein in 25 mM MES pH 5.4+1 mM Calcium chloride+40% Propylene Glycol solution. The reservoir solution contained 2.0M Ammonium sulfate+5% iso-Propanol. Equal amounts of protein solution and reservoir were mixed and allowed to equilibrate. Data was collected on a Bruker X8 Proteum system (Bruker Axis Inc., Madison, Wis., USA). The structure was determined using molecular replacement with the coordinates of *B. lentus* subtilisin pdb entry 1JEA as a starting model. The coordinates for BSP-00801 were fitted in the resulting electron density using the program COOT (Emsley, P et al. Acta Cryst. D66 486-501, 2010). After fitting and refitting adjustments, the coordinates were refined using the REFMAC program with standard defaults in the CCP4 software suite. The final model had good stereochemistry and an R-work of 0.19 and R-free of 0.25 for all data to 2.5 Å.

The structure of the *B. gibsonii*-clade subtilisin BSP-00801 is compared with the main chain fold of another commercial subtilisin: subtilisin BPN' and *B. lentus* subtilisin in FIG. 1. The structures are homologous having a common catalytic triad which in the case of BSP-00801 corresponds to residues Asp 32, His 62 and Ser 215.

The substitutions present in the BSP-00801 variant with respect to the parent *B. gibsonii*-clade Bgi02446 (A37T/N; S39E; I43V; A47V; I80V; N85S; E87D; S99R; T114A; F128A) are shown in FIG. 2. These substitutions are found to be distributed in two regions of the structure. Like most subtilisins, BSP-00801 has two calcium binding sites. The first site is characterized as having very high affinity and has been associated with the stability of the molecule in detergents. Eight of the ten substitutions found in BSP-00801 when compared to Bgi02446 are situated either on the loop that forms the tight binding site, or along a surface extending from this calcium site, as shown in FIG. 2. The surface just mentioned consists of a series of external loops which include the following residues: 25-27, 37-43, 47-48, 55-57, 72-74, 85-87 and 114-117. Three loops for the substrate binding region corresponding to sub-sites S4-S1, they correspond to the following residues in BSP-00801: 97-102, 124-130 and 154-161. The other two substitutions, S99R and F128A, are found on two of these loops, as shown in FIG. 3.

Additional sites have been identified that further enhance the performance of the *B. gibsonii*-clade subtilisin BSP-00801 variants and six of these sites are found to be equally distributed along the two regions previously identified. FIG. 4 is in the same orientation as FIG. 2 to facilitate comparison. In FIG. 4, the ten original substitutions are shown in light gray and the side chains of the residues at the six additional sites are shown as black sticks. The sites N42T, S56Y and N74D are situated along the same surface where eight of the BSP-00801 substitutions are found. FIG. 5 shows in a similar view as FIG. 3 that allows viewing of the N74D site for comparison with three additional sites V102I, S126T and S158T, which are found on the loops forming the sub-sites S4-S1.

One additional substitution, not found in the regions mentioned above, is shown in FIG. 13. In this figure, the location of the N242D substitution can be seen relative to some of the other sites which are visible in this orientation. Surprisingly, this site is situated far removed from the substrate binding surface and the surface near the first calcium binding site. It is found closer to the second calcium binding site.

Example 6

Identification of Homologous Proteases

The amino acid sequence (269 residues) of the predicted mature form of BSP-00801 (SEQ ID NO:18) was subjected to a BLAST search (Altschul et al., Nucleic Acids Res, 25:3389-402, 1997) against the NCBI non-redundant protein database. A similar search was run against the Genome Quest Patent database with search parameters set to default values using SEQ ID NO:18 as the query sequence. Subsets of the search results are shown in Tables 6-1 and 6-2. Percent identity (PID) for both search sets was defined as the number of identical residues divided by the number of aligned residues in the pairwise alignment. The column labeled "Sequence Length" refers to the length (in amino acids) of the protein sequences associated with the listed Accession Nos., while the column labeled "Aligned Length" refers to the length (in amino acids) of the aligned protein sequences, which was used for the PID calculation.

TABLE 6-1

PID Shared by BSP-00801 with Entries in NCBI non-Redundant Protein Database

| Accession No. | PID | Organism | Sequence Length | Alignment Length |
|---|---|---|---|---|
| AGS78407 | 96.3 | *Bacillus gibsonii* | 375 | 269 |
| WP_054704207 | 80.6 | *Bacillus* sp. JCM 19041 | 375 | 268 |
| P41362 | 79.5 | *Bacillus clausii* | 380 | 268 |
| P27693 | 79.1 | *Bacillus alcalophilus* | 380 | 268 |
| P29600 | 78.7 | *Bacillus lentus* | 269 | 268 |
| AFR78140 | 78.7 | Synthetic construct | 269 | 268 |
| BAA06157 | 78.0 | *Bacillus* sp. Sendai | 382 | 268 |
| WP_054794820 | 77.6 | *Bacillus* sp. JCM 19035 | 376 | 268 |
| GAF11832 | 77.2 | *Bacillus* sp. JCM 19045 | 403 | 268 |
| AFK08970 | 77.2 | *Bacillus lehensis* | 378 | 268 |
| BAA25184 | 77.2 | *Bacillus* sp. AprN | 379 | 269 |
| GAF21819 | 76.9 | *Bacillus* sp. JCM 19047 | 379 | 268 |
| ADK62564 | 65.8 | *Bacillus* sp. B001 | 375 | 269 |
| BAA02443 | 63.8 | *Bacillus halodurans* | 361 | 268 |
| BAA05540 | 63.8 | *Bacillus* sp. AprM | 361 | 269 |
| ADD64465 | 63.1 | *Bacillus* sp. JB99 | 361 | 268 |
| ABI26631 | 62.7 | *Bacillus clausii* | 361 | 268 |
| GAE36608 | 61.3 | *Bacillus akibai* JCM 9157 | 373 | 266 |
| BAA06158 | 60.7 | *Bacillus* sp. ALP I | 374 | 272 |
| WP_012957236.1 | 60.7 | *Bacillus pseudofirmus* OF4 | 374 | 272 |
| AAC43580 | 59.9 | *Bacillus* sp. SprC | 378 | 272 |
| WP_003327717.1 (previously known as YP_003972439) | 58.4 | *Bacillus atrophaeus* 1942 (subtilisin E) | 382 | 274 |
| BAD11988 | 57.78 | *Bacillus* sp. KSM-LD1 | 376 | 272 |
| CAA24990 | 56.9 | *Bacillus amyloliquefaciens* | 376 | 274 |
| AGL34969 | 56.5 | *Bacillus subtilis* | 361 | 253 |
| BAD21128 | 56.4 | *Bacillus* sp. KSM-LD1 SB | 377 | 273 |
| BAD02409 | 56.3 | *Bacillus* sp. KSM-LD1 | 404 | 272 |
| BAN09118 | 56.2 | *Bacillus subtilis* | 381 | 274 |
| AAX53176 | 56.2 | *Bacillus subtilis* AP01 | 381 | 274 |
| AAC63365 | 55.9 | *Bacillus subtilis* | 382 | 272 |
| ACI32816 | 55.8 | *Bacillus subtilis* | 274 | 274 |
| CAA74536 | 55.8 | *Bacillus subtilis* str. 168 | 381 | 274 |
| WP_010333625 | 55.5 | *Bacillus mojavensis* | 381 | 274 |
| WP_010329279 | 55.1 | *Bacillus vallismortis* | 381 | 274 |
| ABY25856 | 55.1 | *Geobacillus stearothermophilus* | 382 | 274 |
| AFP23380 | 54.6 | *Bacillus lehensis* | 276 | 273 |
| CAJ70731 | 54.6 | *Bacillus licheniformis* | 379 | 273 |
| WP_007497196 | 54.6 | *Bacillus stratosphericus* | 383 | 273 |
| AAC43581 | 54..2 | *Bacillus* sp. SprD | 379 | 273 |
| WP_006636716 | 53.5 | *Bacillus sonorensis* | 378 | 273 |
| ADN04910 | 54.2 | *Bacillus circulans* | 275 | 273 |
| ADK11996 | 54.2 | *Bacillus pumilus* | 383 | 273 |

TABLE 6-2

| Percent Identity (PID) Shared by BSP-00801 with Entries in Genome Quest Database | | | | |
|---|---|---|---|---|
| Patent - SEQ ID NO/Accession No. listed in Genome Quest | PID | Organism | Sequence Length | Alignment Length |
| US20090275493-0004 | 95.9 | *B. gibsonii* | 269 | 269 |
| WO03054184-0001 | 95.9 | *B. gibsonii* | 383 | 269 |
| WO2007131657-0001 | 94.8 | *B. gibsonii* | 383 | 269 |
| US20090275493-0003 | 94.8 | *B. gibsonii* | 269 | 269 |
| WO2008086916-0001 | 93.7 | *B. gibsonii* | 383 | 269 |
| WO2012119955-0001 | 89.6 | *Bacillus* sp. | 269 | 269 |
| WO03054185-0001 | 89.6 | *B. gibsonii* | 383 | 269 |
| DE102007044415_AWJ12891 | 89.6 | *B. gibsonii* | 269 | 269 |
| WO2011110625-0002 | 89.2 | *Bacillus* sp. | 269 | 269 |
| WO2012119955-0005 | 88.5 | *Bacillus* sp. | 269 | 269 |
| U.S. Pat. No. 7,507,569-0002 | 88.4 | Artificial Sequence | 269 | 268 |
| WO2012119955-0004 | 88.1 | *Bacillus* sp. | 269 | 269 |
| WO2012119955-0006 | 88.1 | *Bacillus* sp. | 269 | 269 |
| U.S. Pat. No. 7,642,080-0002 | 87.4 | *Bacillus* sp. strain Zi344 | 381 | 269 |
| U.S. Pat. No. 7,507,569-0004 | 86.6 | Artificial Sequence | 269 | 268 |
| U.S. Pat. No. 7,507,569-0006 | 86.2 | Artificial Sequence | 269 | 268 |
| U.S. Pat. No. 7,642,080-0006 | 85.5 | *Bacillus* sp. strain p203 | 383 | 269 |
| U.S. Pat. No. 7,642,080-0004 | 85.5 | *Bacillus* sp. strain EP655 | 383 | 269 |

Example 7

Sequence Analysis of *B. gibsonii*-Clade Subtilisins

An alignment of the amino acid sequences of the predicted mature forms of the *B. gibsonii*-clade subtilisins of Table 3; *B. gibsonii*-clade subtilisins DSM 9728, DSM 9729, DSM 9730, DSM 9731 and Bgi02446 disclosed in International Patent Application No. PCT/US2014/070107; and the amino acid sequences of multiple proteases listed in Tables 6-1 and 6-2 is shown in FIG. 6A-F. An alignment of the amino acid sequences of the predicted mature forms of the *B. gibsonii*-clade subtilisins of Table 4; *B. gibsonii*-clade subtilisin Bgi02446; and the amino acid sequences of multiple proteases listed in Table 6-1 is shown in FIG. 7A-F. An alignment of the amino acid sequences of the predicted mature forms of multiple *B. gibsonii*-clade BSP-00801 variant subtilisins of Table 5; *B. gibsonii*-clade subtilisin Bgi02446; and the amino acid sequences of multiple proteases listed in Table 6-1 is shown in FIG. 8A-F. The sequences were aligned using CLUSTALW software (Thompson et al., Nucleic Acids Research, 22:4673-4680, 1994) with default parameters.

The phylogenetic tree set forth in FIG. 9 was built using the amino acid sequences of the predicted mature forms of the *B. gibsonii*-clade subtilisins of Table 3; the *B. gibsonii*-clade subtilisins DSM 9728, DSM 9729, DSM 9730, DSM 9731 and Bgi02446 disclosed in International Patent Application No. PCT/US2014/070107; and the amino acid sequences of multiple proteases listed in Tables 6-1 and 6-2. As seen in FIG. 9, the Table 3 subtilisins cluster in the same region as the DSM 9728, DSM 9729, DSM 9730, DSM 9731 and Bgi02446 subtilisins disclosed in WO2015/089447 that form the *B. gibsonii*-clade, and therefore the Table 3 subtilisins are part of the *B. gibsonii*-clade.

The phylogenetic tree set forth in FIG. 10 was built using the amino acid sequences of the predicted mature forms of the *B. gibsonii*-clade subtilisins of Table 4; *B. gibsonii*-clade subtilisin Bgi02446; and the amino acid sequences of multiple proteases listed in Table 7-1. As seen in FIGS. 9 and 10, the Table 4 subtilisins cluster in the same region as the DSM 9728, DSM 9729, DSM 9730, DSM 9731 and Bgi02446 subtilisins, and therefore the Table 4 subtilisins are part of the *B. gibsonii*-clade.

The phylogenetic tree set forth in FIG. 11 was built using the amino acid sequences of the predicted mature forms of multiple *B. gibsonii*-clade BSP-00801 variant subtilisins of Table 5; *B. gibsonii*-clade subtilisin Bgi02446; and the amino acid sequences of multiple proteases listed in Table 7-1. As seen in FIGS. 9 and 11, the Table 5 subtilisins cluster in the same region as the DSM 9728, DSM 9729, DSM 9730, DSM 9731 and Bgi02446 subtilisins, and therefore the Table 5 subtilisins are part of the *B. gibsonii*-clade. When a phylogenetic tree of all of the *B. gibsonii*-clade BSP-00801 variant subtilisins of Table 5 was generated they all fell in the *B. gibsonii*-clade (data not shown).

The sequences were entered in the Vector NTI Advance suite and a Guide Tree was created using the Neighbor Joining (NJ) method (Saitou and Nei, Mol Biol Evol, 4:406-425, 1987). The NJ method works on a matrix of distances between all pairs of sequences to be analyzed. These distances are related to the degree of divergence between the sequences. The Guide Tree is calculated after the sequences are aligned. The tree construction was calculated using the following parameters: Kimura's correction for sequence distance and ignoring positions with gaps. The MEGA 6 program was used to display the phylogenetic trees shown in FIGS. 9-11.

Example 8

Unique Features of *B. gibsonii*-Clade Proteases Listed in Table 3

The amino acid sequences of the predicted mature forms of the *B. gibsonii*-clade subtilisins of Table 3 and Bgi02446 were aligned using CLUSTALW software (Thompson et al., Nucleic Acids Research, 22:4673-4680, 1994) with default parameters. The alignment showed that the Table 3 subtilisins share a motif extending between Asp(D)32 and His(H) 65, which alignment is set forth in FIG. 12A-C. In all these enzymes, the catalytic triad is formed by Asp (D)32, His (H)62 and Ser (S)215. The motif DXGIXXHSDLXXXG-GASXXXXXPTTADLNX HGTH (SEQ ID NO:71) or DXGIXXHSDLXXXGGASXXXXXXTTADLXXHGTH (SEQ ID NO:72) contains the sequence TTADL that is unique to the *B. gibsonii*-clade subtilisins of Table 3 as well as the previously identified *B. gibsonii* subtilisins disclosed in WO2015/089447. All of the *B. gibsonii*-clade subtilisins aligned in FIG. 6A-F share the motif DXGIXXHSDLXXXGG ASXXXXXPTTADLNXHGTH (SEQ ID NO:71) or DXGIXXHSDLXXXG-GASXXXXXXTT ADLXXHGTH (SEQ ID NO:72), which motifs are more fully described in WO2015/089447

Example 9

Measuring Cleaning Performance and Stability of Additional *B. gibsonii*-Clade Subtilisins The additional *B. gibsonii*-clade subtilisins shown below in Table 7 were tested in the microswatch scale cleaning performance and stability tests described on Example 3. These proteins were generated as described in Example 2 using the *B. lentus* propeptide sequence for expression.

TABLE 7

Cleaning Performance and Stability of *B. gibsonii*-clade Subtilisins

| | | PI versus Bgi02446 | | | | |
|---|---|---|---|---|---|---|
| *B. gibsonii*-clade Subtilisin | Mutations With Respect To Bgi02446 | ADW pH 10.5 Rinsed Egg stain | ADW pH 10.5 Unrinsed Egg stain | Stability in EDTA | Boron-free HDL pH 8.2, BMI Stain | Amino acid SEQ ID NO: |
| BSP-03386 | S099R | 1.0 | 3.4 | 0.8 | 0.6 | 205 |
| BSP-03486 | I080V | 1.1 | 3.4 | 0.8 | 0.6 | 212 |
| BSP-03385 | E087D | 1.0 | 1.1 | 0.8 | 1.0 | 204 |
| BSP-03390 | F128A | 1.0 | 1.1 | 0.9 | 1.0 | 208 |
| BSP-03392 | N242D | 1.0 | 1.6 | 0.9 | 1.3 | 209 |
| BSP-03388 | T114A | 0.9 | 1.1 | 1.0 | 1.2 | 206 |
| BSP-03467 | N085S | 1.0 | 1.2 | 1.1 | 1.0 | 211 |
| BSP-03389 | S126T | 0.9 | 1.0 | 1.1 | 1.0 | 207 |
| BSP-03380 | A037T | 1.0 | 1.2 | 1.1 | 1.0 | 200 |
| BSP-03407 | T114Q | 1.0 | 1.2 | 1.2 | 1.0 | 210 |
| BSP-03383 | A047V | 1.0 | 1.0 | 1.2 | 1.0 | 202 |
| BSP-03384 | T056Y | 1.0 | 1.0 | 1.2 | 1.1 | 203 |
| BSP-03381 | S039E | 1.8 | 1.0 | 1.6 | 1.0 | 201 |
| BSP-03344 | S099R-F128A | 1.2 | 1.1 | 3.4 | 1.3 | 223 |
| BSP-03331 | S099R-S126T | 1.2 | 7.0 | 0.8 | 0.9 | 219 |
| BSP-03396 | S126T-F128A | 1.1 | 5.3 | 1.1 | 0.6 | 229 |
| BSP-03346 | T056Y-T114Q | 1.1 | 1.1 | 1.3 | 1.3 | 224 |
| BSP-03304 | S039E-E087D | 1.2 | 1.0 | 1.7 | 1.0 | 213 |
| BSP-03372 | S099R-F128A-N242D | 1.2 | 1.1 | 3.3 | 1.4 | 226 |
| BSP-03333 | S099R-S126T-N242D | 1.3 | 4.1 | 0.7 | 0.9 | 220 |
| BSP-03435 | S099R-S126T-F128A | 1.1 | 3.0 | 1.1 | 0.7 | 232 |
| BSP-03343 | T056Y-T114Q-N242D | 1.2 | 4.3 | 1.2 | 0.8 | 222 |
| BSP-03397 | S039E-S099R-S126T | 1.4 | 1.2 | 1.6 | 1.4 | 230 |
| BSP-03398 | S039E-S099R-F128A | 1.0 | 3.9 | 2.9 | 0.8 | 231 |
| BSP-03309 | S039E-E087D-N242D | 1.2 | 4.5 | 2.9 | 1.1 | 214 |
| BSP-03321 | T056Y-S099R-T114Q-F128A | 1.2 | 1.1 | 3.6 | 1.6 | 217 |
| BSP-03351 | T056Y-S099R-T114Q-S126T | 1.6 | 2.3 | 1.3 | 0.8 | 225 |
| BSP-03662 | S039E-T056Y-S099R-F128A | 1.6 | 5.4 | 1.7 | 0.6 | 252 |
| BSP-03575 | S039E-S099R-T114Q-F128A | 1.6 | 5.8 | 2.8 | 1.3 | 244 |
| BSP-03324 | S039E-E087D-S099R-S126T | 1.6 | 3.9 | 2.8 | 1.3 | 218 |
| BSP-03563 | S039E-N085S-S099R-F128A | 1.4 | 5.9 | 2.8 | 0.8 | 243 |
| BSP-03678 | S039E-S099R-T114A-S126T | 2.0 | 4.3 | 2.9 | 1.4 | 255 |
| BSP-03311 | S039E-E087D-S099R-F128A | 1.5 | 4.4 | 2.9 | 0.7 | 215 |
| BSP-03393 | S039E-S099R-S126T-F128A | 1.1 | 8.2 | 3.1 | 1.3 | 227 |
| BSP-03334 | S039E-T056Y-E087D-T114Q | 1.6 | 4.0 | 3.4 | 1.1 | 221 |
| BSP-03476 | S039E-E087D-S099R-S126T-F128A | 1.5 | 1.1 | 3.4 | 1.5 | 235 |
| BSP-03394 | S039E-T056Y-S099R-S126T-F128A | 1.7 | 4.0 | 3.1 | 1.3 | 228 |
| BSP-03318 | S039E-E087D-S099R-F128A-N242D | 1.6 | 3.9 | 3.4 | 1.0 | 216 |
| BSP-03512 | A037T-S039E-E087D-S099R-T114A-F128A | 1.5 | 4.9 | 3.4 | 1.4 | 240 |
| BSP-03477 | S039E-T056Y-E087D-S099R-S126T-F128A | 1.5 | 4.7 | 2.9 | 1.2 | 236 |
| BSP-03688 | S039E-S099R-T114Q-S126T-F128A-N242D | 1.5 | 3.6 | 3.2 | 1.1 | 256 |
| BSP-03473 | A037T-S039E-S099R-T114Q-S126T-F128A-N242D | 1.5 | 2.9 | 3.6 | 1.1 | 234 |
| BSP-03493 | A037T-S039E-T056Y-S099R-S126T-F128A-N242D | 1.7 | 2.7 | 3.7 | 1.5 | 238 |
| BSP-03653 | A037T-S039E-T056Y-N085S-E087D-S099R-T114Q-F128A | 1.4 | 2.5 | 3.8 | 1.4 | 251 |
| BSP-03559 | A037T-S039E-A047V-T056Y-S099R-T114Q-S126T-F128A | 1.2 | 5.6 | 2.9 | 1.2 | 241 |
| BSP-03623 | A037T-S039E-A047V-T056Y-S099R-T114A-S126T-F128A | 1.5 | 3.8 | 3.2 | 1.4 | 246 |
| BSP-03604 | A037T-S039E-T056Y-S099R-T114Q-S126T-F128A-N242D | 1.6 | 4.9 | 3.4 | 1.0 | 245 |
| BSP-03562 | S039E-A047V-E087D-S099R-T114Q-S126T-F128A-N242D | 1.7 | 2.2 | 3.7 | 1.2 | 242 |
| BSP-03652 | S039E-A047V-T056Y-N085S-E087D-S099R-T114Q-S126T-F128A | 1.5 | 2.8 | 3.7 | 1.2 | 250 |
| BSP-03663 | S039E-A047V-I080V-E087D-S099R-T114A-S126T-F128A-N242D | 1.4 | 6.1 | 3.2 | 1.2 | 253 |
| BSP-03639 | A037T-S039E-T056Y-N085S-S099R-T114Q-S126T-F128A-N242D | 1.4 | 3.8 | 3.2 | 1.2 | 248 |
| BSP-03631 | S039E-A047V-T056Y-E087D-S099R-T114A-S126T-F128A-N242D | 1.4 | 3.6 | 3.3 | 1.2 | 247 |
| BSP-03463 | S039E-A047V-T056Y-E087D-S099R-T114Q-S126T-F128A-N242D | 1.6 | 4.2 | 3.6 | 1.5 | 233 |
| BSP-03503 | A037T-S039E-A047V-I080V-N085S-E087D-S099R-T114A-S126T-F128A | 2.1 | 2.9 | 3.8 | 1.2 | 239 |

TABLE 7-continued

Cleaning Performance and Stability of *B. gibsonii*-clade Subtilisins

| | | PI versus Bgi02446 | | | | |
|---|---|---|---|---|---|---|
| *B. gibsonii*-clade Subtilisin | Mutations With Respect To Bgi02446 | ADW pH 10.5 Rinsed Egg stain | ADW pH 10.5 Unrinsed Egg stain | Stability in EDTA | Boron-free HDL pH 8.2, BMI Stain | Amino acid SEQ ID NO: |
| BSP-03482 | A037T-S039E-I080V-N085S-E087D-S099R-T114Q-S126T-F128A-N242D | 1.6 | 4.1 | 3.1 | 1.0 | 237 |
| BSP-03675 | A037T-S039E-T056Y-N085S-E087D-S099R-T114A-S126T-F128A-N242D | 1.6 | 6.7 | 3.3 | 1.5 | 254 |
| BSP-03647 | A037T-S039E-A047V-T056Y-E087D-S099R-T114A-S126T-F128A-N242D | 1.6 | 3.7 | 3.8 | 1.5 | 249 |

Example 10

Sequence Analysis of *B. gibsonii*-clade Subtilisins

An alignment of the amino acid sequences of Bgi02446, *B. gibsonii*-clade BSP-00801 variant subtilisin and mature forms of multiple *B. gibsonii*-clade variant subtilisins of Table 7 is shown in FIG. 14A-F. The sequences were aligned using CLUSTALW software (Thompson et al., Nucleic Acids Research, 22:4673-4680, 1994) with default parameters. The phylogenetic tree set forth in FIG. 15 was built using the amino acid sequences of the mature forms of the *B. gibsonii*-clade subtilisins of Table 7, the *B. gibsonii*-clade subtilisins DSM 9728, DSM 9729, DSM 9730, DSM 9731 and Bgi02446 disclosed in WO2015/089447; the amino acid sequences of multiple proteases listed in Tables 6-1 and 6-2, and the amino acid sequences of BgAP variants ML2, ML4, MT1, MT2, MF1 (described in Martinez et al, Biotechnology and Bioengineering, 2012).

SEQUENCE LISTING

```
<160> NUMBER OF SEQ ID NOS: 257

<210> SEQ ID NO 1
<211> LENGTH: 608
<212> TYPE: DNA
<213> ORGANISM: B. subtilis

<400> SEQUENCE: 1

gaattctcca ttttcttctg ctatcaaaat aacagactcg tgattttcca aacgagcttt     60

caaaaaagcc tctgcccctt gcaaatcgga tgcctgtcta taaaattccc gatattggtt    120

aaacagcggc gcaatggcgg ccgcatctga tgtctttgct tggcgaatgt tcatcttatt    180

tcttcctccc tctcaataat tttttcattc tatccctttt ctgtaaagtt tatttttcag    240

aatactttta tcatcatgct ttgaaaaaat atcacgataa tatccattgt tctcacggaa    300

gcacacgcag gtcatttgaa cgaatttttt cgacaggaat ttgccgggac tcaggagcat    360

ttaacctaaa aaagcatgac atttcagcat aatgaacatt tactcatgtc tattttcgtt    420

cttttctgta tgaaaatagt tatttcgagt ctctacggaa atagcgagag atgatatacc    480

taaatagaga taaaatcatc tcaaaaaaat gggtctacta aaatattatt ccatctatta    540

caataaattc acagaatagt cttttaagta agtctactct gaattttttt aaaaggagag    600

ggtaaaga                                                             608


<210> SEQ ID NO 2
<211> LENGTH: 87
<212> TYPE: DNA
<213> ORGANISM: B. subtilis

<400> SEQUENCE: 2

gtgagaagca aaaaattgtg gatcagcttg ttgtttgcgt taacgttaat ctttacgatg     60

gcgttcagca acatgtctgc tagcgca                                         87


<210> SEQ ID NO 3
<211> LENGTH: 29
<212> TYPE: PRT
<213> ORGANISM: B. subtilis
```

<400> SEQUENCE: 3

Met Arg Ser Lys Lys Leu Trp Ile Ser Leu Leu Phe Ala Leu Thr Leu
1 5 10 15

Ile Phe Thr Met Ala Phe Ser Asn Met Ser Ala Ser Ala
20 25

<210> SEQ ID NO 4
<211> LENGTH: 261
<212> TYPE: DNA
<213> ORGANISM: B. gibsonii

<400> SEQUENCE: 4
gcagaagaaa aagtaaaata cttaataggt ttcgaagaag aagcagaact tgaagccttc 60
actgaggaaa ttgaccaagt tggtgtattt tctgttgaag aacaaagtgt agctgaggat 120
acgttagata ttgatgtaga cattattgat gaatatgatt atattgatgt gttagctgta 180
gaattagatc ctgaggatgt agatgcgtta agtgaagaag caggtatctc atttattgaa 240
gaagacattg aactgtctat t 261

<210> SEQ ID NO 5
<211> LENGTH: 252
<212> TYPE: DNA
<213> ORGANISM: B. lentus

<400> SEQUENCE: 5
gctgaagaag caaaagaaaa atatttaatt ggctttaatg agcaggaagc tgtcagtgag 60
tttgtagaac aagtagaggc aaatgacgag gtcgccattc tctctgagga agaggaagtc 120
gaaattgaat tgcttcatga atttgaaacg attcctgttt tatccgttga gttaagccca 180
gaagatgtgg acgcgcttga gctcgatcca gcgatttctt atattgaaga ggatgcagaa 240
gtaacgacaa tg 252

<210> SEQ ID NO 6
<211> LENGTH: 807
<212> TYPE: DNA
<213> ORGANISM: B. gibsonii

<400> SEQUENCE: 6
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caacgactgc tgatttaaat 180
gggcatggca cgcatgtggc tgggacggta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcag caaataacat gcacattgct 360
aatatgagtt taggaagcga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcaatcatc taaagaatac ggcaacgaat ttaggaaact cttcacaatt tggaagcgga 780

-continued

```
cttgtcaatg cagaagcggc aacacgc                                        807


<210> SEQ ID NO 7
<211> LENGTH: 42
<212> TYPE: DNA
<213> ORGANISM: artificial sequence
<220> FEATURE:
<223> OTHER INFORMATION: primer

<400> SEQUENCE: 7

gaggatgcag aagtaacgac aatgcaacaa acagtgccat gg                        42


<210> SEQ ID NO 8
<211> LENGTH: 52
<212> TYPE: DNA
<213> ORGANISM: artificial sequence
<220> FEATURE:
<223> OTHER INFORMATION: primer

<400> SEQUENCE: 8

ccaaggccgg ttttttatgt atctagatta gcgtgttgcc gcttctgcat tg             52


<210> SEQ ID NO 9
<211> LENGTH: 42
<212> TYPE: DNA
<213> ORGANISM: artificial sequence
<220> FEATURE:
<223> OTHER INFORMATION: primer

<400> SEQUENCE: 9

gaagaagaca ttgaactgtc tattcaacaa acagtgccat gg                        42


<210> SEQ ID NO 10
<211> LENGTH: 52
<212> TYPE: DNA
<213> ORGANISM: artificial sequence
<220> FEATURE:
<223> OTHER INFORMATION: primer

<400> SEQUENCE: 10

caatgcagaa gcggcaacac gctaatctag atacataaaa aaccggcctt gg             52


<210> SEQ ID NO 11
<211> LENGTH: 42
<212> TYPE: DNA
<213> ORGANISM: artificial sequence
<220> FEATURE:
<223> OTHER INFORMATION: primer

<400> SEQUENCE: 11

ccatggcact gtttgttgca ttgtcgttac ttctgcatcc tc                        42


<210> SEQ ID NO 12
<211> LENGTH: 42
<212> TYPE: DNA
<213> ORGANISM: artificial sequence
<220> FEATURE:
<223> OTHER INFORMATION: primer

<400> SEQUENCE: 12

ccatggcact gtttgttgaa tagacagttc aatgtcttct tc                        42


<210> SEQ ID NO 13
<211> LENGTH: 93
<212> TYPE: DNA
<213> ORGANISM: artificial sequence
```

<220> FEATURE:
<223> OTHER INFORMATION: terminator

<400> SEQUENCE: 13
ggttaccttg aatgtatata aacattctca aagggatttc taataaaaaa cgctcggttg 60
ccgccgggcg tttttatgc atcgatggaa ttc 93

<210> SEQ ID NO 14
<211> LENGTH: 21
<212> TYPE: DNA
<213> ORGANISM: artificial sequence
<220> FEATURE:
<223> OTHER INFORMATION: B. gibsonii-clade subtilisin

<400> SEQUENCE: 14
ggatcctgac tgcctgagct t 21

<210> SEQ ID NO 15
<211> LENGTH: 1155
<212> TYPE: DNA
<213> ORGANISM: artificial sequence
<220> FEATURE:
<223> OTHER INFORMATION: B. gibsonii-clade subtilisin

<400> SEQUENCE: 15
atgagaagca aaaaattgtg gatcagcttg ttgtttgcgt taacgttaat ctttacgatg 60
gcgttcagca acatgtctgc tagcgcagca gaagaaaaag taaaatactt aataggtttc 120
gaagaagaag cagaacttga agccttcact gaggaaattg accaagttgg tgtattttct 180
gttgaagaac aaagtgtagc tgaggatacg ttagatattg atgtagacat tattgatgaa 240
tatgattata ttgatgtgtt agctgtagaa ttagatcctg aggatgtaga tgcgttaagt 300
gaagaagcag gtatctcatt tattgaagaa gacattgaac tgtctattca acaaacagtg 360
ccatggggaa ttactcgtgt gcaagcccca gctgttcata accgtggaat tacaggttct 420
ggtgtaagag ttgctatcct cgattcaggt atttccacac atgaagactt aaatgttcgt 480
ggtggcgtta gctttgtacc aggggaacca acgactgctg atttaaatgg gcatggcacg 540
catgtggctg ggacggtagc tgctttaaac aattcgattg gcgttgttgg cgtagcaccg 600
tcagcggatc tatacgctgt taaagtatta ggggcgaatg gtagaggttc ggtcagcggg 660
attgcccaag gattggaatg ggcagcagca aataacatgc acattgctaa tatgagttta 720
ggaagcgatg caccaagttc tacacttgag cgtgctgtta attatgcgac ttctagagat 780
gttcttgtta ttgcggcaac tgggaataac ggttctggct cagtaggcta tccggcccgt 840
tatgcgaacg caatggcagt cggagctact gaccaaaaca acagacgcgc caacttttca 900
cagtatggca cggggattga cattgtcgca ccaggtgtaa acgtgcagag cacataccca 960
ggtaaccgtt atgtgagcat gaacggtaca tcgatggcta ctcctcatgt tgcaggtgca 1020
gcagcccttg ttaaacaacg ctatccatct tggaatgcga ctcaaatccg caatcatcta 1080
aagaatacgg caacgaattt aggaaactct tcacaatttg gaagcggact tgtcaatgca 1140
gaagcggcaa cacgc 1155

<210> SEQ ID NO 16
<211> LENGTH: 385
<212> TYPE: PRT
<213> ORGANISM: artificial sequence
<220> FEATURE:
<223> OTHER INFORMATION: B. gibsonii-clade subtilisin

<400> SEQUENCE: 16

Met Arg Ser Lys Lys Leu Trp Ile Ser Leu Leu Phe Ala Leu Thr Leu
1 5 10 15

Ile Phe Thr Met Ala Phe Ser Asn Met Ser Ala Ser Ala Ala Glu Glu
20 25 30

Lys Val Lys Tyr Leu Ile Gly Phe Glu Glu Glu Ala Glu Leu Glu Ala
35 40 45

Phe Thr Glu Glu Ile Asp Gln Val Gly Val Phe Ser Val Glu Glu Gln
50 55 60

Ser Val Ala Glu Asp Thr Leu Asp Ile Asp Val Asp Ile Ile Asp Glu
65 70 75 80

Tyr Asp Tyr Ile Asp Val Leu Ala Val Glu Leu Asp Pro Glu Asp Val
85 90 95

Asp Ala Leu Ser Glu Glu Ala Gly Ile Ser Phe Ile Glu Glu Asp Ile
100 105 110

Glu Leu Ser Ile Gln Gln Thr Val Pro Trp Gly Ile Thr Arg Val Gln
115 120 125

Ala Pro Ala Val His Asn Arg Gly Ile Thr Gly Ser Gly Val Arg Val
130 135 140

Ala Ile Leu Asp Ser Gly Ile Ser Thr His Glu Asp Leu Asn Val Arg
145 150 155 160

Gly Gly Val Ser Phe Val Pro Gly Glu Pro Thr Thr Ala Asp Leu Asn
165 170 175

Gly His Gly Thr His Val Ala Gly Thr Val Ala Ala Leu Asn Asn Ser
180 185 190

Ile Gly Val Val Gly Val Ala Pro Ser Ala Asp Leu Tyr Ala Val Lys
195 200 205

Val Leu Gly Ala Asn Gly Arg Gly Ser Val Ser Gly Ile Ala Gln Gly
210 215 220

Leu Glu Trp Ala Ala Ala Asn Asn Met His Ile Ala Asn Met Ser Leu
225 230 235 240

Gly Ser Asp Ala Pro Ser Ser Thr Leu Glu Arg Ala Val Asn Tyr Ala
245 250 255

Thr Ser Arg Asp Val Leu Val Ile Ala Ala Thr Gly Asn Asn Gly Ser
260 265 270

Gly Ser Val Gly Tyr Pro Ala Arg Tyr Ala Asn Ala Met Ala Val Gly
275 280 285

Ala Thr Asp Gln Asn Asn Arg Arg Ala Asn Phe Ser Gln Tyr Gly Thr
290 295 300

Gly Ile Asp Ile Val Ala Pro Gly Val Asn Val Gln Ser Thr Tyr Pro
305 310 315 320

Gly Asn Arg Tyr Val Ser Met Asn Gly Thr Ser Met Ala Thr Pro His
325 330 335

Val Ala Gly Ala Ala Ala Leu Val Lys Gln Arg Tyr Pro Ser Trp Asn
340 345 350

Ala Thr Gln Ile Arg Asn His Leu Lys Asn Thr Ala Thr Asn Leu Gly
355 360 365

Asn Ser Ser Gln Phe Gly Ser Gly Leu Val Asn Ala Glu Ala Ala Thr
370 375 380

Arg
385

<210> SEQ ID NO 17

<211> LENGTH: 356
<212> TYPE: PRT
<213> ORGANISM: artificial sequence
<220> FEATURE:
<223> OTHER INFORMATION: B. gibsonii-clade subtilisin

<400> SEQUENCE: 17

```
Ala Glu Glu Lys Val Lys Tyr Leu Ile Gly Phe Glu Glu Glu Ala Glu
1               5                   10                  15

Leu Glu Ala Phe Thr Glu Glu Ile Asp Gln Val Gly Val Phe Ser Val
            20                  25                  30

Glu Glu Gln Ser Val Ala Glu Asp Thr Leu Asp Ile Asp Val Asp Ile
        35                  40                  45

Ile Asp Glu Tyr Asp Tyr Ile Asp Val Leu Ala Val Glu Leu Asp Pro
    50                  55                  60

Glu Asp Val Asp Ala Leu Ser Glu Glu Ala Gly Ile Ser Phe Ile Glu
65                  70                  75                  80

Glu Asp Ile Glu Leu Ser Ile Gln Gln Thr Val Pro Trp Gly Ile Thr
                85                  90                  95

Arg Val Gln Ala Pro Ala Val His Asn Arg Gly Ile Thr Gly Ser Gly
            100                 105                 110

Val Arg Val Ala Ile Leu Asp Ser Gly Ile Ser Thr His Glu Asp Leu
        115                 120                 125

Asn Val Arg Gly Gly Val Ser Phe Val Pro Gly Glu Pro Thr Thr Ala
    130                 135                 140

Asp Leu Asn Gly His Gly Thr His Val Ala Gly Thr Val Ala Ala Leu
145                 150                 155                 160

Asn Asn Ser Ile Gly Val Val Gly Val Ala Pro Ser Ala Asp Leu Tyr
                165                 170                 175

Ala Val Lys Val Leu Gly Ala Asn Gly Arg Gly Ser Val Ser Gly Ile
            180                 185                 190

Ala Gln Gly Leu Glu Trp Ala Ala Ala Asn Asn Met His Ile Ala Asn
        195                 200                 205

Met Ser Leu Gly Ser Asp Ala Pro Ser Ser Thr Leu Glu Arg Ala Val
    210                 215                 220

Asn Tyr Ala Thr Ser Arg Asp Val Leu Val Ile Ala Ala Thr Gly Asn
225                 230                 235                 240

Asn Gly Ser Gly Ser Val Gly Tyr Pro Ala Arg Tyr Ala Asn Ala Met
                245                 250                 255

Ala Val Gly Ala Thr Asp Gln Asn Asn Arg Arg Ala Asn Phe Ser Gln
            260                 265                 270

Tyr Gly Thr Gly Ile Asp Ile Val Ala Pro Gly Val Asn Val Gln Ser
        275                 280                 285

Thr Tyr Pro Gly Asn Arg Tyr Val Ser Met Asn Gly Thr Ser Met Ala
    290                 295                 300

Thr Pro His Val Ala Gly Ala Ala Ala Leu Val Lys Gln Arg Tyr Pro
305                 310                 315                 320

Ser Trp Asn Ala Thr Gln Ile Arg Asn His Leu Lys Asn Thr Ala Thr
                325                 330                 335

Asn Leu Gly Asn Ser Ser Gln Phe Gly Ser Gly Leu Val Asn Ala Glu
            340                 345                 350

Ala Ala Thr Arg
        355
```

<210> SEQ ID NO 18

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 18

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 19
<211> LENGTH: 268
<212> TYPE: PRT
<213> ORGANISM: B. gibsonii

<400> SEQUENCE: 19

Gln Thr Val Pro Trp Gly Ile Thr Arg Val Gln Ala Pro Ala Val His
1 5 10 15

Asn Arg Gly Ile Thr Gly Ser Gly Val Arg Val Ala Ile Leu Asp Ser
20 25 30

Gly Ile Ser Ala His Ser Asp Leu Asn Ile Arg Gly Gly Ala Ser Phe
35 40 45

Val Pro Gly Glu Pro Thr Thr Ala Asp Leu Asn Gly His Gly Thr His
50 55 60

```
Val Ala Gly Thr Val Ala Ala Leu Asn Asn Ser Ile Gly Val Ile Gly
65                  70                  75                  80

Val Ala Pro Asn Ala Glu Leu Tyr Ala Val Lys Val Leu Gly Ala Asn
                85                  90                  95

Gly Ser Gly Ser Val Ser Gly Ile Ala Gln Gly Leu Glu Trp Ala Ala
            100                 105                 110

Thr Asn Asn Met His Ile Ala Asn Met Ser Leu Gly Ser Asp Phe Pro
        115                 120                 125

Ser Ser Thr Leu Glu Arg Ala Val Asn Tyr Ala Thr Ser Arg Asp Val
    130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
    210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265


<210> SEQ ID NO 20
<211> LENGTH: 268
<212> TYPE: PRT
<213> ORGANISM: artificial sequence
<220> FEATURE:
<223> OTHER INFORMATION: B. gibsonii-clade subtilisin

<400> SEQUENCE: 20

Gln Thr Val Pro Trp Gly Ile Thr Arg Val Gln Ala Pro Ala Val His
1               5                   10                  15

Asn Arg Gly Ile Thr Gly Ser Gly Val Arg Val Ala Ile Leu Asp Ser
            20                  25                  30

Gly Ile Ser Thr His Glu Asp Leu Asn Val Arg Gly Gly Val Ser Phe
        35                  40                  45

Val Pro Gly Glu Pro Thr Thr Ala Asp Leu Asn Gly His Gly Thr His
    50                  55                  60

Val Ala Gly Thr Val Ala Ala Leu Asn Asn Ser Ile Gly Val Val Gly
65                  70                  75                  80

Val Ala Pro Ser Ala Asp Leu Tyr Ala Val Lys Val Leu Gly Ala Asn
                85                  90                  95

Gly Arg Gly Ser Val Ser Gly Ile Ala Gln Gly Leu Glu Trp Ala Ala
            100                 105                 110

Ala Asn Asn Met His Ile Ala Asn Met Ser Leu Gly Ser Asp Ala Pro
        115                 120                 125

Ser Ser Thr Leu Glu Arg Ala Val Asn Tyr Ala Thr Ser Arg Asp Val
    130                 135                 140

Leu Val Ile Ala Ala Thr Gly Asn Asn Gly Ser Gly Ser Val Gly Tyr
145                 150                 155                 160
```

-continued

```
Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
    210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265
```

<210> SEQ ID NO 21
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 21

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaaatattc gtggtggcgt tagctttgta ccaggggaac caacgactgc tgatttaaat    180

gggcatggca cgcatgtggc tgggacggta gctgctttag acaattcgat tggcgttgtt    240

ggcgtagcac cgtcagcgga tctatacgct gttaaagtat taggggcgaa tggtagaggt    300

tcgattagcg ggattgccca aggattggaa tgggcagcac aaaataacat gcacattgct    360

aatatgagtt taggaacaga tgcaccaagt tctacacttg agcgtgctgt taattatgcg    420

acttctagag atgttcttgt tattgcggca actgggaata acggttctgg cacagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaatt tggaagcgga    780

cttgtcaatg cagaagcggc aacacgc                                         807
```

<210> SEQ ID NO 22
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 22

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
```

-continued

```
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 23
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 23

```
caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caggcactgc tgatttaaat     180

gggcatggca cgcatgtggc tgggacggta gctgctttag acaattcgat tggcgttgtt     240

ggcgtagcac cgaacgcgga actatacgct gttaaagtat taggggcgaa tggtagaggt     300

tcgattagcg ggattgccca aggattggaa tgggcagcac aaaataacat gcacattgct     360

aatatgagtt taggaacaga tgcaccaagt tctacacttg agcgtgctgt taattatgcg     420

acttctagag atgttcttgt tattgcggca actgggaata acggttctgg ctcagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcaatcatc taaagaatac ggcaacgaat ttaggaaact cttcacaatt tggaagcgga     780

cttgtcaatg cagaagcggc aacacgc                                         807
```

<210> SEQ ID NO 24
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 24

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 25
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 25

```
caacaaacag tgccatgggg aattactcgt gtgcaagccc cagctgttca taaccgtgga      60

attacaggtt ctggtgtaag agttgctatc ctcgattcag gtatttccac acatgaagac     120

ttaacaattc gtggtggcgc tagctttgta ccaggggaac caacgactgc tgatttaaat     180

gggcatggca cgcatgtggc tgggacggta gctgctttag acaattcgat tggcgttatt     240
```

-continued

```
ggcgtagcac cgaacgcgga actatacgct gttaaagtat taggggcgaa tggtagaggt    300

tcgattagcg ggattgccca aggattggaa tgggcagcaa ccaataacat gcacattgct    360

aatatgagtt taggaacaga tgcaccaagt tctacacttg agcgtgctgt taattatgcg    420

acttctagag atgttcttgt tattgcggca actgggaata acggttctgg cacagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaatt tggaagcgga    780

cttgtcaatg cagaagcggc aacacgc                                        807


<210> SEQ ID NO 26
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 26

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
```

260 265

<210> SEQ ID NO 27
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 27
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caacgactgc tgatttaaat 180
gggcatggca cgcatgtggc tgggacggta gctgctttag acaattcgat tggcgttgtt 240
ggcgtagcac cgaacgcgga actatacgct gttaaagtat taggggcgaa tggtagaggt 300
tcgattagcg ggattgccca aggattggaa tgggcagcac aaaataacat gcacattgct 360
aatatgagtt taggaacaga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcgaccatc taaagaatac ggcaacgaat ttaggaaact cttcacaatt tggaagcgga 780
cttgtcaatg cagaagcggc aacacgc 807

<210> SEQ ID NO 28
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 28

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Asn Ala Glu Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

```
Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 29
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 29

```
caacaaacag tgccatgggg aattactcgt gtgcaagccc cagctgttca taaccgtgga      60

attacaggtt ctggtgtaaa agttgctatc ctcgattcag gtatttccac acatgaagac     120

ttaaatattc gtggtggcgt tagctttgta ccaggggaac caggctatgc tgatttaaat     180

gggcatggca cgcatgtggc tgggacggta gctgctttag acaattcgat tggcgttatt     240

ggcgtagcac cgaacgcgga actatacgct gttaaagtat taggggcgaa tggtagaggt     300

tcgattagcg ggattgccca aggattggaa tgggcagcaa ccaataacat gcacattgct     360

aatatgagtt taggaacaga tgcaccaagt tctacacttg agcgtgctgt taattatgcg     420

acttctagag atgttcttgt tattgcggca actgggaata acggttctgg ctcagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcgaccatc taaagaatac ggcaacgaat ttaggaaact cttcacaatt tggaagcgga     780

cttgtcaatg cagaagcggc aacacgc                                         807
```

<210> SEQ ID NO 30
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 30

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Ile Arg Gly Gly Val Ser
        35                  40                  45
```

```
Phe Val Pro Gly Glu Pro Gly Tyr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 31
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 31

```
caacaaacag tgccatgggg aattactcgt gtgcaagccc cagctgttca taaccgtgga      60

attacaggtt ctggtgtaag agttgctatc ctcgactcag gtatttccac acatgaagac     120

ttaacaattc gtggtggcgt tagctttgta ccaggggaac caacgtatgc tgatttaaat     180

gggcatggca cgcatgtggc tgggacggta gctgctttag acaattcgat tggcgttgtt     240

ggcgtagcac cgtcagcgga tctatacgct gttaaagtat taggggcgaa tggtagaggt     300

tcggtcagcg ggattgccca aggattggaa tgggcagcac aaaataacat gcacattgct     360

aatatgagtt taggaacaga tgcaccaagt tctacacttg agcgtgctgt taattatgcg     420

acttctagag atgttcttgt tattgcggca actgggaata acggttctgg ctcagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcaatcatc taaagaatac ggcaacgaat ttaggaaact cttcacaatt tggaagcgga     780

cttgtcaatg cagaagcggc aacacgc                                         807
```

<210> SEQ ID NO 32
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 32

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 33
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 33

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaaatgttc gtggtggcgt tagctttgta ccaggggaac caggctatgc tgatttaaat    180

gggcatggca cgcatgtggc tgggacggta gctgctttag acaattcgat tggcgttgtt    240
```

```
ggcgtagcac cgtcagcgga tctatacgct gttaaagtat taggggcgaa tggtagaggt    300

tcgattagcg ggattgccca aggattggaa tgggcagcac aaaataacat gcacattgct    360

aatatgagtt taggaacaga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaatt tggaagcgga    780

cttgtcaatg cagaagcggc aacacgc                                        807
```

<210> SEQ ID NO 34
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 34

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Tyr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255
```

-continued

```
Phe Gly Ser Gly Leu Val Asn Ala Glu Ala Ala Thr Arg
            260                 265


<210> SEQ ID NO 35
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 35

caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caggcactgc tgatttaaat     180

gggcatggca cgcatgtggc tgggacggta gctgctttaa acaattcgat tggcgttgtt     240

ggcgtagcac cgtcagcgga tctatacgct gttaaagtat taggggcgaa tggtagaggt     300

tcgattagcg ggattgccca aggattggaa tgggcagcag caaataacat gcacattgct     360

aatatgagtt taggaacaga tgcaccaagt tctacacttg agcgtgctgt taattatgcg     420

acttctagag atgttcttgt tattgcggca actgggaata acggttctgg cacagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcaatcatc taaagaatac ggcaacgaat ttaggaaact cttcacaatt tggaagcgga     780

cttgtcaatg cagaagcggc aacacgc                                         807


<210> SEQ ID NO 36
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 36

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
```

```
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 37
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 37

```
caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caacgactgc tgatttaaat     180

gggcatggca cgcatgtggc tgggacggta gctgctttaa acaattcgat tggcgttgtt     240

ggcgtagcac cgtcagcgga tctatacgct gttaaagtat taggggcgaa tggtagaggt     300

tcggtcagcg ggattgccca aggattggaa tgggcagcag caaataacat gcacattgct     360

aatatgagtt taggaacaga tgcaccaagt tctacacttg agcgtgctgt taattatgcg     420

acttctagag atgttcttgt tattgcggca actgggaata acggttctgg ctcagtaggc     480

tatccggctc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcgaccatc taaagaatac ggcaacgaat ttaggaaact cttcacaatt tggaagcgga     780

cttgtcaatg cagaagcggc aacacgc                                         807
```

<210> SEQ ID NO 38
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 38

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45
```

```
Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 39
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 39

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaaatgttc gtggtggcgt tagctttgta ccaggggaac caacgactgc tgatttaaat    180

gggcatggca cgcatgtggc tgggacggta gctgctttaa acaattcgat tggcgttgtt    240

ggcgtagcac cgtcagcgga tctatacgct gttaaagtat taggggcgaa tggtagaggt    300

tcggtcagcg ggattgccca aggattggaa tgggcagcac aaaataacat gcacattgct    360

aatatgagtt taggaacaga tgcaccaagt tctacacttg agcgtgctgt taattatgcg    420

acttctgcag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcaatcatc taaagaatac ggcaacgaat ttaggaaact cttcacaatt tggaagcgga    780
```

cttgtcaatg cagaagcggc aacacgc 807

<210> SEQ ID NO 40
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 40

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Ala Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 41
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 41
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caacgactgc tgatttaaat 180
gggcatggca cgcatgtggc tgggactgta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcac aaaataacat gcacattgct 360
aatatgagtt taggaagcga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcgaccatc taaagaatac ggcaacgaat ttaggaaact cttcacaatt tggaagcgga 780
cttgtcaatg cagaagcggc aacacgc 807

<210> SEQ ID NO 42
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 42

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

```
Phe Gly Ser Gly Leu Val Asn Ala Glu Ala Ala Thr Arg
            260                 265


<210> SEQ ID NO 43
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 43

caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caacgtatgc tgatttaaat     180

gggcatggca cgcatgtggc tgggacggta gctgctttaa acaattcgat tggcgttgtt     240

ggcgtagcac cgtcagcgga tctatacgct gttaaagtat taggggcgaa tggtagaggt     300

tcggtcagcg ggattgccca aggattggaa tgggcagcac aaaataacat gcacattgct     360

aatatgagtt taggaacaga tgcaccaagt tctacacttg agcgtgctgt taattatgcg     420

acttctagag atgttcttgt tattgcggca actgggaata acggttctgg cacagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcgaccatc taaagaatac ggcaacgaat ttaggaaact cttcacaatt tggaagcgga     780

cttgtcaatg cagaagcggc aacacgc                                         807


<210> SEQ ID NO 44
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 44

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140
```

```
Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 45
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 45

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaacagttt caggtggcgt tagctttgta ccaggggaac caacgactgc tgatttaaat    180

gggcatggca cgcatgtggc tgggacggta gctgctttag acaattcgat tggcgttgtt    240

ggcgtagcac cgtcagcgga tctatacgct gttaaagtat taggggcgaa tggtagaggt    300

tcggtcagcg ggattgccca aggattggaa tgggcagcag caaataacat gcacattgct    360

aatatgagtt taggaacaga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcaatcatc taaagaatac ggcaacgaat ttaggaaact cttcacaatt tggaagcgga    780

cttgtcaatg cagaagcggc aacacgc                                        807
```

<210> SEQ ID NO 46
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 46

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Val Ser Gly Gly Val Ser
```

-continued

```
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 47

<400> SEQUENCE: 47

000

<210> SEQ ID NO 48

<400> SEQUENCE: 48

000

<210> SEQ ID NO 49
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 49

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaacagttt caggtggcgt tagctttgta ccaggggaac caacgactgc tgatttaaat    180

gggcatggca cgcatgtggc tgggacggta gctgctttaa acaattcgat tggcgttgtt    240

ggcgtagcac cgtcagcgga tctatacgct gttaaagtat taggggcgaa tggtagaggt    300

tcggtcagcg ggattgccca aggattggaa tgggcagcag caaataacat gcacattgct    360
```

-continued

```
aatatgagtt taggaacaga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaatt tggaagcgga    780

cttgtcaatg cagaagcggc aacacgc                                        807
```

<210> SEQ ID NO 50
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 50

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Val Ser Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 51
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 51
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caggcactgc tgatttaaat 180
gggcatggca cgcatgtggc tgggacggta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcac aaaataacat gcacattgct 360
aatatgagtt taggaacaga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcaatcatc taaagaatac ggcaacgaat ttaggaaact cttcacaatt tggaagcgga 780
cttgtcaatg cagaagcggc aacacgc 807

<210> SEQ ID NO 52
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 52

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Gly Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

```
Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 53
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 53

caacaaacag tgccatgggg aattactcgt gtgcaagccc cagctgttca taaccgtgga      60

attacaggtt ctggtgtaaa agttgctatc ctcgattcag gtatttccac acatgaagac     120

ttaaatgttc gtggtggcgt tagctttgta ccaggggaac caacgtatgc tgatttaaat     180

gggcatggca cgcatgtggc tgggacggta gctgctttaa acaattcgat tggcgttgtt     240

ggcgtagcac cgtcagcgga tctatacgct gttaaagtat taggggcgaa tggtagaggt     300

tcggtcagcg ggattgccca aggattggaa tgggcagcac aaaataacat gcacattgct     360

aatatgagtt taggaacaga tgcaccaagt tctacacttg agcgtgctgt taattatgcg     420

acttctagag atgttcttgt tattgcggca actgggaata acggttctgg cacagtaagc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcgaccatc taaagaatac ggcaacgaat ttaggaaact cttcacaata tggaagcgga     780

cttgtcaatg cagaagcggc aacacgc                                         807


<210> SEQ ID NO 54
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 54

Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60
```

```
His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 55
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 55

```
caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caacgactgc tgatttaaat     180

gggcatggca cgcatgtggc tggacggta gctgctttag acaattcgat tggcgttgtt      240

ggcgtagcac cgtcagcgga tctatacgct gttaaagtat taggggcgaa tggtagaggt     300

tcggtcagcg ggattgccca aggattggaa tgggcagcag caaataacat gcacattgct     360

aatatgagtt taggaacaga tgcaccaagt tctacacttg agcgtgctgt taattatgcg     420

acttctagag atgttcttgt tattgcggca actgggaata acggttctgg ctcagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg cagcagccct tgttaaacaa cgctatccat cttggaatgc gactcaaatc     720

cgcgaccatc taaagaatac ggcaacgaat ttaggaaact cttcacaatt tggaagcgga     780

cttgtcaatg cagaagcggc aacacgc                                         807
```

<210> SEQ ID NO 56

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 56

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 57
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 57
caacaaacag tgccatgggg aattactcgt gtgcaagccc cagctgttca taaccgtgga 60
attacaggtt ctggtgtaaa agttgctatc ctcgattcag gtatttccac acatgaagac 120
ttaaatattc gtggtggcgt tagctttgta ccaggggaac caacgtatgc tgatttaaat 180
gggcatggca cgcatgtggc tgggacggta gctgctttag acaattcgat tggcgttgtt 240
ggcgtagcac cgtcagcgga tctatacgct gttaaagtat taggggcgaa tggtagaggt 300

-continued

```
tcggtcagcg ggattgccca aggattggaa tgggcagcac aaaataacat gcacgttgct    360

aatatgagtt taggaacaga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaata tggaagcgga    780

cttgtcaatg cagaagcggc aacacgc                                        807


<210> SEQ ID NO 58
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 58

Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 59
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 59
caacaaacag tgccatgggg aattactcgt gtgcaagccc cagctgttca taaccgtgga 60
attacaggtt ctggtgtaaa agttgctatc ctcgattcag gtatttccac acatgaagac 120
ttaaatgttc gtggtggcgt tagctttgta ccaggggaac caacgactgc tgatttaaat 180
gggcatggca cgcatgtggc tgggacggta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcag caaataacat gcacattgct 360
aatatgagtt taggaacaga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcgaccatc taaagaatac ggcaacgaat ttaggaaact cttcacaatt tggaagcgga 780
cttgtcaatg cagaagcggc aacacgc 807

<210> SEQ ID NO 60
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 60

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
```

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 61
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 61

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaaatgttc gtggtggcgt tagctttgta ccaggggaac caacgtatgc tgatttaaat    180

gggcatggca cgcatgtggc tgggacggta gctgctttaa acaattcgat tggcgttgtt    240

ggcgtagcac cgtcagcgga tctatacgct gttaaagtat taggggcgaa tggtagaggt    300

tcggtcagcg ggattgccca aggattggaa tgggcagcag caaataacat gcacattgct    360

aatatgagtt taggaacaga tgcaccaagt tctacacttg agcgtgctgt taattatgcg    420

acttctgcag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcaatcatc taaagaatac ggcaacgaat ttaggaaact cttcacaatt tggaagcgga    780

cttgtcaatg cagaagcggc aacacgc                                        807
```

<210> SEQ ID NO 62
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 62

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60
```

-continued

```
His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 63
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 63

```
caacaaacaa ttccatgggg aattagccgt gtgcaagccc cagctgttca taaccgtgga     60

attacaggtt ctggtgtaag agttgctatc ctcgattcag gtatttccac acatgaagac    120

ttaaatgttc gtggtggcgt tagctttgta ccaggggaac caacgactgc tgatttaaat    180

gggcatggca cgcatgtggc tgggacggta gctgctttaa acaattcgat tggcgttgtt    240

ggcgtagcac cgtcagcgga tctatacgct gttaaagtat taggggcgaa tggtagaggt    300

tcggtcagcg ggattgccca aggattggaa tgggcagcag caaataacat gcacattgct    360

aatatgagtt taggaagcga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg ttgcagccct tgttaaacaa cgctatccat cttggaatgc gactcaaatc    720

cgcaatcatc tactgaatac ggcaacgaat ttaggaaact ctaaccaatt tggaagcgga    780

cttgtcaatg cagaagcggc aacacgc                                         807
```

<210> SEQ ID NO 64
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 64

```
Gln Gln Thr Ile Pro Trp Gly Ile Ser Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Leu Asn Thr Ala Thr Asn Leu Gly Asn Ser Asn Gln
                245                 250                 255

Phe Gly Ser Gly Leu Val Asn Ala Glu Ala Ala Thr Arg
            260                 265
```

<210> SEQ ID NO 65
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 65

```
caacaaacag tgccatgggg aattactcgt gtgcaagccc cagctgttca taaccgtgga     60

attacaggtt ctggtgtaag agttgctatc ctcgattcag gtatttccac acatgaagac    120

ttaaatgttc gtggtggcgt tagctttgta ccaggggaac caacgtatgc tgatttaaat    180

gggcatggca cgcatgtggc tgggacggta gctgctttaa acaattcgat tggcgttgtt    240

ggcgtagcac cgtcagcgga tctatacgct gttaaagtat taggggcgaa tggtagaggt    300
```

```
tcggtcagcg ggattgccca aggattggaa tgggcagcac aaaataacat gcacattgct    360

aatatgagtt taggaacaga tgcaccaagt tctacacttg agcgtgctgt taattatgcg    420

acttctagag atgttcttgt tattgcggca actgggaata acggttctgg ctcagtaggc    480

tatccggccc gttatgcgaa cgcaatggca gtcggagcta ctgaccaaaa caacagacgc    540

gccaactttt cacagtatgg cacggggatt gacattgtcg caccaggtgt aaacgtgcag    600

agcacatacc caggtaaccg ttatgtgagc atgaacggta catcgatggc tactcctcat    660

gttgcaggtg cagcagccct tgttaaacaa cgctatccat cttggaatgc gactcaaatc    720

cgcgaccatc taaagaatac ggcaacgaat ttaggaaact cttcacaatt tggaagcgga    780

cttgtcaatg cagaagcggc aacacgc                                        807
```

<210> SEQ ID NO 66
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 66

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 67
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 67
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caacgtatgc tgatttaaat 180
gggcatggca cgcatgtggc tgggacggta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcac aaaataacat gcacgttgct 360
aatatgagtt taggaacaga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcgaccatc taaagaatac ggcaacgaat ttaggaaact cttcacaatt tggaagcgga 780
cttgtcaatg cagaagcggc aacacgc 807

<210> SEQ ID NO 68
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 68

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

-continued

```
Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 69
<211> LENGTH: 807
<212> TYPE: DNA
<213> ORGANISM: artificial sequence
<220> FEATURE:
<223> OTHER INFORMATION: B. gibsonii-clade subtilisin

<400> SEQUENCE: 69

caacaaacag tgccatgggg aattactcgt gtgcaagccc cagctgttca taaccgtgga      60

attacaggtt ctggtgtaag agttgctatc ctcgattcag gtatttccac acatgaagac     120

ttaaatgttc gtggtggcgt tagctttgta ccaggggaac caacgactgc tgatttaaat     180

gggcatggca cgcatgtggc tgggacggta gctgctttag acaattcgat tggcgttgtt     240

ggcgtagcac cgtcagcgga tctatacgct gttaaagtat taggggcgaa tggtagaggt     300

tcgattagcg ggattgccca aggattggaa tgggcagcag caaataacat gcacattgct     360

aatatgagtt taggaagcga tgcaccaagt tctacacttg agcgtgctgt taattatgcg     420

acttctcaag atgttcttgt tattgcggca actgggaata acggttctgg cacagtaggc     480

tatccggccc gttatgcgaa cgcaatggca gtcggagcta ctgaccaaaa caacagacgc     540

gccaactttt cacagtatgg cacggggatt gacattgtcg caccaggtgt aaacgtgcag     600

agcacatacc caggtaaccg ttatgtgagc atgaacggta catcgatggc tactcctcat     660

gttgcaggtg ttgcagccct tgttaaacaa cgctatccat cttggaatgc gactcaaatc     720

cgcaatcatc taaagaatac ggcaacgaat ttaggaaact ctaaccaatt tggaagcgga     780

cttgtcaatg cagaagcggc aacacgc                                         807


<210> SEQ ID NO 70
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 70

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
```

```
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Asn Gln
                245                 250                 255

Phe Gly Ser Gly Leu Val Asn Ala Glu Ala Ala Thr Arg
            260                 265
```

<210> SEQ ID NO 71
<211> LENGTH: 34
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(34)
<223> OTHER INFORMATION: where the initial D is the active site Aspartic acid residue, the penultimate H is the active site Histidine, and X is any amino acid, and where the amino acid positions of the variant are numbered by correspondence with the amino acid sequence of SEQ ID
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (11)..(13)
<223> OTHER INFORMATION: Xaa is any amino acid
<220> FEATURE:
<221> NAME/KEY: MISC_FEATURE
<222> LOCATION: (18)..(22)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid

<400> SEQUENCE: 71

-continued

```
Asp Xaa Gly Ile Xaa Xaa His Ser Asp Leu Xaa Xaa Xaa Gly Gly Ala
1               5                   10                  15

Ser Xaa Xaa Xaa Xaa Xaa Pro Thr Thr Ala Asp Leu Asn Xaa His Gly
            20                  25                  30

Thr His


<210> SEQ ID NO 72
<211> LENGTH: 34
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(34)
<223> OTHER INFORMATION: where the initial D is the active site Aspartic
      acid residue, the penultimate H is the active site Histidine, and
      X is any amino acid, and where the amino acid positions of the
      variant are numbered by correspondence with the amino acid
      sequence of SEQ ID
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (11)..(13)
<223> OTHER INFORMATION: Xaa is any amino acid
<220> FEATURE:
<221> NAME/KEY: MISC_FEATURE
<222> LOCATION: (18)..(23)
<223> OTHER INFORMATION: Xaa is any amino acid
<220> FEATURE:
<221> NAME/KEY: MISC_FEATURE
<222> LOCATION: (29)..(30)
<223> OTHER INFORMATION: Xaa is any amino acid

<400> SEQUENCE: 72

Asp Xaa Gly Ile Xaa Xaa His Ser Asp Leu Xaa Xaa Xaa Gly Gly Ala
1               5                   10                  15

Ser Xaa Xaa Xaa Xaa Xaa Xaa Thr Thr Ala Asp Leu Xaa Xaa His Gly
            20                  25                  30

Thr His


<210> SEQ ID NO 73

<400> SEQUENCE: 73

000


<210> SEQ ID NO 74
<211> LENGTH: 275
<212> TYPE: PRT
<213> ORGANISM: B. amyloliquefaciens

<400> SEQUENCE: 74

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
```

```
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 75
<211> LENGTH: 275
<212> TYPE: PRT
<213> ORGANISM: G. stearothermophilus

<400> SEQUENCE: 75

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Tyr Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140
```

-continued

```
Ser Gly Ile Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
            180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
        275


<210> SEQ ID NO 76
<211> LENGTH: 275
<212> TYPE: PRT
<213> ORGANISM: B. subtilis

<400> SEQUENCE: 76

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ala
    130                 135                 140

Ser Gly Ile Val Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ser Tyr Asn Gly Thr Ser Met Ala Thr
    210                 215                 220

Pro His Val Ala Gly Ala Ala Ala Leu Ile Leu Ser Lys His Pro Thr
225                 230                 235                 240
```

```
Trp Ser Asn Ala Gln Val Arg Asp Arg Leu Glu Ser Thr Ala Thr Asn
            245                 250                 255

Leu Gly Ser Ser Phe Tyr Tyr Gly Lys Gly Leu Ile Asn Val Gln Ala
        260                 265                 270

Ala Ala Gln
    275


<210> SEQ ID NO 77
<211> LENGTH: 275
<212> TYPE: PRT
<213> ORGANISM: B. atrophaeus

<400> SEQUENCE: 77

Ala Gln Ser Val Pro Tyr Gly Ile Ser Gln Ile Lys Ala Pro Ala Val
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ser Gly Gly Ala
        35                  40                  45

Ser Phe Val Pro Ser Glu Pro Asn Pro Phe Gln Asp Gly Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Ser Ser Ser Gly Ser Gly Asp Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Gln Gly Ser Thr Ala Leu Lys Ala Val Val Asp Lys Ala Val Ser
    130                 135                 140

Gln Gly Ile Val Val Val Ala Ala Ala Gly Asn Ser Gly Ser Ser Gly
145                 150                 155                 160

Ser Thr Ser Thr Val Gly Tyr Pro Ala Lys Tyr Pro Ser Val Ile Ala
                165                 170                 175

Val Gly Ala Val Asp Ser Asn Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Ser Ser Tyr Gly Ser Tyr Asn Gly Thr Ser Met Ala Ser
    210                 215                 220

Pro His Val Ala Gly Ala Ala Ala Leu Val Leu Ser Lys His Pro Asn
225                 230                 235                 240

Trp Thr Asn Ser Gln Val Arg Asn Ser Leu Glu Ser Thr Ala Thr Asn
                245                 250                 255

Leu Gly Asn Ser Phe Tyr Tyr Gly Lys Gly Leu Ile Asn Val Gln Ala
            260                 265                 270

Ala Ala Gln
        275


<210> SEQ ID NO 78
<211> LENGTH: 275
<212> TYPE: PRT
<213> ORGANISM: B. circulans

<400> SEQUENCE: 78
```

```
Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Arg Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
            260                 265                 270

Ala Ser Asn
        275
```

<210> SEQ ID NO 79
<211> LENGTH: 275
<212> TYPE: PRT
<213> ORGANISM: B. pumilus

<400> SEQUENCE: 79

```
Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
```

```
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Ala Ser Gly Ser Thr Ala Leu Lys Asn Ala Val Asp Thr Ala Asn Asn
    130                 135                 140

Arg Gly Val Val Val Val Ala Ala Ala Gly Asn Ser Gly Ser Ser Gly
145                 150                 155                 160

Ser Arg Ser Thr Val Gly Tyr Pro Ala Lys Tyr Glu Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
        275


<210> SEQ ID NO 80
<211> LENGTH: 274
<212> TYPE: PRT
<213> ORGANISM: B. licheniformis

<400> SEQUENCE: 80

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175
```

```
Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln


<210> SEQ ID NO 81
<211> LENGTH: 275
<212> TYPE: PRT
<213> ORGANISM: unknown
<220> FEATURE:
<223> OTHER INFORMATION: Bacillus sp.

<400> SEQUENCE: 81

Ala Gln Thr Thr Pro Trp Gly Val Thr His Ile Asn Ala His Arg Ala
1               5                   10                  15

His Ser Ser Gly Val Thr Gly Ser Gly Val Lys Val Ala Ile Leu Asp
            20                  25                  30

Thr Gly Ile His Ala Ser His Pro Asp Leu Asn Val Arg Gly Gly Ala
        35                  40                  45

Ser Phe Ile Ser Gly Glu Ser Asn Pro Tyr Ile Asp Ser Asn Gly His
    50                  55                  60

Gly Thr His Val Ala Gly Thr Val Ala Ala Leu Asn Asn Thr Val Gly
65                  70                  75                  80

Val Leu Gly Val Ala Tyr Asn Ala Glu Leu Tyr Ala Val Lys Val Leu
                85                  90                  95

Ser Ala Ser Gly Ser Gly Thr Leu Ser Gly Ile Ala Gln Gly Val Glu
            100                 105                 110

Trp Ser Ile Ala Asn Lys Met Asp Val Ile Asn Met Ser Leu Gly Gly
        115                 120                 125

Ser Ser Gly Ser Thr Ala Leu Gln Arg Ala Val Asp Asn Ala Tyr Arg
    130                 135                 140

Asn Asn Ile Val Val Val Ala Ala Ala Gly Asn Ser Gly Ala Gln Gly
145                 150                 155                 160

Asn Arg Asn Thr Ile Gly Tyr Pro Ala Arg Tyr Ser Ser Val Ile Ala
                165                 170                 175

Val Gly Ala Val Asp Ser Asn Asn Asn Arg Ala Ser Phe Ser Ser Val
            180                 185                 190

Gly Ser Glu Leu Glu Val Met Ala Pro Gly Val Ser Ile Leu Ser Thr
        195                 200                 205

Val Pro Gly Ser Ser Tyr Ala Ser Tyr Asn Gly Thr Ser Met Ala Ser
    210                 215                 220

Pro His Val Ala Gly Ala Ala Ala Leu Leu Lys Ala Lys Tyr Pro Asn
225                 230                 235                 240

Trp Ser Ala Ala Gln Ile Arg Asn Lys Leu Asn Ser Thr Thr Thr Tyr
                245                 250                 255

Leu Gly Ser Ser Phe Tyr Tyr Gly Asn Gly Val Ile Asn Val Glu Arg
```

```
            260                 265                 270

Ala Leu Gln
        275


<210> SEQ ID NO 82
<211> LENGTH: 275
<212> TYPE: PRT
<213> ORGANISM: unknown
<220> FEATURE:
<223> OTHER INFORMATION: bacillus sp.

<400> SEQUENCE: 82

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
    130                 135                 140

Arg Gly Ile Val Val Ile Ala Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
        275


<210> SEQ ID NO 83
<211> LENGTH: 269
<212> TYPE: PRT
<213> ORGANISM: unknown
<220> FEATURE:
<223> OTHER INFORMATION: bacillus sp.

<400> SEQUENCE: 83
```

```
Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
            20                  25                  30

Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
    130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Val Asn Ser Thr Tyr Thr Gly Asn Arg Tyr
        195                 200                 205

Val Ser Leu Ser Gly Thr Ser Met Ala Thr Pro His Val Ala Gly Val
    210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265


<210> SEQ ID NO 84
<211> LENGTH: 269
<212> TYPE: PRT
<213> ORGANISM: B. lentus

<400> SEQUENCE: 84

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110
```

Gly Asn Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 85
<211> LENGTH: 269
<212> TYPE: PRT
<213> ORGANISM: B. gibsonii

<400> SEQUENCE: 85

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Thr Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala

```
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 86
<211> LENGTH: 269
<212> TYPE: PRT
<213> ORGANISM: B. gibsonii

<400> SEQUENCE: 86

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 87
<211> LENGTH: 269
<212> TYPE: PRT
<213> ORGANISM: B. gibsonii

<400> SEQUENCE: 87

Gln Gln Thr Val Pro Trp Gly Ile Thr Arg Val Gln Ala Pro Ala Val
```

-continued

```
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 88
<211> LENGTH: 269
<212> TYPE: PRT
<213> ORGANISM: B. gibsonii

<400> SEQUENCE: 88

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110
```

```
Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 89
<211> LENGTH: 269
<212> TYPE: PRT
<213> ORGANISM: B. gibsonii

<400> SEQUENCE: 89

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ser Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220
```

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 90
<211> LENGTH: 269
<212> TYPE: PRT
<213> ORGANISM: B. gibsonii

<400> SEQUENCE: 90

Gln Gln Thr Val Pro Trp Gly Ile Thr Arg Val Gln Ala Pro Ala Val
1 5 10 15

His Asn Arg Gly Val Thr Gly Ser Gly Val Arg Val Ala Ile Leu Asp
20 25 30

Ser Gly Ile Ser Thr His Ser Asp Leu Thr Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ile Thr Leu Glu Arg Ala Val Asn Tyr Ala Thr Ser Gln Gly
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Ala Ser Leu Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 91
<211> LENGTH: 269
<212> TYPE: PRT
<213> ORGANISM: B. gibsonii

<400> SEQUENCE: 91

Gln Gln Thr Val Pro Trp Gly Ile Thr Arg Val Gln Ala Pro Thr Val
1 5 10 15

```
His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265


<210> SEQ ID NO 92
<211> LENGTH: 269
<212> TYPE: PRT
<213> ORGANISM: B. gibsonii

<400> SEQUENCE: 92

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Gln His Ser Asp Leu Thr Ile Arg Gly Gly Ala Ser
        35                  40                  45

Phe Ile Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
```

```
        115                 120                 125

Pro Ser Ser Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 93
<211> LENGTH: 269
<212> TYPE: PRT
<213> ORGANISM: B. gibsonii

<400> SEQUENCE: 93

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Gln His Ser Asp Leu Thr Ile Arg Gly Gly Ala Ser
        35                  40                  45

Phe Val Pro Gly Glu Pro Thr Thr Glu Asp Leu Asn Gly His Gly Thr
    50                  55                  60

His Val Ala Gly Thr Val Ala Ala Leu Asn Asn Ser Phe Gly Val Ile
65                  70                  75                  80

Gly Val Ala Pro Ser Ala Asp Leu Tyr Ala Val Lys Val Leu Gly Ala
                85                  90                  95

Gly Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
        115                 120                 125

Pro Ser Ser Thr Leu Glu Arg Ala Val Asn Tyr Ala Thr Ser Arg Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Val
    210                 215                 220
```

-continued

```
Ala Ala Leu Val Lys Gln Arg Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Ile Arg
            260                 265
```

<210> SEQ ID NO 94
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 94

```
Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Ile His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 95
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 95

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Thr Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Gln Gly
130 135 140

Val Leu Val Ile Ala Ala Thr Gly Asn Asn Gly Ser Gly Thr Ile Ser
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Gly Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 96
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 96

Ala Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Asn Ala Glu Leu Tyr Ala Val Lys Val Leu Gly Ala
85 90 95

```
Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Ala Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Leu Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Thr Asn Leu
                245                 250                 255

Tyr Gly Ser Gly Leu Val Asn Ala Glu Ala Ala Thr Arg
            260                 265
```

<210> SEQ ID NO 97
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 97

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190
```

```
Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 98
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 98

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 99
```

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 99

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Ile Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 100
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 100

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
```

```
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 101
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 101

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
```

```
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 102
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 102

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
```

```
                245                 250                 255

Tyr Gly Ser Gly Leu Val Asn Ala Glu Ala Ala Thr Arg
            260                 265


<210> SEQ ID NO 103
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 103

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 104
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 104

Gln Gln Thr Val Pro Trp Gly Ile Thr Arg Val Gln Ala Pro Ala Val
1               5                   10                  15
```

```
His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 105
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 105

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110
```

-continued

Ala Gln Asn Asn Met His Val Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Thr Val Ser
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Ser Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Tyr Gly Ser Gly Leu Val Asn Ala Glu Ala Ala Thr Arg
260 265

<210> SEQ ID NO 106
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 106

Gln Gln Thr Val Pro Trp Gly Ile Thr Arg Val Gln Ala Pro Ala Val
1 5 10 15

His Asn Arg Gly Ile Thr Gly Ser Gly Val Lys Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Val Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Thr Ile Ser
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Ala Gly Ile Asp Ile
180 185 190

Val Ala Pro Gly Val Asn Val Gln Ser Thr Tyr Pro Gly Asn Arg Tyr
195 200 205

```
Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 107
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 107

Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Thr Ile Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 108
<211> LENGTH: 269
<212> TYPE: PRT
<213> ORGANISM: artificial sequence
<220> FEATURE:
```

<223> OTHER INFORMATION: B. gibsonii-clade subtilisin

<400> SEQUENCE: 108

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 109
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 109

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80
```

```
Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 110
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 110

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 111
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 111

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 112
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 112

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 113
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 113

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
```

```
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 114
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 114

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
```

```
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 115
<211> LENGTH: 275
<212> TYPE: PRT
<213> ORGANISM: artificial sequence
<220> FEATURE:
<223> OTHER INFORMATION: Consensus sequence Figure 6
<220> FEATURE:
<221> NAME/KEY: MISC_FEATURE
<222> LOCATION: (37)..(37)
<223> OTHER INFORMATION: Xaa can be any amino acid
<220> FEATURE:
<221> NAME/KEY: MISC_FEATURE
<222> LOCATION: (57)..(57)
<223> OTHER INFORMATION: Xaa can be any amino acid
<220> FEATURE:
<221> NAME/KEY: MISC_FEATURE
<222> LOCATION: (82)..(82)
<223> OTHER INFORMATION: Xaa can be any amino acid
<220> FEATURE:
<221> NAME/KEY: MISC_FEATURE
<222> LOCATION: (104)..(104)
<223> OTHER INFORMATION: Xaa can be any amino acid
<220> FEATURE:
<221> NAME/KEY: MISC_FEATURE
<222> LOCATION: (116)..(116)
<223> OTHER INFORMATION: Xaa can be any amino acid
<220> FEATURE:
<221> NAME/KEY: MISC_FEATURE
<222> LOCATION: (128)..(128)
<223> OTHER INFORMATION: Xaa can be any amino acid
<220> FEATURE:
<221> NAME/KEY: MISC_FEATURE
<222> LOCATION: (145)..(146)
<223> OTHER INFORMATION: Xaa can be any amino acid
<220> FEATURE:
<221> NAME/KEY: MISC_FEATURE
<222> LOCATION: (159)..(162)
<223> OTHER INFORMATION: Xaa can be any amino acid
<220> FEATURE:
<221> NAME/KEY: MISC_FEATURE
<222> LOCATION: (248)..(248)
<223> OTHER INFORMATION: Xaa can be any amino acid

<400> SEQUENCE: 115

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Xaa Ala His Ser Asp Leu Asn Ile Arg Gly Gly Ala
```

```
        35                  40                  45

Ser Phe Val Pro Gly Glu Pro Thr Xaa Thr Ala Asp Leu Asn Gly His
    50                  55                  60

Gly Thr His Val Ala Gly Thr Val Ala Ala Leu Asn Asn Ser Ile Gly
65                  70                  75                  80

Val Xaa Gly Val Ala Pro Ser Ala Asp Leu Tyr Ala Val Lys Val Leu
                85                  90                  95

Gly Ala Asn Gly Arg Gly Ser Xaa Ser Gly Ile Ala Gln Gly Leu Glu
            100                 105                 110

Trp Ala Ala Xaa Asn Asn Met His Ile Ala Asn Met Ser Leu Gly Xaa
        115                 120                 125

Asp Ala Pro Ser Ser Thr Leu Glu Arg Ala Val Asn Tyr Ala Thr Ser
    130                 135                 140

Xaa Xaa Val Leu Val Ile Ala Ala Thr Gly Asn Asn Gly Ser Xaa Xaa
145                 150                 155                 160

Xaa Xaa Gly Ser Val Gly Tyr Pro Ala Arg Tyr Ala Asn Ala Met Ala
                165                 170                 175

Val Gly Ala Thr Asp Gln Asn Asn Arg Arg Ala Asn Phe Ser Gln Tyr
            180                 185                 190

Gly Thr Gly Ile Asp Ile Val Ala Pro Gly Val Asn Val Gln Ser Thr
        195                 200                 205

Tyr Pro Gly Asn Arg Tyr Val Ser Met Asn Gly Thr Ser Met Ala Thr
    210                 215                 220

Pro His Val Ala Gly Ala Ala Ala Leu Val Lys Gln Arg Tyr Pro Ser
225                 230                 235                 240

Trp Asn Ala Thr Gln Ile Arg Xaa His Leu Lys Asn Thr Ala Thr Asn
                245                 250                 255

Leu Gly Asn Ser Ser Gln Phe Gly Ser Gly Leu Val Asn Ala Glu Ala
            260                 265                 270

Ala Thr Arg
        275


<210> SEQ ID NO 116
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 116

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
```

```
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 117
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 117

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
```

```
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 118
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 118

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 119
<211> LENGTH: 269
<212> TYPE: PRT
<213> ORGANISM: artificial sequence
<220> FEATURE:
<223> OTHER INFORMATION: B. gibsonii-clade subtilisin
```

<400> SEQUENCE: 119

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Thr Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 120
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 120

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

```
Gly Val Ala Pro Asn Ala Glu Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 121
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 121

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 122
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 122

Gln Gln Thr Val Pro Trp Gly Ile Thr Arg Val Gln Ala Pro Ala Val
1               5                   10                  15

His Asn Arg Gly Ile Thr Gly Phe Gly Val Arg Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 123

<400> SEQUENCE: 123

000

<210> SEQ ID NO 124
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 124

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 125
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 125

```
Gln Gln Thr Val Pro Trp Gly Ile Thr Arg Val Gln Ala Pro Ala Val
```

```
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 126
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 126

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
```

-continued

```
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 127
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 127

Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
```

```
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 128
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 128

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 129
<211> LENGTH: 269
<212> TYPE: PRT
```

<213> ORGANISM: artificial sequence
<220> FEATURE:
<223> OTHER INFORMATION: B. gibsonii-clade subtilisin

<400> SEQUENCE: 129

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Ser Asp Ala
115 120 125

Pro Ser Ser Thr Leu Glu Arg Ala Val Asn Tyr Ala Thr Ser Ala Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 130
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 130

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

```
His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 131

<400> SEQUENCE: 131

000

<210> SEQ ID NO 132

<400> SEQUENCE: 132

000

<210> SEQ ID NO 133
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 133

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
```

```
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 134
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 134

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
```

180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 135
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 135

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 136
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 136

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Ser Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 137
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 137

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Thr Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 138
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 138

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 139
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 139

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

```
Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 140
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 140

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ala Ala His Glu Asp Leu Asn Val Arg Gly Gly Val Ser
        35                  40                  45

Phe Val Pro Gly Glu Pro Met Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 141
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 141

Gln Gln Thr Val Pro Trp Gly Ile Thr Arg Val Gln Ala Pro Ala Val
1               5                   10                  15
```

```
His Asn Arg Gly Ile Thr Gly Ser Gly Val Arg Val Ala Ile Leu Asp
            20                  25                  30

Ser Gly Ile Ala Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 142
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 142

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ala Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110
```

```
Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Asn Gln
                245                 250                 255

Phe Gly Ser Gly Leu Val Asn Ala Glu Ala Ala Thr Arg
            260                 265


<210> SEQ ID NO 143
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 143

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205
```

```
Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Leu Ser Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 144
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 144

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Lys Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 145
<211> LENGTH: 269
<212> TYPE: PRT
<213> ORGANISM: artificial sequence

```
<220> FEATURE:
<223> OTHER INFORMATION: B. gibsonii-clade subtilisin

<400> SEQUENCE: 145

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 146
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 146

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
```

65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Thr Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Ser Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 147
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 147

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asp Asn Ser Ile Gly Val Ile
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 148
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 148

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
```

260 265

<210> SEQ ID NO 149
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 149

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Ser Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 150
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 150

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

```
Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Gln His Leu Leu Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 151
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 151

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125
```

```
Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Leu Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 152
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 152

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220
```

```
Ala Ala Leu Val Lys Gln Arg Tyr Pro Ser Trp Asn Ala Thr Gln Ile
225                 230                 235                 240

Arg Gln His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 153
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 153

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 154
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 154
```

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 155
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 155

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95
```

```
Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 156
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 156

Gln Gln Thr Val Pro Trp Gly Ile Ser Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190
```

```
Val Ala Pro Gly Ile Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 157
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 157

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 158
```

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 158

Gln Gln Thr Ile Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 159
<211> LENGTH: 275
<212> TYPE: PRT
<213> ORGANISM: artificial sequence
<220> FEATURE:
<223> OTHER INFORMATION: Consensus sequence of Figure 7
<220> FEATURE:
<221> NAME/KEY: MISC_FEATURE
<222> LOCATION: (38)..(38)
<223> OTHER INFORMATION: Xaa can be any amino acid
<220> FEATURE:
<221> NAME/KEY: MISC_FEATURE
<222> LOCATION: (57)..(57)
<223> OTHER INFORMATION: Xaa can be any amino acid
<220> FEATURE:
<221> NAME/KEY: MISC_FEATURE
<222> LOCATION: (116)..(116)
<223> OTHER INFORMATION: Xaa can be any amino acid
<220> FEATURE:

<221> NAME/KEY: MISC_FEATURE
<222> LOCATION: (159)..(162)
<223> OTHER INFORMATION: Xaa can be any amino acid

<400> SEQUENCE: 159

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr Xaa His Glu Asp Leu Asn Val Arg Gly Gly Val
        35                  40                  45

Ser Phe Val Pro Gly Glu Pro Thr Xaa Thr Ala Asp Leu Asn Gly His
    50                  55                  60

Gly Thr His Val Ala Gly Thr Val Ala Ala Leu Asn Asn Ser Ile Gly
65                  70                  75                  80

Val Val Gly Val Ala Pro Ser Ala Asp Leu Tyr Ala Val Lys Val Leu
                85                  90                  95

Gly Ala Asn Gly Arg Gly Ser Val Ser Gly Ile Ala Gln Gly Leu Glu
            100                 105                 110

Trp Ala Ala Xaa Asn Asn Met His Ile Ala Asn Met Ser Leu Gly Ser
        115                 120                 125

Asp Ala Pro Ser Ser Thr Leu Glu Arg Ala Val Asn Tyr Ala Thr Ser
    130                 135                 140

Arg Asp Val Leu Val Ile Ala Ala Thr Gly Asn Asn Gly Ser Xaa Xaa
145                 150                 155                 160

Xaa Xaa Gly Ser Val Gly Tyr Pro Ala Arg Tyr Ala Asn Ala Met Ala
                165                 170                 175

Val Gly Ala Thr Asp Gln Asn Asn Arg Arg Ala Asn Phe Ser Gln Tyr
            180                 185                 190

Gly Thr Gly Ile Asp Ile Val Ala Pro Gly Val Asn Val Gln Ser Thr
        195                 200                 205

Tyr Pro Gly Asn Arg Tyr Val Ser Met Asn Gly Thr Ser Met Ala Thr
    210                 215                 220

Pro His Val Ala Gly Ala Ala Ala Leu Val Lys Gln Arg Tyr Pro Ser
225                 230                 235                 240

Trp Asn Ala Thr Gln Ile Arg Asn His Leu Lys Asn Thr Ala Thr Asn
                245                 250                 255

Leu Gly Asn Ser Ser Gln Phe Gly Ser Gly Leu Val Asn Ala Glu Ala
            260                 265                 270

Ala Thr Arg
        275
```

<210> SEQ ID NO 160
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 160

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45
```

```
Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Gln His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 161
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 161

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140
```

```
Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Gln His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 162
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 162

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240
```

```
Arg Gln His Leu Leu Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 163
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 163

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 164
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 164

```
Gln Gln Thr Val Pro Trp Gly Ile Thr Arg Val Gln Ala Pro Ala Val
1               5                   10                  15
```

```
His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Gln His Leu Leu Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

```
<210> SEQ ID NO 165
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 165

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110
```

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Thr Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Ser Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Leu Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 166
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 166

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Val Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Ser Asp Phe
115 120 125

Pro Ser Ser Thr Leu Glu Arg Ala Val Asn Tyr Ala Thr Ser Ala Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

```
Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 167
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 167

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Thr Val Ser Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 168
<211> LENGTH: 269
<212> TYPE: PRT
<213> ORGANISM: artificial sequence
```

<220> FEATURE:
<223> OTHER INFORMATION: B. gibsonii-clade subtilisin

<400> SEQUENCE: 168

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Gly Thr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Thr Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 169
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 169

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Gly Thr Ala Asp Leu Asn Gly His Gly Thr
50 55 60

His Val Ala Gly Thr Val Ala Ala Leu Asp Asn Ser Ile Gly Val Val

```
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 170
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 170

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
```

-continued

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 171
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 171

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Gly Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
```

260 265

<210> SEQ ID NO 172
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 172

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Ala Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 173
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 173

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

```
Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 174
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 174

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125
```

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 175
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 175

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Pro Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Thr Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Lys Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 176
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 176

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Thr Ile Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 177
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 177

-continued

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Ala Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 178
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 178

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95
```

Asn Gly Arg Gly Ser Val Ser Gly Ile Ala Gln Gly Leu Glu Trp Ala
100 105 110

Ala Gln Asn Asn Met His Val Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Tyr Gly Ser Gly Leu Val Asn Ala Glu Ala Ala Thr Arg
260 265

<210> SEQ ID NO 179
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 179

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Val Arg Gly Gly Val Ser
35 40 45

Phe Val Pro Gly Glu Pro Gly Tyr Ala Asp Leu Asn Gly His Gly Thr
50 55 60

His Val Ala Gly Thr Val Ala Ala Leu Asp Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Ile Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

```
Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 180
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 180

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 181
```

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 181

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 182
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 182

```
Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Asn Ala Asp Leu Asn Gly His Gly Thr
```

```
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Pro Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Thr Asp
    130                 135                 140

Val Leu Val Ile Ala Ala Thr Gly Asn Asn Gly Ser Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Thr Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 183
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 183

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
```

```
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 184
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 184

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Ile Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
```

```
                245                 250                 255

Tyr Gly Ser Gly Leu Val Asn Ala Glu Ala Ala Thr Arg
            260                 265


<210> SEQ ID NO 185
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 185

Gln Gln Thr Val Pro Trp Gly Ile Thr Arg Val Gln Ala Pro Ala Val
1               5                   10                  15

His Asn Arg Gly Ile Thr Gly Ser Gly Val Lys Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265


<210> SEQ ID NO 186
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 186

Gln Gln Thr Val Pro Trp Gly Ile Thr Arg Val Gln Ala Pro Ala Val
1               5                   10                  15
```

-continued

```
His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Tyr Gly Ser Gly Leu Val Asn Ala Glu Ala Ala Thr Arg
            260                 265
```

<210> SEQ ID NO 187
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 187

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ala Asn His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110
```

```
Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Leu Ser Thr Ala Thr Asn Leu Gly Asn Ser Asn Gln
                245                 250                 255

Phe Gly Ser Gly Leu Val Asn Ala Glu Ala Ala Thr Arg
            260                 265


<210> SEQ ID NO 188
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 188

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ala Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205
```

Val Ser Met Asn Gly Thr Ser Met Ala Thr Pro His Val Ala Gly Val
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Asn Gln
245 250 255

Phe Gly Ser Gly Leu Val Asn Ala Glu Ala Ala Thr Arg
260 265

<210> SEQ ID NO 189
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 189

Gln Gln Thr Val Pro Trp Gly Ile Ser Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ala Ala His Glu Asp Leu Asn Val Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Ser Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Gln Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Ser Phe Ser Gln Tyr Gly Ala Gly Leu Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 190
<211> LENGTH: 269
<212> TYPE: PRT
<213> ORGANISM: artificial sequence
<220> FEATURE:

<223> OTHER INFORMATION: B. gibsonii-clade subtilisin

<400> SEQUENCE: 190

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Ser Thr Tyr Gln Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Thr Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Asn Gln
                245                 250                 255

Phe Gly Ser Gly Leu Val Asn Ala Glu Ala Ala Thr Arg
            260                 265
```

<210> SEQ ID NO 191
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 191

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80
```

```
Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Ser Gly Thr Ser Met Ala Thr Pro His Val Ala Gly Val
    210                 215                 220

Ala Ala Leu Val Lys Gln Arg Asn Pro Ser Trp Asn Ala Thr Gln Ile
225                 230                 235                 240

Arg Asn His Leu Leu Ser Thr Ala Thr Asn Leu Gly Asn Ser Asn Gln
                245                 250                 255

Phe Gly Ser Gly Leu Val Asn Ala Glu Ala Ala Thr Arg
            260                 265


<210> SEQ ID NO 192
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 192

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asp His Leu Lys Ser Thr Ala Thr Asn Leu Gly Asn Ser Asn Gln
                245                 250                 255

Phe Gly Ser Gly Leu Val Asn Ala Glu Ala Ala Thr Arg
            260                 265


<210> SEQ ID NO 193
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 193

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Leu Ser Thr Ala Thr Asn Leu Gly Asn Ser Asn Gln
                245                 250                 255

Phe Gly Ser Gly Leu Val Asn Ala Glu Ala Ala Thr Arg
            260                 265
```

<210> SEQ ID NO 194
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 194

```
Gln Gln Thr Ile Pro Trp Gly Ile Ser Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ile
    210                 215                 220

Ala Ala Leu Val Lys Gln Lys Tyr Pro Ser Trp Asn Ala Thr Gln Ile
225                 230                 235                 240

Arg Asn His Leu Leu Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 195
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 195

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
```

```
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Gln Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 196
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 196

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Ser Met Ser Leu Gly Ser Asp Ala
        115                 120                 125

Pro Ser Ser Thr Leu Glu Arg Ala Val Asn Tyr Ala Thr Ser Arg Asp
```

```
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Ser Thr Ala Thr Asn Leu Gly Asn Ser Asn Gln
                245                 250                 255

Phe Gly Ser Gly Leu Val Asn Ala Glu Ala Ala Thr Arg
            260                 265
```

<210> SEQ ID NO 197
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 197

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Val Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
```

```
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 198
<211> LENGTH: 275
<212> TYPE: PRT
<213> ORGANISM: artificial sequence
<220> FEATURE:
<223> OTHER INFORMATION: Consensus sequence Figure 8
<220> FEATURE:
<221> NAME/KEY: MISC_FEATURE
<222> LOCATION: (37)..(37)
<223> OTHER INFORMATION: Xaa can be any amino acid
<220> FEATURE:
<221> NAME/KEY: MISC_FEATURE
<222> LOCATION: (57)..(57)
<223> OTHER INFORMATION: Xaa can be any amino acid
<220> FEATURE:
<221> NAME/KEY: MISC_FEATURE
<222> LOCATION: (116)..(116)
<223> OTHER INFORMATION: Xaa can be any amino acid
<220> FEATURE:
<221> NAME/KEY: MISC_FEATURE
<222> LOCATION: (161)..(164)
<223> OTHER INFORMATION: Xaa can be any amino acid
<220> FEATURE:
<221> NAME/KEY: MISC_FEATURE
<222> LOCATION: (248)..(248)
<223> OTHER INFORMATION: Xaa can be any amino acid

<400> SEQUENCE: 198

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Xaa Thr His Glu Asp Leu Asn Val Arg Gly Gly Val
        35                  40                  45

Ser Phe Val Pro Gly Glu Pro Thr Xaa Thr Ala Asp Leu Asn Gly His
    50                  55                  60

Gly Thr His Val Ala Gly Thr Val Ala Ala Leu Asn Asn Ser Ile Gly
65                  70                  75                  80

Val Val Gly Val Ala Pro Ser Ala Asp Leu Tyr Ala Val Lys Val Leu
                85                  90                  95

Gly Ala Asn Gly Arg Gly Ser Val Ser Gly Ile Ala Gln Gly Leu Glu
            100                 105                 110

Trp Ala Ala Xaa Asn Asn Met His Ile Ala Asn Met Ser Leu Gly Thr
        115                 120                 125

Asp Ala Pro Ser Ser Thr Leu Glu Arg Ala Val Asn Tyr Ala Thr Ser
    130                 135                 140

Arg Asp Val Leu Val Ile Ala Ala Thr Gly Asn Asn Gly Ser Gly Ser
145                 150                 155                 160

Xaa Xaa Xaa Xaa Val Gly Tyr Pro Ala Arg Tyr Ala Asn Ala Met Ala
                165                 170                 175

Val Gly Ala Thr Asp Gln Asn Asn Arg Arg Ala Asn Phe Ser Gln Tyr
            180                 185                 190

Gly Thr Gly Ile Asp Ile Val Ala Pro Gly Val Asn Val Gln Ser Thr
        195                 200                 205

Tyr Pro Gly Asn Arg Tyr Val Ser Met Asn Gly Thr Ser Met Ala Thr
    210                 215                 220
```

```
Pro His Val Ala Gly Ala Ala Ala Leu Val Lys Gln Arg Tyr Pro Ser
225                 230                 235                 240

Trp Asn Ala Thr Gln Ile Arg Xaa His Leu Lys Asn Thr Ala Thr Asn
                245                 250                 255

Leu Gly Asn Ser Ser Gln Phe Gly Ser Gly Leu Val Asn Ala Glu Ala
            260                 265                 270

Ala Thr Arg
        275


<210> SEQ ID NO 199
<211> LENGTH: 269
<212> TYPE: PRT
<213> ORGANISM: artificial sequence
<220> FEATURE:
<223> OTHER INFORMATION: Consensus sequence Figure 12
<220> FEATURE:
<221> NAME/KEY: MISC_FEATURE
<222> LOCATION: (143)..(143)
<223> OTHER INFORMATION: Xaa can be any amino acid

<400> SEQUENCE: 199

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asp Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Ile Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Xaa Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 200
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 200

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 201
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 201

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45
```

```
Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 202
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 202

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140
```

```
Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 203
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 203

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240
```

```
Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 204
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 204

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 205
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 205

Gln Gln Thr Val Pro Trp Gly Ile Thr Arg Val Gln Ala Pro Ala Val
1               5                   10                  15
```

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 206
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 206

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Ala Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 207
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 207

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Thr Asn Asn Met His Ile Ala Asn Met Ser Leu Gly Thr Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

```
Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 208
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 208

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 209
<211> LENGTH: 269
<212> TYPE: PRT
<213> ORGANISM: artificial sequence
```

<220> FEATURE:
<223> OTHER INFORMATION: B. gibsonii-clade subtilisin

<400> SEQUENCE: 209

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Thr Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 210
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 210

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile

```
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 211
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 211

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
```

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 212
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 212

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
```

```
            260                 265


<210> SEQ ID NO 213
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 213

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 214
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 214

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30
```

```
Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 215
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 215

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125
```

```
Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 216
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 216

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220
```

```
Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 217
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 217

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 218
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 218

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Thr Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 219
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 219

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

```
Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 220
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 220

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190
```

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 221
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 221

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Asp Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Gln Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 222

<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 222

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 223
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 223

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
```

50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 224
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 224

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Ser Gly Ser Val Ser Gly Ile Ala Gln Gly Leu Glu Trp Ala
100 105 110

Ala Gln Asn Asn Met His Ile Ala Asn Met Ser Leu Gly Ser Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly 145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 225
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 225

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Phe
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln 245 250 255

Phe Gly Ser Gly Leu Val Asn Ala Glu Ala Ala Thr Arg
260 265

<210> SEQ ID NO 226
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 226

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 227
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 227

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 228
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 228

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

```
Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 229
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 229

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205
```

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 230
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 230

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 231
<211> LENGTH: 269
<212> TYPE: PRT
<213> ORGANISM: artificial sequence
<220> FEATURE:

<223> OTHER INFORMATION: B. gibsonii-clade subtilisin

<400> SEQUENCE: 231

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Thr Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 232
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 232

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Ser Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

```
Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 233
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 233

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 234
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 234

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 235
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 235

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 236
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 236

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
```

```
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 237
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 237

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
```

```
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 238
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 238

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
```

```
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 239
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 239

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 240
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 240
```

-continued

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 241
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 241

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Val Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

```
Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 242
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 242

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190
```

```
Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 243
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 243

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 244
<211> LENGTH: 269
```

<212> TYPE: PRT
<213> ORGANISM: artificial sequence
<220> FEATURE:
<223> OTHER INFORMATION: B. gibsonii-clade subtilisin

<400> SEQUENCE: 244

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Ser Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 245
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 245

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 246
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 246

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Val Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

```
Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 247
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 247

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255
```

Phe Gly Ser Gly Leu Val Asn Ala Glu Ala Ala Thr Arg
260 265

<210> SEQ ID NO 248
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 248

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Ser Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 249
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 249

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp

```
            20                  25                  30

Ser Gly Ile Ser Thr His Glu Asp Leu Asn Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 250
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 250

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
```

```
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 251
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 251

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
```

```
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 252
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 252

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 253
<211> LENGTH: 269
<212> TYPE: PRT
<213> ORGANISM: artificial sequence
<220> FEATURE:
<223> OTHER INFORMATION: B. gibsonii-clade subtilisin
```

<400> SEQUENCE: 253

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Val Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Val
65 70 75 80

Gly Val Ala Pro Asn Ala Asp Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Ala Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 254
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 254

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Thr His Glu Asp Leu Asn Ile Arg Gly Gly Ala Ser
35 40 45

Phe Val Pro Gly Glu Pro Thr Tyr Ala Asp Leu Asn Gly His Gly Thr
50 55 60

His Val Ala Gly Thr Val Ala Ala Leu Asn Asn Ser Ile Gly Val Ile
65 70 75 80

```
Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 255
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 255

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Thr Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asn His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

<210> SEQ ID NO 256
<211> LENGTH: 269
<212> TYPE: PRT
<213> ORGANISM: artificial sequence
<220> FEATURE:
<223> OTHER INFORMATION: B. gibsonii-clade subtilisin

<400> SEQUENCE: 256

Gln Gln Thr Val Pro Trp Gly Ile Thr Arg Val Gln Ala Pro Ala Val
1 5 10 15

His Asn Arg Gly Ile Thr Gly Ser Gly Val Arg Val Ala Ile Leu Asp
20 25 30

Ser Gly Ile Ser Ala His Glu Asp Leu Asn Ile Arg Gly Gly Ala Ser
35 40 45

Phe Val Pro Gly Glu Pro Thr Thr Ala Asp Leu Asn Gly His Gly Thr
50 55 60

His Val Ala Gly Thr Val Ala Ala Leu Asn Asn Ser Ile Gly Val Ile
65 70 75 80

Gly Val Ala Pro Asn Ala Glu Leu Tyr Ala Val Lys Val Leu Gly Ala
85 90 95

Asn Gly Arg Gly Ser Val Ser Gly Ile Ala Gln Gly Leu Glu Trp Ala
100 105 110

Ala Gln Asn Asn Met His Ile Ala Asn Met Ser Leu Gly Thr Asp Ala
115 120 125

Pro Ser Ser Thr Leu Glu Arg Ala Val Asn Tyr Ala Thr Ser Arg Asp
130 135 140

Val Leu Val Ile Ala Ala Thr Gly Asn Asn Gly Ser Gly Ser Val Gly
145 150 155 160

Tyr Pro Ala Arg Tyr Ala Asn Ala Met Ala Val Gly Ala Thr Asp Gln
165 170 175

Asn Asn Arg Arg Ala Asn Phe Ser Gln Tyr Gly Thr Gly Ile Asp Ile
180 185 190

Val Ala Pro Gly Val Asn Val Gln Ser Thr Tyr Pro Gly Asn Arg Tyr
195 200 205

Val Ser Met Asn Gly Thr Ser Met Ala Thr Pro His Val Ala Gly Ala
210 215 220

Ala Ala Leu Val Lys Gln Arg Tyr Pro Ser Trp Asn Ala Thr Gln Ile
225 230 235 240

Arg Asp His Leu Lys Asn Thr Ala Thr Asn Leu Gly Asn Ser Ser Gln
245 250 255

Phe Gly Ser Gly Leu Val Asn Ala Glu Ala Ala Thr Arg
260 265

-continued

```
<210> SEQ ID NO 257
<211> LENGTH: 269
<212> TYPE: PRT
<213> ORGANISM: artificial sequence
<220> FEATURE:
<223> OTHER INFORMATION: Consensus sequence Figure 14
<220> FEATURE:
<221> NAME/KEY: MISC_FEATURE
<222> LOCATION: (114)..(114)
<223> OTHER INFORMATION: Xaa can be any amino acid

<400> SEQUENCE: 257

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Xaa Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

We claim:

1. An isolated subtilisin variant having protease activity, wherein said variant comprises an amino acid sequence having at least 90% sequence identity to the amino acid sequence of SEQ ID NO: 18, wherein said variant comprises the amino acid substitutions that correspond to substitutions S039E-S099R-F128A in the polypeptide of SEQ ID NO:85, and wherein said variant has one or more improved properties compared to the reference subtilisin having the amino acid sequence of SEQ ID NO:85 selected from the group consisting of improved protease activity, improved cleaning activity and improved thermostability in the presence of a detergent.

2. The isolated subtilisin variant of claim 1, wherein said variant comprises one or more amino acid substitutions that correspond to substitutions in the polypeptide of SEQ ID NO:85 selected from:

A037T-S039E-N042T-S099R-V102I-T114Q-S126T-F128A-N242D;

A037T-S039E-S099R-V102I-T114Q-S126T-F128A-R143A-N212S-N242D;

A037T-S039E-N074D-S099R-V102I-S126T-F128A-R143A-N212S-N242D;
A037T-S039E-N042T-N074D-S099R-V102I-S126T-F128A-S158T-N242D;
A037T-S039E-I043V-A047V-I080V-N085S-E087D-5099R-T114A-F128A;
A037T-S039E-I043V-A047V-T055G-5099R-V102I-T114Q-S126T-F128A-N212S;
A037T-S039E-I043V-A047V-I080V-N085S-E087D-5099R-T114Q-F128A-N242D;
A037T-S039E-I043V-A047V-I080V-N085S-E087D-5099R-T114A-F128A-N242D;
A037T-S039E-A047V-I080V-N0855-E087D-5099R-T114Q-F128A-R143A-N242D;
S036A-S039E-I043V-A047V-T055M-I080V-N085S-E087D-5099R-T114A-F128A;
A037T-S039E-I043V-A047V-I080V-N085S-E087D-5099R-V102I-T114Q-F128A;
A037T-S039E-I043V-A047V-N074D-N0855-E087D-5099R-T114A-F128A-S158T-N212S;
A037T-S039E-N074D-I080V-N085S-E087D-5099R-V102I-T114Q-S126T-F128A-R143A;
A037T-S039E-I043V-A047V-T055G-N074D-I080V-5099R-V102I-T114Q-S126T-F128A;
A037T-S039E-I043V-A047V-N074D-I080V-5099R-V102I-T114Q-S126T-F128A-N242D;
R027K-A037T-S039E-A047V-T055G-T056Y-N074D-5099R-V102I-S126T-F128A-N242D;
A037T-S039E-N042T-A047V-N074D-I080V-N0855-E087D-5099R-T114Q-F128A-N242D;
A037T-S039E-I043V-A047V-I080V-N0855-E087D-5099R-T114A-S126T-F128A-N212S;
A037T-S039E-I043V-A047V-I080V-N085S-E087D-5099R-T114A-S126T-F128A-N242D;
A037T-S039E-I043V-A047V-I080V-N0855-E087D-5099R-T114Q-S126T-F128A-R143A;
A037T-S039E-I043V-A047V-I080V-N085S-E087D-5099R-V102I-T114A-F128A-N212S;
A037T-S039E-N042T-A047V-I080V-N0855-E087D-5099R-V102I-T114Q-F128A-N242D;
A037T-S039E-I043V-A047V-T056Y-I080V-N085S-E087D-5099R-T114A-F128A-N242D;
A037T-S039E-I043V-A047V-I080V-N085S-E087D-S099R-T114Q-F128A-N212S-N242D;
A037T-S039E-A047V-I080V-N085S-E087D-S099R-V102I-T114Q-F128A-R143A-N242D;
A037T-S039E-I043V-A047V-T055G-I080V-N085S-E087D-S099R-T114Q-S126T-F128A;
R027K-A037T-S039E-A047V-I080V-N085S-E087D-S099R-T114Q-F128A-N212S-N242D;
T009S-A037T-S039E-I043V-A047V-I080V-N085S-E087D-S099R-T114A-F128A-V1971;
S039E-I043V-A047V-I080V-N085S-E087D-S099R-T114A-F128A-N212S-K245L-N246S;
A037T-S039E-I043V-A047V-I080V-N085S-E087D-S099R-T114A-F128A-I190L-A224V;
S036A-S039E-I043V-A047V-I080V-N085S-E087D-S099R-T114A-N121S-F128A-R143Q;
S036A-S039E-I043V-A047V-I080V-N085S-E087D-S099R-T114A-F128A-N212S-S255N;
S039E-I043V-A047V-I080V-N085S-E087D-S099R-T114A-F128A-R143Q-N242D-N246K;
A037T-S039E-I043V-A047V-N074D-N085S-E087D-S099R-T114A-S126T-F128A-N212S;
A037T-S039E-I043V-A047V-N074D-I080V-N085S-E087D-S099R-T114A-F128A-N212S;
A037T-S039E-N042T-A047V-I080V-N085S-E087D-S099R-T114A-F128A-S158T-N212S;
V004I-A037T-S039E-I043V-A047V-I080V-N085S-E087D-S099R-T114A-F128A-N182S;
A037T-S039E-I043V-A047V-N074D-N085S-E087D-S099R-T114A-S126T-F128A-S 158T-N212S;
A037T-S039E-I043V-A047V-N074D-I080V-N085S-E087D-S099R-T114A-F128A-S 158T-N212S;
A037T-S039E-I043V-A047V-N074D-N085S-E087D-S099R-T114A-F128A-N212S-N242Q-K245L;
A037T-S039E-I043V-A047V-N074D-I080V-N085S-E087D-S099R-T114A-F128A-N212S-N242Q;
A037T-S039E-I043V-A047V-N074D-I080V-N085S-E087D-S099R-T114A-F128A-N212S-K245L;
A037T-S039E-A047V-S099R-V102I-T114A-1119V-S126T-F128A-R143A-S158T-G160S-N212S;
A037T-S039E-N042T-A047V-T056Y-N074D-I080V-N085S-E087D-S099R-T114Q-S126T-F128A;
S024F-A037T-S039E-A047V-N074D-I080V-N085S-E087D-S099R-T114Q-S126T-F128A-N212S;
A037T-S039E-I043V-A047V-I080V-N085S-E087D-S099R-T114Q-S126T-F128A-R143A-N242D;
A037T-S039E-I043V-A047V-I080V-N085S-E087D-S099R-T114A-S126T-F128A-A237T-N242D;
A037T-S039E-I043V-A047V-I080V-N085S-E087D-S099R-V102I-T114Q-S126T-F128A-N242D;
A037T-S039E-I043V-A047V-T055G-I080V-N085S-E087D-S099R-V102I-T114Q-F128A-R143A;
A037T-S039E-N042T-A047V-T055G-I080V-N085S-E087D-S099R-T114Q-F128A-N212S-N242D;
A037T-S039E-I043V-A047V-I080V-N085S-E087D-S099R-T114A-F128A;
A037T-S039E-I043V-A047V-I080V-N085S-E087D-S099R-T114A-F128A-N242D;
A037T-S039E-I043V-A047V-I080V-N085S-E087D-S099R-T114Q-F128A-N242D;
A037T-S039E-I043V-A047V-I080V-N085S-E087D-S099R-T114A-S126T-F128A-N242D;
A037T-S039E-I043V-A047V-T056Y-I080V-N085S-E087D-S099R-T114A-F128A-N242D;
A037T-S039E-I043V-A047V-I080V-N085S-E087D-S099R-T114Q-S126T-F128A-R143A;
A037T-S039E-I043V-A047V-T055G-I080V-N085S-E087D-S099R-T114Q-S126T-F128A;
A037T-S039E-I043V-A047V-N074D-I080V-N085S-E087D-S099R-T114A-F128A-S 158T-N212S;
A037T-S039E-I043V-A047V-I080V-N085S-E087D-S099R-T114A-S126T-F128A-A237T-N242D;
A037T-S039E-I043V-A047V-N074D-I080V-N085S-E087D-S099R-T114A-S126T-F128A-N242D;
R027K-A037T-S039E-I043V-A047V-I080V-N085S-E087D-S099R-T114A-S126T-F128A-N242D;
A037T-S039E-I043V-A047V-T056Y-I080V-N085S-E087D-S099R-T114A-S126T-F128A-R143A;
A037T-S039E-I043V-A047V-I080V-N085S-E087D-S099R-T114A-N121S-F128A-N246S-S-255N;
A037T-S039E-A047V-I080V-N085S-E087D-S099R-T114Q-F128A-R143A-N242D;
A037T-S039E-I043V-A047V-N074D-N085S-E087D-S099R-T114A-F128A-S158T-N212S;
A037T-S039E-I043V-A047V-I080V-N085S-E087D-S099R-V102I-T114Q-S126T-F128A-N242D;
A037T-S039E-I043V-A047V-T056Y-I080V-N085S-E087D-S099R-T114Q-S126T-F128A-N242D;
A037T-S039E-I043V-A047V-N074D-I080V-N085S-E087D-S099R-T114Q-I119V-S126T-F128A;

A037T-S039E-I043V-A047V-T055G-I080V-N085S-E087D-S099R-V102I-T114A-S126T-F128A-S158T;
A037T-S039E-I043V-A047V-I080V-N085S-E087D-S099R-T114A-S126T-F128A-R143A-S158T-N242D;
A037T-S039E-N042T-I043V-R044S-A047V-N074D-I080V-N085S-E087D-S099R-T114A-S126T-F128A;
A037T-S039E-N042T-I043V-R044S-A047V-I080V-N085S-E087D-S099R-T114A-S126T-F128A-N242D;
A037T-S039E-I043V-A047V-I080V-N085S-E087D-S099R-V102I-T114A-I119V-S126T-F128A-F257Y;
A037T-S039E-I043V-A047V-N074D-I080V-N085S-E087D-S099R-V102I-T114A-N121S-F128A-R143Q;
A037T-S039E-I043V-A047V-N074D-N085S-E087D-S099R-T114A-S126T-F128A-S 158T-N212S;
S036A-S039E-I043V-A047V-N074D-I080V-N085S-E087D-S099R-T114A-F128A-A224V-S255N;
A037T-S039E-I043V-A047V-T055G-N074D-I080V-N085S-E087D-S099R-T114Q-S126T-F128A-N242D;
A037T-S039E-I043V-A047V-T055G-I080V-N085S-E087D-5099R-V102I-T114Q-S126T-F128A-R143A;
A037T-S039E-I043V-A047V-I080V-N0855-E087D-5099R-V102I-T114Q-S126T-F128A-R143A-N242D;
A037T-S039E-I043V-A047V-T056Y-I080V-N0855-E087D-5099R-T114Q-S126T-F128A-S158T-N242D;
A037T-S039E-I043V-A047V-T056Y-I080V-N085S-E087D-5099R-T114Q-I119V-S126T-F128A-F257Y;
A037T-S039E-I043V-A047V-T056Y-I080V-N085S-E087D-5099R-T114Q-I119V-S126T-F128A-N242D;
A037T-S039E-I043V-A047V-N074D-I080V-N0855-E087D-5099R-T114A-S126T-F128A-S158T-N212S-N242Q;
A037T-S039E-I043V-A047V-N074D-I080V-N0855-E087D-5099R-T114A-S126T-F128A-T188A-I190L-F257Y;
V004I-T0095-A037T-S039E-I043V-A047V-I080V-N0855-E087D-5099R-T114A-F128A-A224V-K245L-S255N;
A037T-S039E-N042T-A047V-T056Y-N074D-I080V-N0855-E087D-5099R-T114Q-S126T-F128A;
A037T-S039E-I043V-A047V-N074D-N085S-E087D-S099R-T114A-S126T-F128A-S 158T-N212S-N242Q;
A037T-S039E-I043V-A047V-N074D-N085S-E087D-S099R-T114A-S126T-F128A-S 158T-N212S-K245L;
A037T-S039E-I043V-A047V-I080V-N085S-E087D-S099R-T114P-S126T-F128A-R143T-S158T-N212K-N242D;
A037T-S039E-I043V-A047V-T056Y-N074D-I080V-N085S-E087D-S099R-T114Q-S126T-F128A-R143A-N242D;
A037T-S039E-I043V-A047V-T055G-T056Y-N074D-I080V-N085S-E087D-S099R-V102I-T114Q-S126T-F128A;
S036A-A037N-S039E-I043V-A047V-I080V-N085S-E087D-S099R-T114A-F128A-N242D-K245L-N246S-S255N;
A037T-S039E-I043V-A047V-N074D-I080V-N085S-E087D-S099R-T114A-S126T-F128A-S158T-N212S-N242Q-K245L;
A037T-S039E-I043V-A047V-I080V-N085S-E087D-S099R-T114A-1119V-S126T-F128A-S158T-G160S-N242D-F257Y;
A037T-S039E-I043V-A047V-I080V-N085S-E087D-S099R-T114A-N121S-F128A-N182S-I190L-K245L-N246S-S255N;
A037T-S039E-N074D-I080V-N085S-E087D-S099R-V102I-T114Q-S126T-F128A-R143A;
A037T-S039E-I043V-A047V-T055G-N074D-I080V-S099R-V102I-T114Q-S126T-F128A;
A037T-S039E-I043V-A047V-N074D-I080V-S099R-V102I-T114Q-S126T-F128A-N242D;
A037T-S039E-A047V-N074D-I080V-N085S-E087D-S099R-V102I-T114Q-S126T-F128A-S158T-N242D;
A037T-S039E-N042T-A047V-N074D-I080V-N085S-E087D-S099R-V102I-T114Q-S126T-F128A-N242D;
A037T-S039E-I043V-A047V-N074D-N085S-E087D-S099R-T114A-S126T-F128A-S 158T-N212S-N242Q-K245L;
T009S-S036A-S039E-I043V-A047V-I080V-N085S-E087D-S099R-T114A-F128A-R143Q-N182S-T188A-I190L;
A037T-S039E-I043V-A047V-T055G-N074D-I080V-N085S-E087D-S099R-V102I-T114Q-S126T-F128A-S158T-N242D;
A037T-S039E-I043V-A047V-T055G-N074D-I080V-N085S-E087D-S099R-T114Q-S126T-F128A-R143A-S158T-N212S;
A037T-S039E-I043V-A047V-I080V-N085S-E087D-S099R-T114A-F128A-R143Q-N212S-A224V-Y232N-K245L-N246S-S255N;
V004I-T009S-A037T-S039E-I043V-A047V-I080V-N085S-E087D-S099R-T114A-N121S-F128A-R143Q-A2241-R231K-K245L;
R027K-A037T-S039E-A047V-I080V-N085S-E087D-S099R-T114Q-I119V-S126T-F128A-G160S-N242D-F257Y;
R027K-A037T-S039E-I043V-A047V-T056Y-I080V-N085S-E087D-S099R-T114Q-S126T-F128A-S 158T-G160S-N242D-F257Y;
R027K-A037T-S039E-I043V-A047V-T056Y-I080V-N085S-E087D-S099R-V102I-T114Q-S126T-F128A-T188A-I190L-F257Y;
R027K-A037T-S039E-I043V-A047V-T056N-I080V-N0855-E087D-5099R-T114P-S126T-F128A-R143T-V1591-N212T-F257Y;
A037T-S039E-I043V-A047V-T056Y-I080V-N085S-E087D-5099R-T114Q-I119V-S126T-F128A-S 158T-V1591-G1605-F257Y;
A037T-S039E-I043V-A047V-T055G-T056Y-N074D-I080V-N0855-E087D-5099R-V102I-T114Q-S126T-F128A-N242D;
R027K-A037T-S039E-A047V-T056Y-N074D-I080V-N0855-E087D-5099R-T114Q-I119V-S126T-F128A-N242D-F257Y;
A037T-S039E-N042T-N074D-S099R-V102I-S126T-F128A-S158T-N242D;
R027K-A037T-S039E-A047V-T055G-T056Y-N074D-5099R-V102I-S126T-F128A-N242D;
S039E-I043V-A047V-I080V-N085S-E087D-5099R-T114A-F128A-A224V-N242D-N2465-S255N;
A037T-S039E-I043V-A047V-N074D-I080V-N0855-E087D-5099R-V102I-T114A-F128A-R143Q-S158T-A224V-S255N;
A037T-S039E-I043V-A047V-P0545-T056Y-A057Q-N074D-I080V-N0855-E087D-5099R-T114A-N121S-F128A-S158T-A224V-S255N;
A037T-S039E-N042T-I043V-R0445-A047V-N074D-I080V-N0855-E087D-5099R-V102I-S126T-F128A-S158T-G160S-N242D;
S039E-T056Y-S099R-F128A;
S039E-S099R-T114Q-F128A;
S039E-N085S-S099R-F128A;
S039E-E087D-S099R-F128A;
S039E-S099R-S126T-F128A;

S039E-E087D-S099R-S126T-F128A;
S039E-T056Y-S099R-S126T-F128A;
S039E-E087D-5099R-F128A-N242D;
A037T-S039E-E087D-5099R-T114A-F128A;
S039E-T056Y-E087D-S099R-S126T-F128A;
S039E-5099R-T114Q-S126T-F128A-N242D;
A037T-S039E-5099R-T114Q-S126T-F128A-N242D;
A037T-S039E-T056Y-S099R-S126T-F128A-N242D;
A037T-S039E-T056Y-N085S-E087D-S099R-T114Q-F128A;
A037T-S039E-A047V-T056Y-5099R-T114Q-S126T-F128A;
A037T-S039E-A047V-T056Y-5099R-T114A-S126T-F128A;
A037T-S039E-T056Y-S099R-T114Q-S126T-F128A-N242D;
S039E-A047V-E087D-S099R-T114Q-S126T-F128A-N242D;
S039E-A047V-T056Y-N085S-E087D-S099R-T114Q-S126T-F128A;
S039E-A047V-I080V-E087D-S099R-T114A-S126T-F128A-N242D;
A037T-S039E-T056Y-N085S-S099R-T114Q-S126T-F128A-N242D;
S039E-A047V-T056Y-E087D-S099R-T114A-S126T-F128A-N242D;
S039E-A047V-T056Y-E087D-S099R-T114Q-S126T-F128A-N242D;
A037T-S039E-A047V-I080V-N085S-E087D-S099R-T114A-S126T-F128A;
A037T-S039E-I080V-N085S-E087D-S099R-T114Q-S126T-F128A-N242D;
A037T-S039E-T056Y-N085S-E087D-S099R-T114A-S126T-F128A-N242D;
A037T-S039E-A047V-T056Y-E087D-S099R-T114A-S126T-F128A-N242D; and
combinations thereof.

3. The isolated subtilisin variant of claim 1, wherein the improved property is (i) improved protease activity, wherein said variant has a performance index (PI) on N-succinyl-alanine-alanine-proline-phenylalanine-p-nitroanilide (N-suc-AAPF-pNA) or dimethyl casein substrate;

(ii) improved cleaning performance in the presence of a detergent, wherein said variant has a blood/milk/ink (BMI) and/or egg stain cleaning PI >1; and/or (iii) improved thermostability in the presence of a detergent, wherein said variant has a stability PI >1.

4. A composition comprising the subtilisin variant of claim 1.

5. The composition of claim 4, wherein said composition is a detergent composition.

6. The composition of claim 5, wherein the detergent composition is selected from a laundry detergent, a fabric softening detergent, a dishwashing detergent, and a hard-surface cleaning detergent.

7. The composition of claim 4, wherein said composition further comprises calcium ions and/or zinc ions; one or more enzyme stabilizers; about 0.001% to about 1.0 weight % of said variant; one or more bleaching agents; one or more adjunct materials; and/or one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

8. The composition of claim 4, wherein said composition is phosphate-free.

9. The composition of claim 4, wherein said composition is a granule, powder, solid, bar, liquid, tablet, gel, paste or unit dose composition.

10. The composition of claim 4, wherein said composition is boron free.

* * * * *